US010077238B2

(12) United States Patent
Breitenstein et al.

(10) Patent No.: US 10,077,238 B2
(45) Date of Patent: Sep. 18, 2018

(54) SMALL MOLECULE LFA-1 INHIBITORS

(71) Applicant: ALLOCYTE PHARMACEUTICALS AG, Basel (CH)

(72) Inventors: Werner Breitenstein, Basel (CH);
Marianne Huerzeler, Daniken (CH);
Terence Kelly, Ridgefield, CT (US);
Riccardo Mancuso, Basel (CH);
Gisbert Schneider, Zurich (CH);
Gabriele Weitz-Schmidt, Bad Krozingen (DE)

(73) Assignee: ALLOCYTE PHARMACEUTICALS AG, Basel (CH)

( * ) Notice: Subject to any disclaimer, the term of this patent is extended or adjusted under 35 U.S.C. 154(b) by 0 days.

(21) Appl. No.: 15/318,278

(22) PCT Filed: Jun. 10, 2015

(86) PCT No.: PCT/EP2015/062931
§ 371 (c)(1),
(2) Date: Dec. 12, 2016

(87) PCT Pub. No.: WO2015/189265
PCT Pub. Date: Dec. 17, 2015

(65) Prior Publication Data
US 2017/0121284 A1    May 4, 2017

(30) Foreign Application Priority Data
Jun. 12, 2014  (EP) .................................... 14172200

(51) Int. Cl.
*C07D 209/52* (2006.01)
*A61K 45/06* (2006.01)
*A61K 31/403* (2006.01)
*A61K 31/5377* (2006.01)
*A61K 31/4439* (2006.01)

(52) U.S. Cl.
CPC .......... *C07D 209/52* (2013.01); *A61K 31/403* (2013.01); *A61K 31/4439* (2013.01); *A61K 31/5377* (2013.01); *A61K 45/06* (2013.01)

(58) Field of Classification Search
CPC ..... C07D 209/52; A61K 45/06; A61K 31/403
USPC ................................................. 548/465, 452
See application file for complete search history.

(56) References Cited

U.S. PATENT DOCUMENTS

2006/0202197 A1   9/2006  Nakayama

FOREIGN PATENT DOCUMENTS

DE      2100800         7/1971
WO    WO 2008/064057    5/2008

OTHER PUBLICATIONS

Prodrug, 2017,https://en.wikipedia.org/wiki/Prodrug.*
Enantiomer, 2017, https://en.wikipedia.org/wiki/Enantiomer.*
RN-500194-36-5 (2003).*
Aggarwal, et al, "A new protocol for the in situ generation of aromatic, heteroaromatic, and unsaturated diazo compounds and its application in catalytic and asymmetric epoxidation of carbonyl compounds. Extensive studies to map out scope and limitations, and rationalization of diastereo- and enantioselectivities" *J Am Chem Soc.*, 2003, 10;125(36):10926-40.
Ahrens, et al., "Therapeutic integrin inhibition: allosteric and activation-specific inhibition strategies may surpass the initial ligand-mimetic strategies" *Thromb Haemost*, 2008, 99(5):803-4.
Harikrishna, et al., "Study of the Chemoselectivity of Grignard Reagent Addition to Substrates Cotaining Both Nitrile and Weinreb Amide Functionalities" *Eur, J. Org, Chem.*, 2013, 4918-4932.
Arefanian, et al. "Short-term administrations of a combination of anti-LFA-1 and anti-CD154 monoclonal antibodies induce tolerance to neonatal porcine islet xenografts in mice," *Diabetes*, 2010, 59(4):958-66.
Bourget, et al., "Biotin-phenyldiazomethane conjugates as labeling reagents at phosphate in mono and polynucleotides," *Bioorg Med Chem.*, 2005, 1;13(5):1453-61.
Chittasupho, et al., "cIBR effectively targets nanoparticles to LFA-1 on acute lymphoblastic T cells," *Mol Pharm.*, 2010, 1;7(1):146-55.
Cook, et al., "Enamidines. Part 1. Synthesis of enamidines and dihydrntriazines by the reaction of organolithium and organomagnesium compounds with aromatic nitrites," *J. Chem. Soc., Perkin Trans. 1*, 1980, 2392-2397.
Dolara, et al., "Cytogenetic effects on human lymphocytes of a mixture of fifteen pesticides commonly used in Italy," *Mutation Research*, 1994, pp. 47-51.
Faia, et al., "Treatment of inflammatory macular edema with humanized anti-CD11a antibody therapy," *Invest Ophthalmol Vis Sci.*, 2011, 1;52(9):6919-24.
Glawe, et al., "Genetic deficiency of Itgb2 or ItgaL prevents autoimmune diabetes through distinctly different mechanisms in NOD/LtJ mice," *Diabetes*, 2009, 58(6):1292-301.
Hogg, et al., "The insider's guide to leukocyte integrin signalling and function," *Nat Rev Immuno,.* 2011, 11(6):416-26.
Jabado, et al., "Bone marrow transplantation from genetically HLA-nonidentical donors in children with fatal inherited disorders excluding severe combined immunodeficiencies: use of two monoclonal antibodies to prevent graft rejection," *Pediatrics*, 1996, 98(3 Pt 1):420-8.
Kapp, et al., "Integrin modulators: a patent review," *Expert Opin Ther Pat.*, 2013, 23(10):1273-1295.
Ke, et al., "Suppression of established experimental autoimmune uveitis by anti-LFA-1alpha Ab," *Invest Ophthalmol Vis Sci.*, 2007, 48(6):2667-75.
Krasovskiy, et al., A LiCl-Meicated Br/Mg Exchange Reaction for the Preparation of Functionalized Aryl- and HeteroarylmagnesiumAngew. *Chem. Int. Ed.* 2004, 43, 3333-3336.
Lebwohl, et al., "A novel targeted T-cell modulator, efalizumab, for plaque psoriasis," *N Engl J Med.*, 2003, 20;349(21):2004-2013.

(Continued)

*Primary Examiner* — Sun Jae Yoo
(74) *Attorney, Agent, or Firm* — Hoxie & Associates LLC

(57) ABSTRACT

The present invention relates to novel compounds which are capable of inhibiting the interaction of LFA-1 with its counter ligands.

18 Claims, No Drawings

(56) References Cited

OTHER PUBLICATIONS

Lee, et al. "Developmental control of integrin expression regulates Th2 effector homing," *J Immunol.*, 2008, 1;180(7):4656-67.
Navarini, et al., "Control of widespread hypertrophic lupus erythematosus with T-cell-directed biologic efalizumab," *Dermatology*, 2010, 220(3):249-53.
Nicolls, et al., "LFA-1 (CD11a) as a therapeutic target," *Am J Transplant*, 2006, 6(1):27-36.
Poria, et al., "Characterization of a radiolabeled small molecule targeting leukocyte function-associated antigen-1 expression in lymphoma and leukemia," *Cancer Biother Radiopharm*, 2006, 21(5):418-26.
Posselt, et al., "Islet transplantation in type 1 diabetics using an immunosuppressive protocol based on the anti-LFA-1 antibody efalizumab," *Am J Transplant*, 2010, 10(8):1870-80.
Reimlinger, *Chem. Ber.* 1964, 97, 3493 (German Language Only).
Salas, et al., Rolling adhesion through an extended conformation of integrin alphaLbeta2 and relation to alpha I and beta I-like domain interaction. Immunity. Apr. 2004;20(4):393-406.
Seminara, et al., "Assessing long-term drug safety: lessons (re) learned from raptiva," *Semin Cutan Med Surg*, 2010, 29(1):16-19.
Sheppard, Lifitegrast ophthalmic solution 5.0% for treatment of dry eye disease: results of the OPUS-1 phase 3 study, *Ophthalmology*, 2014, 121(2):475-483.
Shults, et al., "Thebaine adducts with maleimides. Synthesis and transformations," *Russian Journal of Organic Chemistry*, 2005, 41 (8): 1132-1144.
Suchard, et al., "An LFA-1 (alphaLbeta2) small-molecule antagonist reduces inflammation and joint destruction in murine models of arthritis," *J Immunol.*, 2010, 184(7):3917-26.
Taber, et al., "Simple preparation of alpha-diazo esters," *J Org Chem.*, 2005, 70(7):2851-4.
Tan, "The leucocyte β2 (CD18) integrins: the structure, functional regulation and signalling properties," *Biosci Rep.*, 2012, 32(3):241-69.
Usmani, et al., "Efalizumab in the treatment of discoid lupus erythematosus," *Arch Dermatol.* 2007, 143(7):873-7.
Verma, "Leukocyte function-associated antigen-1/intercellular adhesion molecule-1 interaction induces a novel genetic signature resulting in T-cells refractory to transforming growth factor-β signaling," *J Biol Chem.*, 2012, 3;287(32):27204-16.
Weitz-Schmidt, et al., "Improved lymphocyte function-associated antigen-1 (LFA-1) inhibition by statin derivatives: molecular basis determined by x-ray analysis and monitoring of LFA-1 conformational changes in vitro and ex vivo," *J Biol Chem.*, 2004, 279(45):46764-71.
Weitz-Schmidt, et al., "Cell adhesion assays" *Methods Mol Biol.*, 2012, 757:15-30.
Yuki, et al., "Isoflurane binds and stabilizes a closed conformation of the leukocyte function-associated antigen-1," *FASEB J.*, 2012, 26(11):4408-17.
Zhou, et al., "Catalytic reactions of carbene precursors on bulk gold metal," *J Am Chem Soc.*, 2009, 131(33):11734-43.
International Search Report for International Application No. PCT/EP2015/062931, dated.
Molchanov, et al. "Reactions of Aliphatic Diazo Compounds: IV. Reaction of Diphenyldiazomethane with Substituted Imides of Maleic and Itaconic Acids," *Russian Journal of Organic Chemistry*, vol. 38, No. 2, 2002, pp. 259-263.
Kirino, et al. "Effect of Methyl Groups on the Cyclopropane Ring on Antifungal Activity of N-(3, 5-Dichlorophenyl)-" *Journal of Pesticide Science*, vol. 9, No. 2, 1984, pp. 351-353.
Tamura, et al. "Structural Basis for Androgen Receptor Agonists and Antagonists: Interactio of SPEED 98-listed Chemicals and Related Compounds with the Androgen Receptor Based on an In Vitro Reporter Gene Assay and 3D-QSAR," *Bioorganic & Medicinal Chemistry*, vol. 14, 2006, pp. 7160-7174.
CAS Registry [STN online], entered Oct. 17, 2002, RN: 462091-11-8.
Giblin, et al. "LFA-1 as a Key Regulator of Immune Function: Approaches Toward the Development of LFA-1-Based Therapeutics," *Current Pharmaceutical Design*, vol. 12, No. 22, 2006, pp. 2771-2795.

* cited by examiner

SMALL MOLECULE LFA-1 INHIBITORS

CROSS-REFERENCE TO RELATED APPLICATIONS

This application is a U.S. National Stage application under 35 U.S.C. 371 claiming benefit of PCT/EP2015/062931, filed on Jun. 10, 2015, which claims priority to and the benefit of European Patent Application No. 14172200.9 filed Jun. 12, 2014, the contents of each of which are hereby incorporated by reference in their entireties.

THE FIELD OF THE INVENTION

The present invention relates to novel compounds which are capable of inhibiting the interaction of LFA-1 with its counter ligands and pharmaceutical compositions of these compounds which are useful for diagnostic, preventive and therapeutic use in human and veterinary medicine.

BACKGROUND OF THE INVENTION

Lymphocyte function-associated antigen-1 (LFA-1) (alphaLbeta2, CD11a/CD18), the target receptor of this invention, is a member of the integrin superfamily with 24 members known todate. Integrins are heterodimeric cell-surface receptors composed of one alpha subunit and one beta subunit each. Functionally, integrins are cellular adhesion molecules mediating a wide range of cell-cell, cell-extracellular matrix and cell-pathogen interactions. Within the integrin superfamily, LFA-1 belongs to the beta 2 integrin subfamily, which is defined by a common beta 2 chain and unique alpha chains. The four members of the beta2 integrin subfamily are alphaLbeta2 (LFA-1, CD11a/CD18), alphaMbeta2 (Mac-1, CD11b/CD18), alphaXbeta2 (gp 150, CD11c/CD18) and alphaDbeta2 (CD11d/CD18) [Tan 2012]. A condition termed "Leukocyte Adhesion Deficiency-I" (LAD-I) has been identified in patients having a deficiency in beta2 (CD18) integrins. LAD-I is characterized by serious bacterial and fungal infections.

The expression of LFA-1 is restricted to leukocytes including T-cells, B-cells, neutrophils, monocytes, macrophages, dendritic cells, mast cells, eosinophils, and NK cells. The level of expression varies with cell type and differentiation state. LFA-1 is overexpressed in certain lymphomas and leukemias [Poria 2006, Chittasupho 2010]. The major ligands of LFA-1 identified to date belong to the immunoglobulin (Ig) superfamily. They are the intercellular adhesion molecules ICAM-1, ICAM-2, ICAM-3, ICAM-5 and the junctional adhesion molecule JAM-A (previously JAM-1). These ligands are expressed on various cell types including endothelial cells lining the vessel wall, epithelial and tissue resident cells (e.g. keratinocytes, dendritic cells) and leukocytes [Tan 2012].

LFA-1 plays a central role in the innate and adaptive immune response. Firstly, as a cellular adhesion molecule LFA-1 mediates the firm adhesion of leukocytes to inflamed vessel walls and their extravasation into inflamed tissues. Secondly, LFA-1 is crucial for the activation of immune cells. In this context, LFA-1 is well-characterized as a co-stimulatory receptor which is essential for the formation of the immunological synapse and controls T cell activation and proliferation. The central roles of LFA-1 in the immune response require tight control of LFA-1 activation. Normally, LFA-1 resides on the cell surface in an inactive state. Upon intracellular signaling (so-called "inside-out" signaling) LFA-1 is converted from an inactive to an active, ligand-binding state. This conversion is associated with major conformational changes within the receptor. Upon ligand binding, LFA-1 conveys signals back into the cells (so-called "outside-in" signaling), triggering subsequent steps which depend on the cell type [Hogg 2011].

Given its broad distribution on immunocompetent cells, LFA-1 plays a central role in immune-mediated and inflammatory diseases. This has been established extensively in experimental disease in animals, mostly using knock-out mice and anti-LFA-1 antibodies. Anti-LFA-1 therapy led to prolonged graft survival in various models of allograft transplantation (including cardiac, islet and cornea transplantation). Moreover, in several transplantation models, tolerance could be induced with both anti-LFA-1 therapy used alone or in combination with other modalities [Nicolls 2006, Arefanian 2010]. In other experimental disease models, for example, uveitis, arthritis, multiple sclerosis, diabetes mellitus, asthma and lupus-like disease animals genetically deficient for LFA-1 or treated with anti-LFA-1 agents were found to be protected against disease [Giblin 2006, Ke 2007, Glawe 2009, Lee 2008, Suchard 2010]. LFA-1 has also been identified as a therapeutic target for infectious diseases, including HIV infection [Kapp 2013].

Beyond, LFA-1 has been described as target receptor for drug delivery or for the delivery of marker molecules such as imaging agents (diagnostic usage) to lymphoma and leukemia cells [Chittasupho 2010, Poria 2006].

Further, LFA-1 plays decisive roles in the differentiation of lymphocyte populations [Verma 2012] and may be used as a target allowing the selection or expansion of distinct lymphocyte populations in vitro, ex vivo and in vivo. Increases in regulatory lymphocyte populations have been observed in patients treated with anti-LFA-1 antibodies [Faia 2011, Posselt 2010].

The clinical experience with LFA-1 targeting therapies largely derives from the use of monoclonal anti-LFA-1 antibodies, i.e. odulimumab used for the treatment of graft-versus-host disease [Jabado 1996] and efalizumab for plaque psoriasis [Lebwohl 2003], primarily, with small pilot studies in other autoimmune indications [e.g. Usmani 2007, Navarini 2010, Faia 2011]. Efalizumab was withdrawn from markets because of the occurrence of four cases of a rare, often fatal viral infection of the brain (progressive multifocal leukoencepahlopathy) [Seminara 2010].

Several small molecule inhibitors have been described in patent applications or scientific literature which affect the interaction of LFA-1 with their ligands [Giblin 2006]. To date, these compounds can be grouped into two major classes, based on how they bind to LFA-1 and how they influence LFA-1 conformation. One class of inhibitors, termed alpha I allosteric inhibitors, binds to the ligand binding domain (termed I domain) on the LFA-1 alpha chain, however at a site distal to the ligand binding site (termed alpha L I allosteric site). These inhibitors stabilize LFA-1 in its bent inactive state, preventing the switchblade-like opening of LFA-1 into its extended active state, and the exposure of activation epitopes [Giblin 2006]. Furthermore, the binding of alpha I allosteric inhibitors to LFA-1 can be elegantly detected by the loss of the mAb R7.1 epitope [Weitz-Schmidt 2004]. Major chemical classes of alpha I allosteric inhibitors which have been described so far include hydantoin derivatives, statin (or "mevinolin")-based derivatives, substituted diazepanes and arylthio cinnamide analogues [for review see Giblin 2006 and Kapp 2013]. None of these compounds is reported to be in clinical development, currently.

Another group of inhibitors, termed alpha/beta I allosteric inhibitors, are ligand mimetics, i.e. they are derived from amino acids of the LFA-1 binding region of ICAM [Giblin 2010, Kapp 2013]. Unexpectedly, these ligand mimetics do not bind to the ligand binding site of LFA-1 located on the alpha chain. Instead, they act via the LFA-1 beta chain by competing with the interaction of an internal ligand. As a result the binding domain of LFA-1 remains in a low affinity state whereas the rest of LFA-1 adapts an extended, active conformation, exposing activation epitopes [Giblin 2010]. Cells treated with these inhibitors exhibit paradoxical activities, i.e. they induce "rolling adhesion", in contrast to cells treated with alpha L I allosteric inhibitors [Salas 2004]. Paradoxical agonism has also been observed with ligand mimetics targeting other integrin family members including alpha IIb/beta3 [Ahrens 2008]. Currently, one ligand mimetic LFA-1 inhibitor is in clinical development for the treatment of dry eye disease [Sheppard 2014, Kapp 2013].

Taken together, it is appreciated that LFA-1 is a receptor involved in inflammatory, immune-mediated and infectious diseases and is overexpressed in certain malignant diseases. These diseases are often severe, chronic disorders often requiring life-long therapy. From a clinical perspective, there remains a high need for effective therapies either preventing the conditions or controlling the activity of disease and providing long-term benefit/risk profiles superior to currently available therapies. It is further appreciated that novel LFA-1 inhibitors with improved pharmacologic profiles and devoid of side effects observed with earlier LFA-1 inhibitors will constitute a therapeutic advance.

In conclusion, based on the status of prior art, there remains a need for novel, improved LFA-1 inhibitors of chemical scaffolds different to scaffolds described before. The availability of such inhibitors would provide additional therapeutic and diagnostic options across the spectrum of diseases in which LFA-1 is involved or can be employed as a target for drug delivery, given that different chemical structures will be associated with different pharmacologic profiles. Furthermore, it is appreciated that the function of LFA-1 can be modulated in different ways and that unwanted effects/side-effects observed with certain classes of existing LFA-1 inhibitors, such as anti-LFA-1 monoclonal antibodies, may not be observed with novel types of LFA-1 inhibitors.

SUMMARY OF THE INVENTION

The present invention relates to novel compounds according to formula (Ia) and/or (Ib), which are capable of selectively and potently inhibiting the interaction of LFA-1 with its counter ligands. The present invention provides novel compounds according to formula (Ia)

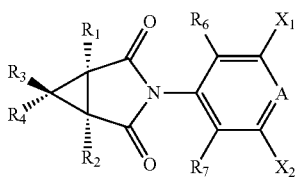

or according to formula (Ib)

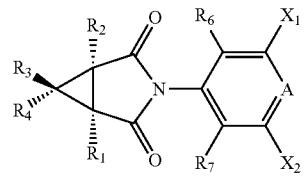

pharmaceutically-acceptable salts, hydrates, solvates, or prodrugs thereof, wherein the substituents have the meaning as described below.

The present invention also provides novel compounds according to formula (Ia)

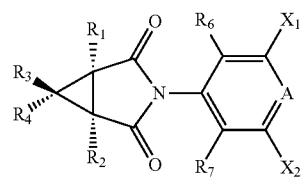

and/or according to formula (Ib),

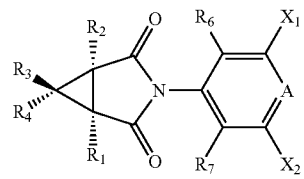

racemates of the compound according to formula (Ia) and the compound according to formula (Ib), diastereomers of the compound according to formula (Ia) or the compound according to formula (Ib), diastereomeric meso forms of the compound according to formula (Ia) wherein $R_1$ and $R_2$ are the same, pharmaceutically-acceptable salts, hydrates, solvates, or prodrugs thereof, wherein the substituents have the meaning as described below.

The present invention also provides novel diastereomeric mesoforms of a compound according to formula (Ia)

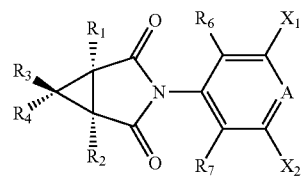

pharmaceutically-acceptable salts, hydrates, solvates, or prodrugs thereof, wherein the substituents have the meaning as described below.

The present invention also relates to pharmaceutical compositions useful for diagnostic, preventive and therapeutic use in human and veterinary medicine comprising compounds of the formula (Ia) and/or (Ib), its racemates, diastereomers, pharmaceutically-acceptable salts, hydrates, solvates, or prodrugs thereof. The present invention is useful in methods in diagnosing, preventing and treating any disorder mediated through LFA-1.

DETAILED DESCRIPTION OF THE INVENTION

The following are definitions of terms used in this specification and appended claims. The initial definition provided for a group or term herein applies to that group or term throughout the specification and claims, individually or as part of another group, unless otherwise indicated.

The term "acyl" as used herein refers to a carbonyl group linked to an organic radical, more particularly, the group C(=O)R, as well as the bivalent groups —C(=O)— or —C(=O) R—, which are linked to organic radicals or a ring in compounds of formula (Ia) or (Ib).

The term "alkenyl" as used herein refers to straight or branched chain hydrocarbon groups having 2 to 6 carbon atoms and at least one double bond.

The term "alkyl" as used herein refers to a saturated straight or branched chain group of 1-6 carbon atoms derived from an alkane by the removal of one hydrogen atom for example methyl, ethyl, n-propyl, i-propyl, n-butyl, i-butyl, tert-butyl, n-pentyl, or n-hexyl. The alkyl groups of this invention can be optionally substituted.

The term "aryl" as used herein refers to a mono- or bicyclic carbocyclic ring system having one or two aromatic rings. The aryl group can also be fused to a cyclohexane, cyclohexene, cyclopentane or cyclopentene ring. The aryl groups of this invention can be optionally substituted. A preferred aryl group and optionally substituted aryl group, respectively of this invention is a phenyl group or substituted phenyl group.

The term "cycloalkyl" as used herein refers to a monovalent saturated cyclic or bicyclic hydrocarbon group of usually 3-6 carbons derived from a cycloalkane by the removal of a single hydrogen atom. Cycloalkyl groups of this invention can be optionally substituted.

The term "fluoroalkyl" as used herein refers to an alkyl group of 1 to 6 carbon atoms, preferably 1 carbon atom, in which one, two or all of the hydrogen atoms of one carbon atom, preferably all of the hydrogen atoms of one carbon atom, have been replaced by fluoride atoms. The term "trifluoroalkyl" as used herein refers to an alkyl group of 1 to 6 carbon atoms preferably 1 carbon atom, in which all of the hydrogen atoms of one carbon atom have been replaced by fluoride atoms.

The terms "halo" or "halogen" as used herein refers to F, Cl, Br, or I.

The term "heteroaryl" as used herein refers to substituted and unsubstituted aromatic 5-, or 6-membered monocyclic groups, 9- or 10-membered bicyclic groups, and 11- to 14-membered tricyclic groups which have at least one heteroatom (O, S or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. Heteroaryl groups of this invention can be optionally substituted. The heteroaryl groups of this invention can be substituted with e.g. alkyl or halogen, preferably with methyl and/or fluorine. Usually, a heteroaryl group and optionally substituted heteroaryl group, respectively of this invention is selected from the group consisting of substituted and/or unsubstituted aromatic 5-, or 6-membered monocyclic groups, which have at least one heteroatom (O, S or N), preferably one heteroatom (O, S or N), more preferably one O or N in the ring. A preferred heteroaryl group and optionally substituted heteroaryl group, respectively of this invention is selected from the group consisting of a pyridinyl group, a substituted pyridinyl group, a furanyl group and a substituted furanyl group. A substituted pyridinyl group and a substituted furanyl group are e.g. fluorinated or methylated furanyl and pyridinyl, respectively e.g. 5-fluorofuran-2-yl, 5-methylfuran-2-yl, 3-fluoro-4-pyridyl, 3,5-difluoro-4-pyridyl, 2-methyl-4-pyridyl, 2,6-dimethyl-4-pyridyl. Most preferably an unsubstituted heteroaryl group, in particular an unsubstituted pyridinyl group or an unsubstituted furanyl group, is used as heteroaryl group in the present invention.

Substituents of the aryl or the heteroaryl group of the present invention include (i) $R_{11}$, which is aryl or heteroaryl selected from phenyl, 2-naphthyl, 2-, 3-, 5- or 6-indolyl, 2- or 3-thiophenyl, 2-, 3- or 4-pyridyl, 2-, 4- or 5-pyrimidinyl, 2- or 3-furyl, 1-, 2- or 3-pyrrolyl, 2-, 4- or 5-oxazolyl, 2-, 4- or 5-thiazolyl, 1-, 3-, 4- or 5-pyrazolyl, 3-, 4- or 5-isoxazolyl, 1-, 2-, 4- or 5-imidazolyl, 3-, 4- or 5-isothiazolyl, 4- or 5-oxadiazolyl, 1-, 4- or 5-triazolyl, 2-thiadiazolyl, 3- or 4-pyridazinyl, 2-pyrazinyl, 2-triazinyl, 2-, 3-, 6- or 7-indolyzinyl, 2-, 3-, 5- or 6-isoindolyl, 2-, 3-, 5- or 6-benzo[b]furanyl, 2-, 3-, 5- or 6-benzo[b]thiophenyl, 3-, 5- or 6-indazolyl, 2-, 5- or 6-benzthiazolyl, 2-, 5- or 6-benzimidazolyl, 2-, 3-, 6- or 7-quinolinyl, 3-, 6- or 7-isoquinolinyl, 2- or 8-purinyl, 2-, 3-, 7- or 8-quinolizinyl, 3-, 6- or 7-cinnolinyl, 6- or 7-phthalazinyl, 2-, 3-, 6- or 7-quinoxalinyl, 2-, 3-, 6- or 7-naphthyridinyl, 2-, 6- or 7-pteridinyl or 2-, 6- or 7-quinazolinyl, wherein one or more of the hydrogen atoms of said aryl or heteroaryl group may be optionally and independently replaced with:

(a) branched or unbranched alkyl of 1 to 6 carbon atoms or cycloalkyl of 3 to 6 carbon atoms, which alkyl or cycloakyl group may be mono or polysubstituted with halogen or oxo, (b) —COOH, (c) —SO$_2$OH, (d) —PO(OH)$_2$, (e) a group of the formula —COOR$_{12}$, wherein R$_{12}$ is unbranched or branched alkyl of 1 to 6 carbon atoms or cycloalkyl of 3 to 6 carbon atoms, (f) a group of the formula —NR$_{13}$R$_{14}$, wherein R$_{13}$ and R$_{14}$ are each, independently, H, alkyl or fluoroalkyl of 1 to 6 carbon atoms, cycloalkyl of 3 to 6 carbon atoms or acyl of 1 to 6 carbon atoms, or wherein R$_{13}$ and R$_{14}$ constitute a saturated hydrocarbon bridge of 3 to 5 carbon atoms which together with the nitrogen atom between them form a heterocyclic ring, (g) a group of the formula —CONR$_{15}$R$_{16}$, wherein R$_{15}$ and R$_{16}$ are each, independently H, alkyl or fluoroalkyl of 1 to 6 carbon atoms or cycloalkyl of 3 to 6 carbon atoms, or wherein R$_{15}$ and R$_{16}$ constitute a saturated hydrocarbon bridge of 3 to 5 carbon atoms which together with the nitrogen atom between them form a heterocyclic ring, (h) a group of the formula —$OR_{17}$, wherein $R_{17}$ is H, alkyl or fluoroalkyl of 1 to 6 carbon atoms or acyl of 1 to 6 carbon atoms, (i) a group of the formula —$SR_{18}$, wherein $R_{18}$ is H, alkyl or fluoroalkyl of 1 to 6 carbon atoms or acyl of 1 to 6 carbon atoms, (j) cyano, (k) nitro, (l) an amidino group of the formula —$C(NR_{19})$—$NR_{20}R_{21}$ wherein $R_{19}$, $R_{20}$ and $R_{21}$ are each, independently, H or alkyl of 1 to 3 carbon atoms, and wherein two of $R_{19}$, $R_{20}$ and $R_{21}$ may additionally constitute a saturated hydrocarbon bridge of 3 to 5 carbon atoms which together with the nitrogen atom(s) between them form a heterocyclic ring, or (m) halogen, (ii) methyl, which may be mono- or polysubstituted with fluorine atoms and additionally may be monosubstituted with $R_{11}$, (iii) branched or unbranched alkyl of 2 to 6 carbon atoms or cycloalkyl of 3 to 6 carbon atoms, which alkyl or cycloakyl group may be mono- or polysubstituted with halogen or oxo, (iv) a group of the formula —$COOR_{22}$, wherein $R_{22}$ is unbranched or branched alkyl of 1 to 6 carbon atoms or cycloalkyl of 3 to 6 carbon atoms, (v) a group of the formula —$NR_{23}R_{24}$, wherein $R_{23}$ and $R_{24}$ are each, independently H, alkyl or fluoroalkyl of 1 to 6 carbon atoms, cycloalkyl of 3 to 6 carbon atoms or acyl of 1 to 6 carbon atoms, or wherein $R_{23}$ and $R_{24}$ constitute a saturated hydrocarbon bridge of 3 to 5 carbon atoms which together with the nitrogen atom between them form a heterocyclic ring, or wherein one of $R_{23}$ and $R_{24}$ is the group $R_{11}$, (vi) a group of the formula —$CONR_{25}R_{26}$, wherein $R_{25}$ and $R_{26}$ are each, independently, H, alkyl or fluoroalkyl of 1 to 6 carbon atoms or cycloalkyl of 3 to 6 carbon atoms, or wherein $R_{25}$ and $R_{26}$ constitute a saturated hydrocarbon bridge of 3 to 5 carbon atoms which together with the nitrogen atom between them form a heterocyclic ring, or wherein one of $R_{25}$ and $R_{26}$ is the group $R_{11}$, (vii) a group of the formula —$COR_{27}$, wherein $R_{27}$ is H, unbranched or branched alkyl of 1 to 6 carbon atoms, cycloalkyl of 3 to 6 carbon atoms or $R_{11}$, (viii) a group of the formula —$OR_{28}$, wherein $R_{28}$ is H, alkyl or fluoroalkyl of 1 to 6 carbon atoms or acyl of 1 to 6 carbon atoms, or $R_{11}$, (ix) a group of the formula —$SR_{29}$, wherein $R_{29}$ is H, alkyl or fluoroalkyl of 1 to 6 carbon atoms or acyl of 1 to 6 carbon atoms, or $R_{11}$, (x) cyano, (xi) nitro, or (xii) halogen.

The term "LFA-1 inhibitor" as used herein includes a compound which is capable of inhibiting the interaction of LFA-1 with its counter ligands.

The term "condition associated with LFA-1 or its counter ligands" as used herein includes any inflammatory, immune-mediated, infectious or malignant conditions, in which LFA-1 bearing cells can be employed as targets for diagnosis, prevention, therapy or drug delivery, The term "LFA-1 counter ligands" or "counter ligands" as used herein includes ICAM-1, ICAM-2, ICAM-3, ICAM-4, ICAM-5 and JAM-1.

Compounds

In a first aspect the present invention provides compounds according to formula (Ia)

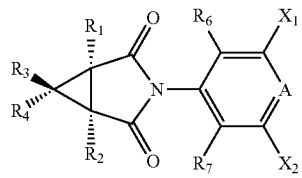

or according to formula (Ib)

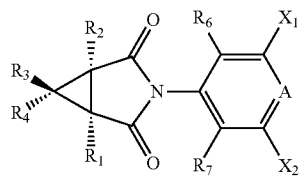

pharmaceutically-acceptable salts, hydrates, solvates, or prodrugs thereof, in which:

$X_1$ is selected from H, halogen or $CF_3$, $X_2$ is selected from H, halogen or $CF_3$, wherein at least one of $X_1$ and $X_2$ is halogen or $CF_3$;

A is N or $CR_5$, wherein $R_5$ is selected from H, halogen, branched or unbranched alkyl of 1 to 6 carbon atoms, branched or unbranched alkenyl of 2 to 6 carbon atoms, $CF_3$, $CCl_3$, CN, $NO_2$, O-alkyl with branched or unbranched alkyl of 1 to 6 carbon atoms, S-alkyl with branched or unbranched alkyl of 1 to 6 carbon atoms, aryl, substituted aryl, heteroaryl or substituted heteroaryl;

$R_1$ is selected from H, branched or unbranched alkyl of 1 to 6 carbon atoms, branched or unbranched alkenyl of 2 to 6 carbon atoms, or cycloalkyl of 3 to 6 carbon atoms;

$R_2$ and $R_4$ are independently selected from (A) H, (B) branched or unbranched alkyl of 1 to 6 carbon atoms or cycloalkyl of 3 to 6 carbon atoms, wherein said alkyl or cycloalkyl group may optionally be substituted with:

(a) a group of the formula —$OR_8$, wherein $R_8$ is an alkyl or acyl group of 1 to 6 carbon atoms, or (b) a group of the formula —$NR_9R_{10}$, wherein $R_9$ and $R_{10}$ are each, independently, an alkyl or acyl group of 1 to 2 carbon atoms, (C) $(CH_2)_n$-aryl, substituted $(CH_2)_n$-aryl, $(CH_2)_n$-heteroaryl or substituted $(CH_2)_n$-heteroaryl, wherein one or more of the hydrogen atoms of the aryl group of said substituted $(CH_2)_n$-aryl group or one or more of the hydrogen atoms of the heteroaryl group of said substituted $(CH_2)_n$-heteroaryl group may be optionally and independently replaced with:

(i) $R_{11}$, which is aryl or heteroaryl selected from phenyl, 2-naphthyl, 2-, 3-, 5- or 6-indolyl, 2- or 3-thiophenyl, 2-, 3- or 4-pyridyl, 2-, 4- or 5-pyrimidinyl, 2- or 3-furyl, 1-, 2- or 3-pyrrolyl, 2-, 4- or 5-oxazolyl, 2-, 4- or 5-thiazolyl, 1-, 3-, 4- or 5-pyrazolyl, 3-, 4- or 5-isoxazolyl, 1-, 2-, 4- or 5-imidazolyl, 3-, 4- or 5-isothiazolyl, 4- or 5-oxadiazolyl, 1-, 4- or 5-triazolyl, 2-thiadiazolyl, 3- or 4-pyridazinyl, 2-pyrazinyl, 2-triazinyl, 2-, 3-, 6- or 7-indolyzinyl, 2-, 3-, 5- or 6-isoindolyl, 2-, 3-, 5- or 6-benzo[b]furanyl, 2-, 3-, 5- or 6-benzo[b] thiophenyl, 3-, 5- or 6-indazolyl, 2-, 5- or 6-benzthiazolyl, 2-, 5- or 6-benzimidazolyl, 2-, 3-, 6- or 7-quinolinyl, 3-, 6- or 7-isoquinolinyl, 2- or 8-purinyl, 2-, 3-, 7- or 8-quinolizinyl, 3-, 6- or 7-cinnolinyl, 6- or 7-phthalazinyl, 2-, 3-, 6- or 7-quinoxalinyl, 2-, 3-, 6- or 7-naphthyridinyl, 2-, 6- or 7-pteridinyl or 2-, 6- or 7-quinazolinyl, wherein one or more of the hydrogen atoms of said aryl or heteroaryl group may be optionally and independently replaced with:
- (a) branched or unbranched alkyl of 1 to 6 carbon atoms or cycloalkyl of 3 to 6 carbon atoms, which alkyl or cycloakyl group may be mono or polysubstituted with halogen or oxo,
- (b) —COOH,
- (c) —SO$_2$OH,
- (d) —PO(OH)$_2$,
- (e) a group of the formula —COOR$_{12}$, wherein R$_{12}$ is unbranched or branched alkyl of 1 to 6 carbon atoms or cycloalkyl of 3 to 6 carbon atoms,
- (f) a group of the formula —NR$_{13}$R$_{14}$, wherein R$_{13}$ and R$_{14}$ are each, independently, H, alkyl or fluoroalkyl of 1 to 6 carbon atoms, cycloalkyl of 3 to 6 carbon atoms or acyl of 1 to 6 carbon atoms, or wherein R$_{13}$ and R$_{14}$ constitute a saturated hydrocarbon bridge of 3 to 5 carbon atoms which together with the nitrogen atom between them form a heterocyclic ring,
- (g) a group of the formula —CONR$_{15}$R$_{16}$, wherein R$_{15}$ and R$_{16}$ are each, independently H, alkyl or fluoroalkyl of 1 to 6 carbon atoms or cycloalkyl of 3 to 6 carbon atoms, or wherein R$_{15}$ and R$_{16}$ constitute a saturated hydrocarbon bridge of 3 to 5 carbon atoms which together with the nitrogen atom between them form a heterocyclic ring,
- (h) a group of the formula —OR$_{17}$, wherein R$_{17}$ is H, alkyl or fluoroalkyl of 1 to 6 carbon atoms or acyl of 1 to 6 carbon atoms,
- (i) a group of the formula —SR$_{18}$, wherein R$_{18}$ is H, alkyl or fluoroalkyl of 1 to 6 carbon atoms or acyl of 1 to 6 carbon atoms,
- (j) cyano,
- (k) nitro,
- (l) an amidino group of the formula —C(NR$_{19}$)—NR$_{20}$R$_{21}$ wherein R$_{19}$, R$_{20}$ and R$_{21}$ are each, independently, H or alkyl of 1 to 3 carbon atoms, and wherein two of R$_{19}$, R$_{20}$ and R$_{21}$ may additionally constitute a saturated hydrocarbon bridge of 3 to 5 carbon atoms which together with the nitrogen atom(s) between them form a heterocyclic ring, or
- (m) halogen,
- (ii) methyl, which may be mono- or polysubstituted with fluorine atoms and additionally may be monosubstituted with R$_{11}$,
- (iii) branched or unbranched alkyl of 2 to 6 carbon atoms or cycloalkyl of 3 to 6 carbon atoms, which alkyl or cycloakyl group may be mono- or polysubstituted with halogen or oxo,
- (iv) a group of the formula —COOR$_{22}$, wherein R$_{22}$ is unbranched or branched alkyl of 1 to 6 carbon atoms or cycloalkyl of 3 to 6 carbon atoms,
- (v) a group of the formula —NR$_{23}$R$_{24}$, wherein R$_{23}$ and R$_{24}$ are each, independently H, alkyl or fluoroalkyl of 1 to 6 carbon atoms, cycloalkyl of 3 to 6 carbon atoms or acyl of 1 to 6 carbon atoms, or wherein R$_{23}$ and R$_{24}$ constitute a saturated hydrocarbon bridge of 3 to 5 carbon atoms which together with the nitrogen atom between them form a heterocyclic ring, or wherein one of R$_{23}$ and R$_{24}$ is the group R$_{11}$,
- (vi) a group of the formula —CONR$_{25}$ R$_{26}$, wherein R$_{25}$ and R$_{26}$ are each, independently, H, alkyl or fluoroalkyl of 1 to 6 carbon atoms or cycloalkyl of 3 to 6 carbon atoms, or wherein R$_{25}$ and R$_{26}$ constitute a saturated hydrocarbon bridge of 3 to 5 carbon atoms which together with the nitrogen atom between them form a heterocyclic ring, or wherein one of R$_{25}$ and R$_{26}$ is the group R$_{11}$,
- (vii) a group of the formula —COR$_{27}$, wherein R$_{27}$ is H, unbranched or branched alkyl of 1 to 6 carbon atoms, cycloalkyl of 3 to 6 carbon atoms or R$_{11}$,
- (viii) a group of the formula —OR$_{28}$, wherein R$_{28}$ is H, alkyl or fluoroalkyl of 1 to 6 carbon atoms or acyl of 1 to 6 carbon atoms, or R$_{11}$,
- (ix) a group of the formula —SR$_{29}$, wherein R$_{29}$ is H, alkyl or fluoroalkyl of 1 to 6 carbon atoms or acyl of 1 to 6 carbon atoms, or R$_{11}$,
- (x) cyano,
- (xi) nitro, or
- (xii) halogen, or,
- (D) a substituent selected from
  - (i) a group of the formula —(CH$_2$)$_n$COOR$_{30}$, wherein R$_{30}$ is independently H, unbranched or branched alkyl of 1 to 6 carbon atoms or cycloalkyl of 3 to 6 carbon atoms and wherein said unbranched or branched alkyl of 1 to 6 carbon atoms or cycloalkyl of 3 to 6 carbon atoms may be optionally and independently substituted with —CH$_2$OR$_{31}$, —COOR$_{31}$, —CON(R$_{31}$)$_2$, —CH$_2$NHCOR$_{31}$, —SO$_2$N(R$_{31}$)$_2$, —CH$_2$NHSO$_2$R$_{31}$, —CH$_2$N(R$_{31}$)$_2$, —SO$_2$OH, —PO(OH)$_2$ wherein R$_{31}$ is independently selected from H, unbranched or branched alkyl of 1 to 6 carbon atoms,
  - (ii) a group of the formula —(CH$_2$)$_n$CONR$_{32}$R$_{33}$, wherein R$_{32}$ and R$_{33}$ are each, independently, H, unbranched or branched alkyl of 1 to 6 carbon atoms or cycloalkyl of 3 to 6 carbon atoms and wherein said unbranched or branched alkyl of 1 to 6 carbon atoms or cycloalkyl of 3 to 6 carbon atoms may be optionally and independently substituted with —CH$_2$OR$_{31}$, —COOR$_{31}$, —CON(R$_{31}$)$_2$, —CH$_2$NHCOR$_{31}$, —SO$_2$N(R$_{31}$)$_2$, —CH$_2$NHSO$_2$R$_{31}$, —CH$_2$N(R$_{31}$)$_2$, —SO$_2$OH, —PO(OH)$_2$ wherein R$_{31}$ is independently selected from H, unbranched or branched alkyl of 1 to 6 carbon atoms or wherein NR$_{32}$ is N-alkyl-4-piperidinylamino, N-carboxymethyl-4-piperidinylamino, pyridin-4-ylmethylamino, 4-amidinobenzylamino, 4-carboxybenzylamino, or 4-hydroxybenzylamino and R$_{33}$ is H or wherein NR$_{32}$R$_{33}$ constitute a heterocyclic ring selected from 4-alkyl-1-piperazinyl, wherein alkyl is unbranched or branched alkyl of 1 to 6 carbon atoms, or 1-morpholinyl,
  - (iii) a group of the formula —(CH$_2$)$_n$NHR$_{34}$, wherein R$_{34}$ is H, unbranched or branched alkyl of 1 to 6 carbon atoms, cycloalkyl of 3 to 6 carbon atoms or an acyl group of 1 to 6 carbon atoms and wherein said unbranched or branched alkyl of 1 to 6 carbon atoms or cycloalkyl of 3 to 6 carbon atoms may be optionally and independently substituted with —CH$_2$OR$_{31}$, —COOR$_{31}$, —CON(R$_{31}$)$_2$, —CH$_2$NHCOR$_{31}$, —SO$_2$N(R$_{31}$)$_2$, —CH$_2$NHSO$_2$R$_{31}$, —CH$_2$N(R$_{31}$)$_2$, —SO$_2$OH, —PO(OH)$_2$ wherein R$_{31}$ is independently selected from H, unbranched or branched alkyl of 1 to 6 carbon atoms or wherein R$_{34}$ is —COR$_{36}$ wherein R$_{36}$ is 1-alkyl-4-piperidyl, wherein alkyl is unbranched or branched alkyl of 1 to 6 carbon atoms, or —(CH$_2$)$_n$COR$_{36}$ wherein R$_{36}$ is 4-pyridyl or 4-hydroxyphenyl,
  - (iv) a group of the formula —(CH$_2$)$_n$PO(OH)$_2$, —(CH$_2$)$_n$SO$_2$OH, —(CH$_2$)$_n$OR$_{31}$, —(CH$_2$)$_n$SO$_2$N(R$_{31}$)$_2$, or —$(CH_2)_n NHSO_2 R_{31}$ wherein $R_{31}$ is independently selected from H, unbranched or branched alkyl of 1 to 6 carbon atoms, (v) $(CH_2)_n$-aryl, substituted $(CH_2)_n$-aryl, $(CH_2)_n$-heteroaryl or substituted $(CH_2)_n$-heteroaryl, wherein one or more of the hydrogen atoms of the aryl group of said substituted $(CH_2)_n$-aryl group or one or more of the hydrogen atoms of the heteroaryl group of said substituted $(CH_2)_n$-heteroaryl group may be optionally and independently replaced with:
- (a) a group of the formula —$COOR_{30}$, wherein $R_{30}$ is independently H, unbranched or branched alkyl of 1 to 6 carbon atoms or cycloalkyl of 3 to 6 carbon atoms and wherein said unbranched or branched alkyl of 1 to 6 carbon atoms or cycloalkyl of 3 to 6 carbon atoms may be optionally and independently substituted with —$CH_2 OR_{31}$, —$COOR_{31}$, —$CON(R_{31})_2$, —$CH_2 NHCOR_{31}$, —$SO_2 N(R_{31})_2$, —$CH_2 NHSO_2 R_{31}$, —$CH_2 N(R_{31})_2$, —$SO_2 OH$, —$PO(OH)_2$ wherein $R_{31}$ is independently selected from H, unbranched or branched alkyl of 1 to 6 carbon atoms,
- (b) a group of the formula —$CONR_{32}R_{33}$, wherein $R_{32}$ and $R_{33}$ are each, independently, H, unbranched or branched alkyl of 1 to 6 carbon atoms or cycloalkyl of 3 to 6 carbon atoms and wherein said unbranched or branched alkyl of 1 to 6 carbon atoms or cycloalkyl of 3 to 6 carbon atoms may be optionally and independently substituted with —$CH_2 OR_{31}$, —$COOR_{31}$, —$CON(R_{31})_2$, —$CH_2 NHCOR_{31}$, —$SO_2 N(R_{31})_2$, —$CH_2 NHSO_2 R_{31}$, —$CH_2 N(R_{31})_2$, —$SO_2 OH$, —$PO(OH)_2$ wherein $R_{31}$ is independently selected from H, unbranched or branched alkyl of 1 to 6 carbon atoms or wherein $NR_{32}$ is N-alkyl-4-piperidinylamino, N-carboxymethyl-4-piperidinylamino, pyridin-4-ylmethylamino, 4-amidinobenzylamino, 4-carboxybenzylamino, or 4-hydroxybenzylamino and $R_{33}$ is H or wherein $NR_{32}R_{33}$ constitute a heterocyclic ring selected from 4-alkyl-1-piperazinyl, wherein alkyl is unbranched or branched alkyl of 1 to 6 carbon atoms, or 1-morpholinyl,
- (c) a group of the formula —$NHR_{35}$, wherein $R_{35}$ is H, unbranched or branched alkyl of 1 to 6 carbon atoms, cycloalkyl of 3 to 6 carbon atoms or an acyl group of 1 to 6 carbon atoms and wherein said unbranched or branched alkyl of 1 to 6 carbon atoms or cycloalkyl of 3 to 6 carbon atoms may be optionally and independently substituted with —$CH_2 OR_{31}$, —$COOR_{31}$, —$CON(R_{31})_2$, —$CH_2 NHCOR_{31}$, —$SO_2 N(R_{31})_2$, —$CH_2 NHSO_2 R_{31}$, —$CH_2 N(R_{31})_2$, —$SO_2 OH$, —$PO(OH)_2$ wherein $R_{31}$ is independently selected from H, unbranched or branched alkyl of 1 to 6 carbon atoms or wherein $R_{35}$ is —$COR_{36}$ wherein $R_{36}$ is 1-alkyl-4-piperidyl, wherein alkyl is unbranched or branched alkyl of 1 to 6 carbon atoms, or —$(CH_2)_n COR_{36}$ wherein $R_{36}$ is 4-pyridyl or 4-hydroxyphenyl,
- (d) a group of the formula —$(CH_2)_n PO(OH)_2$, —$(CH_2)_n SO_2 OH$, —$(CH_2)_n OR_{31}$, —$(CH_2)_n SO_2 N(R_{31})_2$, or —$(CH_2)_n NHSO_2 R_{31}$ wherein $R_{31}$ is independently selected from H, unbranched or branched alkyl of 1 to 6 carbon atoms, $R_3$ is selected from
- (A) H,
- (B) branched or unbranched alkyl of 1 to 6 carbon atoms or cycloalkyl of 3 to 6 carbon atoms, wherein said alkyl or cycloalkyl group may optionally be substituted with a group of the formula —$OR_8$, wherein $R_8$ is an alkyl or acyl group of 1 to 6 carbon atoms,
- (C) $(CH_2)_n$-aryl, substituted $(CH_2)_n$-aryl, $(CH_2)_n$-heteroaryl or substituted $(CH_2)_n$-heteroaryl, wherein one or more of the hydrogen atoms of the aryl group of said substituted $(CH_2)_n$-aryl group or one or more of the hydrogen atoms of the heteroaryl group of said substituted $(CH_2)_n$-heteroaryl group may be optionally and independently replaced with:
  - (i) $R_{11}$, which is aryl or heteroaryl selected from phenyl, 2-naphthyl, 2-, 3-, 5- or 6-indolyl, 2- or 3-thiophenyl, 2-, 3- or 4-pyridyl, 2-, 4- or 5-pyrimidinyl, 2- or 3-furyl, 1-, 2- or 3-pyrrolyl, 2-, 4- or 5-oxazolyl, 2-, 4- or 5-thiazolyl, 1-, 3-, 4- or 5-pyrazolyl, 3-, 4- or 5-isoxazolyl, 1-, 2-, 4- or 5-imidazolyl, 3-, 4- or 5-isothiazolyl, 4- or 5-oxadiazolyl, 1-, 4- or 5-triazolyl, 2-thiadiazolyl, 3- or 4-pyridazinyl, 2-pyrazinyl, 2-triazinyl, 2-, 3-, 6- or 7-indolyzinyl, 2-, 3-, 5- or 6-isoindolyl, 2-, 3-, 5- or 6-benzo[b]furanyl, 2-, 3-, 5- or 6-benzo[b]thiophenyl, 3-, 5- or 6-indazolyl, 2-, 5- or 6-benzthiazolyl, 2-, 5- or 6-benzimidazolyl, 2-, 3-, 6- or 7-quinolinyl, 3-, 6- or 7-isoquinolinyl, 2- or 8-purinyl, 2-, 3-, 7- or 8-quinolizinyl, 3-, 6- or 7-cinnolinyl, 6- or 7-phthalazinyl, 2-, 3-, 6- or 7-quinoxalinyl, 2-, 3-, 6- or 7-naphthyridinyl, 2-, 6- or 7-pteridinyl or 2-, 6- or 7-quinazolinyl, wherein one or more of the hydrogen atoms of said aryl or heteroaryl group may be optionally and independently replaced with:
  - (a) branched or unbranched alkyl of 1 to 6 carbon atoms or cycloalkyl of 3 to 6 carbon atoms, which alkyl or cycloakyl group may be mono or polysubstituted with halogen or oxo,
  - (b) a group of the formula —$COOR_{12}$, wherein $R_{12}$ is unbranched or branched alkyl of 1 to 6 carbon atoms or cycloalkyl of 3 to 6 carbon atoms,
  - (c) a group of the formula —$NR_{13}R_{14}$, wherein $R_{13}$ and $R_{14}$ are each, independently, H, alkyl or fluoroalkyl of 1 to 6 carbon atoms, cycloalkyl of 3 to 6 carbon atoms or acyl of 1 to 6 carbon atoms, or wherein $R_{13}$ and $R_{14}$ constitute a saturated hydrocarbon bridge of 3 to 5 carbon atoms which together with the nitrogen atom between them form a heterocyclic ring,
  - (d) a group of the formula —$CONR_{15}R_{16}$, wherein $R_{15}$ and $R_{16}$ are each independently H, alkyl or fluoroalkyl of 1 to 6 carbon atoms or cycloalkyl of 3 to 6 carbon atoms, or wherein $R_{15}$ and $R_{16}$ constitute a saturated hydrocarbon bridge of 3 to 5 carbon atoms which together with the nitrogen atom between them form a heterocyclic ring,
  - (e) a group of the formula —$OR_{17}$, wherein $R_{17}$ is H, alkyl or fluoroalkyl of 1 to 6 carbon atoms or acyl of 1 to 6 carbon atoms,
  - (f) a group of the formula —$SR_{18}$, wherein $R_{18}$ is H, alkyl or fluoroalkyl of 1 to 6 carbon atoms or acyl of 1 to 6 carbon atoms,
  - (g) cyano,
  - (h) nitro,
  - (i) an amidino group of the formula —$C(NR_{19})$—$NR_{20}R_{21}$ wherein $R_{19}$, $R_{20}$ and $R_{21}$ are each, independently, H or alkyl of 1 to 3 carbon atoms, and wherein two of $R_{19}$, $R_{20}$ and $R_{21}$ may additionally constitute a saturated hydrocarbon bridge of 3 to 5 carbon atoms which together with the nitrogen atom(s) between them form a heterocyclic ring, or (j) halogen,
(ii) methyl, which may be mono- or polysubstituted with fluorine atoms and additionally may be monosubstituted with $R_{11}$,
(iii) branched or unbranched alkyl of 2 to 6 carbon atoms or cycloalkyl of 3 to 6 carbon atoms, which alkyl or cycloakyl group may be mono- or polysubstituted with halogen or oxo,
(iv) a group of the formula —$COOR_{22}$, wherein $R_{22}$ is unbranched or branched alkyl of 1 to 6 carbon atoms or cycloalkyl of 3 to 6 carbon atoms,
(v) a group of the formula —$NR_{23}R_{24}$, wherein $R_{23}$ and $R_{24}$ are each, independently, H, alkyl or fluoroalkyl of 1 to 6 carbon atoms, cycloalkyl of 3 to 6 carbon atoms or acyl of 1 to 6 carbon atoms, or wherein $R_{23}$ and $R_{24}$ constitute a saturated hydrocarbon bridge of 3 to 5 carbon atoms which together with the nitrogen atom between them form a heterocyclic ring, or wherein one of $R_{23}$ and $R_{24}$ is the group $R_{11}$,
(vi) a group of the formula —$CONR_{25}R_{26}$, wherein $R_{25}$ and $R_{26}$ are each, independently, H, alkyl or fluoroalkyl of 1 to 6 carbon atoms or cycloalkyl of 3 to 6 carbon atoms, or wherein $R_{25}$ and $R_{26}$ constitute a saturated hydrocarbon bridge of 3 to 5 carbon atoms which together with the nitrogen atom between them form a heterocyclic ring, or wherein one of $R_{25}$ and $R_{26}$ is the group $R_{11}$,
(vii) a group of the formula —$COR_{27}$, wherein $R_{27}$ is H, unbranched or branched alkyl of 1 to 6 carbon atoms, cycloalkyl of 3 to 6 carbon atoms or $R_{11}$,
(viii) a group of the formula —$OR_{28}$, wherein $R_{28}$ is H, alkyl or fluoroalkyl of 1 to 6 carbon atoms or acyl of 1 to 6 carbon atoms, or $R_{11}$,
(ix) a group of the formula —$SR_{29}$, wherein $R_{29}$ is H, alkyl or fluoroalkyl of 1 to 6 carbon atoms or acyl of 1 to 6 carbon atoms, or $R_{11}$,
(x) cyano,
(xi) nitro, or
(xii) halogen,
wherein at least one of $R_2$ and $R_3$ is $(CH_2)_n$-aryl, substituted $(CH_2)_n$-aryl, $(CH_2)_n$-heteroaryl or substituted $(CH_2)_n$-heteroaryl and wherein $R_1$ and $R_2$ are different from each other; $R_6$ and $R_7$ are independently selected from H, branched or unbranched alkyl of 1 to 6 carbon atoms or cycloalkyl of 3 to 6 carbon atoms, wherein said alkyl or cycloalkyl group may optionally be substituted with:
(a) a group of the formula —$OR_8$, wherein $R_8$ is an alkyl or acyl group of 1 to 6 carbon atoms, or
(b) a group of the formula —$NR_9R_{10}$, wherein $R_9$ and $R_{10}$ are each, independently, an alkyl or acyl group of 1 to 2 carbon atoms;
n is 0, 1, 2 or 3.

In a further aspect the present invention provides compounds according to formula (Ia)

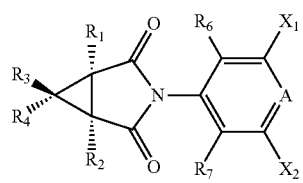

pharmaceutically-acceptable salts, hydrates, solvates, or prodrugs thereof, in which:

$X_1$ is selected from H, halogen or $CF_3$,
$X_2$ is selected from H, halogen or $CF_3$,
wherein at least one of $X_1$ and $X_2$ is halogen or $CF_3$;
A is N or $CR_5$, wherein $R_5$ is selected from H, halogen, branched or unbranched alkyl of 1 to 6 carbon atoms, branched or unbranched alkenyl of 2 to 6 carbon atoms, $CF_3$, $CCl_3$, CN, $NO_2$, O-alkyl with branched or unbranched alkyl of 1 to 6 carbon atoms, S-alkyl with branched or unbranched alkyl of 1 to 6 carbon atoms, aryl, substituted aryl, heteroaryl or substituted heteroaryl;
$R_1$ is selected from H, branched or unbranched alkyl of 1 to 6 carbon atoms, branched or unbranched alkenyl of 2 to 6 carbon atoms, or cycloalkyl of 3 to 6 carbon atoms; $R_2$ and $R_4$ are independently selected from
(A) H,
(B) branched or unbranched alkyl of 1 to 6 carbon atoms or cycloalkyl of 3 to 6 carbon atoms, wherein said alkyl or cycloalkyl group may optionally be substituted with:
(a) a group of the formula —$OR_8$, wherein $R_8$ is an alkyl or acyl group of 1 to 6 carbon atoms, or
(b) a group of the formula —$NR_9R_{10}$, wherein $R_9$ and $R_{10}$ are each, independently, an alkyl or acyl group of 1 to 2 carbon atoms,
(C) $(CH_2)_n$-aryl, substituted $(CH_2)_n$-aryl, $(CH_2)_n$-heteroaryl or substituted $(CH_2)_n$-heteroaryl, wherein one or more of the hydrogen atoms of the aryl group of said substituted $(CH_2)_n$-aryl group or one or more of the hydrogen atoms of the heteroaryl group of said substituted $(CH_2)_n$-heteroaryl group may be optionally and independently replaced with:
(i) $R_{11}$, which is aryl or heteroaryl selected from phenyl, 2-naphthyl, 2-, 3-, 5- or 6-indolyl, 2- or 3-thiophenyl, 2-, 3- or 4-pyridyl, 2-, 4- or 5-pyrimidinyl, 2- or 3-furyl, 1-, 2- or 3-pyrrolyl, 2-, 4- or 5-oxazolyl, 2-, 4- or 5-thiazolyl, 1-, 3-, 4- or 5-pyrazolyl, 3-, 4- or 5-isoxazolyl, 1-, 2-, 4- or 5-imidazolyl, 3-, 4- or 5-isothiazolyl, 4- or 5-oxadiazolyl, 1-, 4- or 5-triazolyl, 2-thiadiazolyl, 3- or 4-pyridazinyl, 2-pyrazinyl, 2-triazinyl, 2-, 3-, 6- or 7-indolyzinyl, 2-, 3-, 5- or 6-isoindolyl, 2-, 3-, 5- or 6-benzo[b]furanyl, 2-, 3-, 5- or 6-benzo[b]thiophenyl, 3-, 5- or 6-indazolyl, 2-, 5- or 6-benzthiazolyl, 2-, 5- or 6-benzimidazolyl, 2-, 3-, 6- or 7-quinolinyl, 3-, 6- or 7-isoquinolinyl, 2- or 8-purinyl, 2-, 3-, 7- or 8-quinolizinyl, 3-, 6- or 7-cinnolinyl, 6- or 7-phthalazinyl, 2-, 3-, 6- or 7-quinoxalinyl, 2-, 3-, 6- or 7-naphthyridinyl, 2-, 6- or 7-pteridinyl or 2-, 6- or 7-quinazolinyl,
wherein one or more of the hydrogen atoms of said aryl or heteroaryl group may be optionally and independently replaced with:
(a) branched or unbranched alkyl of 1 to 6 carbon atoms or cycloalkyl of 3 to 6 carbon atoms, which alkyl or cycloakyl group may be mono or polysubstituted with halogen or oxo,
(b) —COOH,
(c) —$SO_2OH$,
(d) —$PO(OH)_2$,
(e) a group of the formula —$COOR_{12}$, wherein $R_{12}$ is unbranched or branched alkyl of 1 to 6 carbon atoms or cycloalkyl of 3 to 6 carbon atoms,
(f) a group of the formula —$NR_{13}R_{14}$, wherein $R_{13}$ and $R_{14}$ are each, independently, H, alkyl or fluoroalkyl of 1 to 6 carbon atoms, cycloalkyl of 3 to 6 carbon atoms or acyl of 1 to 6 carbon atoms, or wherein $R_{13}$ and $R_{14}$ constitute a saturated hydrocarbon bridge of 3 to 5 carbon atoms which together with the nitrogen atom between them form a heterocyclic ring, (g) a group of the formula —CONR$_{15}$R$_{16}$, wherein R$_{15}$ and R$_{16}$ are each, independently H, alkyl or fluoroalkyl of 1 to 6 carbon atoms or cycloalkyl of 3 to 6 carbon atoms, or wherein R$_{15}$ and R$_{16}$ constitute a saturated hydrocarbon bridge of 3 to 5 carbon atoms which together with the nitrogen atom between them form a heterocyclic ring, (h) a group of the formula —OR$_{17}$, wherein R$_{17}$ is H, alkyl or fluoroalkyl of 1 to 6 carbon atoms or acyl of 1 to 6 carbon atoms, (i) a group of the formula —SR$_{18}$, wherein R$_{18}$ is H, alkyl or fluoroalkyl of 1 to 6 carbon atoms or acyl of 1 to 6 carbon atoms, (j) cyano, (k) nitro, (l) an amidino group of the formula —C(NR$_{19}$)—NR$_{20}$R$_{21}$ wherein R$_{19}$, R$_{20}$ and R$_{21}$ are each, independently, H or alkyl of 1 to 3 carbon atoms, and wherein two of R$_{19}$, R$_{20}$ and R$_{21}$ may additionally constitute a saturated hydrocarbon bridge of 3 to 5 carbon atoms which together with the nitrogen atom(s) between them form a heterocyclic ring, or (m) halogen, (ii) methyl, which may be mono- or polysubstituted with fluorine atoms and additionally may be monosubstituted with R$_{11}$, (iii) branched or unbranched alkyl of 2 to 6 carbon atoms or cycloalkyl of 3 to 6 carbon atoms, which alkyl or cycloakyl group may be mono- or polysubstituted with halogen or oxo, (iv) a group of the formula —COOR$_{22}$, wherein R$_{22}$ is unbranched or branched alkyl of 1 to 6 carbon atoms or cycloalkyl of 3 to 6 carbon atoms, (v) a group of the formula —NR$_{23}$R$_{24}$, wherein R$_{23}$ and R$_{24}$ are each, independently H, alkyl or fluoroalkyl of 1 to 6 carbon atoms, cycloalkyl of 3 to 6 carbon atoms or acyl of 1 to 6 carbon atoms, or wherein R$_{23}$ and R$_{24}$ constitute a saturated hydrocarbon bridge of 3 to 5 carbon atoms which together with the nitrogen atom between them form a heterocyclic ring, or wherein one of R$_{23}$ and R$_{24}$ is the group R$_{11}$, (vi) a group of the formula —CONR$_{25}$R$_{26}$, wherein R$_{25}$ and R$_{26}$ are each, independently, H, alkyl or fluoroalkyl of 1 to 6 carbon atoms or cycloalkyl of 3 to 6 carbon atoms, or wherein R$_{25}$ and R$_{26}$ constitute a saturated hydrocarbon bridge of 3 to 5 carbon atoms which together with the nitrogen atom between them form a heterocyclic ring, or wherein one of R$_{25}$ and R$_{26}$ is the group R$_{11}$, (vii) a group of the formula —COR$_{27}$, wherein R$_{27}$ is H, unbranched or branched alkyl of 1 to 6 carbon atoms, cycloalkyl of 3 to 6 carbon atoms or R$_{11}$, (viii) a group of the formula —OR$_{28}$, wherein R$_{28}$ is H, alkyl or fluoroalkyl of 1 to 6 carbon atoms or acyl of 1 to 6 carbon atoms, or R$_{11}$, (ix) a group of the formula —SR$_{29}$, wherein R$_{29}$ is H, alkyl or fluoroalkyl of 1 to 6 carbon atoms or acyl of 1 to 6 carbon atoms, or R$_{11}$, (x) cyano, (xi) nitro, or (xii) halogen, or, (D) a substituent selected from (i) a group of the formula —(CH$_2$)$_n$COOR$_{30}$, wherein R$_{30}$ is independently H, unbranched or branched alkyl of 1 to 6 carbon atoms or cycloalkyl of 3 to 6 carbon atoms and wherein said unbranched or branched alkyl of 1 to 6 carbon atoms or cycloalkyl of 3 to 6 carbon atoms may be optionally and independently substituted with —CH$_2$OR$_{31}$, —COOR$_{31}$, —CON(R$_{31}$)$_2$, —CH$_2$NHCOR$_{31}$, —SO$_2$N(R$_{31}$)$_2$, —CH$_2$NHSO$_2$R$_{31}$, —CH$_2$N(R$_{31}$)$_2$, —SO$_2$OH, —PO(OH)$_2$ wherein R$_{31}$ is independently selected from H, unbranched or branched alkyl of 1 to 6 carbon atoms, (ii) a group of the formula —(CH$_2$)$_n$CONR$_{32}$R$_{33}$, wherein R$_{32}$ and R$_{33}$ are each, independently, H, unbranched or branched alkyl of 1 to 6 carbon atoms or cycloalkyl of 3 to 6 carbon atoms and wherein said unbranched or branched alkyl of 1 to 6 carbon atoms or cycloalkyl of 3 to 6 carbon atoms may be optionally and independently substituted with —CH$_2$OR$_{31}$, —COOR$_{31}$, —CON(R$_{31}$)$_2$, —CH$_2$NHCOR$_{31}$, —SO$_2$N(R$_{31}$)$_2$, —CH$_2$NHSO$_2$R$_{31}$, —CH$_2$N(R$_{31}$)$_2$, —SO$_2$OH, —PO(OH)$_2$ wherein R$_{31}$ is independently selected from H, unbranched or branched alkyl of 1 to 6 carbon atoms or wherein NR$_{32}$ is N-alkyl-4-piperidinylamino, N-carboxymethyl-4-piperidinylamino, pyridin-4-ylmethylamino, 4-amidinobenzylamino, 4-carboxybenzylamino, or 4-hydroxybenzylamino and R$_{33}$ is H or wherein NR$_{32}$R$_{33}$ constitute a heterocyclic ring selected from 4-alkyl-1-piperazinyl, wherein alkyl is unbranched or branched alkyl of 1 to 6 carbon atoms, or 1-morpholinyl, (iii) a group of the formula —(CH$_2$)$_n$NHR$_{34}$, wherein R$_{34}$ is H, unbranched or branched alkyl of 1 to 6 carbon atoms, cycloalkyl of 3 to 6 carbon atoms or an acyl group of 1 to 6 carbon atoms and wherein said unbranched or branched alkyl of 1 to 6 carbon atoms or cycloalkyl of 3 to 6 carbon atoms may be optionally and independently substituted with —CH$_2$OR$_{31}$, —COOR$_{31}$, —CON(R$_{31}$)$_2$, —CH$_2$NHCOR$_{31}$, —SO$_2$N(R$_{31}$)$_2$, —CH$_2$NHSO$_2$R$_{31}$, —CH$_2$N(R$_{31}$)$_2$, —SO$_2$OH, —PO(OH)$_2$ wherein R$_{31}$ is independently selected from H, unbranched or branched alkyl of 1 to 6 carbon atoms or wherein R$_{34}$ is —COR$_{36}$ wherein R$_{36}$ is 1-alkyl-4-piperidyl, wherein alkyl is unbranched or branched alkyl of 1 to 6 carbon atoms, or —(CH$_2$)$_n$COR$_{36}$ wherein R$_{36}$ is 4-pyridyl or 4-hydroxyphenyl, (iv) a group of the formula —(CH$_2$)$_n$PO(OH)$_2$, —(CH$_2$)$_n$SO$_2$OH, —(CH$_2$)$_n$OR$_{31}$, —(CH$_2$)$_n$SO$_2$N(R$_{31}$)$_2$, or —(CH$_2$)$_n$NHSO$_2$R$_{31}$ wherein R$_{31}$ is independently selected from H, unbranched or branched alkyl of 1 to 6 carbon atoms, (v) (CH$_2$)$_n$-aryl, substituted (CH$_2$)$_n$-aryl, (CH$_2$)$_n$-heteroaryl or substituted (CH$_2$)$_n$-heteroaryl, wherein one or more of the hydrogen atoms of the aryl group of said substituted (CH$_2$)$_n$-aryl group or one or more of the hydrogen atoms of the heteroaryl group of said substituted (CH$_2$)$_n$-heteroaryl group may be optionally and independently replaced with:

(a) a group of the formula —COOR$_{30}$, wherein R$_{30}$ is independently H, unbranched or branched alkyl of 1 to 6 carbon atoms or cycloalkyl of 3 to 6 carbon atoms and wherein said unbranched or branched alkyl of 1 to 6 carbon atoms or cycloalkyl of 3 to 6 carbon atoms may be optionally and independently substituted with —CH$_2$OR$_{31}$, —COOR$_{31}$, —CON(R$_{31}$)$_2$, —CH$_2$NHCOR$_{31}$, —SO$_2$N(R$_{31}$)$_2$, —CH$_2$NHSO$_2$R$_{31}$, —CH$_2$N(R$_{31}$)$_2$, —SO$_2$OH, —PO(OH)$_2$ wherein R$_{31}$ is independently selected from H, unbranched or branched alkyl of 1 to 6 carbon atoms, (b) a group of the formula —CONR$_{32}$R$_{33}$, wherein R$_{32}$ and R$_{33}$ are each, independently, H, unbranched or branched alkyl of 1 to 6 carbon atoms or cycloalkyl of 3 to 6 carbon atoms and wherein said unbranched or branched alkyl of 1 to 6 carbon atoms or cycloalkyl of 3 to 6 carbon atoms may be optionally and independently substituted with —$CH_2OR_{31}$, —$COOR_{31}$, —$CON(R_{31})_2$, —$CH_2NHCOR_{31}$, —$SO_2N(R_{31})_2$, —$CH_2NHSO_2R_{31}$, —$CH_2N(R_{31})_2$, —$SO_2OH$, —$PO(OH)_2$ wherein $R_{31}$ is independently selected from H, unbranched or branched alkyl of 1 to 6 carbon atoms or wherein $NR_{32}$ is N-alkyl-4-piperidinylamino, N-carboxymethyl-4-piperidinylamino, pyridin-4-ylmethylamino, 4-amidinobenzylamino, 4-carboxybenzylamino, or 4-hydroxybenzylamino and $R_{33}$ is H or wherein $NR_{32}R_{33}$ constitute a heterocyclic ring selected from 4-alkyl-1-piperazinyl, wherein alkyl is unbranched or branched alkyl of 1 to 6 carbon atoms, or 1-morpholinyl, (c) a group of the formula —$NHR_{35}$, wherein $R_{35}$ is H, unbranched or branched alkyl of 1 to 6 carbon atoms, cycloalkyl of 3 to 6 carbon atoms or an acyl group of 1 to 6 carbon atoms and wherein said unbranched or branched alkyl of 1 to 6 carbon atoms or cycloalkyl of 3 to 6 carbon atoms may be optionally and independently substituted with —$CH_2OR_{31}$, —$COOR_{31}$, —$CON(R_{31})_2$, —$CH_2NHCOR_{31}$, —$SO_2N(R_{31})_2$, —$CH_2NHSO_2R_{31}$, —$CH_2N(R_{31})_2$, —$SO_2OH$, —$PO(OH)_2$ wherein $R_{31}$ is independently selected from H, unbranched or branched alkyl of 1 to 6 carbon atoms or wherein $R_{35}$ is —$COR_{36}$ wherein $R_{36}$ is 1-alkyl-4-piperidyl, wherein alkyl is unbranched or branched alkyl of 1 to 6 carbon atoms, or —$(CH_2)_nCOR_{36}$ wherein $R_{36}$ is 4-pyridyl or 4-hydroxyphenyl, (d) a group of the formula —$(CH_2)_nPO(OH)_2$, —$(CH_2)_n SO_2OH$, —$(CH_2)_nOR_{31}$, —$(CH_2)_nSO_2N(R_{31})_2$, or —$(CH_2)_nNHSO_2R_{31}$ wherein $R_{31}$ is independently selected from H, unbranched or branched alkyl of 1 to 6 carbon atoms, $R_3$ is selected from (A) H, (B) branched or unbranched alkyl of 1 to 6 carbon atoms or cycloalkyl of 3 to 6 carbon atoms, wherein said alkyl or cycloalkyl group may optionally be substituted with a group of the formula —$OR_8$, wherein $R_8$ is an alkyl or acyl group of 1 to 6 carbon atoms, (C) $(CH_2)_n$-aryl, substituted $(CH_2)_n$-aryl, $(CH_2)_n$-heteroaryl or substituted $(CH_2)_n$-heteroaryl, wherein one or more of the hydrogen atoms of the aryl group of said substituted $(CH_2)_n$-aryl group or one or more of the hydrogen atoms of the heteroaryl group of said substituted $(CH_2)_n$-heteroaryl group may be optionally and independently replaced with:

(i) $R_{11}$, which is aryl or heteroaryl selected from phenyl, 2-naphthyl, 2-, 3-, 5- or 6-indolyl, 2- or 3-thiophenyl, 2-, 3- or 4-pyridyl, 2-, 4- or 5-pyrimidinyl, 2- or 3-furyl, 1-, 2- or 3-pyrrolyl, 2-, 4- or 5-oxazolyl, 2-, 4- or 5-thiazolyl, 1-, 3-, 4- or 5-pyrazolyl, 3-, 4- or 5-isoxazolyl, 1-, 2-, 4- or 5-imidazolyl, 3-, 4- or 5-isothiazolyl, 4- or 5-oxadiazolyl, 1-, 4- or 5-triazolyl, 2-thiadiazolyl, 3- or 4-pyridazinyl, 2-pyrazinyl, 2-triazinyl, 2-, 3-, 6- or 7-indolyzinyl, 2-, 3-, 5- or 6-isoindolyl, 2-, 3-, 5- or 6-benzo[b]furanyl, 2-, 3-, 5- or 6-benzo[b]thiophenyl, 3-, 5- or 6-indazolyl, 2-, 5- or 6-benzthiazolyl, 2-, 5- or 6-benzimidazolyl, 2-, 3-, 6- or 7-quinolinyl, 3-, 6- or 7-isoquinolinyl, 2- or 8-purinyl, 2-, 3-, 7- or 8-quinolizinyl, 3-, 6- or 7-cinnolinyl, 6- or 7-phthalazinyl, 2-, 3-, 6- or 7-quinoxalinyl, 2-, 3-, 6- or 7-naphthyridinyl, 2-, 6- or 7-pteridinyl or 2-, 6- or 7-quinazolinyl, wherein one or more of the hydrogen atoms of said aryl or heteroaryl group may be optionally and independently replaced with:

(a) branched or unbranched alkyl of 1 to 6 carbon atoms or cycloalkyl of 3 to 6 carbon atoms, which alkyl or cycloakyl group may be mono or polysubstituted with halogen or oxo, (b) a group of the formula —$COOR_{12}$, wherein $R_{12}$ is unbranched or branched alkyl of 1 to 6 carbon atoms or cycloalkyl of 3 to 6 carbon atoms, (c) a group of the formula —$NR_{13}R_{14}$, wherein $R_{13}$ and $R_{14}$ are each, independently, H, alkyl or fluoroalkyl of 1 to 6 carbon atoms, cycloalkyl of 3 to 6 carbon atoms or acyl of 1 to 6 carbon atoms, or wherein $R_{13}$ and $R_{14}$ constitute a saturated hydrocarbon bridge of 3 to 5 carbon atoms which together with the nitrogen atom between them form a heterocyclic ring, (d) a group of the formula —$CONR_{15}R_{16}$, wherein $R_{15}$ and $R_{16}$ are each independently H, alkyl or fluoroalkyl of 1 to 6 carbon atoms or cycloalkyl of 3 to 6 carbon atoms, or wherein $R_{15}$ and $R_{16}$ constitute a saturated hydrocarbon bridge of 3 to 5 carbon atoms which together with the nitrogen atom between them form a heterocyclic ring, (e) a group of the formula —$OR_{17}$, wherein $R_{17}$ is H, alkyl or fluoroalkyl of 1 to 6 carbon atoms or acyl of 1 to 6 carbon atoms, (f) a group of the formula —$SR_{18}$, wherein $R_{18}$ is H, alkyl or fluoroalkyl of 1 to 6 carbon atoms or acyl of 1 to 6 carbon atoms, (g) cyano, (h) nitro, (i) an amidino group of the formula —$C(NR_{19})$—$NR_{20}R_{21}$ wherein $R_{19}$, $R_{20}$ and $R_{21}$ are each, independently, H or alkyl of 1 to 3 carbon atoms, and wherein two of $R_{19}$, $R_{20}$ and $R_{21}$ may additionally constitute a saturated hydrocarbon bridge of 3 to 5 carbon atoms which together with the nitrogen atom(s) between them form a heterocyclic ring, or (j) halogen, (ii) methyl, which may be mono- or polysubstituted with fluorine atoms and additionally may be monosubstituted with $R_{11}$, (iii) branched or unbranched alkyl of 2 to 6 carbon atoms or cycloalkyl of 3 to 6 carbon atoms, which alkyl or cycloakyl group may be mono- or polysubstituted with halogen or oxo, (iv) a group of the formula —$COOR_{22}$, wherein $R_{22}$ is unbranched or branched alkyl of 1 to 6 carbon atoms or cycloalkyl of 3 to 6 carbon atoms, (v) a group of the formula —$NR_{23}R_{24}$, wherein $R_{23}$ and $R_{24}$ are each, independently, H, alkyl or fluoroalkyl of 1 to 6 carbon atoms, cycloalkyl of 3 to 6 carbon atoms or acyl of 1 to 6 carbon atoms, or wherein $R_{23}$ and $R_{24}$ constitute a saturated hydrocarbon bridge of 3 to 5 carbon atoms which together with the nitrogen atom between them form a heterocyclic ring, or wherein one of $R_{23}$ and $R_{24}$ is the group $R_{11}$, (vi) a group of the formula —$CONR_{25}R_{26}$, wherein $R_{25}$ and $R_{26}$ are each, independently, H, alkyl or fluoroalkyl of 1 to 6 carbon atoms or cycloalkyl of 3 to 6 carbon atoms, or wherein $R_{25}$ and $R_{26}$ constitute a saturated hydrocarbon bridge of 3 to 5 carbon atoms which together with the nitrogen atom between them form a heterocyclic ring, or wherein one of $R_{25}$ and $R_{26}$ is the group $R_{11}$, (vii) a group of the formula —$COR_{27}$, wherein $R_{27}$ is H, unbranched or branched alkyl of 1 to 6 carbon atoms, cycloalkyl of 3 to 6 carbon atoms or $R_{11}$, (viii) a group of the formula —$OR_{28}$, wherein $R_{28}$ is H, alkyl or fluoroalkyl of 1 to 6 carbon atoms or acyl of 1 to 6 carbon atoms, or $R_{11}$, (ix) a group of the formula —$SR_{29}$, wherein $R_{29}$ is H, alkyl or fluoroalkyl of 1 to 6 carbon atoms or acyl of 1 to 6 carbon atoms, or $R_{11}$, (x) cyano, (xi) nitro, or (xii) halogen, wherein at least one of $R_2$ and $R_3$ is $(CH_2)_n$-aryl, substituted $(CH_2)_n$-aryl, $(CH_2)_n$-heteroaryl or substituted $(CH_2)_n$-heteroaryl and wherein $R_1$ and $R_2$ are different from each other;

$R_6$ and $R_7$ are independently selected from H, branched or unbranched alkyl of 1 to 6 carbon atoms or cycloalkyl of 3 to 6 carbon atoms, wherein said alkyl or cycloalkyl group may optionally be substituted with:

(a) a group of the formula —$OR_8$, wherein $R_8$ is an alkyl or acyl group of 1 to 6 carbon atoms, or (b) a group of the formula —$NR_9R_{10}$, wherein $R_9$ and $R_{10}$ are each, independently, an alkyl or acyl group of 1 to 2 carbon atoms;

n is 0, 1, 2 or 3.

In a further aspect the present invention provides compounds according to formula (Ib)

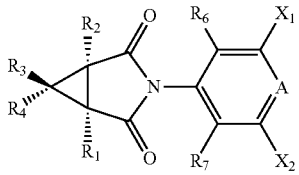

pharmaceutically-acceptable salts, hydrates, solvates, or prodrugs thereof, in which:

$X_1$ is selected from H, halogen or $CF_3$, $X_2$ is selected from H, halogen or $CF_3$, wherein at least one of $X_1$ and $X_2$ is halogen or $CF_3$;

A is N or $CR_5$, wherein $R_5$ is selected from H, halogen, branched or unbranched alkyl of 1 to 6 carbon atoms, branched or unbranched alkenyl of 2 to 6 carbon atoms, $CF_3$, $CCl_3$, CN, $NO_2$, O-alkyl with branched or unbranched alkyl of 1 to 6 carbon atoms, S-alkyl with branched or unbranched alkyl of 1 to 6 carbon atoms, aryl, substituted aryl, heteroaryl or substituted heteroaryl;

$R_1$ is selected from H, branched or unbranched alkyl of 1 to 6 carbon atoms, branched or unbranched alkenyl of 2 to 6 carbon atoms, or cycloalkyl of 3 to 6 carbon atoms;

$R_2$ and $R_4$ are independently selected from (A) H, (B) branched or unbranched alkyl of 1 to 6 carbon atoms or cycloalkyl of 3 to 6 carbon atoms, wherein said alkyl or cycloalkyl group may optionally be substituted with:

(a) a group of the formula —$OR_8$, wherein $R_8$ is an alkyl or acyl group of 1 to 6 carbon atoms, or (b) a group of the formula —$NR_9R_{10}$, wherein $R_9$ and $R_{10}$ are each, independently, an alkyl or acyl group of 1 to 2 carbon atoms, (C) $(CH_2)_n$-aryl, substituted $(CH_2)_n$-aryl, $(CH_2)_n$-heteroaryl or substituted $(CH_2)_n$-heteroaryl, wherein one or more of the hydrogen atoms of the aryl group of said substituted $(CH_2)_n$-aryl group or one or more of the hydrogen atoms of the heteroaryl group of said substituted $(CH_2)_n$-heteroaryl group may be optionally and independently replaced with:

(i) $R_{11}$, which is aryl or heteroaryl selected from phenyl, 2-naphthyl, 2-, 3-, 5- or 6-indolyl, 2- or 3-thiophenyl, 2-, 3- or 4-pyridyl, 2-, 4- or 5-pyrimidinyl, 2- or 3-furyl, 1-, 2- or 3-pyrrolyl, 2-, 4- or 5-oxazolyl, 2-, 4- or 5-thiazolyl, 1-, 3-, 4- or 5-pyrazolyl, 3-, 4- or 5-isoxazolyl, 1-, 2-, 4- or 5-imidazolyl, 3-, 4- or 5-isothiazolyl, 4- or 5-oxadiazolyl, 1-, 4- or 5-triazolyl, 2-thiadiazolyl, 3- or 4-pyridazinyl, 2-pyrazinyl, 2-triazinyl, 2-, 3-, 6- or 7-indolyzinyl, 2-, 3-, 5- or 6-isoindolyl, 2-, 3-, 5- or 6-benzo[b]furanyl, 2-, 3-, 5- or 6-benzo[b]thiophenyl, 3-, 5- or 6-indazolyl, 2-, 5- or 6-benzthiazolyl, 2-, 5- or 6-benzimidazolyl, 2-, 3-, 6- or 7-quinolinyl, 3-, 6- or 7-isoquinolinyl, 2- or 8-purinyl, 2-, 3-, 7- or 8-quinolizinyl, 3-, 6- or 7-cinnolinyl, 6- or 7-phthalazinyl, 2-, 3-, 6- or 7-quinoxalinyl, 2-, 3-, 6- or 7-naphthyridinyl, 2-, 6- or 7-pteridinyl or 2-, 6- or 7-quinazolinyl, wherein one or more of the hydrogen atoms of said aryl or heteroaryl group may be optionally and independently replaced with:

(a) branched or unbranched alkyl of 1 to 6 carbon atoms or cycloalkyl of 3 to 6 carbon atoms, which alkyl or cycloakyl group may be mono or polysubstituted with halogen or oxo, (b) —COOH, (c) —$SO_2OH$, (d) —$PO(OH)_2$, (e) a group of the formula —$COOR_{12}$, wherein $R_{12}$ is unbranched or branched alkyl of 1 to 6 carbon atoms or cycloalkyl of 3 to 6 carbon atoms, (f) a group of the formula —$NR_{13}R_{14}$, wherein $R_{13}$ and $R_{14}$ are each, independently, H, alkyl or fluoroalkyl of 1 to 6 carbon atoms, cycloalkyl of 3 to 6 carbon atoms or acyl of 1 to 6 carbon atoms, or wherein $R_{13}$ and $R_{14}$ constitute a saturated hydrocarbon bridge of 3 to 5 carbon atoms which together with the nitrogen atom between them form a heterocyclic ring, (g) a group of the formula —$CONR_{15}R_{16}$, wherein $R_{15}$ and $R_{16}$ are each, independently H, alkyl or fluoroalkyl of 1 to 6 carbon atoms or cycloalkyl of 3 to 6 carbon atoms, or wherein $R_{15}$ and $R_{16}$ constitute a saturated hydrocarbon bridge of 3 to 5 carbon atoms which together with the nitrogen atom between them form a heterocyclic ring, (h) a group of the formula —$OR_{17}$, wherein $R_{17}$ is H, alkyl or fluoroalkyl of 1 to 6 carbon atoms or acyl of 1 to 6 carbon atoms, (i) a group of the formula —$SR_{18}$, wherein $R_{18}$ is H, alkyl or fluoroalkyl of 1 to 6 carbon atoms or acyl of 1 to 6 carbon atoms, (j) cyano, (k) nitro, (l) an amidino group of the formula —$C(NR_{19})$—$NR_{20}R_{21}$ wherein $R_{19}$, $R_{20}$ and $R_{21}$ are each, independently, H or alkyl of 1 to 3 carbon atoms, and wherein two of $R_{19}$, $R_{20}$ and $R_{21}$ may additionally constitute a saturated hydrocarbon bridge of 3 to 5 carbon atoms which together with the nitrogen atom(s) between them form a heterocyclic ring, or (m) halogen,
(ii) methyl, which may be mono- or polysubstituted with fluorine atoms and additionally may be monosubstituted with $R_{11}$,
(iii) branched or unbranched alkyl of 2 to 6 carbon atoms or cycloalkyl of 3 to 6 carbon atoms, which alkyl or cycloakyl group may be mono- or polysubstituted with halogen or oxo,
(iv) a group of the formula —$COOR_{22}$, wherein $R_{22}$ is unbranched or branched alkyl of 1 to 6 carbon atoms or cycloalkyl of 3 to 6 carbon atoms,
(v) a group of the formula —$NR_{23}R_{24}$, wherein $R_{23}$ and $R_{24}$ are each, independently H, alkyl or fluoroalkyl of 1 to 6 carbon atoms, cycloalkyl of 3 to 6 carbon atoms or acyl of 1 to 6 carbon atoms, or wherein $R_{23}$ and $R_{24}$ constitute a saturated hydrocarbon bridge of 3 to 5 carbon atoms which together with the nitrogen atom between them form a heterocyclic ring, or wherein one of $R_{23}$ and $R_{24}$ 1 S the group $R_{11}$,
(vi) a group of the formula —$CONR_{25}R_{26}$, wherein $R_{25}$ and $R_{26}$ are each, independently, H, alkyl or fluoroalkyl of 1 to 6 carbon atoms or cycloalkyl of 3 to 6 carbon atoms, or wherein $R_{25}$ and $R_{26}$ constitute a saturated hydrocarbon bridge of 3 to 5 carbon atoms which together with the nitrogen atom between them form a heterocyclic ring, or wherein one of $R_{25}$ and $R_{26}$ is the group $R_{11}$,
(vii) a group of the formula —$COR_{27}$, wherein $R_{27}$ is H, unbranched or branched alkyl of 1 to 6 carbon atoms, cycloalkyl of 3 to 6 carbon atoms or $R_{11}$,
(viii) a group of the formula —$OR_{28}$, wherein $R_{28}$ is H, alkyl or fluoroalkyl of 1 to 6 carbon atoms or acyl of 1 to 6 carbon atoms, or $R_{11}$,
(ix) a group of the formula —$SR_{29}$, wherein $R_{29}$ is H, alkyl or fluoroalkyl of 1 to 6 carbon atoms or acyl of 1 to 6 carbon atoms, or $R_{11}$,
(x) cyano,
(xi) nitro, or
(xii) halogen, or,
(D) a substituent selected from
(i) a group of the formula —$(CH_2)_n COOR_{30}$, wherein $R_{30}$ is independently H, unbranched or branched alkyl of 1 to 6 carbon atoms or cycloalkyl of 3 to 6 carbon atoms and wherein said unbranched or branched alkyl of 1 to 6 carbon atoms or cycloalkyl of 3 to 6 carbon atoms may be optionally and independently substituted with —$CH_2OR_{31}$, —$COOR_{31}$, —$CON(R_{31})_2$, —$CH_2NHCOR_{31}$, —$SO_2N(R_{31})_2$, —$CH_2NHSO_2R_{31}$, —$CH_2N(R_{31})_2$, —$SO_2OH$, —$PO(OH)_2$ wherein $R_{31}$ is independently selected from H, unbranched or branched alkyl of 1 to 6 carbon atoms,
(ii) a group of the formula —$(CH_2)_nCONR_{32}R_{33}$, wherein $R_{32}$ and $R_{33}$ are each, independently, H, unbranched or branched alkyl of 1 to 6 carbon atoms or cycloalkyl of 3 to 6 carbon atoms and wherein said unbranched or branched alkyl of 1 to 6 carbon atoms or cycloalkyl of 3 to 6 carbon atoms may be optionally and independently substituted with —$CH_2OR_{31}$, —$COOR_{31}$, —$CON(R_{31})_2$, —$CH_2NHCOR_{31}$, —$SO_2N(R_{31})_2$, —$CH_2NHSO_2R_{31}$, —$CH_2N(R_{31})_2$, —$SO_2OH$, —$PO(OH)_2$ wherein $R_{31}$ is independently selected from H, unbranched or branched alkyl of 1 to 6 carbon atoms or wherein $NR_{32}$ is N-alkyl-4-piperidinylamino, N-carboxymethyl-4-piperidinylamino, pyridin-4-ylmethylamino, 4-amidinobenzylamino, 4-carboxybenzylamino, or 4-hydroxybenzylamino and $R_{33}$ is H or wherein $NR_{32}R_{33}$ constitute a heterocyclic ring selected from 4-alkyl-1-piperazinyl, wherein alkyl is unbranched or branched alkyl of 1 to 6 carbon atoms, or 1-morpholinyl,
(iii) a group of the formula —$(CH_2)_nNHR_{34}$, wherein $R_{34}$ is H, unbranched or branched alkyl of 1 to 6 carbon atoms, cycloalkyl of 3 to 6 carbon atoms or an acyl group of 1 to 6 carbon atoms and wherein said unbranched or branched alkyl of 1 to 6 carbon atoms or cycloalkyl of 3 to 6 carbon atoms may be optionally and independently substituted with —$CH_2OR_{31}$, —$COOR_{31}$, —$CON(R_{31})_2$, —$CH_2NHCOR_{31}$, —$SO_2N(R_{31})_2$, —$CH_2NHSO_2R_{31}$, —$CH_2N(R_{31})_2$, —$SO_2OH$, —$PO(OH)_2$ wherein $R_{31}$ is independently selected from H, unbranched or branched alkyl of 1 to 6 carbon atoms or wherein $R_{34}$ is —$COR_{36}$ wherein $R_{36}$ is 1-alkyl-4-piperidyl, wherein alkyl is unbranched or branched alkyl of 1 to 6 carbon atoms, or —$(CH_2)_n COR_{36}$ wherein $R_{36}$ is 4-pyridyl or 4-hydroxyphenyl,
(iv) a group of the formula —$(CH_2)$—$PO(OH)_2$, —$(CH_2)_n SO_2OH$, —$(CH_2)_nOR_{31}$, —$(CH_2)_nSO_2N(R_{31})_2$, or —$(CH_2)_nNHSO_2R_{31}$ wherein $R_{31}$ is independently selected from H, unbranched or branched alkyl of 1 to 6 carbon atoms,
(v) $(CH_2)_n$-aryl, substituted $(CH_2)_n$-aryl, $(CH_2)_n$-heteroaryl or substituted $(CH_2)_n$-heteroaryl, wherein one or more of the hydrogen atoms of the aryl group of said substituted $(CH_2)_n$-aryl group or one or more of the hydrogen atoms of the heteroaryl group of said substituted $(CH_2)_n$-heteroaryl group may be optionally and independently replaced with:
(a) a group of the formula —$COOR_{30}$, wherein $R_{30}$ is independently H, unbranched or branched alkyl of 1 to 6 carbon atoms or cycloalkyl of 3 to 6 carbon atoms and wherein said unbranched or branched alkyl of 1 to 6 carbon atoms or cycloalkyl of 3 to 6 carbon atoms may be optionally and independently substituted with —$CH_2OR_{31}$, —$COOR_{31}$, —$CON(R_{31})_2$, —$CH_2NHCOR_{31}$, —$SO_2N(R_{31})_2$, —$CH_2NHSO_2R_{31}$, —$CH_2N(R_{31})_2$, —$SO_2OH$, —$PO(OH)_2$ wherein $R_{31}$ is independently selected from H, unbranched or branched alkyl of 1 to 6 carbon atoms,
(b) a group of the formula —$CONR_{32}R_{33}$, wherein $R_{32}$ and $R_{33}$ are each, independently, H, unbranched or branched alkyl of 1 to 6 carbon atoms or cycloalkyl of 3 to 6 carbon atoms and wherein said unbranched or branched alkyl of 1 to 6 carbon atoms or cycloalkyl of 3 to 6 carbon atoms may be optionally and independently substituted with —$CH_2OR_{31}$, —$COOR_{31}$, —$CON(R_{31})_2$, —$CH_2NHCOR_{31}$, —$SO_2N(R_{31})_2$, —$CH_2NHSO_2R_{31}$, —$CH_2N(R_{31})_2$, —$SO_2OH$, —$PO(OH)_2$ wherein $R_{31}$ is independently selected from H, unbranched or branched alkyl of 1 to 6 carbon atoms or wherein $NR_{32}$ is N-alkyl-4-piperidinylamino, N-carboxymethyl-4-piperidinylamino, pyridin-4-ylmethylamino, 4-amidinobenzylamino, 4-carboxybenzylamino, or 4-hydroxybenzylamino and $R_{33}$ is H or wherein $NR_{32}R_{33}$ constitute a heterocyclic ring selected from 4-alkyl-1-piperazinyl, wherein alkyl is unbranched or branched alkyl of 1 to 6 carbon atoms, or 1-morpholinyl,
(c) a group of the formula —$NHR_{35}$, wherein $R_{35}$ is H, unbranched or branched alkyl of 1 to 6 carbon atoms, cycloalkyl of 3 to 6 carbon atoms or an acyl group of 1 to 6 carbon atoms and wherein said unbranched or branched alkyl of 1 to 6 carbon atoms or cycloalkyl of 3 to 6 carbon atoms may be optionally and independently substituted with —CH$_2$OR$_{31}$, —COOR$_{31}$, —CON(R$_{31}$)$_2$, —CH$_2$NHCOR$_{31}$, —SO$_2$N(R$_{31}$)$_2$, —CH$_2$NHSO$_2$R$_{31}$, —CH$_2$N(R$_{31}$)$_2$, —SO$_2$OH, —PO(OH)$_2$ wherein R$_{31}$ is independently selected from H, unbranched or branched alkyl of 1 to 6 carbon atoms or wherein R$_{35}$ is —COR$_{36}$ wherein R$_{36}$ is 1-alkyl-4-piperidyl, wherein alkyl is unbranched or branched alkyl of 1 to 6 carbon atoms, or —(CH$_2$)$_n$COR$_{36}$ wherein R$_{36}$ is 4-pyridyl or 4-hydroxyphenyl, (d) a group of the formula —(CH$_2$)$_n$PO(OH)$_2$, —(CH$_2$)$_n$SO$_2$OH, —(CH$_2$)$_n$OR$_{31}$, —(CH$_2$)$_n$SO$_2$N(R$_{31}$)$_2$, or —(CH$_2$)$_n$NHSO$_2$R$_{31}$ wherein R$_{31}$ is independently selected from H, unbranched or branched alkyl of 1 to 6 carbon atoms, R$_3$ is selected from (A) H, (B) branched or unbranched alkyl of 1 to 6 carbon atoms or cycloalkyl of 3 to 6 carbon atoms, wherein said alkyl or cycloalkyl group may optionally be substituted with a group of the formula —OR$_8$, wherein R$_8$ is an alkyl or acyl group of 1 to 6 carbon atoms, (C) (CH$_2$)$_n$-aryl, substituted (CH$_2$)$_n$-aryl, (CH$_2$)$_n$-heteroaryl or substituted (CH$_2$)$_n$-heteroaryl, wherein one or more of the hydrogen atoms of the aryl group of said substituted (CH$_2$)$_n$-aryl group or one or more of the hydrogen atoms of the heteroaryl group of said substituted (CH$_2$)$_n$-heteroaryl group may be optionally and independently replaced with:

(i) R$_{11}$, which is aryl or heteroaryl selected from phenyl, 2-naphthyl, 2-, 3-, 5- or 6-indolyl, 2- or 3-thiophenyl, 2-, 3- or 4-pyridyl, 2-, 4- or 5-pyrimidinyl, 2- or 3-furyl, 1-, 2- or 3-pyrrolyl, 2-, 4- or 5-oxazolyl, 2-, 4- or 5-thiazolyl, 1-, 3-, 4- or 5-pyrazolyl, 3-, 4- or 5-isoxazolyl, 1-, 2-, 4- or 5-imidazolyl, 3-, 4- or 5-isothiazolyl, 4- or 5-oxadiazolyl, 1-, 4- or 5-triazolyl, 2-thiadiazolyl, 3- or 4-pyridazinyl, 2-pyrazinyl, 2-triazinyl, 2-, 3-, 6- or 7-indolyzinyl, 2-, 3-, 5- or 6-isoindolyl, 2-, 3-, 5- or 6-benzo[b]furanyl, 2-, 3-, 5- or 6-benzo[b]thiophenyl, 3-, 5- or 6-indazolyl, 2-, 5- or 6-benzthiazolyl, 2-, 5- or 6-benzimidazolyl, 2-, 3-, 6- or 7-quinolinyl, 3-, 6- or 7-isoquinolinyl, 2- or 8-purinyl, 2-, 3-, 7- or 8-quinolizinyl, 3-, 6- or 7-cinnolinyl, 6- or 7-phthalazinyl, 2-, 3-, 6- or 7-quinoxalinyl, 2-, 3-, 6- or 7-naphthyridinyl, 2-, 6- or 7-pteridinyl or 2-, 6- or 7-quinazolinyl, wherein one or more of the hydrogen atoms of said aryl or heteroaryl group may be optionally and independently replaced with:

(a) branched or unbranched alkyl of 1 to 6 carbon atoms or cycloalkyl of 3 to 6 carbon atoms, which alkyl or cycloakyl group may be mono or polysubstituted with halogen or oxo, (b) a group of the formula —COOR$_{12}$, wherein R$_{12}$ is unbranched or branched alkyl of 1 to 6 carbon atoms or cycloalkyl of 3 to 6 carbon atoms, (c) a group of the formula —NR$_{13}$R$_{14}$, wherein R$_{13}$ and R$_{14}$ are each, independently, H, alkyl or fluoroalkyl of 1 to 6 carbon atoms, cycloalkyl of 3 to 6 carbon atoms or acyl of 1 to 6 carbon atoms, or wherein R$_{13}$ and R$_{14}$ constitute a saturated hydrocarbon bridge of 3 to 5 carbon atoms which together with the nitrogen atom between them form a heterocyclic ring, (d) a group of the formula —CONR$_{15}$R$_{16}$, wherein R$_{15}$ and R$_{16}$ are each independently H, alkyl or fluoroalkyl of 1 to 6 carbon atoms or cycloalkyl of 3 to 6 carbon atoms, or wherein R$_{15}$ and R$_{16}$ constitute a saturated hydrocarbon bridge of 3 to 5 carbon atoms which together with the nitrogen atom between them form a heterocyclic ring, (e) a group of the formula —OR$_{17}$, wherein R$_{17}$ is H, alkyl or fluoroalkyl of 1 to 6 carbon atoms or acyl of 1 to 6 carbon atoms, (f) a group of the formula —SR$_{18}$, wherein R$_{18}$ is H, alkyl or fluoroalkyl of 1 to 6 carbon atoms or acyl of 1 to 6 carbon atoms, (g) cyano, (h) nitro, (i) an amidino group of the formula —C(NR$_{19}$)—NR$_{20}$R$_{21}$ wherein R$_{19}$, R$_{20}$ and R$_{21}$ are each, independently, H or alkyl of 1 to 3 carbon atoms, and wherein two of R$_{19}$, R$_{20}$ and R$_{21}$ may additionally constitute a saturated hydrocarbon bridge of 3 to 5 carbon atoms which together with the nitrogen atom(s) between them form a heterocyclic ring, or (j) halogen, (ii) methyl, which may be mono- or polysubstituted with fluorine atoms and additionally may be monosubstituted with R$_{11}$, (iii) branched or unbranched alkyl of 2 to 6 carbon atoms or cycloalkyl of 3 to 6 carbon atoms, which alkyl or cycloakyl group may be mono- or polysubstituted with halogen or oxo, (iv) a group of the formula —COOR$_{22}$, wherein R$_{22}$ is unbranched or branched alkyl of 1 to 6 carbon atoms or cycloalkyl of 3 to 6 carbon atoms, (v) a group of the formula —NR$_{23}$R$_{24}$, wherein R$_{23}$ and R$_{24}$ are each, independently, H, alkyl or fluoroalkyl of 1 to 6 carbon atoms, cycloalkyl of 3 to 6 carbon atoms or acyl of 1 to 6 carbon atoms, or wherein R$_{23}$ and R$_{24}$ constitute a saturated hydrocarbon bridge of 3 to 5 carbon atoms which together with the nitrogen atom between them form a heterocyclic ring, or wherein one of R$_{23}$ and R$_{24}$ is the group R$_{11}$, (vi) a group of the formula —CONR$_{25}$R$_{26}$, wherein R$_{25}$ and R$_{26}$ are each, independently, H, alkyl or fluoroalkyl of 1 to 6 carbon atoms or cycloalkyl of 3 to 6 carbon atoms, or wherein R$_{25}$ and R$_{26}$ constitute a saturated hydrocarbon bridge of 3 to 5 carbon atoms which together with the nitrogen atom between them form a heterocyclic ring, or wherein one of R$_{25}$ and R$_{26}$ is the group R$_{11}$, (vii) a group of the formula —COR$_{27}$, wherein R$_{27}$ is H, unbranched or branched alkyl of 1 to 6 carbon atoms, cycloalkyl of 3 to 6 carbon atoms or R$_{11}$, (viii) a group of the formula —OR$_{28}$, wherein R$_{28}$ is H, alkyl or fluoroalkyl of 1 to 6 carbon atoms or acyl of 1 to 6 carbon atoms, or R$_{11}$, (ix) a group of the formula —SR$_{29}$, wherein R$_{29}$ is H, alkyl or fluoroalkyl of 1 to 6 carbon atoms or acyl of 1 to 6 carbon atoms, or R$_{11}$, (x) cyano, (xi) nitro, or (xii) halogen, wherein at least one of R$_2$ and R$_3$ is (CH$_2$)$_n$-aryl, substituted (CH$_2$)$_n$-aryl, (CH$_2$)$_n$-heteroaryl or substituted (CH$_2$)$_n$-heteroaryl and wherein R$_1$ and R$_2$ are different from each other; R$_6$ and R$_7$ are independently selected from H, branched or unbranched alkyl of 1 to 6 carbon atoms or cycloalkyl of 3 to 6 carbon atoms, wherein said alkyl or cycloalkyl group may optionally be substituted with:

(a) a group of the formula —OR$_8$, wherein R$_8$ is an alkyl or acyl group of 1 to 6 carbon atoms, or
(b) a group of the formula —NR$_9$R$_{10}$, wherein R$_9$ and R$_{10}$ are each, independently, an alkyl or acyl group of 1 to 2 carbon atoms;

n is 0, 1, 2 or 3.

In a further aspect the present invention provides compounds according to formula (Ia)

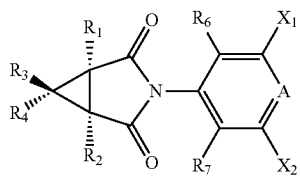

and/or according to formula (Ib),

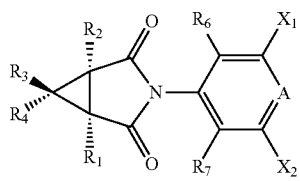

racemates of the compound according to formula (Ia) and the compound according to formula (Ib), diastereomers of the compound according to formula (Ia) or the compound according to formula (Ib), diastereomeric meso forms of the compound according to formula (Ia) wherein R$_1$ and R$_2$ are the same, pharmaceutically-acceptable salts, hydrates, solvates, or prodrugs thereof, in which:

X$_1$ is selected from H, halogen or CF$_3$,
X$_2$ is selected from H, halogen or CF$_3$,
wherein at least one of X$_1$ and X$_2$ is halogen or CF$_3$;
A is N or CR$_5$, wherein R$_5$ is selected from H, halogen, branched or unbranched alkyl of 1 to 6 carbon atoms, branched or unbranched alkenyl of 2 to 6 carbon atoms, CF$_3$, CCl$_3$, CN, NO$_2$, O-alkyl with branched or unbranched alkyl of 1 to 6 carbon atoms, S-alkyl with branched or unbranched alkyl of 1 to 6 carbon atoms, aryl, substituted aryl, heteroaryl or substituted heteroaryl;
R$_1$ is selected from H, branched or unbranched alkyl of 1 to 6 carbon atoms, branched or unbranched alkenyl of 2 to 6 carbon atoms, or cycloalkyl of 3 to 6 carbon atoms;
R$_2$ and R$_4$ are independently selected from
(A) H,
(B) branched or unbranched alkyl of 1 to 6 carbon atoms or cycloalkyl of 3 to 6 carbon atoms, wherein said alkyl or cycloalkyl group may optionally be substituted with:
 (a) a group of the formula —OR$_8$, wherein R$_8$ is an alkyl or acyl group of 1 to 6 carbon atoms, or
 (b) a group of the formula —NR$_9$R$_{10}$, wherein R$_9$ and R$_{10}$ are each, independently, an alkyl or acyl group of 1 to 2 carbon atoms,
(C) (CH$_2$)$_n$-aryl, substituted (CH$_2$)$_n$-aryl, (CH$_2$)$_n$-heteroaryl or substituted (CH$_2$)$_n$-heteroaryl, wherein one or more of the hydrogen atoms of the aryl group of said substituted (CH$_2$)$_n$-aryl group or one or more of the hydrogen atoms of the heteroaryl group of said substituted (CH$_2$)$_n$-heteroaryl group may be optionally and independently replaced with:

(i) R$_{11}$, which is aryl or heteroaryl selected from phenyl, 2-naphthyl, 2-, 3-, 5- or 6-indolyl, 2- or 3-thiophenyl, 2-, 3- or 4-pyridyl, 2-, 4- or 5-pyrimidinyl, 2- or 3-furyl, 1-, 2- or 3-pyrrolyl, 2-, 4- or 5-oxazolyl, 2-, 4- or 5-thiazolyl, 1-, 3-, 4- or 5-pyrazolyl, 3-, 4- or 5-isoxazolyl, 1-, 2-, 4- or 5-imidazolyl, 3-, 4- or 5-isothiazolyl, 4- or 5-oxadiazolyl, 1-, 4- or 5-triazolyl, 2-thiadiazolyl, 3- or 4-pyridazinyl, 2-pyrazinyl, 2-triazinyl, 2-, 3-, 6- or 7-indolyzinyl, 2-, 3-, 5- or 6-isoindolyl, 2-, 3-, 5- or 6-benzo[b]furanyl, 2-, 3-, 5- or 6-benzo[b]thiophenyl, 3-, 5- or 6-indazolyl, 2-, 5- or 6-benzthiazolyl, 2-, 5- or 6-benzimidazolyl, 2-, 3-, 6- or 7-quinolinyl, 3-, 6- or 7-isoquinolinyl, 2- or 8-purinyl, 2-, 3-, 7- or 8-quinolizinyl, 3-, 6- or 7-cinnolinyl, 6- or 7-phthalazinyl, 2-, 3-, 6- or 7-quinoxalinyl, 2-, 3-, 6- or 7-naphthyridinyl, 2-, 6- or 7-pteridinyl or 2-, 6- or 7-quinazolinyl, wherein one or more of the hydrogen atoms of said aryl or heteroaryl group may be optionally and independently replaced with:
 (a) branched or unbranched alkyl of 1 to 6 carbon atoms or cycloalkyl of 3 to 6 carbon atoms, which alkyl or cycloakyl group may be mono or polysubstituted with halogen or oxo,
 (b) —COOH,
 (c) —SO$_2$OH,
 (d) —PO(OH)$_2$,
 (e) a group of the formula —COOR$_{12}$, wherein R$_{12}$ is unbranched or branched alkyl of 1 to 6 carbon atoms or cycloalkyl of 3 to 6 carbon atoms,
 (f) a group of the formula —NR$_{13}$R$_{14}$, wherein R$_{13}$ and R$_{14}$ are each, independently, H, alkyl or fluoroalkyl of 1 to 6 carbon atoms, cycloalkyl of 3 to 6 carbon atoms or acyl of 1 to 6 carbon atoms, or wherein R$_{13}$ and R$_{14}$ constitute a saturated hydrocarbon bridge of 3 to 5 carbon atoms which together with the nitrogen atom between them form a heterocyclic ring,
 (g) a group of the formula —CONR$_{15}$R$_{16}$, wherein R$_{15}$ and R$_{16}$ are each, independently H, alkyl or fluoroalkyl of 1 to 6
carbon atoms or cycloalkyl of 3 to 6 carbon atoms, or wherein R$_{15}$ and R$_{16}$ constitute a saturated hydrocarbon bridge of 3 to 5 carbon atoms which together with the nitrogen atom between them form a heterocyclic ring,
 (h) a group of the formula —OR$_{17}$, wherein R$_{17}$ is H, alkyl or fluoroalkyl of 1 to 6 carbon atoms or acyl of 1 to 6 carbon atoms,
 (i) a group of the formula —SR$_{18}$, wherein R$_{18}$ is H, alkyl or fluoroalkyl of 1 to 6 carbon atoms or acyl of 1 to 6 carbon atoms,
 (j) cyano,
 (k) nitro,
 (l) an amidino group of the formula —C(NR$_{19}$)—NR$_{20}$R$_{21}$
 wherein R$_{19}$, R$_{20}$ and R$_{21}$ are each, independently, H or alkyl of 1 to 3 carbon atoms, and wherein two of R$_{19}$, R$_{20}$ and R$_{21}$ may additionally constitute a saturated hydrocarbon bridge of 3 to 5 carbon atoms which together with the nitrogen atom(s) between them form a heterocyclic ring, or
 (m) halogen,
(ii) methyl, which may be mono- or polysubstituted with fluorine atoms and additionally may be monosubstituted with R$_{11}$, (iii) branched or unbranched alkyl of 2 to 6 carbon atoms or cycloalkyl of 3 to 6 carbon atoms, which alkyl or cycloakyl group may be mono- or polysubstituted with halogen or oxo, (iv) a group of the formula —COOR$_{22}$, wherein R$_{22}$ is unbranched or branched alkyl of 1 to 6 carbon atoms or cycloalkyl of 3 to 6 carbon atoms, (v) a group of the formula —NR$_{23}$R$_{24}$, wherein R23 and R24 are each, independently, H, alkyl or fluoroalkyl of 1 to 6 carbon atoms, cycloalkyl of 3 to 6 carbon atoms or acyl of 1 to 6 carbon atoms, or wherein R$_{23}$ and R$_{24}$ constitute a saturated hydrocarbon bridge of 3 to 5 carbon atoms which together with the nitrogen atom between them form a heterocyclic ring, or wherein one of R$_{23}$ and R$_{24}$ is the group R$_{11}$, (vi) a group of the formula —CONR$_{25}$R$_{26}$, wherein R$_{25}$ and R$_{26}$ are each, independently, H, alkyl or fluoroalkyl of 1 to 6 carbon atoms or cycloalkyl of 3 to 6 carbon atoms, or wherein R$_{25}$ and R$_{26}$ constitute a saturated hydrocarbon bridge of 3 to 5 carbon atoms which together with the nitrogen atom between them form a heterocyclic ring, or wherein one of R$_{25}$ and R$_{26}$ is the group R$_{11}$, (vii) a group of the formula —COR$_{27}$, wherein R$_{27}$ is H, unbranched or branched alkyl of 1 to 6 carbon atoms, cycloalkyl of 3 to 6 carbon atoms or R$_{11}$, (viii) a group of the formula —OR$_{28}$, wherein R$_{28}$ is H, alkyl or fluoroalkyl of 1 to 6 carbon atoms or acyl of 1 to 6 carbon atoms, or R$_{11}$, (ix) a group of the formula —SR$_{29}$, wherein R$_{29}$ is H, alkyl or fluoroalkyl of 1 to 6 carbon atoms or acyl of 1 to 6 carbon atoms, or R$_{11}$, (x) cyano, (xi) nitro, or (xii) halogen, or, (D) a substituent selected from (i) a group of the formula —(CH$_2$)$_n$COOR$_{30}$, wherein R$_{30}$ is independently H, unbranched or branched alkyl of 1 to 6 carbon atoms or cycloalkyl of 3 to 6 carbon atoms and wherein said unbranched or branched alkyl of 1 to 6 carbon atoms or cycloalkyl of 3 to 6 carbon atoms may be optionally and independently substituted with —CH$_2$OR$_{31}$, —COOR$_{31}$, —CON(R$_{31}$)$_2$, —CH$_2$NHCOR$_{31}$, —SO$_2$N(R$_{31}$)$_2$, —CH$_2$NHSO$_2$R$_{31}$, —CH$_2$N(R$_{31}$)$_2$, —SO$_2$OH, —PO(OH)$_2$ wherein R$_{31}$ is independently selected from H, unbranched or branched alkyl of 1 to 6 carbon atoms, (ii) a group of the formula —(CH$_2$)$_n$CONR$_{32}$R$_{33}$, wherein R$_{32}$ and R$_{33}$ are each, independently, H, unbranched or branched alkyl of 1 to 6 carbon atoms or cycloalkyl of 3 to 6 carbon atoms and wherein said unbranched or branched alkyl of 1 to 6 carbon atoms or cycloalkyl of 3 to 6 carbon atoms may be optionally and independently substituted with —CH$_2$OR$_{31}$, —COOR$_{31}$, —CON(R$_{31}$)$_2$, —CH$_2$NHCOR$_{31}$, —SO$_2$N(R$_{31}$)$_2$, —CH$_2$NHSO$_2$R$_{31}$, —CH$_2$N(R$_{31}$)$_2$, —SO$_2$OH, —PO(OH)$_2$ wherein R$_{31}$ is independently selected from H, unbranched or branched alkyl of 1 to 6 carbon atoms or wherein NR$_{32}$ is N-alkyl-4-piperidinylamino, N-carboxymethyl-4-piperidinylamino, pyridin-4-ylmethylamino, 4-amidinobenzylamino, 4-carboxybenzylamino, or 4-hydroxybenzylamino and R$_{33}$ is H or wherein NR$_{32}$R$_{33}$ constitute a heterocyclic ring selected from 4-alkyl-1-piperazinyl, wherein alkyl is unbranched or branched alkyl of 1 to 6 carbon atoms, or 1-morpholinyl, (iii) a group of the formula —(CH$_2$)$_n$NHR$_{34}$, wherein R$_{34}$ is H, unbranched or branched alkyl of 1 to 6 carbon atoms, cycloalkyl of 3 to 6 carbon atoms or an acyl group of 1 to 6 carbon atoms and wherein said unbranched or branched alkyl of 1 to 6 carbon atoms or cycloalkyl of 3 to 6 carbon atoms may be optionally and independently substituted with —CH$_2$OR$_{31}$, —COOR$_{31}$, —CON(R$_{31}$)$_2$, —CH$_2$NHCOR$_{31}$, —SO$_2$N(R$_{31}$)$_2$, —CH$_2$NHSO$_2$R$_{31}$, —CH$_2$N(R$_{31}$)$_2$, —SO$_2$OH, —PO(OH)$_2$ wherein R$_{31}$ is independently selected from H, unbranched or branched alkyl of 1 to 6 carbon atoms or wherein R$_{34}$ is —COR$_{36}$ wherein R$_{36}$ is 1-alkyl-4-piperidyl, wherein alkyl is unbranched or branched alkyl of 1 to 6 carbon atoms, or —(CH$_2$)$_n$COR$_{36}$ wherein R$_{36}$ is 4-pyridyl or 4-hydroxyphenyl, (iv) a group of the formula —(CH$_2$)$_n$PO(OH)$_2$, —(CH$_2$)$_n$SO$_2$OH, —(CH$_2$)$_n$OR$_{31}$, —(CH$_2$)$_n$SO$_2$N(R$_{31}$)$_2$, or —(CH$_2$)$_1$NHSO$_2$R$_{31}$ wherein R$_{31}$ is independently selected from H, unbranched or branched alkyl of 1 to 6 carbon atoms, (v) (CH$_2$)$_n$-aryl, substituted (CH$_2$)$_n$-aryl, (CH$_2$)$_n$-heteroaryl or substituted (CH$_2$)$_n$-heteroaryl, wherein one or more of the hydrogen atoms of the aryl group of said substituted (CH$_2$)$_n$-aryl group or one or more of the hydrogen atoms of the heteroaryl group of said substituted (CH$_2$)$_n$-heteroaryl group may be optionally and independently replaced with:

(a) a group of the formula —COOR$_{30}$, wherein R$_{30}$ is independently H, unbranched or branched alkyl of 1 to 6 carbon atoms or cycloalkyl of 3 to 6 carbon atoms and wherein said unbranched or branched alkyl of 1 to 6 carbon atoms or cycloalkyl of 3 to 6 carbon atoms may be optionally and independently substituted with —CH$_2$OR$_{31}$, —COOR$_{31}$, —CON(R$_{31}$)$_2$, —CH$_2$NHCOR$_{31}$, —SO$_2$N(R$_{31}$)$_2$, —CH$_2$NHSO$_2$R$_{31}$, —CH$_2$N(R$_{31}$)$_2$, —SO$_2$OH, —PO(OH)$_2$ wherein R$_{31}$ is independently selected from H, unbranched or branched alkyl of 1 to 6 carbon atoms, (b) a group of the formula —CONR$_{32}$R$_{33}$, wherein R$_{32}$ and R$_{33}$ are each, independently, H, unbranched or branched alkyl of 1 to 6 carbon atoms or cycloalkyl of 3 to 6 carbon atoms and wherein said unbranched or branched alkyl of 1 to 6 carbon atoms or cycloalkyl of 3 to 6 carbon atoms may be optionally and independently substituted with —CH$_2$OR$_{31}$, —COOR$_{31}$, —CON(R$_{31}$)$_2$, —CH$_2$NHCOR$_{31}$, —SO$_2$N(R$_{31}$)$_2$, —CH$_2$NHSO$_2$R$_{31}$, —CH$_2$N(R$_{31}$)$_2$, —SO$_2$OH, —PO(OH)$_2$ wherein R$_{31}$ is independently selected from H, unbranched or branched alkyl of 1 to 6 carbon atoms or wherein NR$_{32}$ is N-alkyl-4-piperidinylamino, N-carboxymethyl-4-piperidinylamino, pyridin-4-ylmethylamino, 4-amidinobenzylamino, 4-carboxybenzylamino, or 4-hydroxybenzylamino and R$_{33}$ is H or wherein NR$_{32}$R$_{33}$ constitute a heterocyclic ring selected from 4-alkyl-1-piperazinyl, wherein alkyl is unbranched or branched alkyl of 1 to 6 carbon atoms, or 1-morpholinyl, (c) a group of the formula —NHR$_{35}$, wherein R$_{35}$ is H, unbranched or branched alkyl of 1 to 6 carbon atoms, cycloalkyl of 3 to 6 carbon atoms or an acyl group of 1 to 6 carbon atoms and wherein said unbranched or branched alkyl of 1 to 6 carbon atoms or cycloalkyl of 3 to 6 carbon atoms may be optionally and independently substituted with —CH$_2$OR$_{31}$, —COOR$_{31}$, —CON(R$_{31}$)$_2$, —CH$_2$NHCOR$_{31}$, —SO$_2$N(R$_{31}$)$_2$, —CH$_2$NHSO$_2$R$_{31}$, —CH$_2$N(R$_{31}$)$_2$, —SO$_2$OH, —PO(OH)$_2$ wherein R$_{31}$ is independently selected from H, unbranched or branched alkyl of 1 to 6 carbon atoms or wherein R$_{35}$ is —COR$_{36}$ wherein R$_{36}$ is 1-alkyl-4-piperidyl, wherein alkyl is unbranched or branched alkyl of 1 to 6 carbon atoms, or —(CH$_2$)$_n$COR$_{36}$ wherein R$_{36}$ is 4-pyridyl or 4-hydroxyphenyl,
  (d) a group of the formula —(CH$_2$)$_n$PO(OH)$_2$, —(CH$_2$)$_n$ SO$_2$OH, —(CH$_2$)$_n$OR$_{31}$, —(CH$_2$)$_n$SO$_2$N(R$_{31}$)$_2$, or —(CH$_2$)—NHSO$_2$R$_{31}$ wherein R$_{31}$ is independently selected from H, unbranched or branched alkyl of 1 to 6 carbon atoms;

R$_3$ is selected from
(A) H,
(B) branched or unbranched alkyl of 1 to 6 carbon atoms or cycloalkyl of 3 to 6 carbon atoms, wherein said alkyl or cycloalkyl group may optionally be substituted with a group of the formula —OR$_8$, wherein R$_8$ is an alkyl or acyl group of 1 to 6 carbon atoms,
(C) (CH$_2$)$_n$-aryl, substituted (CH$_2$)$_n$-aryl, (CH$_2$)$_n$-heteroaryl or substituted (CH$_2$)$_n$-heteroaryl, wherein one or more of the hydrogen atoms of the aryl group of said substituted (CH$_2$)$_n$-aryl group or one or more of the hydrogen atoms of the heteroaryl group of said substituted (CH$_2$)$_n$-heteroaryl group may be optionally and independently replaced with:
  (i) R$_{11}$, which is aryl or heteroaryl selected from phenyl, 2-naphthyl, 2-, 3-, 5- or 6-indolyl, 2- or 3-thiophenyl, 2-, 3- or 4-pyridyl, 2-, 4- or 5-pyrimidinyl, 2- or 3-furyl, 1-, 2- or 3-pyrrolyl, 2-, 4- or 5-oxazolyl, 2-, 4- or 5-thiazolyl, 1-, 3-, 4- or 5-pyrazolyl, 3-, 4- or 5-isoxazolyl, 1-, 2-, 4- or 5-imidazolyl, 3-, 4- or 5-isothiazolyl, 4- or 5-oxadiazolyl, 1-, 4- or 5-triazolyl, 2-thiadiazolyl, 3- or 4-pyridazinyl, 2-pyrazinyl, 2-triazinyl, 2-, 3-, 6- or 7-indolyzinyl, 2-, 3-, 5- or 6-isoindolyl, 2-, 3-, 5- or 6-benzo[b]furanyl, 2-, 3-, 5- or 6-benzo[b]thiophenyl, 3-, 5- or 6-indazolyl, 2-, 5- or 6-benzthiazolyl, 2-, 5- or 6-benzimidazolyl, 2-, 3-, 6- or 7-quinolinyl, 3-, 6- or 7-isoquinolinyl, 2- or 8-purinyl, 2-, 3-, 7- or 8-quinolizinyl, 3-, 6- or 7-cinnolinyl, 6- or 7-phthalazinyl, 2-, 3-, 6- or 7-quinoxalinyl, 2-, 3-, 6- or 7-naphthyridinyl, 2-, 6- or 7-pteridinyl or 2-, 6- or 7-quinazolinyl,
  wherein one or more of the hydrogen atoms of said aryl or heteroaryl group may be optionally and independently replaced with:
    (a) branched or unbranched alkyl of 1 to 6 carbon atoms or cycloalkyl of 3 to 6 carbon atoms, which alkyl or cycloakyl group may be mono or polysubstituted with halogen or oxo,
    (b) a group of the formula —COOR$_{12}$, wherein R$_{12}$ is unbranched or branched alkyl of 1 to 6 carbon atoms or cycloalkyl of 3 to 6 carbon atoms,
    (c) a group of the formula —NR$_{13}$R$_{14}$, wherein R$_{13}$ and R$_{14}$ are each, independently, H, alkyl or fluoroalkyl of 1 to 6 carbon atoms, cycloalkyl of 3 to 6 carbon atoms or acyl of 1 to 6 carbon atoms, or wherein R$_{13}$ and R$_{14}$ constitute a saturated hydrocarbon bridge of 3 to 5 carbon atoms which together with the nitrogen atom between them form a heterocyclic ring,
    (d) a group of the formula —CONR$_{15}$R$_{16}$, wherein R$_{15}$ and R$_{16}$ are each independently H, alkyl or fluoroalkyl of 1 to 6 carbon atoms or cycloalkyl of 3 to 6 carbon atoms, or wherein R$_{15}$ and R$_{16}$ constitute a saturated hydrocarbon bridge of 3 to 5 carbon atoms which together with the nitrogen atom between them form a heterocyclic ring,
    (e) a group of the formula —OR$_{17}$, wherein R$_{17}$ is H, alkyl or fluoroalkyl of 1 to 6 carbon atoms or acyl of 1 to 6 carbon atoms,
    (f) a group of the formula —SR$_{18}$, wherein R$_{18}$ is H, alkyl or fluoroalkyl of 1 to 6 carbon atoms or acyl of 1 to 6 carbon atoms,
    (g) cyano,
    (h) nitro,
    (i) an amidino group of the formula —C(NR$_{19}$)—NR$_{20}$R$_{21}$ wherein R$_{19}$, R$_{20}$ and R$_{21}$ are each, independently, H or alkyl of 1 to 3 carbon atoms, and wherein two of R$_{19}$, R$_{20}$ and R$_{21}$ may additionally constitute a saturated hydrocarbon bridge of 3 to 5 carbon atoms which together with the nitrogen atom(s) between them form a heterocyclic ring, or
    (j) halogen,
  (ii) methyl, which may be mono- or polysubstituted with fluorine atoms and additionally may be monosubstituted with R$_{11}$,
  (iii) branched or unbranched alkyl of 2 to 6 carbon atoms or cycloalkyl of 3 to 6 carbon atoms, which alkyl or cycloakyl group may be mono- or polysubstituted with halogen or oxo,
  (iv) a group of the formula —COOR$_{22}$, wherein R$_{22}$ is unbranched or branched alkyl of 1 to 6 carbon atoms or cycloalkyl of 3 to 6 carbon atoms,
  (v) a group of the formula —NR$_{23}$R$_{24}$, wherein R$_{23}$ and R$_{24}$ are each, independently, H, alkyl or fluoroalkyl of 1 to 6 carbon atoms, cycloalkyl of 3 to 6 carbon atoms or acyl of 1 to 6 carbon atoms, or wherein R$_{23}$ and R$_{24}$ constitute a saturated hydrocarbon bridge of 3 to 5 carbon atoms which together with the nitrogen atom between them form a heterocyclic ring, or wherein one of R$_{23}$ and R$_{24}$ is the group R$_{11}$,
  (vi) a group of the formula —CONR$_{25}$R$_{26}$, wherein R$_{25}$ and R$_{26}$ are each, independently, H, alkyl or fluoroalkyl of 1 to 6 carbon atoms or cycloalkyl of 3 to 6 carbon atoms, or wherein R$_{25}$ and R$_{26}$ constitute a saturated hydrocarbon bridge of 3 to 5 carbon atoms which together with the nitrogen atom between them form a heterocyclic ring, or wherein one of R$_{25}$ and R$_{26}$ is the group R$_{11}$,
  (vii) a group of the formula —COR$_{27}$, wherein R$_{27}$ is H, unbranched or branched alkyl of 1 to 6 carbon atoms, cycloalkyl of 3 to 6 carbon atoms or R$_{11}$,
  (viii) a group of the formula —OR$_{28}$, wherein R$_{28}$ is H, alkyl or fluoroalkyl of 1 to 6 carbon atoms or acyl of 1 to 6 carbon atoms, or R$_{11}$,
  (ix) a group of the formula —SR$_{29}$, wherein R$_{29}$ is H, alkyl or fluoroalkyl of 1 to 6 carbon atoms or acyl of 1 to 6 carbon atoms, or R$_{11}$,
  (x) cyano,
  (xi) nitro, or
  (xii) halogen,
wherein at least one of R$_2$ and R$_3$ is (CH$_2$)$_n$-aryl, substituted (CH$_2$)$_n$-aryl, (CH$_2$)$_n$-heteroaryl or substituted (CH$_2$)$_n$-heteroaryl;
R$_6$ and R$_7$ are independently selected from H, branched or unbranched alkyl of 1 to 6 carbon atoms or cycloalkyl of 3 to 6 carbon atoms, wherein said alkyl or cycloalkyl group may optionally be substituted with:
  (a) a group of the formula —OR$_8$, wherein R$_8$ is an alkyl or acyl group of 1 to 6 carbon atoms, or (b) a group of the formula —NR$_9$R$_{10}$, wherein R$_9$ and R$_{10}$ are each, independently, an alkyl or acyl group of 1 to 2 carbon atoms;

n is 0, 1, 2 or 3.

In a further aspect the present invention provides diastereomeric mesoforms of a compound according to formula (Ia)

pharmaceutically-acceptable salts, hydrates, solvates, or prodrugs thereof, in which:

X$_1$ is selected from H, halogen or CF$_3$,
X$_2$ is selected from H, halogen or CF$_3$,
wherein at least one of X$_1$ and X$_2$ is halogen or CF$_3$;
A is N or CR$_5$, wherein R$_5$ is selected from H, halogen, branched or unbranched alkyl of 1 to 6 carbon atoms, branched or unbranched alkenyl of 2 to 6 carbon atoms, CF$_3$, CCl$_3$, CN, NO$_2$, O-alkyl with branched or unbranched alkyl of 1 to 6 carbon atoms, S-alkyl with branched or unbranched alkyl of 1 to 6 carbon atoms, aryl, substituted aryl, heteroaryl or substituted heteroaryl;
R$_1$ and R$_2$ are the same and are selected from H, branched or unbranched alkyl of 1 to 6 carbon atoms, or cycloalkyl of 3 to 6 carbon atoms;
R$_4$ is H;
R$_3$ is selected from (CH$_2$)$_n$-aryl, substituted (CH$_2$)$_n$-aryl, (CH$_2$)$_n$-heteroaryl or substituted (CH$_2$)$_n$-heteroaryl, wherein one or more of the hydrogen atoms of the aryl group of said substituted (CH$_2$)$_n$-aryl group or one or more of the hydrogen atoms of the heteroaryl group of said substituted (CH$_2$)$_n$-heteroaryl group may be optionally and independently replaced with:
  (i) R$_{11}$, which is aryl or heteroaryl selected from phenyl, 2-naphthyl, 2-, 3-, 5- or 6-indolyl, 2- or 3-thiophenyl, 2-, 3- or 4-pyridyl, 2-, 4- or 5-pyrimidinyl, 2- or 3-furyl, 1-, 2- or 3-pyrrolyl, 2-, 4- or 5-oxazolyl, 2-, 4- or 5-thiazolyl, 1-, 3-, 4- or 5-pyrazolyl, 3-, 4- or 5-isoxazolyl, 1-, 2-, 4- or 5-imidazolyl, 3-, 4- or 5-isothiazolyl, 4- or 5-oxadiazolyl, 1-, 4- or 5-triazolyl, 2-thiadiazolyl, 3- or 4-pyridazinyl, 2-pyrazinyl, 2-triazinyl, 2-, 3-, 6- or 7-indolyzinyl, 2-, 3-, 5- or 6-isoindolyl, 2-, 3-, 5- or 6-benzo[b]furanyl, 2-, 3-, 5- or 6-benzo[b]thiophenyl, 3-, 5- or 6-indazolyl, 2-, 5- or 6-benzthiazolyl, 2-, 5- or 6-benzimidazolyl, 2-, 3-, 6- or 7-quinolinyl, 3-, 6- or 7-isoquinolinyl, 2- or 8-purinyl, 2-, 3-, 7- or 8-quinolizinyl, 3-, 6- or 7-cinnolinyl, 6- or 7-phthalazinyl, 2-, 3-, 6- or 7-quinoxalinyl, 2-, 3-, 6- or 7-naphthyridinyl, 2-, 6- or 7-pteridinyl or 2-, 6- or 7-quinazolinyl,
wherein one or more of the hydrogen atoms of said aryl or heteroaryl group may be optionally and independently replaced with:
  (a) branched or unbranched alkyl of 1 to 6 carbon atoms or cycloalkyl of 3 to 6 carbon atoms, which alkyl or cycloakyl group may be mono or polysubstituted with halogen or oxo,
  (b) a group of the formula —COOR$_{12}$, wherein R$_{12}$ is unbranched or branched alkyl of 1 to 6 carbon atoms or cycloalkyl of 3 to 6 carbon atoms,
  (c) a group of the formula —NR$_{13}$R$_{14}$, wherein R$_{13}$ and R$_{14}$ are each, independently, H, alkyl or fluoroalkyl of 1 to 6 carbon atoms, cycloalkyl of 3 to 6 carbon atoms or acyl of 1 to 6 carbon atoms, or wherein R$_{13}$ and R$_{14}$ constitute a saturated hydrocarbon bridge of 3 to 5 carbon atoms which together with the nitrogen atom between them form a heterocyclic ring,
  (d) a group of the formula —CONR$_{15}$R$_{16}$, wherein R$_{15}$ and R$_{16}$ are each independently H, alkyl or fluoroalkyl of 1 to 6 carbon atoms or cycloalkyl of 3 to 6 carbon atoms, or wherein R$_{15}$ and R$_{16}$ constitute a saturated hydrocarbon bridge of 3 to 5 carbon atoms which together with the nitrogen atom between them form a heterocyclic ring,
  (e) a group of the formula —OR$_{17}$, wherein R$_{17}$ is H, alkyl or fluoroalkyl of 1 to 6 carbon atoms or acyl of 1 to 6 carbon atoms,
  (f) a group of the formula —SR$_{18}$, wherein R$_{18}$ is H, alkyl or fluoroalkyl of 1 to 6 carbon atoms or acyl of 1 to 6 carbon atoms,
  (g) cyano,
  (h) nitro,
  (i) an amidino group of the formula —C(NR$_{19}$)—NR$_{20}$R$_{21}$ wherein R$_{19}$, R$_{20}$ and R$_{21}$ are each, independently, H or alkyl of 1 to 3 carbon atoms, and wherein two of R$_{19}$, R$_{20}$ and R$_{21}$ may additionally constitute a saturated hydrocarbon bridge of 3 to 5 carbon atoms which together with the nitrogen atom(s) between them form a heterocyclic ring, or
  (j) halogen,
(ii) methyl, which may be mono- or polysubstituted with fluorine atoms and additionally may be monosubstituted with R$_{11}$,
(iii) branched or unbranched alkyl of 2 to 6 carbon atoms or cycloalkyl of 3 to 6 carbon atoms, which alkyl or cycloakyl group may be mono- or polysubstituted with halogen or oxo,
(iv) a group of the formula —COOR$_{22}$, wherein R$_{22}$ is unbranched or branched alkyl of 1 to 6 carbon atoms or cycloalkyl of 3 to 6 carbon atoms,
(v) a group of the formula —NR$_{23}$R$_{24}$, wherein R$_{23}$ and R$_{24}$ are each, independently, H, alkyl or fluoroalkyl of 1 to 6 carbon atoms, cycloalkyl of 3 to 6 carbon atoms or acyl of 1 to 6 carbon atoms, or wherein R$_{23}$ and R$_{24}$ constitute a saturated hydrocarbon bridge of 3 to 5 carbon atoms which together with the nitrogen atom between them form a heterocyclic ring, or wherein one of R$_{23}$ and R$_{24}$ is the group R$_{11}$,
(vi) a group of the formula —CONR$_{25}$R$_{26}$, wherein R$_{25}$ and R$_{26}$ are each, independently, H, alkyl or fluoroalkyl of 1 to 6 carbon atoms or cycloalkyl of 3 to 6 carbon atoms, or wherein R$_{25}$ and R$_{26}$ constitute a saturated hydrocarbon bridge of 3 to 5 carbon atoms which together with the nitrogen atom between them form a heterocyclic ring, or wherein one of R$_{25}$ and R$_{26}$ is the group R$_{11}$,
(vii) a group of the formula —COR$_{27}$, wherein R$_{27}$ is H, unbranched or branched alkyl of 1 to 6 carbon atoms, cycloalkyl of 3 to 6 carbon atoms or R$_{11}$,
(viii) a group of the formula —OR$_{28}$, wherein R$_{28}$ is H, alkyl or fluoroalkyl of 1 to 6 carbon atoms or acyl of 1 to 6 carbon atoms, or R$_{11}$,
(ix) a group of the formula —SR$_{29}$, wherein R$_{29}$ is H, alkyl or fluoroalkyl of 1 to 6 carbon atoms or acyl of 1 to 6 carbon atoms, or R$_{11}$,
(x) cyano,
(xi) nitro, or
(xii) halogen;

$R_6$ and $R_7$ are independently selected from H, branched or unbranched alkyl of 1 to 6 carbon atoms or cycloalkyl of 3 to 6 carbon atoms, wherein said alkyl or cycloalkyl group may optionally be substituted with:

(a) a group of the formula —$OR_8$, wherein $R_8$ is an alkyl or acyl group of 1 to 6 carbon atoms, or (b) a group of the formula —$NR_9R_{10}$, wherein $R_9$ and $R_{10}$ are each, independently, an alkyl or acyl group of 1 to 2 carbon atoms;

n is 0, 1, 2 or 3.

In some embodiments the following compounds are excluded from the invention:

Ethyl 3-(3-chlorophenyl)-1-(4-chlorophenyl)-2,4-dioxo-3-azabicyclo[3.1.0]hexane-6-carboxylate
3-(3-Chlorophenyl)-6,6-diphenyl-3-azabicyclo[3.1.0]hexane-2,4-dione
3-(3-Bromophenyl)-6,6-diphenyl-3-azabicyclo[3.1.0]hexane-2,4-dione
3-(3-Chlorophenyl)-1-methyl-6,6-diphenyl-3-azabicyclo[3.1.0]hexane-2,4-dione
3-(3,5-Dichlorophenyl)-6,6-diphenyl-3-azabicyclo[3.1.0]hexane-2,4-dione
3-(3,5-Dichlorophenyl)-1-methyl-6,6-diphenyl-3-azabicyclo[3.1.0]hexane-2,4-dione
3-(3,4-Dichlorophenyl)-1-methyl-6,6-diphenyl-3-azabicyclo[3.1.0]hexane-2,4-dione
3-(3-Bromophenyl)-1-methyl-6,6-diphenyl-3-azabicyclo[3.1.0]hexane-2,4-dione
1-Methyl-6,6-diphenyl-3-(3-(trifluoromethyl)phenyl)-3-azabicyclo[3.1.0]hexane-2,4-dione
3-(3-Chlorophenyl)-1,6,6-triphenyl-3-azabicyclo[3.1.0]hexane-2,4-dione
3-(3,4-Dichlorophenyl)-1,6,6-triphenyl-3-azabicyclo[3.1.0]hexane-2,4-dione
1,6,6-Triphenyl-3-(3-(trifluoromethyl)phenyl)-3-azabicyclo[3.1.0]hexane-2,4-dione
3-(3-Bromophenyl)-1,6,6-triphenyl-3-azabicyclo[3.1.0]hexane-2,4-dione
3-(3-Chlorophenyl)-1-(4-chlorophenyl)-6,6-diphenyl-3-azabicyclo[3.1.0]hexane-2,4-dione
1-(4-Chlorophenyl)-3-(3,5-dichlorophenyl)-6,6-diphenyl-3-azabicyclo[3.1.0]hexane-2,4-dione
3-(3,5-Dichlorophenyl)-1-(4-nitrophenyl)-6,6-diphenyl-3-azabicyclo[3.1.0]hexane-2,4-dione
3-(3,4-Dichlorophenyl)-1-(4-nitrophenyl)-6,6-diphenyl-3-azabicyclo[3.1.0]hexane-2,4-dione
1-(4-Nitrophenyl)-6,6-diphenyl-3-[3-(trifluoromethyl)phenyl]-3-azabicyclo[3.1.0]hexane-2,4-dione
1-(4-Nitrophenyl)-6,6-diphenyl-3-(3-chloro-4-methyl-phenyl)-3-azabicyclo[3.1.0]hexane-2,4-dione
3-(3-Chloro-6-methoxy-phenyl)-6,6-diphenyl-3-azabicyclo[3.1.0]hexane-2,4-dione. In some embodiments procymidone (3-(3,5-dichlorophenyl)-1,5-dimethyl-3-azabicyclo[3.1.0]hexane-2,4-dione) is excluded from the invention alone or is excluded in addition to the excluded compounds as described supra.

The compounds excluded from the present invention comprise usually racemates, diastereomers, and/or diastereomeric meso forms of the excluded compounds mentioned supra.

Preferably A is $CR_5$ and wherein $R_5$ is H or halogen. More preferably A is $CR_5$ and at least two of $X_1$ and $X_2$ and $R_5$ are halogen.

Preferably both $X_1$ and $X_2$ are halogen or CF3, more preferably both are halogen.

Preferably $R_1$ is selected from H, branched or unbranched alkyl of 1 to 6 carbon atoms. More preferably $R_1$ is selected from H, unbranched alkyl group having 1 to 3 carbon atoms. Particularly preferably $R_1$ is selected from H or methyl.

Preferably $R_2$ is selected from H, branched or unbranched alkyl of 1 to 6 carbon atoms or from a substituent of (D) selected from (i) a group of the formula —$(CH_2)_n COOR_{30}$, wherein $R_{30}$ is independently H, unbranched or branched alkyl of 1 to 6 carbon atoms or cycloalkyl of 3 to 6 carbon atoms and wherein said unbranched or branched alkyl of 1 to 6 carbon atoms or cycloalkyl of 3 to 6 carbon atoms may be optionally and independently substituted with —$CH_2OR_{31}$, —$COOR_{31}$, —$CON(R_{31})_2$, —$CH_2NHCOR_{31}$, —$SO_2N(R_{31})_2$, —$CH_2NHSO_2R_{31}$, —$CH_2N(R_{31})_2$, —$SO_2OH$, —$PO(OH)_2$ wherein $R_{31}$ is independently selected from H, unbranched or branched alkyl of 1 to 6 carbon atoms, or (ii) a group of the formula —$(CH_2)_n CONR_{32}R_{33}$, wherein $R_{32}$ and $R_{33}$ are each, independently, H, unbranched or branched alkyl of 1 to 6 carbon atoms or cycloalkyl of 3 to 6 carbon atoms and wherein said unbranched or branched alkyl of 1 to 6 carbon atoms or cycloalkyl of 3 to 6 carbon atoms may be optionally and independently substituted with —$CH_2OR_{31}$, —$COOR_{31}$, —$CON(R_{31})_2$, —$CH_2NHCOR_{31}$, —$SO_2N(R_{31})_2$, —$CH_2NHSO_2R_{31}$, —$CH_2N(R_{31})_2$, —$SO_2OH$, —$PO(OH)_2$ wherein $R_{31}$ is independently selected from H, unbranched or branched alkyl of 1 to 6 carbon atoms or wherein $NR_{32}$ is N-alkyl-4-piperidinylamino, N-carboxymethyl-4-piperidinylamino, pyridin-4-ylmethylamino, 4-amidinobenzylamino, 4-carboxybenzylamino, or 4-hydroxybenzylamino and $R_{33}$ is H or wherein $NR_{32}R_{33}$ constitute a heterocyclic ring selected from 4-alkyl-1-piperazinyl, wherein alkyl is unbranched or branched alkyl of 1 to 6 carbon atoms, or 1-morpholinyl.

More preferably $R_2$ is selected from H, branched or unbranched alkyl of 1 to 6 carbon atoms or from a substituent of (D) selected from a group of the formula —$(CH_2)_n COOR_{30}$, wherein $R_{30}$ is independently H, unbranched or branched alkyl of 1 to 6 carbon atoms or cycloalkyl of 3 to 6 carbon atoms and wherein said unbranched or branched alkyl of 1 to 6 carbon atoms or cycloalkyl of 3 to 6 carbon atoms may be optionally and independently substituted with —$CH_2OR_{31}$, —$COOR_{31}$, —$CON(R_{31})_2$, —$CH_2NHCOR_{31}$, —$SO_2N(R_{31})_2$, —$CH_2NHSO_2R_{31}$, —$CH_2N(R_{31})_2$, —$SO_2OH$, —$PO(OH)_2$ wherein $R_{31}$ is independently selected from H, unbranched or branched alkyl of 1 to 6 carbon atoms.

Even more preferably $R_2$ is selected from H, branched or unbranched alkyl of 1 to 6 carbon atoms. Most preferably $R_2$ is selected from H, or unbranched alkyl group having 1 to 3 carbon atoms. Particularly preferably $R_2$ is selected from H or methyl.

Preferably $R_3$ is selected from H, $(CH2)_n$-aryl, substituted $(CH2)_n$-aryl, $(CH2)_n$-heteroaryl or substituted $(CH2)_n$-heteroaryl, wherein one or more of the hydrogen atoms of the aryl group of said substituted $(CH2)_n$-aryl group or one or more of the hydrogen atoms of the heteroaryl group of said substituted $(CH2)_n$-heteroaryl group may be optionally and independently replaced with:

(i) $R_{11}$, which is aryl or heteroaryl selected from phenyl, 2-naphthyl, 2-, 3-, 5- or 6-indolyl, 2- or 3-thiophenyl, 2-, 3- or 4-pyridyl, 2-, 4- or 5-pyrimidinyl, 2- or 3-furyl, 1-, 2- or 3-pyrrolyl, 2-, 4- or 5-oxazolyl, 2-, 4- or 5-thiazolyl, 1-, 3-, 4- or 5-pyrazolyl, 3-, 4- or 5-isoxazolyl, 1-, 2-, 4- or 5-imidazolyl, 3-, 4- or 5-isothiazolyl, 4- or 5-oxadiazolyl, 1-, 4- or 5-triazolyl, 2-thiadiazolyl, 3- or 4-pyridazinyl, 2-pyrazinyl, 2-triazinyl, 2-, 3-, 6- or 7-indolyzinyl, 2-, 3-, 5- or 6-isoindolyl, 2-, 3-, 5- or 6-benzo[b]furanyl, 2-, 3-, 5- or 6-benzo[b]thiophenyl, 3-, 5- or 6-indazolyl, 2-, 5- or 6-benzthiazolyl, 2-, 5- or 6-benzimidazolyl, 2-, 3-, 6- or 7-quinolinyl, 3-, 6- or 7-isoquinolinyl, 2- or 8-purinyl, 2-, 3-, 7- or 8-quinolizinyl, 3-, 6- or 7-cinnolinyl, 6- or 7-phthalazinyl, 2-, 3-, 6- or 7-quinoxalinyl, 2-, 3-, 6- or 7-naphthyridinyl, 2-, 6- or 7-pteridinyl or 2-, 6- or 7-quinazolinyl, (ii) methyl, which may be mono- or polysubstituted with fluorine atoms and additionally may be monosubstituted with $R_{11}$, (iii) branched or unbranched alkyl of 2 to 6 carbon atoms or cycloalkyl of 3 to 6 carbon atoms, which alkyl or cycloakyl group may be mono- or polysubstituted with halogen or oxo, (iv) a group of the formula $—OR_{28}$, wherein $R_{28}$ is H, alkyl or fluoroalkyl of 1 to 6 carbon atoms or acyl of 1 to 6 carbon atoms, or $R_{11}$, (v) cyano, or (vi) halogen.

More preferably $R_3$ is selected from H, $(CH_2)_n$-aryl, substituted $(CH_2)_n$-aryl, $(CH_2)_n$-heteroaryl or substituted $(CH_2)_n$-heteroaryl, wherein one or more of the hydrogen atoms of the aryl group of said substituted $(CH_2)_n$-aryl group or one or more of the hydrogen atoms of the heteroaryl group of said substituted $(CH_2)_n$-heteroaryl group may be optionally and independently replaced with:

(i) methyl, which may be mono- or polysubstituted with fluorine atoms, (ii) branched or unbranched alkyl of 2 to 6 carbon atoms or cycloalkyl of 3 to 6 carbon atoms, which alkyl or cycloakyl group may be mono- or polysubstituted with halogen or oxo, (iii) a group of the formula $—OR_{28}$, wherein $R_{28}$ is H, alkyl or fluoroalkyl of 1 to 6 carbon atoms or acyl of 1 to 6 carbon atoms, (iv) cyano, or (v) halogen.

More preferably $R_3$ is selected from H, $(CH_2)_n$-aryl, substituted $(CH_2)_n$-aryl, $(CH_2)_n$-heteroaryl, wherein one or more of the hydrogen atoms of the aryl group of said substituted $(CH_2)_n$-aryl group may be optionally and independently replaced with:

(i) methyl, which may be mono- or polysubstituted with fluorine atoms, (ii) branched or unbranched alkyl of 2 to 6 carbon atoms or cycloalkyl of 3 to 6 carbon atoms, which alkyl or cycloakyl group may be mono- or polysubstituted with halogen or oxo, (iii) a group of the formula $—OR_{28}$, wherein $R_{28}$ is H, alkyl or fluoroalkyl of 1 to 6 carbon atoms or acyl of 1 to 6 carbon atoms, (iv) cyano, or (v) halogen.

More preferably $R_3$ is selected from H, $(CH_2)_n$-aryl, or substituted $(CH_2)_n$-aryl, wherein one or more of the hydrogen atoms of the aryl group of said substituted $(CH_2)_n$-aryl group may be optionally replaced with:

(i) methyl, which may be mono- or polysubstituted with fluorine atoms, (ii) branched or unbranched alkyl of 2 to 6 carbon atoms or cycloalkyl of 3 to 6 carbon atoms, which alkyl or cycloakyl group may be mono- or polysubstituted with halogen or oxo, (iii) a group of the formula $—OR_{28}$, wherein $R_{28}$ is H, alkyl or fluoroalkyl of 1 to 6 carbon atoms or acyl of 1 to 6 carbon atoms, (iv) cyano, or (v) halogen, wherein n of $(CH_2)_n$-aryl or substituted $(CH_2)_n$-aryl is 0 or 1, more preferably 0.

Preferably $R_4$ is selected from H, $(CH_2)_n$-aryl, substituted $(CH_2)_n$-aryl, $(CH_2)_n$-heteroaryl or substituted $(CH_2)_n$-heteroaryl, wherein one or more of the hydrogen atoms of the aryl group of said substituted $(CH_2)_n$-aryl group or one or more of the hydrogen atoms of the heteroaryl group of said substituted $(CH_2)_n$-heteroaryl group may be optionally and independently replaced with:

(i) $R_{11}$, which is aryl or heteroaryl selected from phenyl, 2-naphthyl, 2-, 3-, 5- or 6-indolyl, 2- or 3-thiophenyl, 2-, 3- or 4-pyridyl, 2-, 4- or 5-pyrimidinyl, 2- or 3-furyl, 1-, 2- or 3-pyrrolyl, 2-, 4- or 5-oxazolyl, 2-, 4- or 5-thiazolyl, 1-, 3-, 4- or 5-pyrazolyl, 3-, 4- or 5-isoxazolyl, 1-, 2-, 4- or 5-imidazolyl, 3-, 4- or 5-isothiazolyl, 4- or 5-oxadiazolyl, 1-, 4- or 5-triazolyl, 2-thiadiazolyl, 3- or 4-pyridazinyl, 2-pyrazinyl, 2-triazinyl, 2-, 3-, 6- or 7-indolyzinyl, 2-, 3-, 5- or 6-isoindolyl, 2-, 3-, 5- or 6-benzo[b]furanyl, 2-, 3-, 5- or 6-benzo[b]thiophenyl, 3-, 5- or 6-indazolyl, 2-, 5- or 6-benzthiazolyl, 2-, 5- or 6-benzimidazolyl, 2-, 3-, 6- or 7-quinolinyl, 3-, 6- or 7-isoquinolinyl, 2- or 8-purinyl, 2-, 3-, 7- or 8-quinolizinyl, 3-, 6- or 7-cinnolinyl, 6- or 7-phthalazinyl, 2-, 3-, 6- or 7-quinoxalinyl, 2-, 3-, 6- or 7-naphthyridinyl, 2-, 6- or 7-pteridinyl or 2-, 6- or 7-quinazolinyl, (ii) methyl, which may be mono- or polysubstituted with fluorine atoms and additionally may be monosubstituted with $R_{11}$, (iii) branched or unbranched alkyl of 2 to 6 carbon atoms or cycloalkyl of 3 to 6 carbon atoms, which alkyl or cycloakyl group may be mono- or polysubstituted with halogen or oxo, (iv) a group of the formula $—OR_{28}$, wherein $R_{28}$ is H, alkyl or fluoroalkyl of 1 to 6 carbon atoms or acyl of 1 to 6 carbon atoms, or $R_{11}$, (v) cyano, or (vi) halogen, or from a substituent of (D) selected from (i) a group of the formula $—(CH_2)_nCOOR_{30}$, wherein $R_{30}$ is independently H, unbranched or branched alkyl of 1 to 6 carbon atoms or cycloalkyl of 3 to 6 carbon atoms and wherein said unbranched or branched alkyl of 1 to 6 carbon atoms or cycloalkyl of 3 to 6 carbon atoms may be optionally and independently substituted with $—CH_2OR_{31}$, $—COOR_{31}$, $—CON(R_{31})_2$, $—CH_2NHCOR_{31}$, $—SO_2N(R_{31})_2$, $—CH_2NHSO_2R_{31}$, $—CH_2N(R_{31})_2$, $—SO_2OH$, $—PO(OH)_2$ wherein $R_{31}$ is independently selected from H, unbranched or branched alkyl of 1 to 6 carbon atoms; or (ii) a group of the formula $—(CH_2)_nCONR_{32}R_{33}$, wherein $R_{32}$ and $R_{33}$ are each, independently, H, unbranched or branched alkyl of 1 to 6 carbon atoms or cycloalkyl of 3 to 6 carbon atoms and wherein said unbranched or branched alkyl of 1 to 6 carbon atoms or cycloalkyl of 3 to 6 carbon atoms may be optionally and independently substituted with $—CH_2OR_{31}$, $—COOR_{31}$, $—CON(R_{31})_2$, $—CH_2NHCOR_{31}$, $—SO_2N(R_{31})_2$, $—CH_2NHSO_2R_{31}$, $—CH_2N(R_{31})_2$, $—SO_2OH$, $—PO(OH)_2$ wherein $R_{31}$ is independently selected from H, unbranched or branched alkyl of 1 to 6 carbon atoms or wherein $NR_{32}$ is N-alkyl-4-piperidinylamino, N-carboxymethyl-4-piperidinylamino, pyridin-4-ylmethylamino, 4-amidinobenzylamino, 4-carboxybenzylamino, or 4-hydroxybenzylamino and $R_{33}$ is H or wherein $NR_{32}R_{33}$ constitute a heterocyclic ring selected from 4-alkyl-1-piperazinyl, wherein alkyl is unbranched or branched alkyl of 1 to 6 carbon atoms, or 1-morpholinyl, (iii) a group of the formula —$(CH_2)_n NHR_{34}$, wherein $R_{34}$ is H, unbranched or branched alkyl of 1 to 6 carbon atoms, cycloalkyl of 3 to 6 carbon atoms or an acyl group of 1 to 6 carbon atoms and wherein said unbranched or branched alkyl of 1 to 6 carbon atoms or cycloalkyl of 3 to 6 carbon atoms may be optionally and independently substituted with —$CH_2OR_{31}$, —$COOR_{31}$, —$CON(R_{31})_2$, —$CH_2NHCOR_{31}$, —$SO_2N(R_{31})_2$, —$CH_2NHSO_2R_{31}$, —$CH_2N(R_{31})_2$, —$SO_2OH$, —$PO(OH)_2$ wherein $R_{31}$ is independently selected from H, unbranched or branched alkyl of 1 to 6 carbon atoms or wherein $R_{34}$ is —$COR_{36}$ wherein $R_{36}$ is 1-alkyl-4-piperidyl, wherein alkyl is unbranched or branched alkyl of 1 to 6 carbon atoms, or —$(CH_2)_n COR_{36}$ wherein $R_{36}$ is 4-pyridyl or 4-hydroxyphenyl, (iv) a group of the formula —$(CH_2)_n PO(OH)_2$, —$(CH_2)_n SO_2OH$, —$(CH_2)_n OR_{31}$, —$(CH_2)_n SO_2N(R_{31})_2$, or —$(CH_2)_n NHSO_2R_{31}$ wherein $R_{31}$ is independently selected from H, unbranched or branched alkyl of 1 to 6 carbon atoms.

More preferably $R_4$ is selected from H, $(CH_2)_n$-aryl, substituted $(CH_2)_n$-aryl, or $(CH_2)_n$-heteroaryl, wherein one or more of the hydrogen atoms of the aryl group of said substituted $(CH_2)_n$-aryl group may be optionally replaced with:
(i) methyl, which may be mono- or polysubstituted with fluorine atoms,
(ii) branched or unbranched alkyl of 2 to 6 carbon atoms or cycloalkyl of 3 to 6 carbon atoms, which alkyl or cycloakyl group may be mono- or polysubstituted with halogen or oxo,
(iii) a group of the formula —$OR_{28}$, wherein $R_{28}$ is H, alkyl or fluoroalkyl of 1 to 6 carbon atoms or acyl of 1 to 6 carbon atoms,
(iv) cyano,
(v) halogen, or from a substituent of (D) selected from
(i) a group of the formula —$(CH_2)_n COOR_{30}$, wherein $R_{30}$ is independently H, unbranched or branched alkyl of 1 to 6 carbon atoms or cycloalkyl of 3 to 6 carbon atoms and wherein said unbranched or branched alkyl of 1 to 6 carbon atoms or cycloalkyl of 3 to 6 carbon atoms may be optionally and independently substituted with —$CH_2OR_{31}$, —$COOR_{31}$, —$CON(R_{31})_2$, —$CH_2NHCOR_{31}$, —$SO_2N(R_{31})_2$, —$CH_2NHSO_2R_{31}$, —$CH_2N(R_{31})_2$, —$SO_2OH$, —$PO(OH)_2$ wherein $R_{31}$ is independently selected from H, unbranched or branched alkyl of 1 to 6 carbon atoms,
(ii) a group of the formula —$(CH_2)_n CONR_{32}R_{33}$, wherein $R_{32}$ and $R_{33}$ are each, independently, H, unbranched or branched alkyl of 1 to 6 carbon atoms or cycloalkyl of 3 to 6 carbon atoms and wherein said unbranched or branched alkyl of 1 to 6 carbon atoms or cycloalkyl of 3 to 6 carbon atoms may be optionally and independently substituted with —$CH_2OR_{31}$, —$COOR_{31}$, —$CON(R_{31})_2$, —$CH_2NHCOR_{31}$, —$SO_2N(R_{31})_2$, —$CH_2NHSO_2R_{31}$, —$CH_2N(R_{31})_2$, —$SO_2OH$, —$PO(OH)_2$ wherein $R_{31}$ is independently selected from H, unbranched or branched alkyl of 1 to 6 carbon atoms or wherein $NR_{32}$ is N-alkyl-4-piperidinylamino, N-carboxymethyl-4-piperidinylamino, pyridin-4-ylmethylamino, 4-amidinobenzylamino, 4-carboxybenzylamino, or 4-hydroxybenzylamino and $R_{33}$ is H or wherein $NR_{32}R_{33}$ constitute a heterocyclic ring selected from 4-alkyl-1-piperazinyl, wherein alkyl is unbranched or branched alkyl of 1 to 6 carbon atoms, or 1-morpholinyl.

constitute a heterocyclic ring selected from 4-alkyl-1-piperazinyl, wherein alkyl is unbranched or branched alkyl of 1 to 6 carbon atoms, or 1-morpholinyl, in particular a group of the formula —$(CH_2)_n CONR_{32}R_{33}$, wherein $NR_{32}R_{33}$ constitute a heterocyclic ring selected from 4-alkyl-1-piperazinyl, wherein alkyl is unbranched or branched alkyl of 1 to 6 carbon atoms, or 1-morpholinyl.

Equally more preferably $R_4$ is selected from H, $(CH_2)_n$-aryl, or substituted $(CH_2)_n$-aryl, wherein one or more of the hydrogen atoms of the aryl group of said substituted $(CH_2)_n$-aryl group may be optionally replaced with:
(i) methyl, which may be mono- or polysubstituted with fluorine atoms,
(ii) branched or unbranched alkyl of 2 to 6 carbon atoms or cycloalkyl of 3 to 6 carbon atoms, which alkyl or cycloakyl group may be mono- or polysubstituted with halogen or oxo,
(iii) a group of the formula —$OR_{28}$, wherein $R_{28}$ is H, alkyl or fluoroalkyl of 1 to 6 carbon atoms or acyl of 1 to 6 carbon atoms,
(iv) cyano,
(v) halogen, or from a substituent of (D) selected from
(i) a group of the formula —$(CH_2)_n COOR_{30}$, wherein $R_{30}$ is independently H, unbranched or branched alkyl of 1 to 6 carbon atoms or cycloalkyl of 3 to 6 carbon atoms and wherein said unbranched or branched alkyl of 1 to 6 carbon atoms or cycloalkyl of 3 to 6 carbon atoms may be optionally and independently substituted with —$CH_2OR_{31}$, —$COOR_{31}$, —$CON(R_{31})_2$, —$CH_2NHCOR_{31}$, —$SO_2N(R_{31})_2$, —$CH_2NHSO_2R_{31}$, —$CH_2N(R_{31})_2$, —$SO_2OH$, —$PO(OH)_2$ wherein $R_{31}$ is independently selected from H, unbranched or branched alkyl of 1 to 6 carbon atoms,
(ii) a group of the formula —$(CH_2)_n CONR_{32}R_{33}$, wherein $R_{32}$ and $R_{33}$ are each, independently, H, unbranched or branched alkyl of 1 to 6 carbon atoms or cycloalkyl of 3 to 6 carbon atoms and wherein said unbranched or branched alkyl of 1 to 6 carbon atoms or cycloalkyl of 3 to 6 carbon atoms may be optionally and independently substituted with —$CH_2OR_{31}$, —$COOR_{31}$, —$CON(R_{31})_2$, —$CH_2NHCOR_{31}$, —$SO_2N(R_{31})_2$, —$CH_2NHSO_2R_{31}$, —$CH_2N(R_{31})_2$, —$SO_2OH$, —$PO(OH)_2$ wherein $R_{31}$ is independently selected from H, unbranched or branched alkyl of 1 to 6 carbon atoms or wherein $NR_{32}$ is N-alkyl-4-piperidinylamino, N-carboxymethyl-4-piperidinylamino, pyridin-4-ylmethylamino, 4-amidinobenzylamino, 4-carboxybenzylamino, or 4-hydroxybenzylamino and $R_{33}$ is H or wherein $NR_{32}R_{33}$ constitute a heterocyclic ring selected from 4-alkyl-1-piperazinyl, wherein alkyl is unbranched or branched alkyl of 1 to 6 carbon atoms, or 1-morpholinyl.

Even more preferably $R_4$ is selected from H, $(CH_2)_n$-aryl, substituted $(CH_2)_n$-aryl, or $(CH_2)_n$-heteroaryl, wherein one or more of the hydrogen atoms of the aryl group of said substituted $(CH_2)_n$-aryl group may be optionally replaced with:
(i) methyl, which may be mono- or polysubstituted with fluorine atoms,
(ii) branched or unbranched alkyl of 2 to 6 carbon atoms or cycloalkyl of 3 to 6 carbon atoms, which alkyl or cycloakyl group may be mono- or polysubstituted with halogen or oxo,
(iii) a group of the formula —$OR_{28}$, wherein $R_{28}$ is H, alkyl or fluoroalkyl of 1 to 6 carbon atoms or acyl of 1 to 6 carbon atoms, (iv) cyano,
(v) halogen, or
from a substituent of (D) selected from
(i) a group of the formula —$(CH_2)_n COOR_{30}$, wherein $R_{30}$ is independently H, unbranched or branched alkyl of 1 to 6 carbon atoms,
(ii) a group of the formula —$(CH_2)_n CONR_{32}R_{33}$, wherein $NR_{32}R_{33}$ constitute a heterocyclic ring selected from 4-alkyl-1-piperazinyl, wherein alkyl is unbranched or branched alkyl of 1 to 6 carbon atoms, or 1-morpholinyl, wherein n of $(CH_2)_n$-aryl, substituted $(CH_2)_n$-aryl, or $(CH_2)_n$-heteroaryl is 0 or 1, more preferably 0.

Equally even more preferably $R_4$ is selected from H, $(CH_2)_n$-aryl, or substituted $(CH_2)_n$-aryl, wherein one or more of the hydrogen atoms of the aryl group of said substituted $(CH_2)_n$-aryl group may be optionally replaced with:
(i) methyl, which may be mono- or polysubstituted with fluorine atoms,
(ii) branched or unbranched alkyl of 2 to 6 carbon atoms or cycloalkyl of 3 to 6 carbon atoms, which alkyl or cycloakyl group may be mono- or polysubstituted with halogen or oxo,
(iii) a group of the formula —$OR_{28}$, wherein $R_{28}$ is H, alkyl or fluoroalkyl of 1 to 6 carbon atoms or acyl of 1 to 6 carbon atoms,
(iv) cyano,
(v) halogen, or
from a substituent of (D) selected from
a group of the formula —$(CH_2)_n COOR_{30}$, wherein $R_{30}$ is independently H, unbranched or branched alkyl of 1 to 6 carbon atoms, wherein n of $(CH_2)_n$-aryl or substituted $(CH_2)_n$-aryl is 0 or 1, more preferably 0.

In particular $R_4$ is H, or a substituent of (D) selected from a group of the formula —$(CH_2)_n COOR_{30}$, wherein $R_{30}$ is independently H, unbranched or branched alkyl of 1 to 6 carbon atoms.

Equally in particular $R_4$ is selected from a substituent of (D) selected from
(i) a group of the formula —$(CH_2)_n COOR_{30}$, wherein $R_{30}$ is independently H, unbranched or branched alkyl of 1 to 6 carbon atoms or cycloalkyl of 3 to 6 carbon atoms and wherein said unbranched or branched alkyl of 1 to 6 carbon atoms or cycloalkyl of 3 to 6 carbon atoms may be optionally and independently substituted with —$CH_2OR_{31}$, —$COOR_{31}$, —$CON(R_{31})_2$, —$CH_2NHCOR_{31}$, —$SO_2N(R_{31})_2$, —$CH_2NHSO_2R_{31}$, —$CH_2N(R_{31})_2$, —$SO_2OH$, —$PO(OH)_2$ wherein $R_{31}$ is independently selected from H, unbranched or branched alkyl of 1 to 6 carbon atoms,
(ii) a group of the formula —$(CH_2)_n CONR_{32}R_{33}$, wherein $R_{32}$ and $R_{33}$ are each, independently, H, unbranched or branched alkyl of 1 to 6 carbon atoms or cycloalkyl of 3 to 6 carbon atoms and wherein said unbranched or branched alkyl of 1 to 6 carbon atoms or cycloalkyl of 3 to 6 carbon atoms may be optionally and independently substituted with —$CH_2OR_{31}$,—$COOR_{31}$,—$CON(R_{31})_2$, —$CH_2NHCOR_{31}$, —$SO_2N(R_{31})_2$, —$CH_2NHSO_2R_{31}$, —$CH_2N(R_{31})_2$, —$SO_2OH$, —$PO(OH)_2$ wherein $R_{31}$ is independently selected from H, unbranched or branched alkyl of 1 to 6 carbon atoms or wherein $NR_{32}$ is N-alkyl-4-piperidinylamino, N-carboxymethyl-4-piperidinylamino, pyridin-4-ylmethylamino, 4-amidinobenzylamino, 4-carboxybenzylamino, or 4-hydroxybenzylamino and $R_{33}$ is H or wherein $NR_{32}R_{33}$ constitute a heterocyclic ring selected from 4-alkyl-1-piperazinyl, wherein alkyl is unbranched or branched alkyl of 1 to 6 carbon atoms, or 1-morpholinyl,
(iii) a group of the formula —$(CH_2)_n NHR_{34}$, wherein $R_{34}$ is H, unbranched or branched alkyl of 1 to 6 carbon atoms, cycloalkyl of 3 to 6 carbon atoms or an acyl group of 1 to 6 carbon atoms and wherein said unbranched or branched alkyl of 1 to 6 carbon atoms or cycloalkyl of 3 to 6 carbon atoms may be optionally and independently substituted with —$CH_2OR_{31}$, —$COOR_{31}$, —$CON(R_{31})_2$, —$CH_2NHCOR_{31}$, —$SO_2N(R_{31})_2$, —$CH_2NHSO_2R_{31}$, —$CH_2N(R_{31})_2$, —$SO_2OH$, —$PO(OH)_2$ wherein $R_{31}$ is independently selected from H, unbranched or branched alkyl of 1 to 6 carbon atoms or wherein $R_{34}$ is —$COR_{36}$ wherein $R_{36}$ is 1-alkyl-4-piperidyl, wherein alkyl is unbranched or branched alkyl of 1 to 6 carbon atoms, or —$(CH_2)_n COR_{36}$ wherein $R_{36}$ is 4-pyridyl or 4-hydroxyphenyl,
(iv) a group of the formula —$(CH_2)_n PO(OH)_2$, —$(CH_2)_n SO_2OH$, —$(CH_2)_n OR_{31}$, —$(CH_2)_n SO_2N(R_{31})_2$, or —$(CH_2)$—$NHSO_2R_{31}$ wherein $R_{31}$ is independently selected from H, unbranched or branched alkyl of 1 to 6 carbon atoms.

Preferably at least one, more preferably only one, of $R_2$ and $R_4$ is as defined by (D).

Preferably a substituent of (D) is selected from
(i) a group of the formula —$(CH_2)_n COOR_{30}$, wherein $R_{30}$ is independently H, unbranched or branched alkyl of 1 to 6 carbon atoms or cycloalkyl of 3 to 6 carbon atoms and wherein said unbranched or branched alkyl of 1 to 6 carbon atoms or cycloalkyl of 3 to 6 carbon atoms may be optionally and independently substituted with —$CH_2OR_{31}$, —$COOR_{31}$, —$CON(R_{31})_2$, —$CH_2NHCOR_{31}$, —$SO_2N(R_{31})_2$, —$CH_2NHSO_2R_{31}$, —$CH_2N(R_{31})_2$, —$SO_2OH$, —$PO(OH)_2$ wherein $R_{31}$ is independently selected from H, unbranched or branched alkyl of 1 to 6 carbon atoms,
(ii) a group of the formula —$(CH_2)_n CONR_{32}R_{33}$, wherein $R_{32}$ and $R_{33}$ are each, independently, H, unbranched or branched alkyl of 1 to 6 carbon atoms or cycloalkyl of 3 to 6 carbon atoms and wherein said unbranched or branched alkyl of 1 to 6 carbon atoms or cycloalkyl of 3 to 6 carbon atoms may be optionally and independently substituted with —$CH_2OR_{31}$, —$COOR_{31}$, —$CON(R_{31})_2$, —$CH_2NHCOR_{31}$, —$SO_2N(R_{31})_2$, —$CH_2NHSO_2R_{31}$, —$CH_2N(R_{31})_2$, —$SO_2OH$, —$PO(OH)_2$ wherein $R_{31}$ is independently selected from H, unbranched or branched alkyl of 1 to 6 carbon atoms or wherein $NR_{32}$ is N-alkyl-4-piperidinylamino, N-carboxymethyl-4-piperidinylamino, pyridin-4-ylmethylamino, 4-amidinobenzylamino, 4-carboxybenzylamino, or 4-hydroxybenzylamino and $R_{33}$ is H or wherein $NR_{32}R_{33}$ constitute a heterocyclic ring selected from 4-alkyl-1-piperazinyl, wherein alkyl is unbranched or branched alkyl of 1 to 6 carbon atoms, or 1-morpholinyl,
(iii) a group of the formula —$(CH_2)$—$NHR_{34}$, wherein $R_{34}$ is H, unbranched or branched alkyl of 1 to 6 carbon atoms, cycloalkyl of 3 to 6 carbon atoms or an acyl group of 1 to 6 carbon atoms and wherein said unbranched or branched alkyl of 1 to 6 carbon atoms or cycloalkyl of 3 to 6 carbon atoms may be optionally and independently substituted with —$CH_2OR_{31}$, —$COOR_{31}$, —$CON(R_{31})_2$, —$CH_2NHCOR_{31}$, —$SO_2N(R_{31})_2$, —$CH_2NHSO_2R_{31}$, —$CH_2N(R_{31})_2$, —$SO_2OH$, —$PO(OH)_2$ wherein $R_{31}$ is independently selected from H, unbranched or branched alkyl of 1 to 6 carbon atoms or wherein $R_{34}$ is —$COR_{36}$ wherein $R_{36}$ is 1-alkyl-4-piperidyl, wherein alkyl is unbranched or branched alkyl of 1 to 6 carbon atoms, or —$(CH_2)_nCOR_{36}$ wherein $R_{36}$ is 4-pyridyl or 4-hydroxyphenyl, (iv) a group of the formula —$(CH_2)_nPO(OH)_2$, —$(CH_2)_nSO_2OH$, —$(CH_2)_nOR_{31}$, —$(CH_2)_nSO_2N(R_{31})_2$, or —$(CH_2)_nNHSO_2R_{31}$ wherein $R_{31}$ is independently selected from H, unbranched or branched alkyl of 1 to 6 carbon atoms.

Preferably $R_6$ and $R_7$ are independently selected from H, branched or unbranched alkyl of 1 to 6 carbon atoms. More preferably $R_6$ and $R_7$ are independently selected from H, unbranched alkyl group having 1 to 3 carbon atoms. Particularly preferably $R_6$ and $R_7$ are independently selected from H and methyl, most preferably $R_6$ and $R_7$ are both H.

Preferably n is 0 or 1, more preferably 0.

Preferably only one of $R_2$ and $R_3$, more preferably only $R_3$ of $R_2$ and $R_3$ is $(CH2)_n$-aryl, substituted $(CH2)_n$-aryl, $(CH2)_n$-heteroaryl or substituted $(CH2)_n$-heteroaryl, even more preferably only $R_3$ of $R_2$ and $R_3$ is $(CH2)_n$-aryl, substituted $(CH2)_n$-aryl, $(CH2)_n$-heteroaryl or substituted $(CH2)_n$-heteroaryl, wherein n is 0 or 1, more preferably 0.

Preferably at least one of $R_3$ and $R_4$, more preferably both of $R_3$ and $R_4$ are independently substituted $(CH2)_n$-aryl, $(CH2)_n$-heteroaryl or substituted $(CH2)_n$-heteroaryl. More preferably at least one of $R_3$ and $R_4$, in particular both of $R_3$ and $R_4$ are independently substituted $(CH2)_n$-aryl or substituted $(CH2)_n$-heteroaryl, more particular both of $R_3$ and $R_4$ are independently substituted $(CH2)_n$-aryl.

Preferably the groups $R_3$ and $R_1$ and the groups $R_3$ and $R_2$ are in trans position to each other.

More preferred compounds of formula (Ia) or formula (Ib), pharmaceutically-acceptable salts, hydrates, solvates, or prodrugs thereof are those wherein A is $CR_5$, wherein $R_5$ is H or halogen;

$R_1$ is selected from H, branched or unbranched alkyl of 1 to 6 carbon atoms;

$R_2$ and $R_4$ are independently selected from H, $(CH_2)_n$-aryl, substituted $(CH_2)_n$-aryl or $(CH2)_n$-heteroaryl, wherein one or more of the hydrogen atoms of the aryl group of said substituted $(CH_2)_n$-aryl group may be optionally replaced with:

(i) $R_{11}$, which is aryl or heteroaryl selected from phenyl, 2-naphthyl, 2-, 3-, 5- or 6-indolyl, 2- or 3-thiophenyl, 2-, 3- or 4-pyridyl, 2-, 4- or 5-pyrimidinyl, 2- or 3-furyl, 1-, 2- or 3-pyrrolyl, 2-, 4- or 5-oxazolyl, 2-, 4- or 5-thiazolyl, 1-, 3-, 4- or 5-pyrazolyl, 3-, 4- or 5-isoxazolyl, 1-, 2-, 4- or 5-imidazolyl, 3-, 4- or 5-isothiazolyl, 4- or 5-oxadiazolyl, 1-, 4- or 5-triazolyl, 2-thiadiazolyl, 3- or 4-pyridazinyl, 2-pyrazinyl, 2-triazinyl, 2-, 3-, 6- or 7-indolyzinyl, 2-, 3-, 5- or 6-isoindolyl, 2-, 3-, 5- or 6-benzo[b]furanyl, 2-, 3-, 5- or 6-benzo[b]thiophenyl, 3-, 5- or 6-indazolyl, 2-, 5- or 6-benzthiazolyl, 2-, 5- or 6-benzimidazolyl, 2-, 3-, 6- or 7-quinolinyl, 3-, 6- or 7-isoquinolinyl, 2- or 8-purinyl, 2-, 3-, 7- or 8-quinolizinyl, 3-, 6- or 7-cinnolinyl, 6- or 7-phthalazinyl, 2-, 3-, 6- or 7-quinoxalinyl, 2-, 3-, 6- or 7-naphthyridinyl, 2-, 6- or 7-pteridinyl or 2-, 6- or 7-quinazolinyl, (ii) methyl, which may be mono- or polysubstituted with fluorine atoms and additionally may be monosubstituted with $R_{11}$, (iii) branched or unbranched alkyl of 2 to 6 carbon atoms or cycloalkyl of 3 to 6 carbon atoms, which alkyl or cycloakyl group may be mono- or polysubstituted with halogen or oxo, (iv) a group of the formula —$OR_{28}$, wherein $R_{28}$ is H, alkyl or fluoroalkyl of 1 to 6 carbon atoms or acyl of 1 to 6 carbon atoms, or $R_{11}$, (v) cyano, (vi) halogen, or from a substituent of (D) selected from (i) a group of the formula —$(CH_2)_nCOOR_{30}$, wherein $R_{30}$ is independently H, unbranched or branched alkyl of 1 to 6 carbon atoms or cycloalkyl of 3 to 6 carbon atoms and wherein said unbranched or branched alkyl of 1 to 6 carbon atoms or cycloalkyl of 3 to 6 carbon atoms may be optionally and independently substituted with —$CH_2OR_{31}$, —$COOR_{31}$, —$CON(R_{31})_2$, —$CH_2NHCOR_{31}$, —$SO_2N(R_{31})_2$, —$CH_2NHSO_2R_{31}$, —$CH_2N(R_{31})_2$, —$SO_2OH$, —$PO(OH)_2$ wherein $R_{31}$ is independently selected from H, unbranched or branched alkyl of 1 to 6 carbon atoms; or (ii) a group of the formula —$(CH_2)_nCONR_{32}R_{33}$, wherein $R_{32}$ and $R_{33}$ are each, independently, H, unbranched or branched alkyl of 1 to 6 carbon atoms or cycloalkyl of 3 to 6 carbon atoms and wherein said unbranched or branched alkyl of 1 to 6 carbon atoms or cycloalkyl of 3 to 6 carbon atoms may be optionally and independently substituted with —$CH_2OR_{31}$, —$COOR_{31}$, —$CON(R_{31})_2$, —$CH_2NHCOR_{31}$, —$SO_2N(R_{31})_2$, —$CH_2NHSO_2R_{31}$, —$CH_2N(R_{31})_2$, —$SO_2OH$, —$PO(OH)_2$ wherein $R_{31}$ is independently selected from H, unbranched or branched alkyl of 1 to 6 carbon atoms or wherein $NR_{32}$ is N-alkyl-4-piperidinylamino, N-carboxymethyl-4-piperidinylamino, pyridin-4-ylmethylamino, 4-amidinobenzylamino, 4-carboxybenzylamino, or 4-hydroxybenzylamino and $R_{33}$ is H or wherein $NR_{32}R_{33}$ constitute a heterocyclic ring selected from 4-alkyl-1-piperazinyl, wherein alkyl is unbranched or branched alkyl of 1 to 6 carbon atoms, or 1-morpholinyl;

$R_3$ is selected from H, $(CH_2)_n$-aryl, substituted $(CH_2)_n$-aryl, $(CH_2)_n$-heteroaryl and substituted $(CH_2)_n$-heteroaryl, wherein one or more of the hydrogen atoms of the aryl group of said substituted $(CH_2)_n$-aryl group or one or more of the hydrogen atoms of the heteroaryl group of said substituted $(CH_2)_n$-heteroaryl group may be optionally and independently replaced with:

(i) $R_{11}$, which is aryl or heteroaryl selected from phenyl, 2-naphthyl, 2-, 3-, 5- or 6-indolyl, 2- or 3-thiophenyl, 2-, 3- or 4-pyridyl, 2-, 4- or 5-pyrimidinyl, 2- or 3-furyl, 1-, 2- or 3-pyrrolyl, 2-, 4- or 5-oxazolyl, 2-, 4- or 5-thiazolyl, 1-, 3-, 4- or 5-pyrazolyl, 3-, 4- or 5-isoxazolyl, 1-, 2-, 4- or 5-imidazolyl, 3-, 4- or 5-isothiazolyl, 4- or 5-oxadiazolyl, 1-, 4- or 5-triazolyl, 2-thiadiazolyl, 3- or 4-pyridazinyl, 2-pyrazinyl, 2-triazinyl, 2-, 3-, 6- or 7-indolyzinyl, 2-, 3-, 5- or 6-isoindolyl, 2-, 3-, 5- or 6-benzo[b]furanyl, 2-, 3-, 5- or 6-benzo[b]thiophenyl, 3-, 5- or 6-indazolyl, 2-, 5- or 6-benzthiazolyl, 2-, 5- or 6-benzimidazolyl, 2-, 3-, 6- or 7-quinolinyl, 3-, 6- or 7-isoquinolinyl, 2- or 8-purinyl, 2-, 3-, 7- or 8-quinolizinyl, 3-, 6- or 7-cinnolinyl, 6- or 7-phthalazinyl, 2-, 3-, 6- or 7-quinoxalinyl, 2-, 3-, 6- or 7-naphthyridinyl, 2-, 6- or 7-pteridinyl or 2-, 6- or 7-quinazolinyl, (ii) methyl, which may be mono- or polysubstituted with fluorine atoms and additionally may be monosubstituted with $R_{11}$, (iii) branched or unbranched alkyl of 2 to 6 carbon atoms or cycloalkyl of 3 to 6 carbon atoms, which alkyl or cycloakyl group may be mono- or polysubstituted with halogen or oxo, (iv) a group of the formula —$OR_{28}$, wherein $R_{28}$ is H, alkyl or fluoroalkyl of 1 to 6 carbon atoms or acyl of 1 to 6 carbon atoms, or $R_{11}$, (v) cyano, or (vi) halogen;

$R_6$ and $R_7$ are both H;

and n is 0, 1 or 2. Preferably at least one of $R_2$ and $R_3$ is $(CH_2)_n$-aryl, substituted $(CH_2)_n$-aryl, $(CH_2)_n$-heteroaryl or substituted $(CH_2)_n$-heteroaryl and $R_1$ and $R_2$ are different from each other.

More preferred compounds of formula (Ia) and/or formula (Ib) racemates of the compound according to formula (Ia) and the compound according to formula (Ib), diastereomers of the compound according to formula (Ia) or the compound according to formula (Ib), and the diastereomeric meso forms of the compound according to formula (Ia) wherein $R_1$ and $R_2$ are the same, pharmaceutically-acceptable salts, hydrates, solvates, or prodrugs thereof are those wherein A is $CR_5$, wherein $R_5$ is H or halogen;

$R_1$ is selected from H, branched or unbranched alkyl of 1 to 6 carbon atoms;

$R_2$ and $R_4$ are independently selected from H, $(CH_2)_n$-aryl, substituted $(CH_2)_n$-aryl or $(CH2)_n$-heteroaryl, wherein one or more of the hydrogen atoms of the aryl group of said substituted $(CH_2)_n$-aryl group may be optionally replaced with:

(i) $R_{11}$, which is aryl or heteroaryl selected from phenyl, 2-naphthyl, 2-, 3-, 5- or 6-indolyl, 2- or 3-thiophenyl, 2-, 3- or 4-pyridyl, 2-, 4- or 5-pyrimidinyl, 2- or 3-furyl, 1-, 2- or 3-pyrrolyl, 2-, 4- or 5-oxazolyl, 2-, 4- or 5-thiazolyl, 1-, 3-, 4- or 5-pyrazolyl, 3-, 4- or 5-isoxazolyl, 1-, 2-, 4- or 5-imidazolyl, 3-, 4- or 5-isothiazolyl, 4- or 5-oxadiazolyl, 1-, 4- or 5-triazolyl, 2-thiadiazolyl, 3- or 4-pyridazinyl, 2-pyrazinyl, 2-triazinyl, 2-, 3-, 6- or 7-indolyzinyl, 2-, 3-, 5- or 6-isoindolyl, 2-, 3-, 5- or 6-benzo[b]furanyl, 2-, 3-, 5- or 6-benzo[b]thiophenyl, 3-, 5- or 6-indazolyl, 2-, 5- or 6-benzthiazolyl, 2-, 5- or 6-benzimidazolyl, 2-, 3-, 6- or 7-quinolinyl, 3-, 6- or 7-isoquinolinyl, 2- or 8-purinyl, 2-, 3-, 7- or 8-quinolizinyl, 3-, 6- or 7-cinnolinyl, 6- or 7-phthalazinyl, 2-, 3-, 6- or 7-quinoxalinyl, 2-, 3-, 6- or 7-naphthyridinyl, 2-, 6- or 7-pteridinyl or 2-, 6- or 7-quinazolinyl, (ii) methyl, which may be mono- or polysubstituted with fluorine atoms and additionally may be monosubstituted with $R_{11}$, (iii) branched or unbranched alkyl of 2 to 6 carbon atoms or cycloalkyl of 3 to 6 carbon atoms, which alkyl or cycloakyl group may be mono- or polysubstituted with halogen or oxo, (iv) a group of the formula $-OR_{28}$, wherein $R_{28}$ is H, alkyl or fluoroalkyl of 1 to 6 carbon atoms or acyl of 1 to 6 carbon atoms, or $R_{11}$, (v) cyano, (vi) halogen, or from a substituent of (D) selected from (i) a group of the formula $-(CH_2)_nCOOR_{30}$, wherein $R_{30}$ is independently H, unbranched or branched alkyl of 1 to 6 carbon atoms or cycloalkyl of 3 to 6 carbon atoms and wherein said unbranched or branched alkyl of 1 to 6 carbon atoms or cycloalkyl of 3 to 6 carbon atoms may be optionally and independently substituted with $-CH_2OR_{31}$, $-COOR_{31}$, $-CON(R_{31})_2$, $-CH_2NHCOR_{31}$, $-SO_2N(R_{31})_2$, $-CH_2NHSO_2R_{31}$, $-CH_2N(R_{31})_2$, $-SO_2OH$, $-PO(OH)_2$ wherein $R_{31}$ is independently selected from H, unbranched or branched alkyl of 1 to 6 carbon atoms; or (ii) a group of the formula $-(CH_2)_nCONR_{32}R_{33}$, wherein $R_{32}$ and $R_{33}$ are each, independently, H, unbranched or branched alkyl of 1 to 6 carbon atoms or cycloalkyl of 3 to 6 carbon atoms and wherein said unbranched or branched alkyl of 1 to 6 carbon atoms or cycloalkyl of 3 to 6 carbon atoms may be optionally and independently substituted with $-CH_2OR_{31}$, $-COOR_{31}$, $-CON(R_{31})_2$, $-CH_2NHCOR_{31}$, $-SO_2N(R_{31})_2$, $-CH_2NHSO_2R_{31}$, $-CH_2N(R_{31})_2$, $-SO_2OH$, $-PO(OH)_2$ wherein $R_{31}$ is independently selected from H, unbranched or branched alkyl of 1 to 6 carbon atoms or wherein $NR_{32}$ is N-alkyl-4-piperidinylamino, N-carboxymethyl-4-piperidinylamino, pyridin-4-ylmethylamino, 4-amidinobenzylamino, 4-carboxybenzylamino, or 4-hydroxybenzylamino and $R_{33}$ is H or wherein $NR_{32}R_{33}$ constitute a heterocyclic ring selected from 4-alkyl-1-piperazinyl, wherein alkyl is unbranched or branched alkyl of 1 to 6 carbon atoms, or 1-morpholinyl;

$R_3$ is selected from H, $(CH_2)_n$-aryl, substituted $(CH_2)_n$-aryl, $(CH_2)_n$-heteroaryl and substituted $(CH_2)_n$-heteroaryl, wherein one or more of the hydrogen atoms of the aryl group of said substituted $(CH_2)_n$-aryl group or one or more of the hydrogen atoms of the heteroaryl group of said substituted $(CH_2)_n$-heteroaryl group may be optionally and independently replaced with:

(i) $R_{11}$, which is aryl or heteroaryl selected from phenyl, 2-naphthyl, 2-, 3-, 5- or 6-indolyl, 2- or 3-thiophenyl, 2-, 3- or 4-pyridyl, 2-, 4- or 5-pyrimidinyl, 2- or 3-furyl, 1-, 2- or 3-pyrrolyl, 2-, 4- or 5-oxazolyl, 2-, 4- or 5-thiazolyl, 1-, 3-, 4- or 5-pyrazolyl, 3-, 4- or 5-isoxazolyl, 1-, 2-, 4- or 5-imidazolyl, 3-, 4- or 5-isothiazolyl, 4- or 5-oxadiazolyl, 1-, 4- or 5-triazolyl, 2-thiadiazolyl, 3- or 4-pyridazinyl, 2-pyrazinyl, 2-triazinyl, 2-, 3-, 6- or 7-indolyzinyl, 2-, 3-, 5- or 6-isoindolyl, 2-, 3-, 5- or 6-benzo[b]furanyl, 2-, 3-, 5- or 6-benzo[b]thiophenyl, 3-, 5- or 6-indazolyl, 2-, 5- or 6-benzthiazolyl, 2-, 5- or 6-benzimidazolyl, 2-, 3-, 6- or 7-quinolinyl, 3-, 6- or 7-isoquinolinyl, 2- or 8-purinyl, 2-, 3-, 7- or 8-quinolizinyl, 3-, 6- or 7-cinnolinyl, 6- or 7-phthalazinyl, 2-, 3-, 6- or 7-quinoxalinyl, 2-, 3-, 6- or 7-naphthyridinyl, 2-, 6- or 7-pteridinyl or 2-, 6- or 7-quinazolinyl, (ii) methyl, which may be mono- or polysubstituted with fluorine atoms and additionally may be monosubstituted with $R_{11}$, (iii) branched or unbranched alkyl of 2 to 6 carbon atoms or cycloalkyl of 3 to 6 carbon atoms, which alkyl or cycloakyl group may be mono- or polysubstituted with halogen or oxo, (iv) a group of the formula $-OR_{28}$, wherein $R_{28}$ is H, alkyl or fluoroalkyl of 1 to 6 carbon atoms or acyl of 1 to 6 carbon atoms, or $R_{11}$, (v) cyano, or (vi) halogen;

$R_6$ and $R_7$ are both H;

and n is 0, 1 or 2, wherein at least one of $R_3$ and $R_4$, preferably $R_3$ is $(CH_2)_n$-aryl, substituted $(CH_2)_n$-aryl or $(CH_2)_n$-heteroaryl and wherein the following compounds are excluded:

3-(3-Chlorophenyl)-6,6-diphenyl-3-azabicyclo[3.1.0]hexane-2,4-dione 3-(3-Bromophenyl)-6,6-diphenyl-3-azabicyclo[3.1.0]hexane-2,4-dione 3-(3-Chlorophenyl)-1-methyl-6,6-diphenyl-3-azabicyclo[3.1.0]hexane-2,4-dione 3-(3,5-Dichlorophenyl)-6,6-diphenyl-3-azabicyclo[3.1.0]hexane-2,4-dione 3-(3,5-Dichlorophenyl)-1-methyl-6,6-diphenyl-3-azabicyclo[3.1.0]hexane-2,4-dione 3-(3,4-Dichlorophenyl)-1-methyl-6,6-diphenyl-3-azabicyclo[3.1.0]hexane-2,4-dione 3-(3-Bromophenyl)-1-methyl-6,6-diphenyl-3-azabicyclo[3.1.0]hexane-2,4-dione 1-Methyl-6,6-diphenyl-3-(3-(trifluoromethyl)phenyl)-3-azabicyclo[3.1.0]hexane-2,4-dione.

Most preferred compounds of formula (Ia) or formula (Ib), pharmaceutically-acceptable salts, hydrates, solvates, or prodrugs thereof are those wherein $X_1$ and $X_2$ are halogen;

A is $CR_5$, wherein $R_5$ is H or halogen;

$R_1$ is selected from H, branched or unbranched alkyl of 1 to 6 carbon atoms;

$R_2$ is selected from H, branched or unbranched alkyl of 1 to 6 carbon atoms;

$R_4$ is selected from H, $(CH_2)_n$-aryl, substituted $(CH_2)_n$-aryl or $(CH_2)_n$-heteroaryl, wherein one or more of the hydrogen atoms of the aryl group of said substituted $(CH_2)_n$-aryl group may be optionally replaced with:

(i) methyl, which may be mono- or polysubstituted with fluorine atoms, (ii) branched or unbranched alkyl of 2 to 6 carbon atoms or cycloalkyl of 3 to 6 carbon atoms, which alkyl or cycloakyl group may be mono- or polysubstituted with halogen or oxo, (iii) a group of the formula —$OR_{28}$, wherein $R_{28}$ is H, alkyl or fluoroalkyl of 1 to 6 carbon atoms or acyl of 1 to 6 carbon atoms, (iv) cyano, or (v) halogen, or from a substituent of (D) selected from i) a group of the formula —$(CH_2)_n COOR_{30}$, wherein $R_{30}$ is independently H, unbranched or branched alkyl of 1 to 6 carbon atoms, (ii) a group of the formula —$(CH_2)_n CONR_{32}R_{33}$, wherein $NR_{32}R_{33}$ constitute a heterocyclic ring selected from 4-alkyl-1-piperazinyl, wherein alkyl is unbranched or branched alkyl of 1 to 6 carbon atoms, or 1-morpholinyl;

$R_3$ is selected from H, $(CH_2)_n$-aryl, substituted $(CH_2)_n$-aryl, or $(CH_2)_n$-heteroaryl, wherein one or more of the hydrogen atoms of the aryl group of said substituted $(CH_2)_n$-aryl group may be optionally and independently replaced with:

(i) methyl, which may be mono- or polysubstituted with fluorine atoms and additionally may be monosubstituted with $R_{11}$, (ii) branched or unbranched alkyl of 2 to 6 carbon atoms or cycloalkyl of 3 to 6 carbon atoms, which alkyl or cycloakyl group may be mono- or polysubstituted with halogen or oxo, (iii) a group of the formula —$OR_{28}$, wherein $R_{28}$ is H, alkyl or fluoroalkyl of 1 to 6 carbon atoms or acyl of 1 to 6 carbon atoms, or $R_{11}$, (iv) cyano, or (v) halogen;

$R_6$ and $R_7$ are both H;

and n is 0. Preferably at least one of $R_2$ and $R_3$ is $(CH_2)_n$-aryl, substituted $(CH_2)_n$-aryl, $(CH_2)_n$-heteroaryl or substituted $(CH_2)_n$-heteroaryl and $R_1$ and $R_2$ are different from each other.

Particularly preferred compounds of formula (Ia) or formula (Ib), pharmaceutically-acceptable salts, hydrates, solvates, or prodrugs thereof are those wherein 1) A is $CR_5$ and wherein $R_5$ is H or halogen, preferably H, 2) Both $X_1$ and $X_2$ are halogen or $CF_3$, more preferably both are halogen, 3) $R_1$ is H or branched or unbranched alkyl of 1 to 6 carbon atoms, preferably methyl, 4) $R_2$ is H or branched or unbranched alkyl of 1 to 6 carbon atoms, preferably H, 5) $R_3$ is selected from H, $(CH2)_n$-aryl, substituted $(CH2)_n$-aryl or $(CH2)_n$-heteroaryl, wherein aryl of $(CH2)_n$-aryl or substituted $(CH2)_n$-aryl is preferably phenyl and wherein heteroaryl of $(CH2)_n$-heteroaryl is preferably pyridinyl or furanyl, wherein one or more of the hydrogen atoms of the aryl group of said substituted $(CH2)_n$-aryl group may be optionally and independently replaced with:

(i) a group of the formula —$OR_{28}$, wherein $R_{28}$ is H, alkyl or fluoroalkyl of 1 to 6, carbon atoms, preferably trifluoromethyl (ii) cyano, or (iii) halogen, 6) $R_4$ is selected from H, $(CH2)_n$-aryl, substituted $(CH2)_n$-aryl or $(CH2)_n$-heteroaryl, wherein aryl of $(CH2)_n$-aryl or substituted $(CH2)_n$-aryl is preferably phenyl and wherein heteroaryl of $(CH2)_n$-heteroaryl is preferably pyridinyl, wherein one or more of the hydrogen atoms of the aryl group of said substituted $(CH_2)_n$-aryl group may be optionally replaced with:

(i) a group of the formula —$OR_{28}$, wherein $R_{28}$ is H, alkyl or fluoroalkyl of 1 to 6 carbon atoms, preferably trifluoromethyl (ii) cyano, or (iii) halogen, or is a substituent of (D) which is selected from (i) a group of the formula —$(CH_2)_n COOR_{30}$, wherein $R_{30}$ is independently H, unbranched or branched alkyl of 1 to 6 carbon atoms or cycloalkyl of 3 to 6 carbon atoms, preferably H, (ii) a ii) a group of the formula —$(CH_2)_n CONR_{32}R_{33}$, wherein $NR_{32}R_{33}$ constitute a heterocyclic ring selected from 4-alkyl-1-piperazinyl, wherein alkyl is unbranched or branched alkyl of 1 to 6 carbon atoms, or 1-morpholinyl, wherein n of $(CH_2)_n$-aryl or substituted $(CH_2)_n$-aryl is 0 or 1, more preferably 0, and 7) $R_6$ and $R_7$ are independently selected from H and methyl, most preferably $R_6$ and $R_7$ are both H;

wherein at least one of $R_3$ and $R_4$, preferably $R_3$ is $(CH_2)_n$-aryl or substituted $(CH_2)_n$-aryl. Preferably at least one of $R_2$ and $R_3$ is $(CH_2)_n$-aryl, substituted $(CH_2)_n$-aryl, $(CH_2)_n$-heteroaryl or substituted $(CH_2)_n$-heteroaryl and $R_1$ and $R_2$ are different from each other.

Particularly preferred compounds of formula (Ia) or formula (Ib), pharmaceutically-acceptable salts, hydrates, solvates, or prodrugs thereof are those wherein 1) A is $CR_5$ and wherein $R_5$ is H or halogen, preferably H, 2) Both $X_1$ and $X_2$ are halogen or $CF_3$, more preferably both are halogen, 3) $R_1$ is H or branched or unbranched alkyl of 1 to 6 carbon atoms, preferably methyl, 4) $R_2$ is H or branched or unbranched alkyl of 1 to 6 carbon atoms, preferably H, 5) $R_3$ is selected from H, $(CH2)_n$-aryl or substituted $(CH2)_n$-aryl, wherein aryl of $(CH2)_n$-aryl or substituted $(CH2)_n$-aryl is preferably phenyl, wherein one or more of the hydrogen atoms of the aryl group of said substituted $(CH2)_n$-aryl group may be optionally and independently replaced with:

(i) a group of the formula —$OR_{28}$, wherein $R_{28}$ is H, alkyl or fluoroalkyl of 1 to 6, carbon atoms, preferably trifluoromethyl (ii) cyano, or (iii) halogen, 6) $R_4$ is selected from H, $(CH_2)_n$-aryl, or substituted $(CH_2)_n$-aryl, wherein aryl of $(CH_2)_n$-aryl or substituted $(CH_2)_n$-aryl is preferably phenyl, wherein one or more of the hydrogen atoms of the aryl group of said substituted $(CH_2)_n$-aryl group may be optionally replaced with:
(i) a group of the formula —OR$_{28}$, wherein R$_{28}$ is H, alkyl or fluoroalkyl of 1 to 6 carbon atoms, preferably trifluoromethyl
(ii) cyano, or
(iii) halogen, or
is a substituent of (D) which is a group of the formula —(CH$_2$)$_n$COOR$_{30}$, wherein R$_{30}$ is independently H, unbranched or branched alkyl of 1 to 6 carbon atoms or cycloalkyl of 3 to 6 carbon atoms, preferably H, wherein n of $(CH_2)_n$-aryl or substituted $(CH_2)_n$-aryl is 0 or 1, more preferably 0, and
7) R$_6$ and R$_7$ are independently selected from H and methyl, most preferably R$_6$ and R$_7$ are both H;
wherein at least one of R$_3$ and R$_4$, preferably R$_3$ is $(CH_2)_n$-aryl or substituted $(CH_2)_n$-aryl, and
wherein R$_1$ and R$_2$ are different from each other.

Particularly preferred compounds of formula (Ia) and/or formula (Ib) racemates of the compound according to formula (Ia) and the compound according to formula (Ib), diastereomers of the compound according to formula (Ia) or the compound according to formula (Ib), and the diastereomeric meso forms of the compound according to formula (Ia) wherein R$_1$ and R$_2$ are the same, pharmaceutically-acceptable salts, hydrates, solvates, or prodrugs thereof are those wherein
1) A is CR5 and wherein R5 is H or halogen, preferably H,
2) Both X1 and X2 are halogen or CF3, more preferably both are halogen,
3) R1 is H or branched or unbranched alkyl of 1 to 6 carbon atoms, preferably methyl,
4) R2 is H or branched or unbranched alkyl of 1 to 6 carbon atoms, preferably H,
5) R3 is selected from H, (CH2)n-aryl, substituted (CH2)n-aryl or (CH2)n-heteroaryl, wherein aryl of (CH2)n-aryl or substituted (CH2)n-aryl is preferably phenyl and wherein heteroaryl of (CH2)n-heteroaryl is preferably pyridinyl or furanyl, wherein one or more of the hydrogen atoms of the aryl group of said substituted (CH2)n-aryl group may be optionally and independently replaced with:
(i) a group of the formula —OR28, wherein R28 is H, alkyl or fluoroalkyl of 1 to 6, carbon atoms, preferably trifluoromethyl
(ii) cyano, or
(iii) halogen,
6) R4 is selected from H, (CH2)$_n$-aryl, substituted (CH2)$_n$-aryl or (CH2)n-heteroaryl, wherein aryl of (CH2)n-aryl or substituted (CH2)n-aryl is preferably phenyl and wherein heteroaryl of (CH2)n-heteroaryl is preferably pyridinyl, wherein one or more of the hydrogen atoms of the aryl group of said substituted (CH2)n-aryl group may be optionally replaced with:
(i) a group of the formula —OR28, wherein R28 is H, alkyl or fluoroalkyl of 1 to 6 carbon atoms, preferably trifluoromethyl
(ii) cyano, or
(iii) halogen, or
is a substituent of (D) which is selected from
(i) a group of the formula —(CH2)nCOOR30, wherein R30 is independently H, unbranched or branched alkyl of 1 to 6 carbon atoms or cycloalkyl of 3 to 6 carbon atoms, preferably H, (ii) a
ii) a group of the formula —(CH2)nCONR32R33, wherein NR32R33 constitute a heterocyclic ring selected from 4-alkyl-1-piperazinyl, wherein alkyl is unbranched or branched alkyl of 1 to 6 carbon atoms, or 1-morpholinyl,
wherein n of (CH2)n-aryl or substituted (CH2)n-aryl is 0 or 1, more preferably 0, and
7) R6 and R7 are independently selected from H and methyl, most preferably R6 and R7 are both H;
wherein at least one of R$_3$ and R$_4$, preferably R$_3$ is $(CH_2)_n$-aryl, substituted $(CH_2)_n$-aryl or $(CH_2)_n$-heteroaryl and wherein the following compounds are excluded:
3-(3-Chlorophenyl)-6,6-diphenyl-3-azabicyclo[3.1.0] hexane-2,4-dione
3-(3-Bromophenyl)-6,6-diphenyl-3-azabicyclo[3.1.0] hexane-2,4-dione
3-(3-Chlorophenyl)-1-methyl-6,6-diphenyl-3-azabicyclo [3.1.0]hexane-2,4-dione
3-(3,5-Dichlorophenyl)-6,6-diphenyl-3-azabicyclo[3.1.0] hexane-2,4-dione
3-(3,5-Dichlorophenyl)-1-methyl-6,6-diphenyl-3-azabicyclo[3.1.0]hexane-2,4-dione
3-(3,4-Dichlorophenyl)-1-methyl-6,6-diphenyl-3-azabicyclo[3.1.0]hexane-2,4-dione
3-(3-Bromophenyl)-1-methyl-6,6-diphenyl-3-azabicyclo [3.1.0]hexane-2,4-dione
1-Methyl-6,6-diphenyl-3-(3-(trifluoromethyl)phenyl)-3-azabicyclo[3.1.0]hexane-2,4-dione.

Particularly preferred compounds of formula (Ia) and/or formula (Ib) racemates of the compound according to formula (Ia) and the compound according to formula (Ib), diastereomers of the compound according to formula (Ia) or the compound according to formula (Ib), and the diastereomeric meso forms of the compound according to formula (Ia) wherein R$_1$ and R$_2$ are the same, pharmaceutically-acceptable salts, hydrates, solvates, or prodrugs thereof are those wherein
1) A is CR$_5$ and wherein R$_5$ is H or halogen, preferably H,
2) Both X$_1$ and X$_2$ are halogen or CF$_3$, more preferably both are halogen,
3) R$_1$ is H or branched or unbranched alkyl of 1 to 6 carbon atoms, preferably methyl,
4) R$_2$ is H or branched or unbranched alkyl of 1 to 6 carbon atoms, preferably H,
5) R$_3$ is selected from H, $(CH2)_n$-aryl or substituted $(CH2)_n$-aryl, wherein aryl of $(CH2)_n$-aryl or substituted $(CH2)_n$-aryl is preferably phenyl, wherein one or more of the hydrogen atoms of the aryl group of said substituted $(CH2)_n$-aryl group may be optionally and independently replaced with:
(i) a group of the formula —OR$_{28}$, wherein R$_{28}$ is H, alkyl or fluoroalkyl of 1 to 6, carbon atoms, preferably trifluoromethyl
(ii) cyano, or
(iii) halogen,
6) R$_4$ is selected from H, $(CH2)_n$-aryl, or substituted $(CH2)_n$-aryl, wherein aryl of $(CH2)_n$-aryl or substituted $(CH2)_n$-aryl is preferably phenyl, wherein one or more of the hydrogen atoms of the aryl group of said substituted $(CH_2)_n$-aryl group may be optionally replaced with:
(i) a group of the formula —OR$_{28}$, wherein R$_{28}$ is H, alkyl or fluoroalkyl of 1 to 6 carbon atoms, preferably trifluoromethyl
(ii) cyano, or
(iii) halogen, or
is a substituent of (D) which is a group of the formula —(CH$_2$)$_n$COOR$_{30}$, wherein R$_{30}$ is independently H, unbranched or branched alkyl of 1 to 6 carbon atoms or cycloalkyl of 3 to 6 carbon atoms, preferably H, wherein n of $(CH_2)_n$-aryl or substituted $(CH_2)_n$-aryl is 0 or 1, more preferably 0, and 7) $R_6$ and $R_7$ are independently selected from H and methyl, most preferably $R_6$ and $R_7$ are both H;

wherein at least one of $R_3$ and $R_4$, preferably $R_3$ is $(CH_2)_n$-aryl or substituted $(CH_2)_n$-aryl and wherein the following compounds are excluded:

3-(3-Chlorophenyl)-6,6-diphenyl-3-azabicyclo[3.1.0]hexane-2,4-dione
3-(3-Bromophenyl)-6,6-diphenyl-3-azabicyclo[3.1.0]hexane-2,4-dione
3-(3-Chlorophenyl)-1-methyl-6,6-diphenyl-3-azabicyclo[3.1.0]hexane-2,4-dione
3-(3,5-Dichlorophenyl)-6,6-diphenyl-3-azabicyclo[3.1.0]hexane-2,4-dione
3-(3,5-Dichlorophenyl)-1-methyl-6,6-diphenyl-3-azabicyclo[3.1.0]hexane-2,4-dione
3-(3,4-Dichlorophenyl)-1-methyl-6,6-diphenyl-3-azabicyclo[3.1.0]hexane-2,4-dione
3-(3-Bromophenyl)-1-methyl-6,6-diphenyl-3-azabicyclo[3.1.0]hexane-2,4-dione
1-Methyl-6,6-diphenyl-3-(3-(trifluoromethyl)phenyl)-3-azabicyclo[3.1.0]hexane-2,4-dione.

Particularly preferred compounds of diastereomeric mesoforms of a compound according to formula (Ia), pharmaceutically-acceptable salts, hydrates, solvates, or prodrugs thereof are those wherein
1) A is $CR_5$ and wherein $R_5$ is H or halogen, preferably H,
2) Both $X_1$ and $X_2$ are halogen or $CF_3$, more preferably both are halogen,
3) $R_1$ and $R_2$ are the same and are H or branched or unbranched alkyl of 1 to 6 carbon atoms, preferably H,
4) $R_3$ is selected from $(CH2)_n$-aryl or substituted $(CH2)_n$-aryl, wherein aryl of $(CH2)_n$-aryl or substituted $(CH2)_n$-aryl is preferably phenyl, wherein one or more of the hydrogen atoms of the aryl group of said substituted $(CH2)_n$-aryl group may be optionally and independently replaced with:
(i) a group of the formula —$OR_{28}$, wherein $R_{28}$ is H, alkyl or fluoroalkyl of 1 to 6, carbon atoms, preferably trifluoromethyl
(ii) cyano, or
(iii) halogen,
5) $R_4$ is H;
6) $R_6$ and $R_7$ are independently selected from H and methyl, most preferably $R_6$ and $R_7$ are both H.

More particular preferred compounds are the following compounds, including racemates, diastereomers, and/or diastereomeric meso forms thereof where applicable:

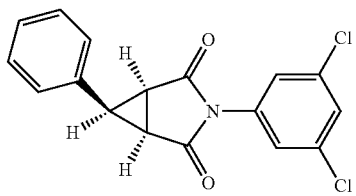
4'c

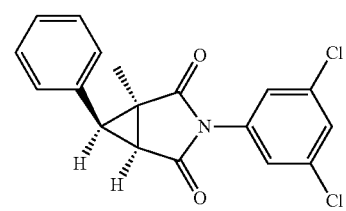
4'd

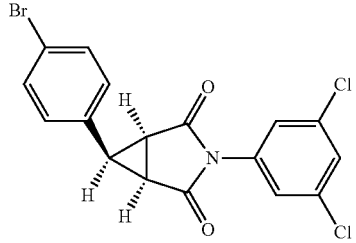
4'e

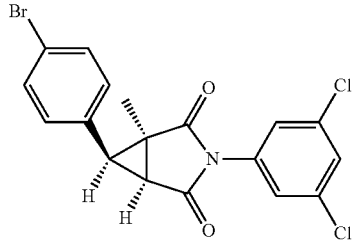
4'f

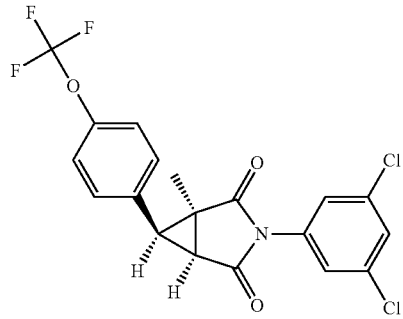
4'g

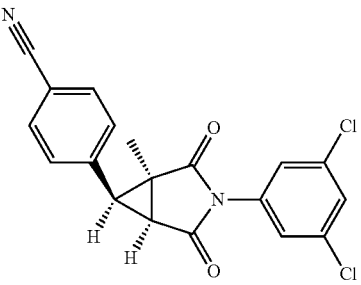
4'h

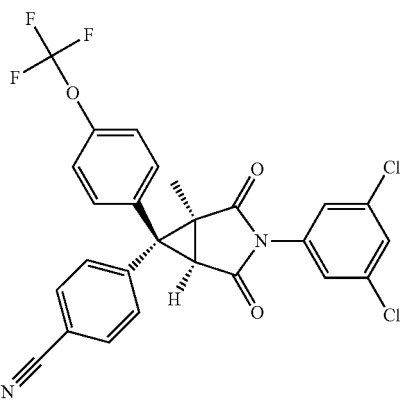
4i or 4'i

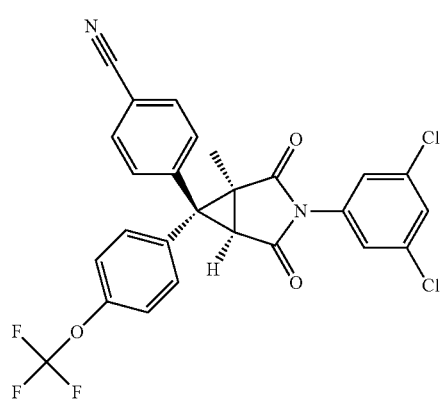
4i or 4'i
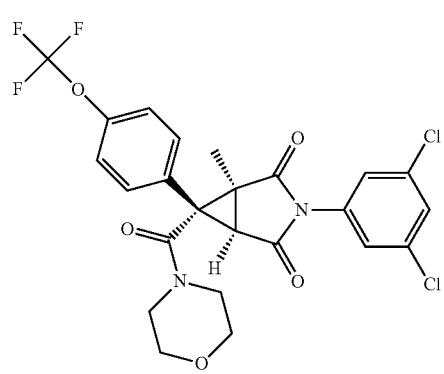
4'm
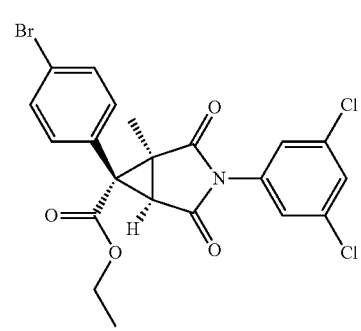
4'j
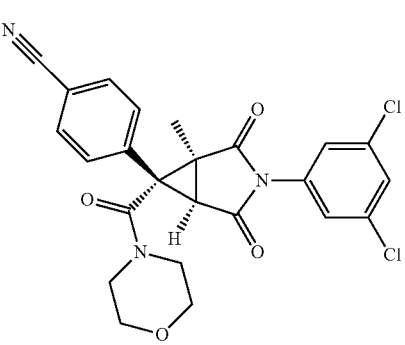
4'n
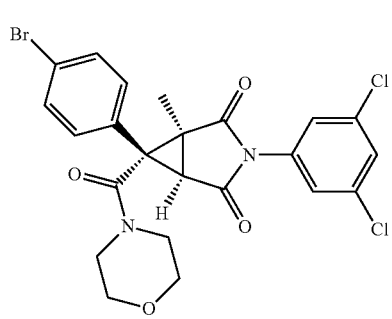
4'k
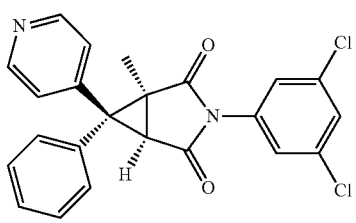
4o or 4'o
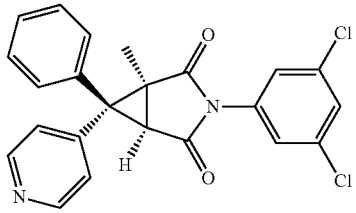
4o or 4'o
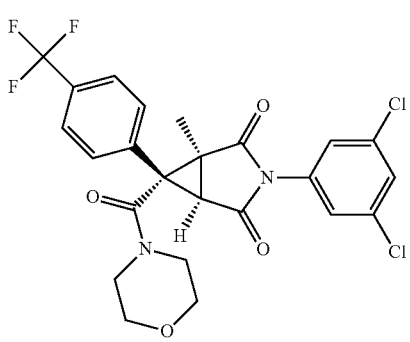
4'l
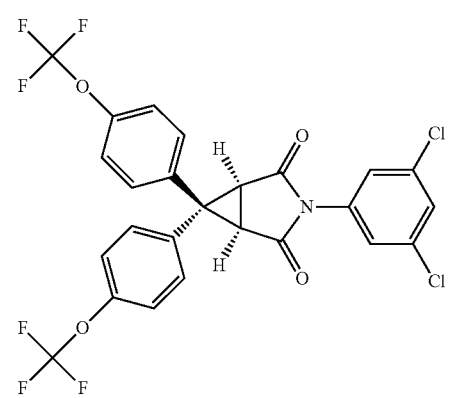
4p

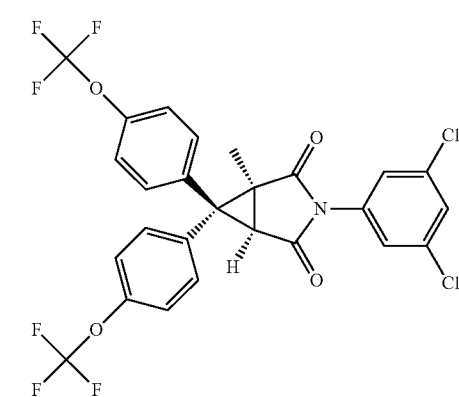
4q
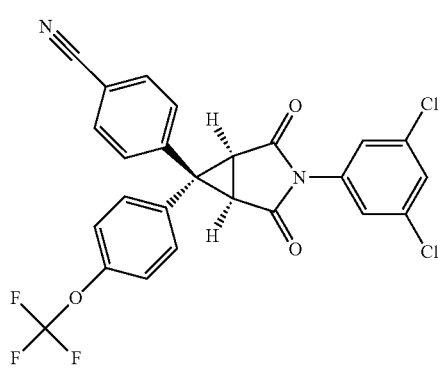
4r or 4′r
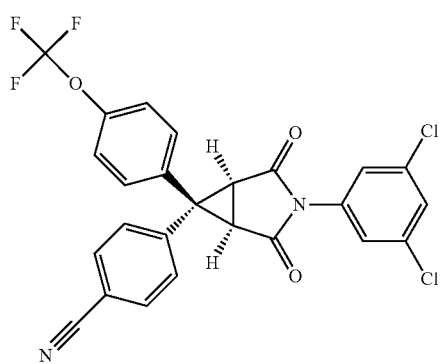
4r or 4′r
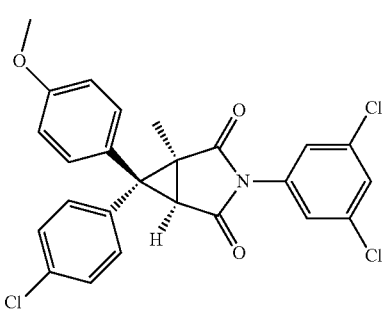
4s or 4′s
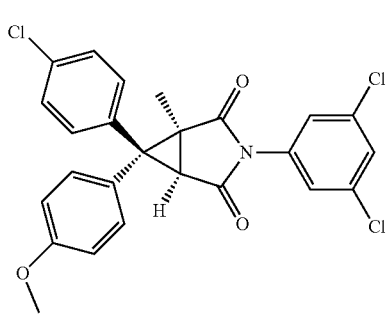
4s or 4′s
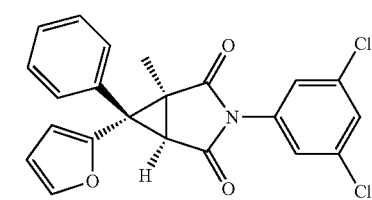
4t or 4′t
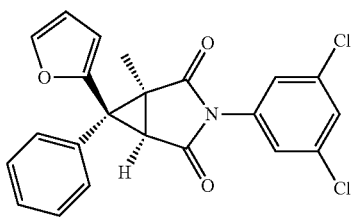
4t or 4′t
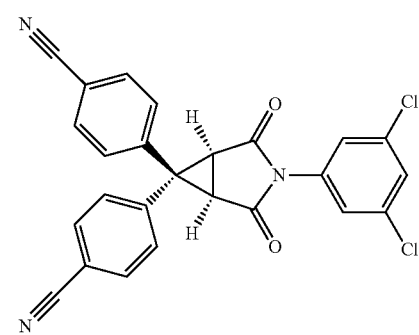
4u
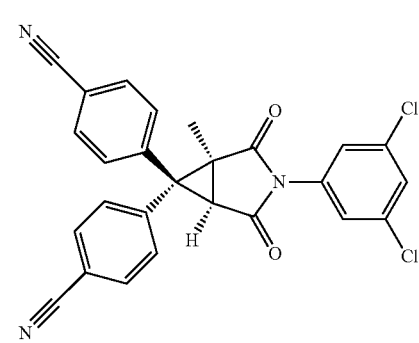
4v

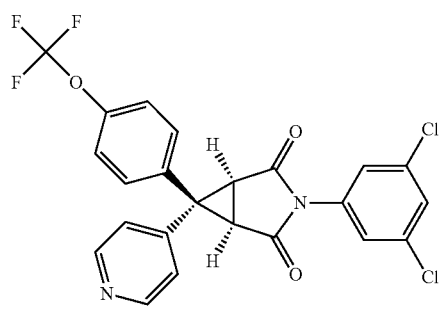
4w or 4'w
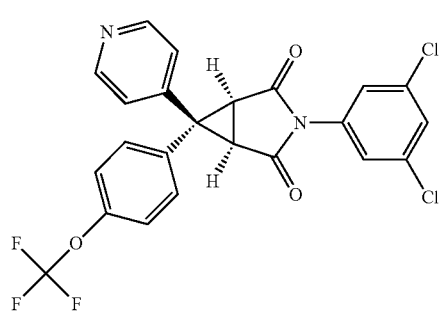
4w or 4'w
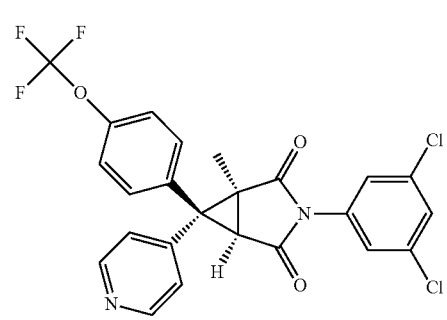
4x or 4'x
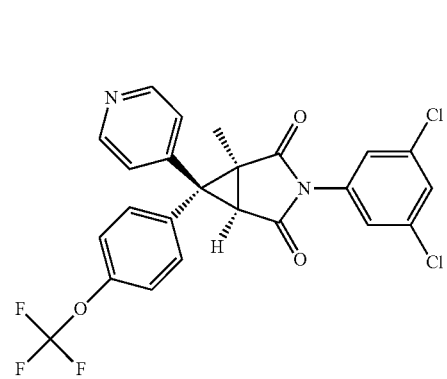
4x or 4'x
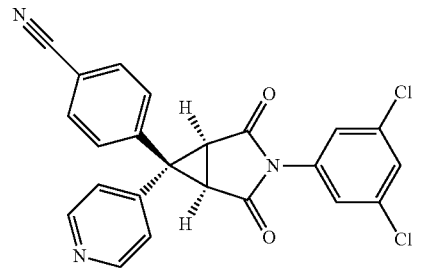
4y or 4'y
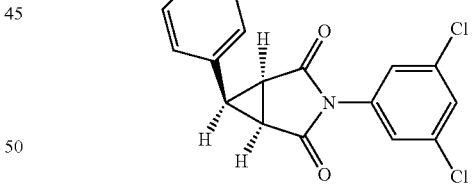
4y or 4'y
4z or 4'z
4z or 4'z
Equally more particular preferred compounds are the following compounds, including racemates, diastereomers, and/or diastereomeric meso forms thereof where applicable:
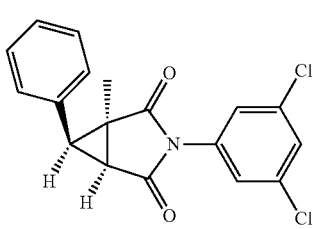
4'c
4'd

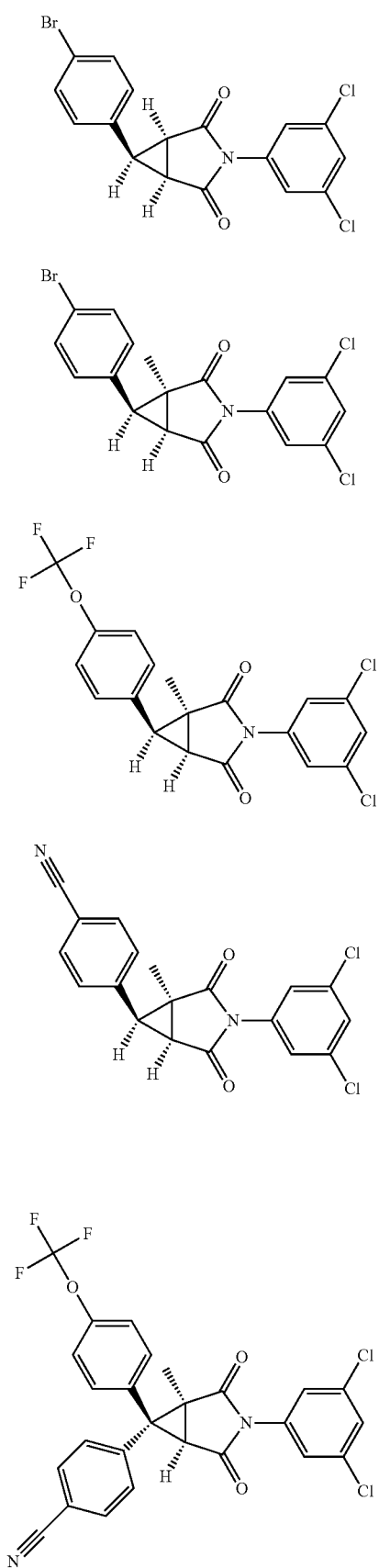
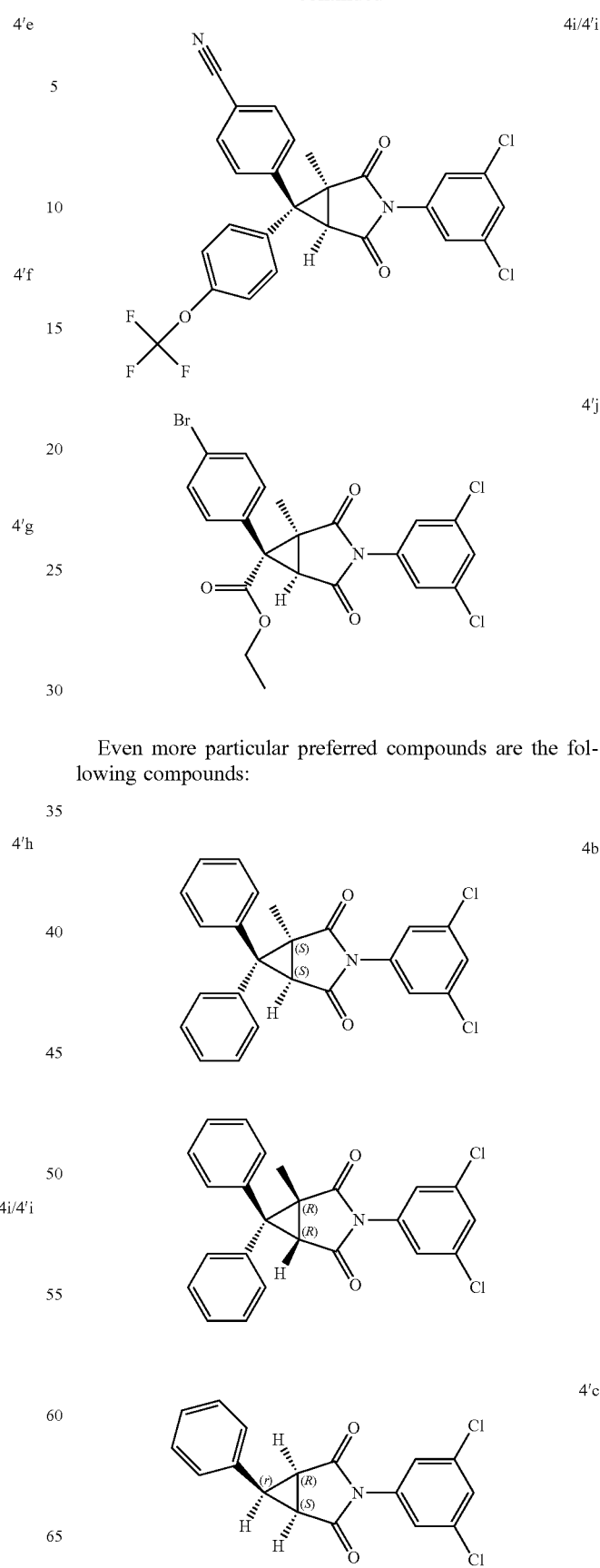
Even more particular preferred compounds are the following compounds:
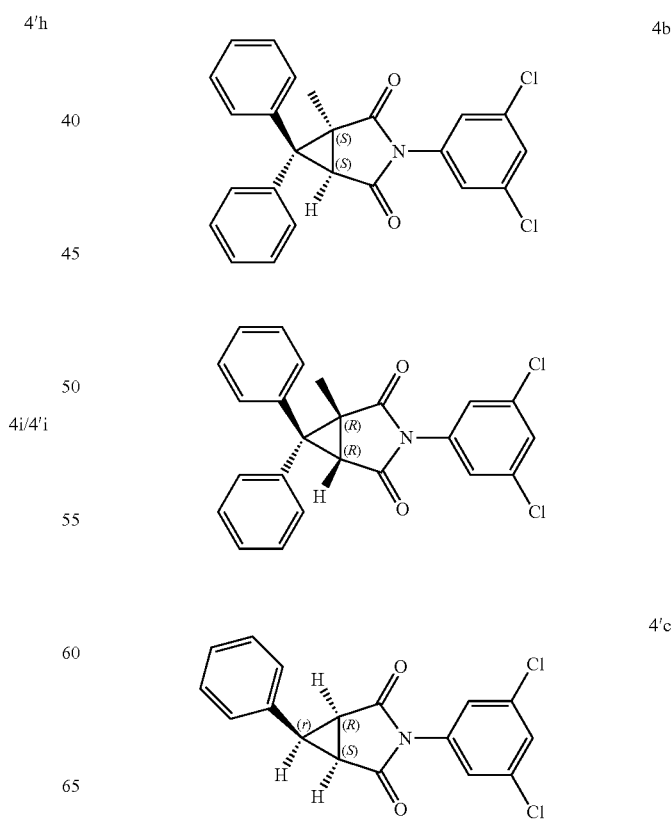

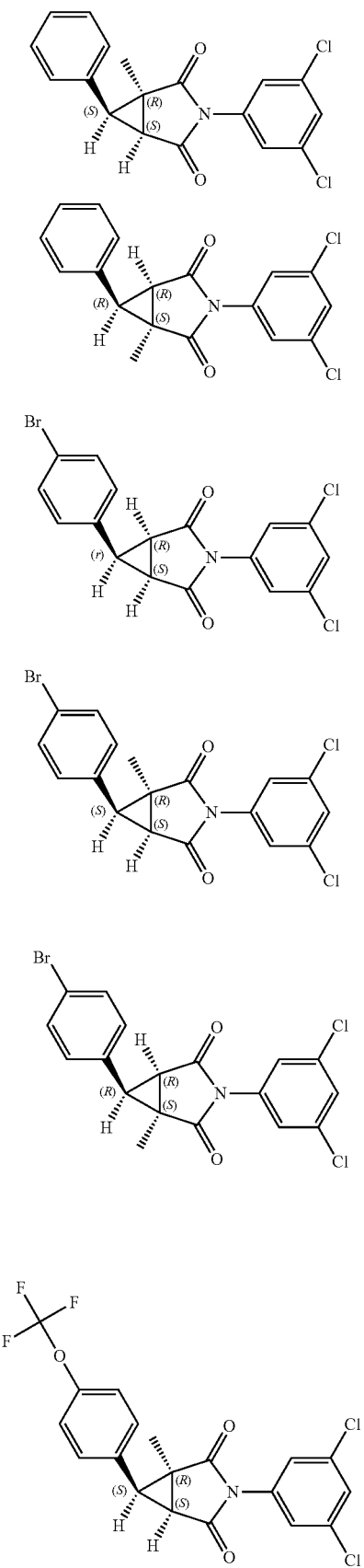
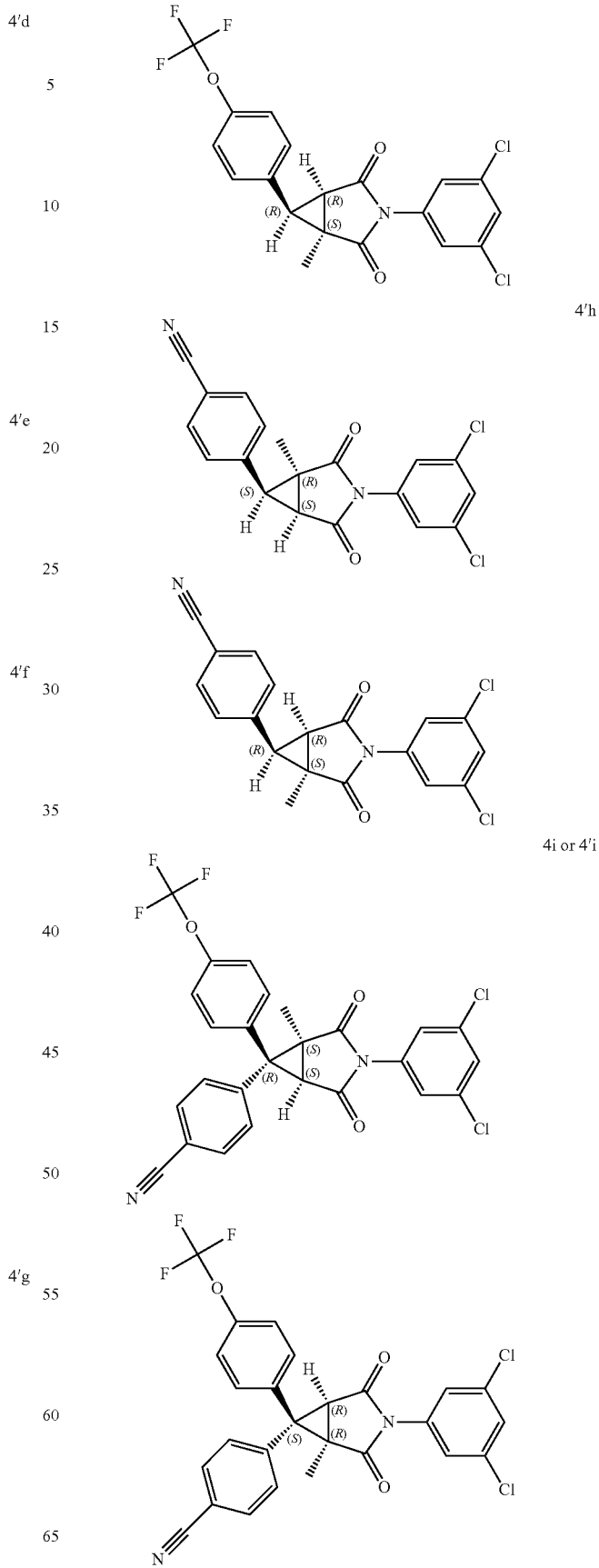

-continued
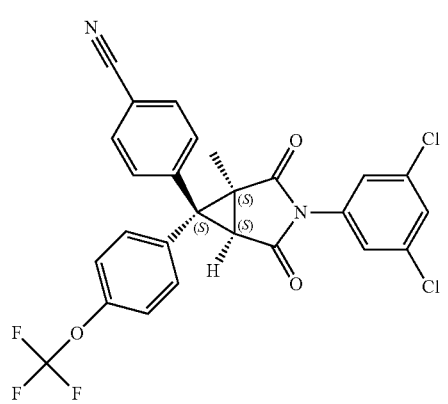
4i or 4'i
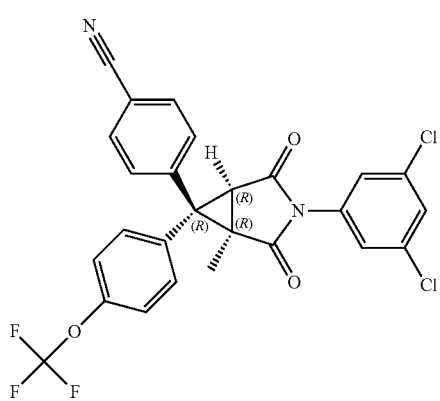
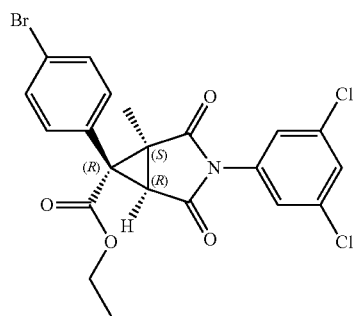
4j
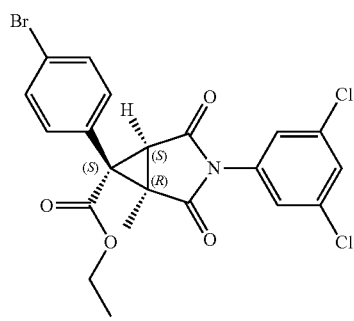
-continued
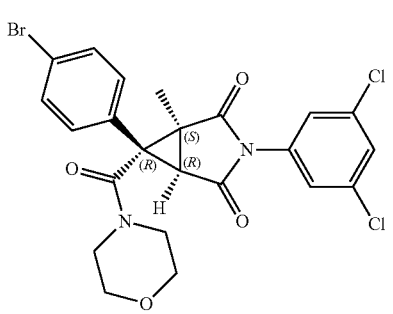
4'k
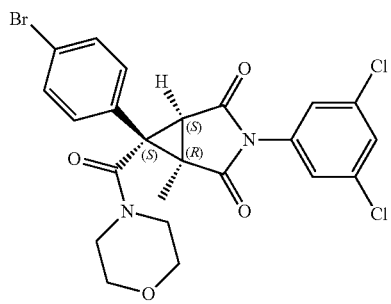
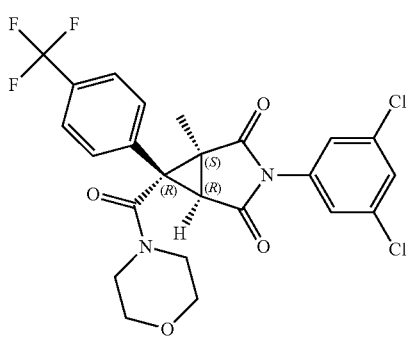
4'l
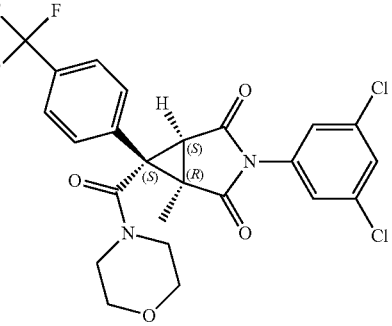
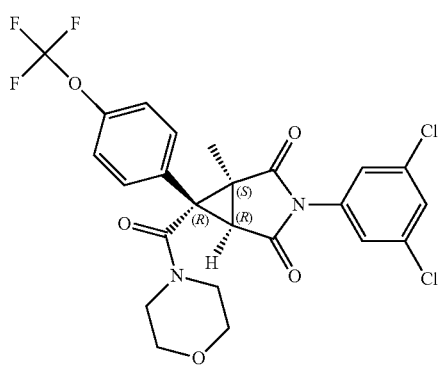
4'm

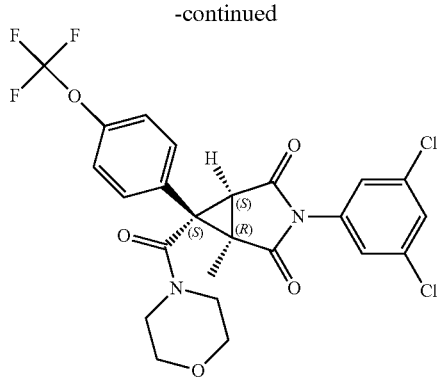
4'n
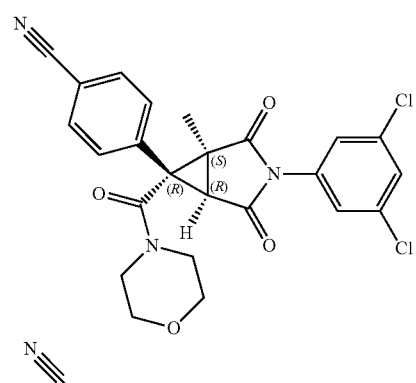
4o or 4'o
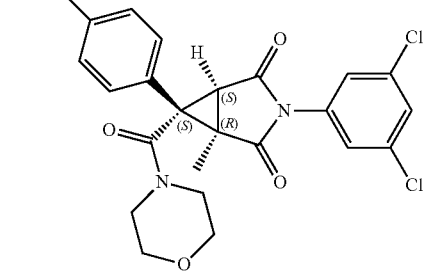
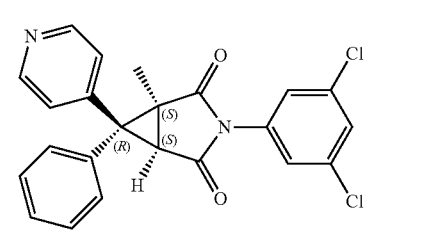
4o or 4'o
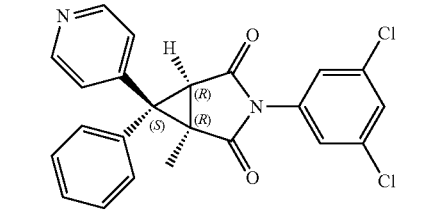
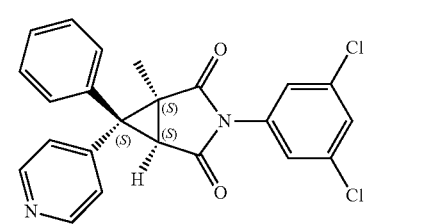
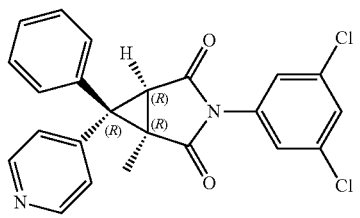
4p
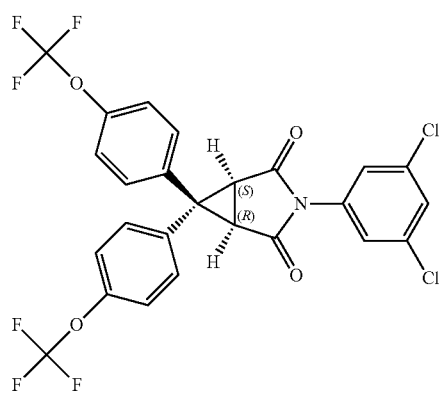
4q
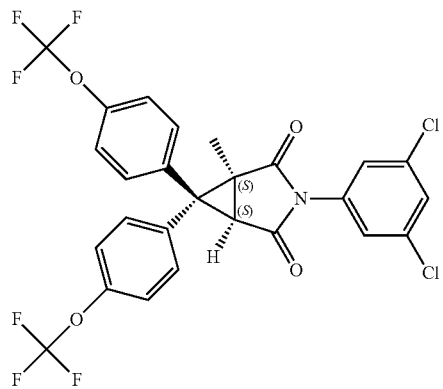
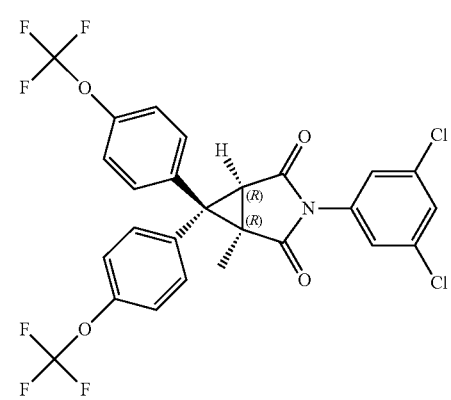

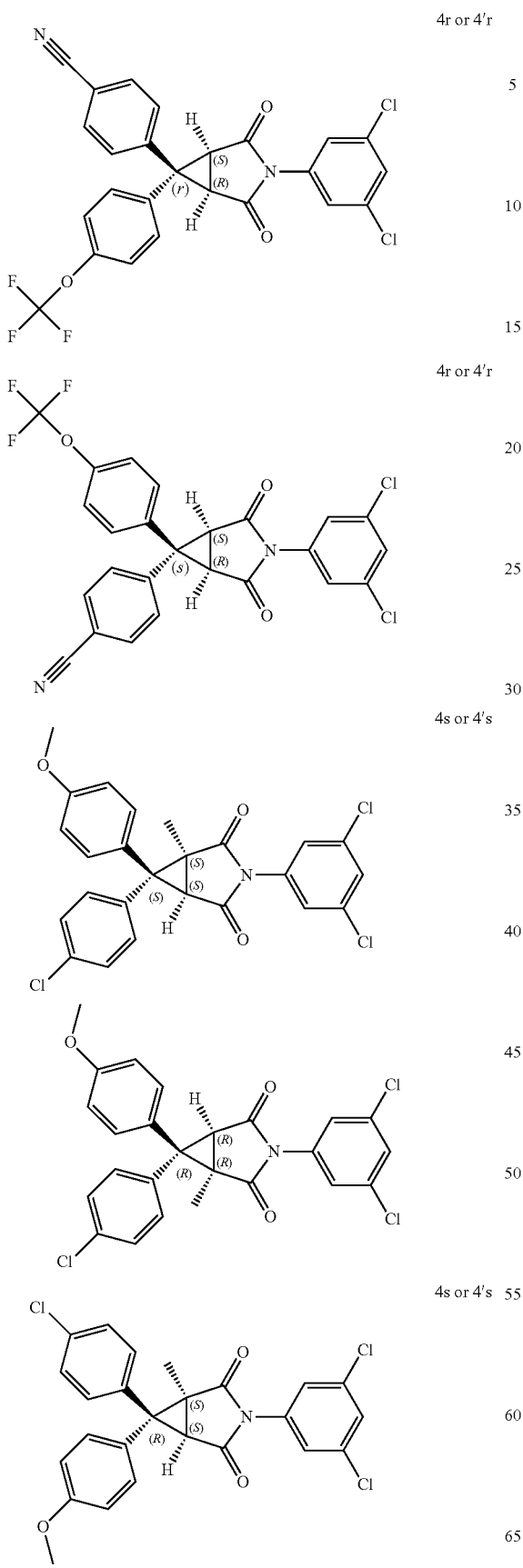
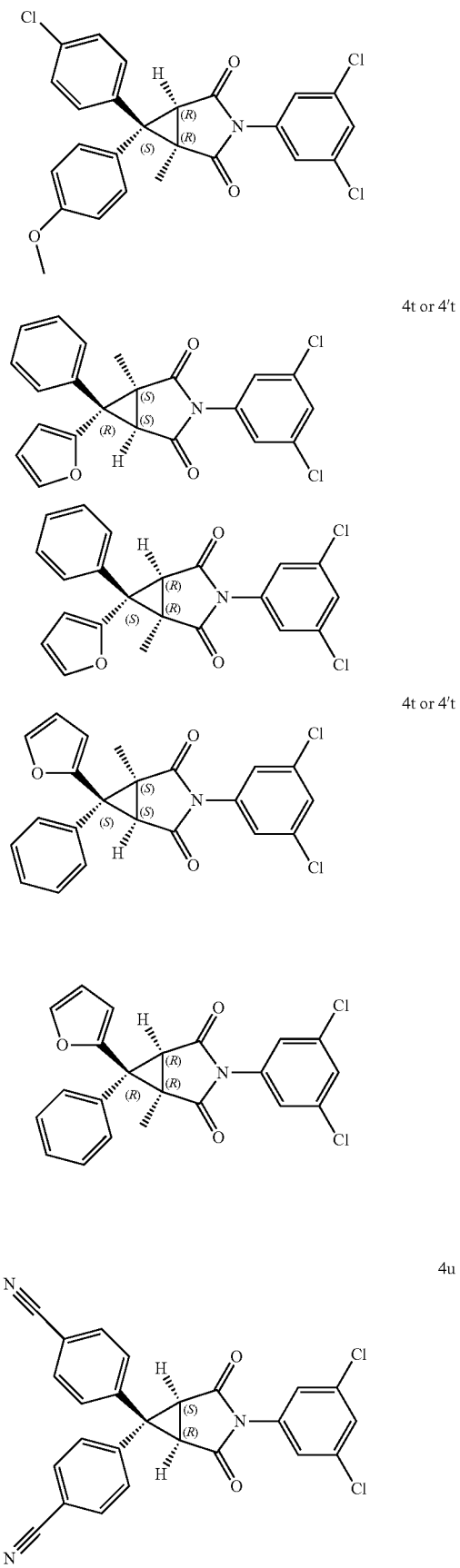

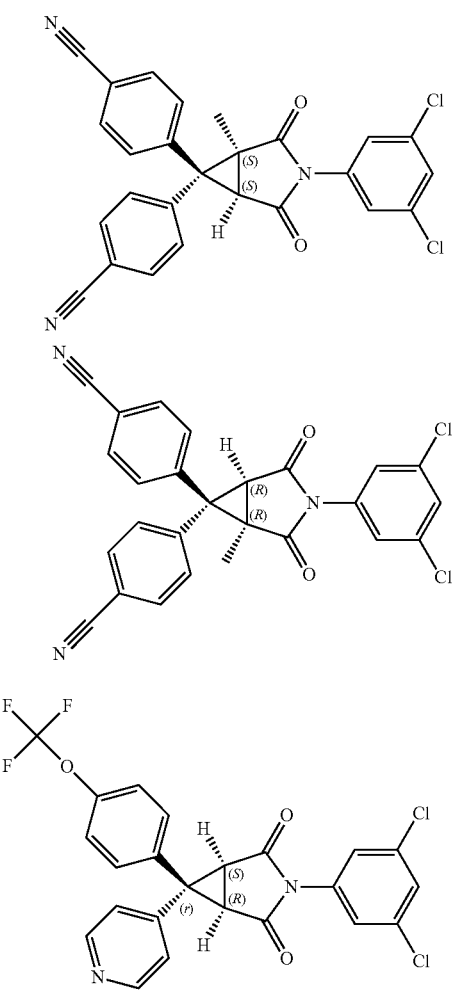
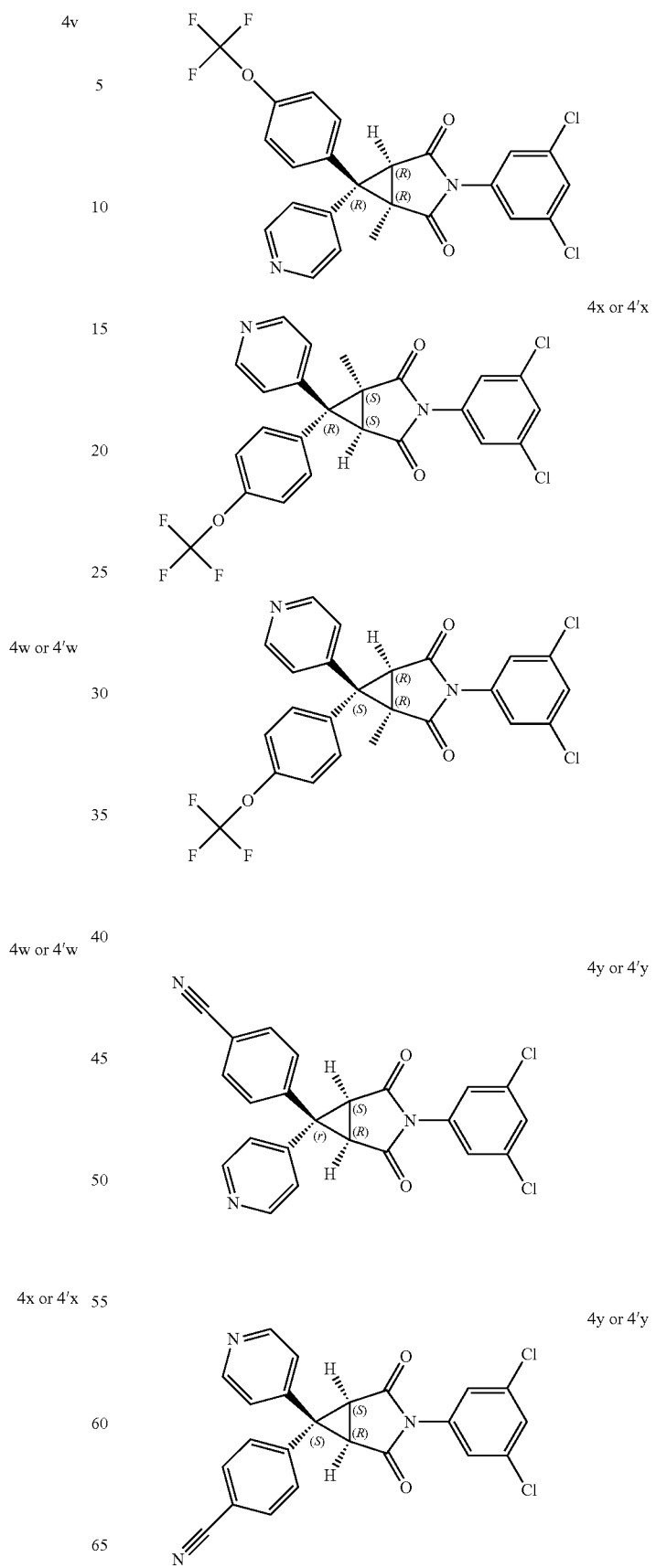

-continued
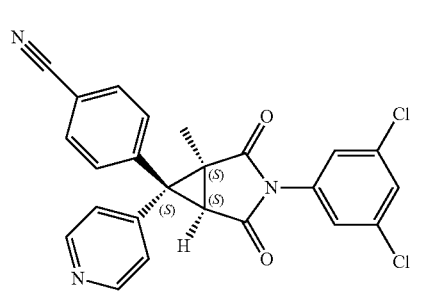
4z or 4′z
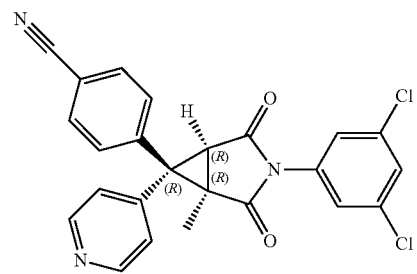
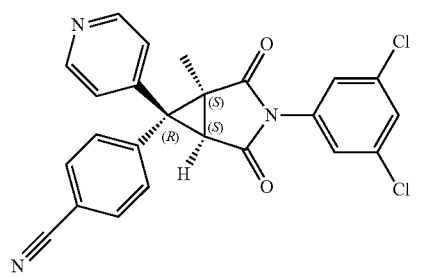
4z or 4′z
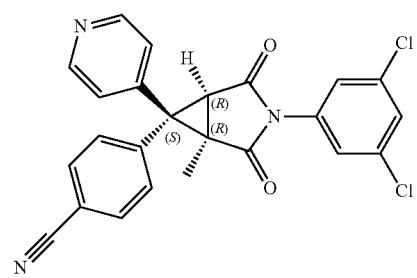
Equally even more particular preferred compounds are the following compounds:
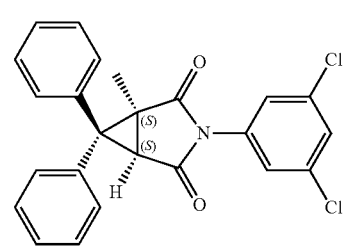
4b
-continued
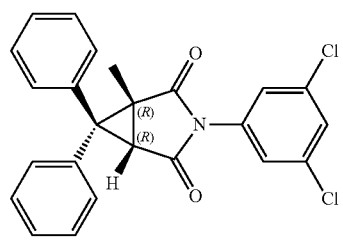
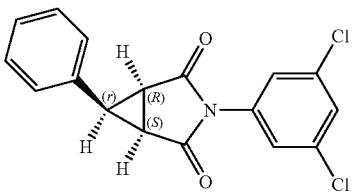
4′c
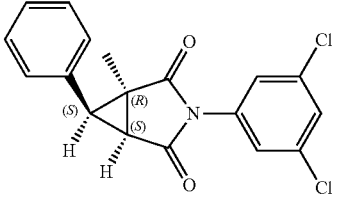
4′d
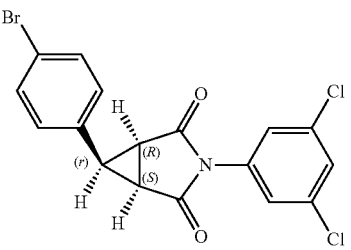
4′e
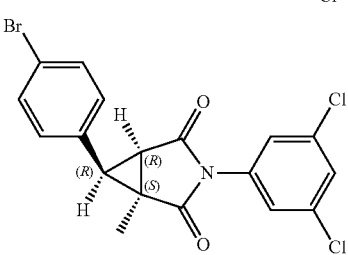
4′f

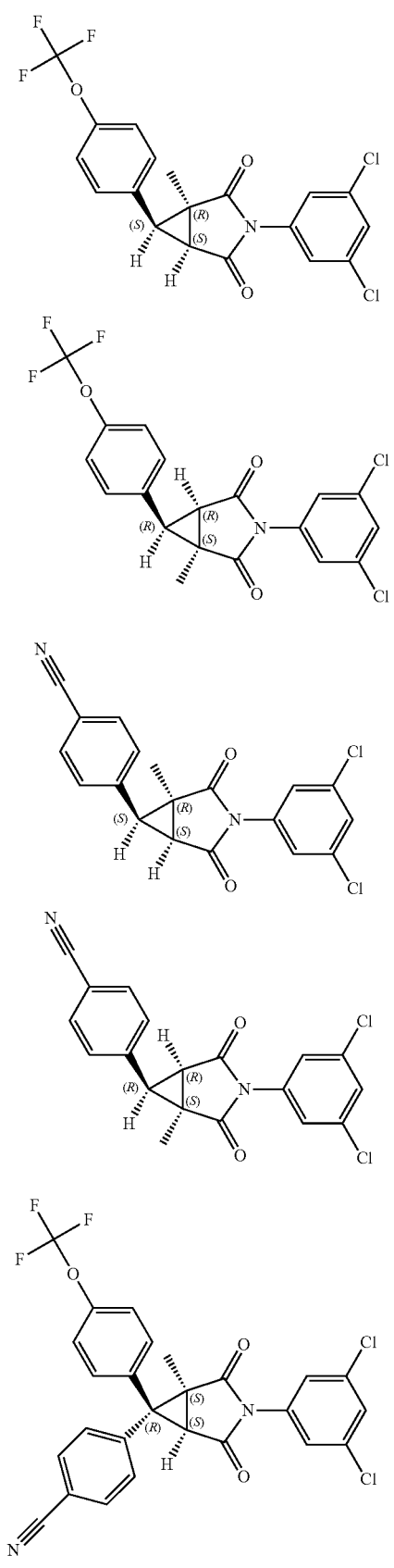
4'g
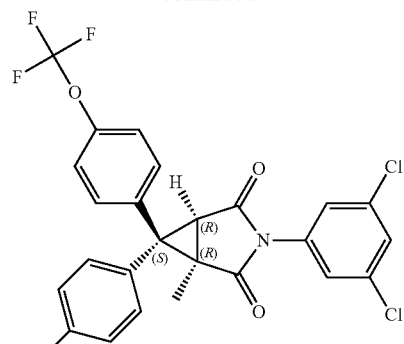
4'h
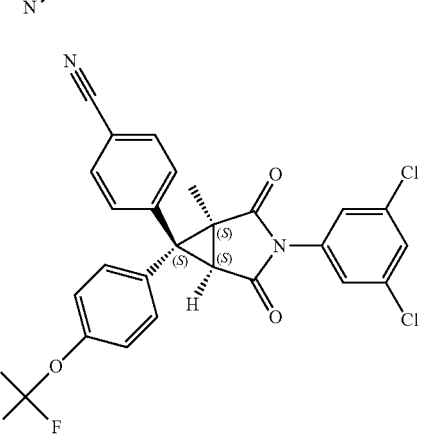
4i/4'i
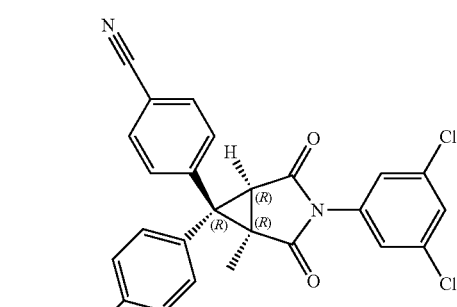
4'j
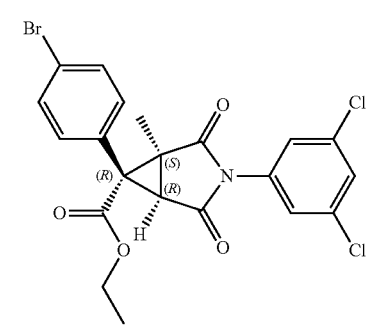

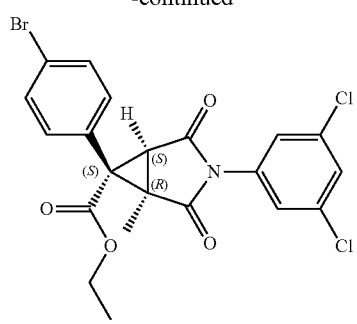
Most particular preferred compounds are the following compounds:
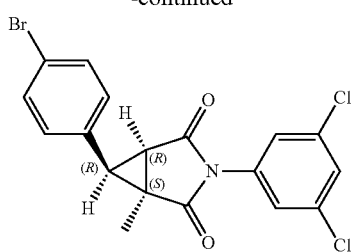
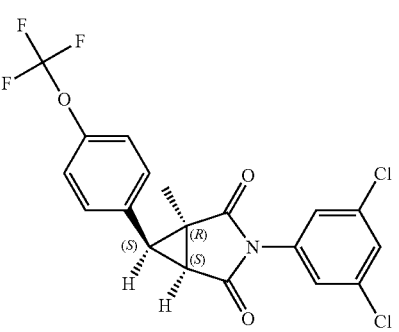
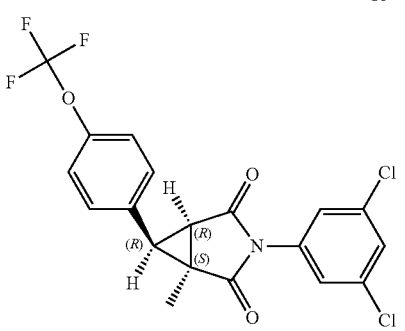
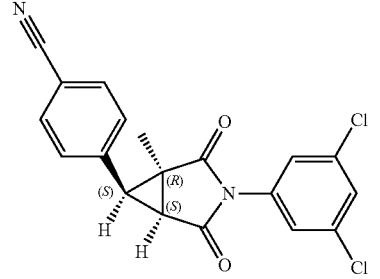
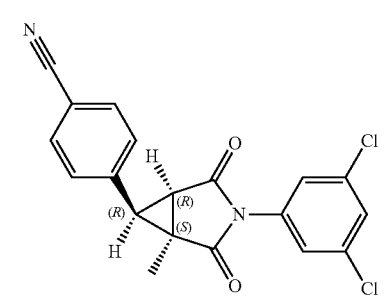

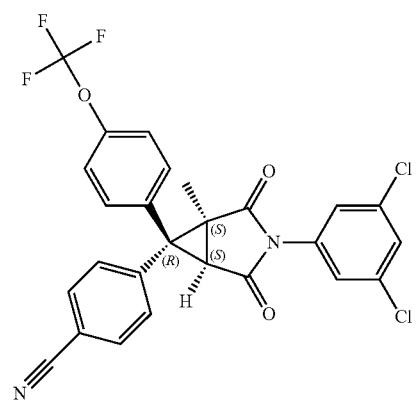
4i or 4'i
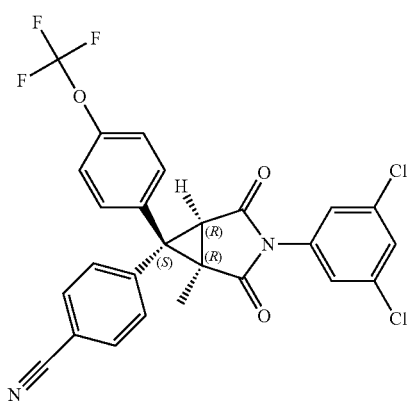
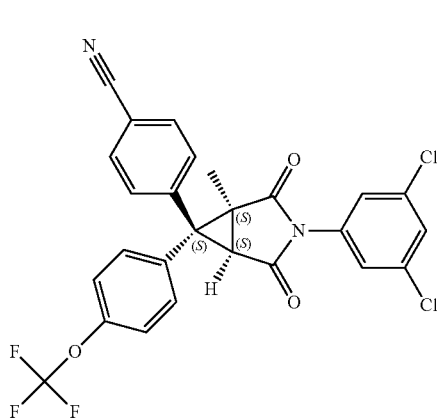
4i or 4'i
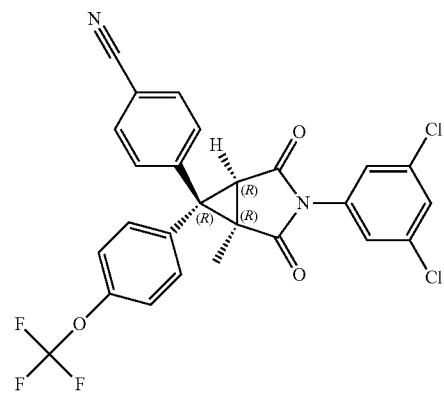
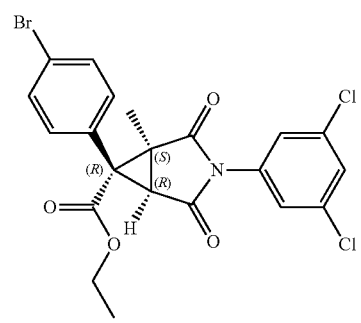
4'j
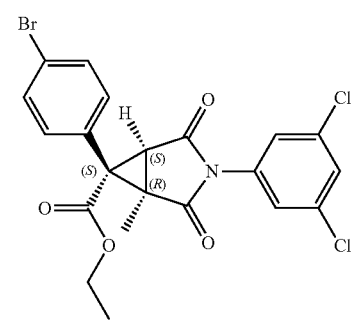
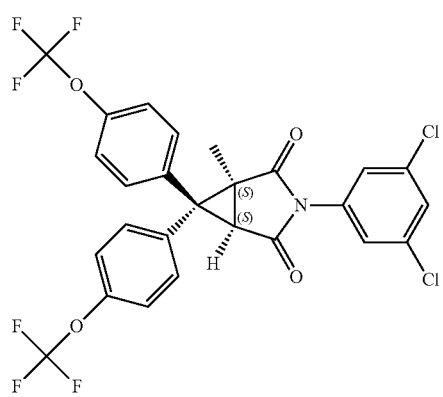
4q
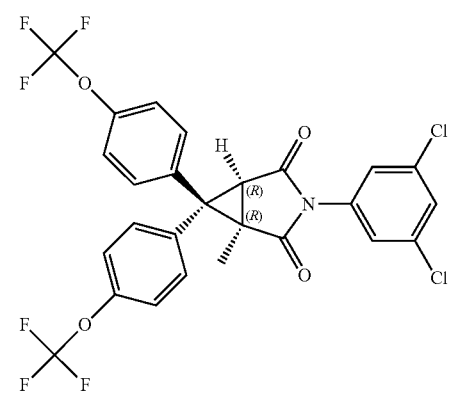

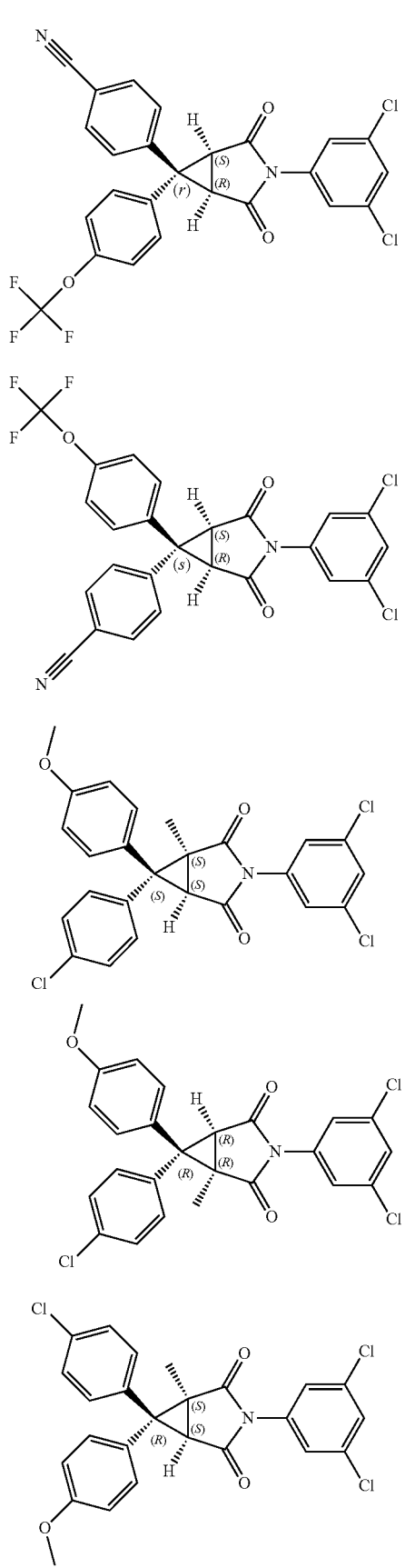
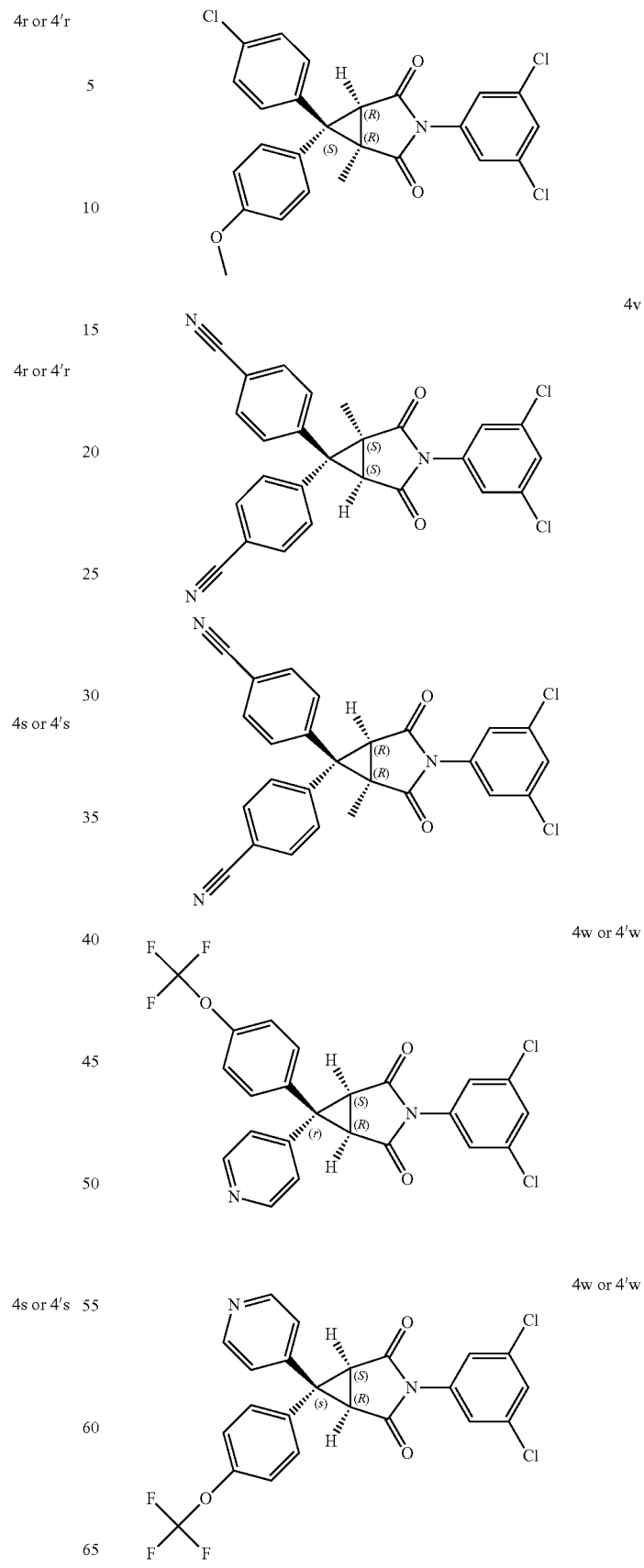

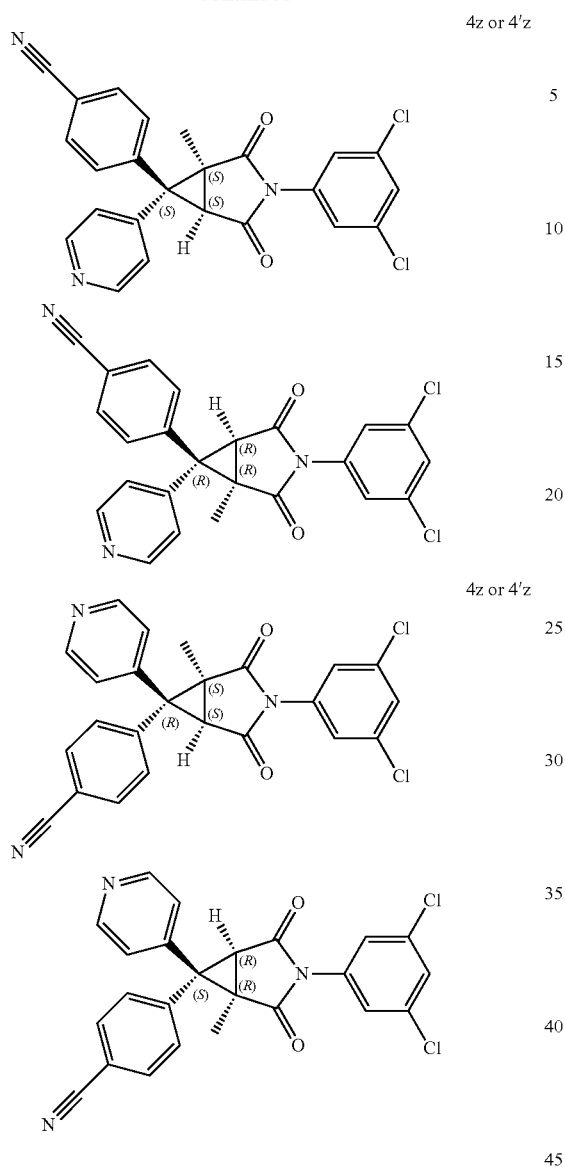
Equally most particular preferred compounds are the following compounds:
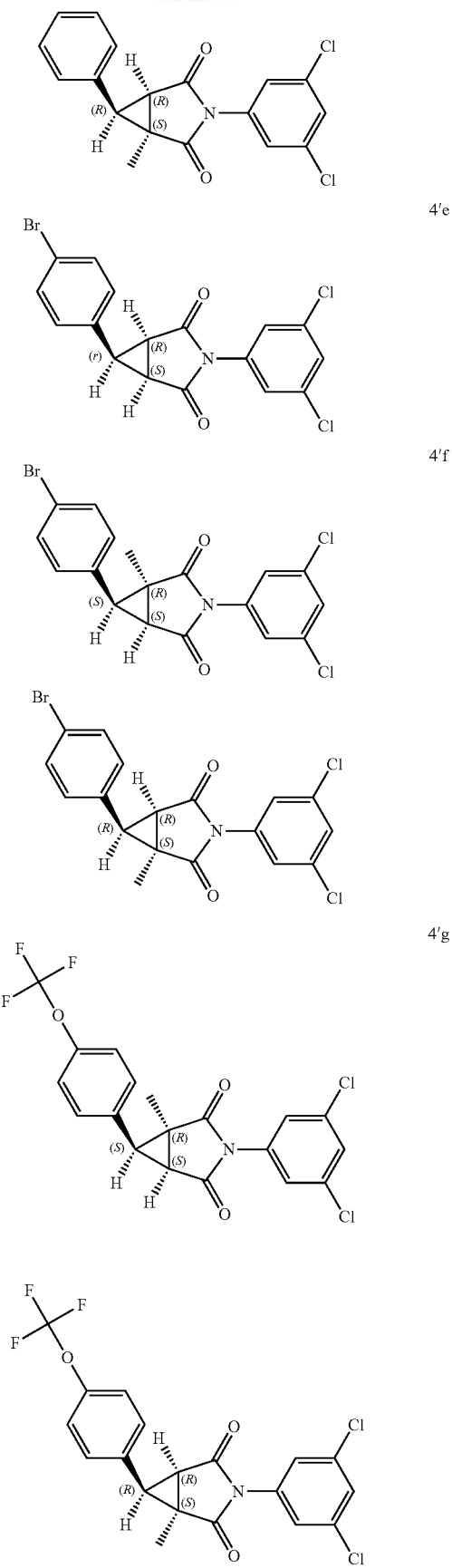

81
-continued

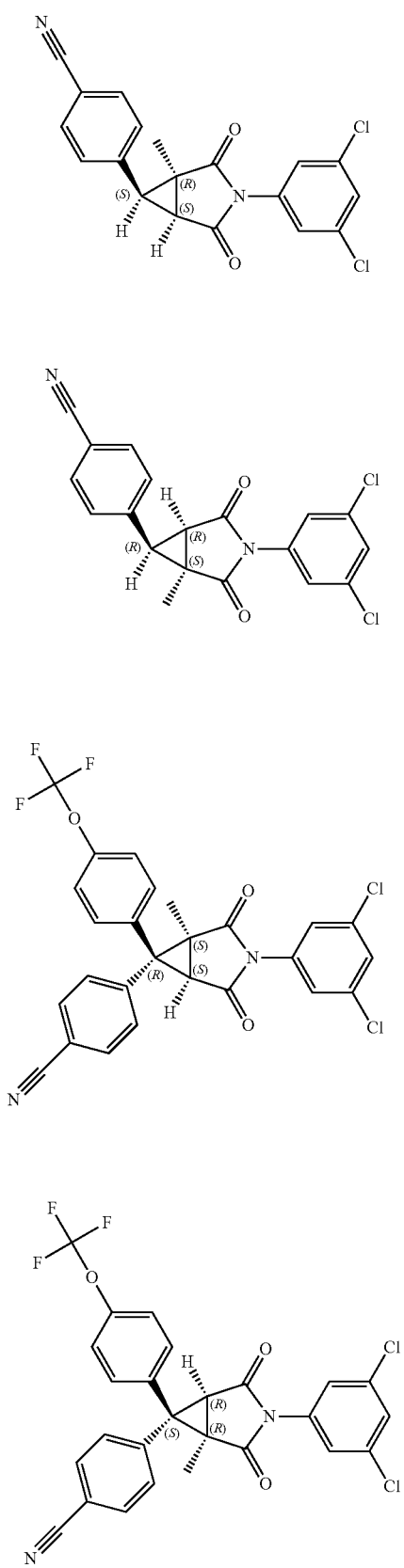

4'h

82
-continued

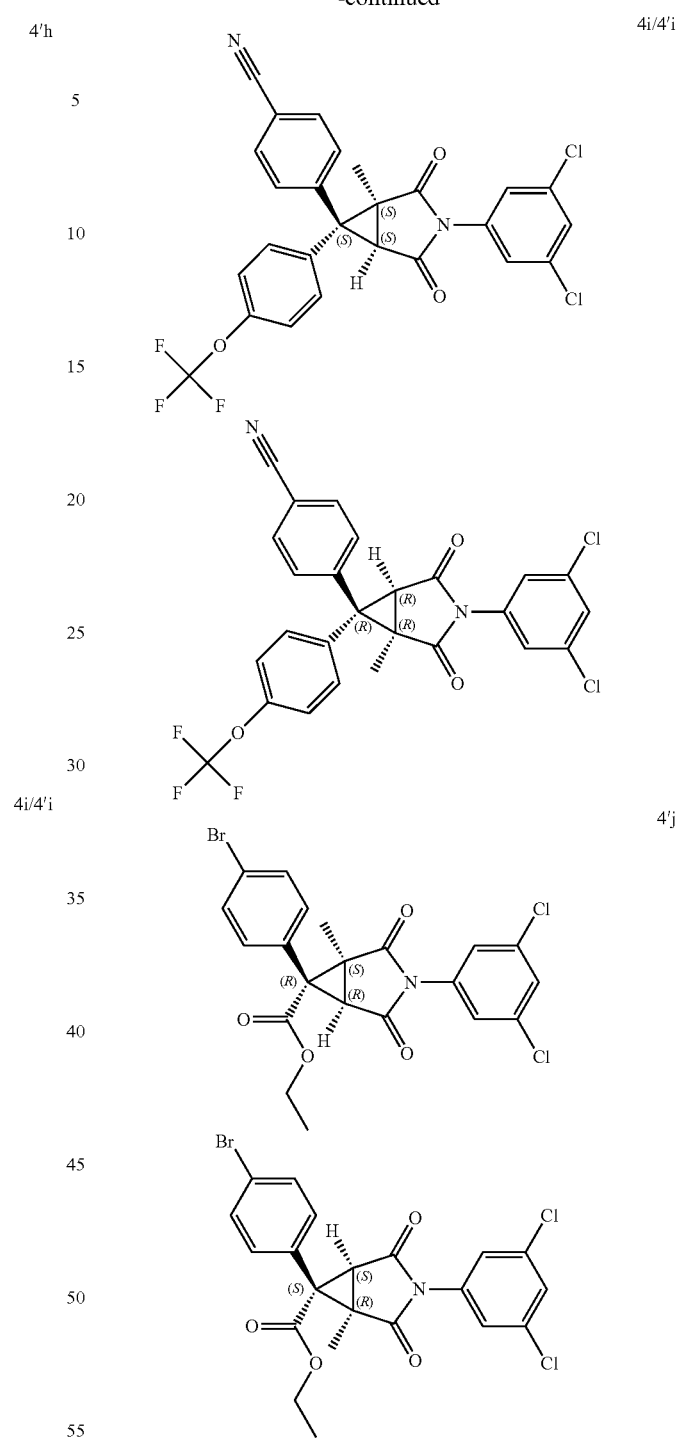

4i/4'i

4i/4'i

4'j

Compounds of the present invention can exist as stereoisomers wherein asymmetric or chiral centers are present. These compounds are designated by the symbols "R" or "S", depending on the configuration of substituents around the chiral carbon atom. The present invention contemplates various stereoisomers and mixtures thereof. Stereoisomers include enantiomers and diastereomers, and mixtures of enantiomers or diastereomers. Individual stereoisomers of compounds of the present invention can be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, or (3) direct separation of the mixture of optical enantiomers on chiral chromatographic columns.

Geometric isomers can also exist in the compounds of the present invention. The present invention contemplates the various geometric isomers and mixtures thereof resulting from the arrangement of substituents around a carbon-carbon double bond or arrangement of substituents around a carbocyclic ring.

Compounds of the present invention can also exist as racemates which is given the descriptor "rac". The term racemate, as used herein, means an equimolar mixture of a pair of enantiomers. A racemate is usually formed when synthesis results in the generation of a stereocenter. As used herein, the term racemic mixture means racemate. Compounds of the present invention can also exist as diastereomeric meso forms which is given the descriptor "rel". The term diastereomeric meso form as used herein means achiral forms with a pseudostereogenic C-atom, which is given the descriptor "r" or "s", respectively.

Salts

The compounds of the present invention may be used in the form of pharmaceutically-acceptable salts derived from inorganic or organic acids. By "pharmaceutically-acceptable salt" is meant those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically-acceptable salts are well-known in the art. The salts may be prepared in situ during the final isolation and purification of the compounds of the invention or separately by reacting a free base function with a suitable acid.

Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethanesulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quatemized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically-acceptable basic addition salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like.

Prodrugs/Solvates/Hydrates

Compounds of the formula I may have prodrug forms. Any compound e.g. the compound according to formula (Ia) and/or (Ib) which will be converted in vivo to provide the bioactive agent for example, by hydrolysis in blood is a prodrug within the scope of this invention. Various forms of prodrugs are well known in the art It should be appreciated that solvates and hydrates of the compound according to formula (Ia) and or (Ib) are also within the scope of the present application. Methods of solvation are generally known in the art.

A further embodiment of the present invention may also include compounds, which are identical to the compounds of formula (Ia) and/or (Ib) except that one or more atoms are replaced by an atom having an atomic mass number or mass different from the atomic mass number or mass usually found in nature, e.g. compounds enriched in $^2$H (D), $^3$H, $^{13}$C, $^{127}$I etc. These isotopic analogs and their pharmaceutical salts and formulations are considered useful agents in therapy and/or diagnosis, for example, but not limited to, where a fine-tuning of in vivo half-life time could lead to an optimized dosage regimen.

Preparation of the Compounds

The compounds of the invention may be prepared by the exemplary processes described in the following reaction schemes or by the processes described in the examples below. Exemplary reagents and procedures for these reactions appear hereinafter. Starting materials can be purchased or readily prepared by one of ordinary skill in the art.

Scheme A

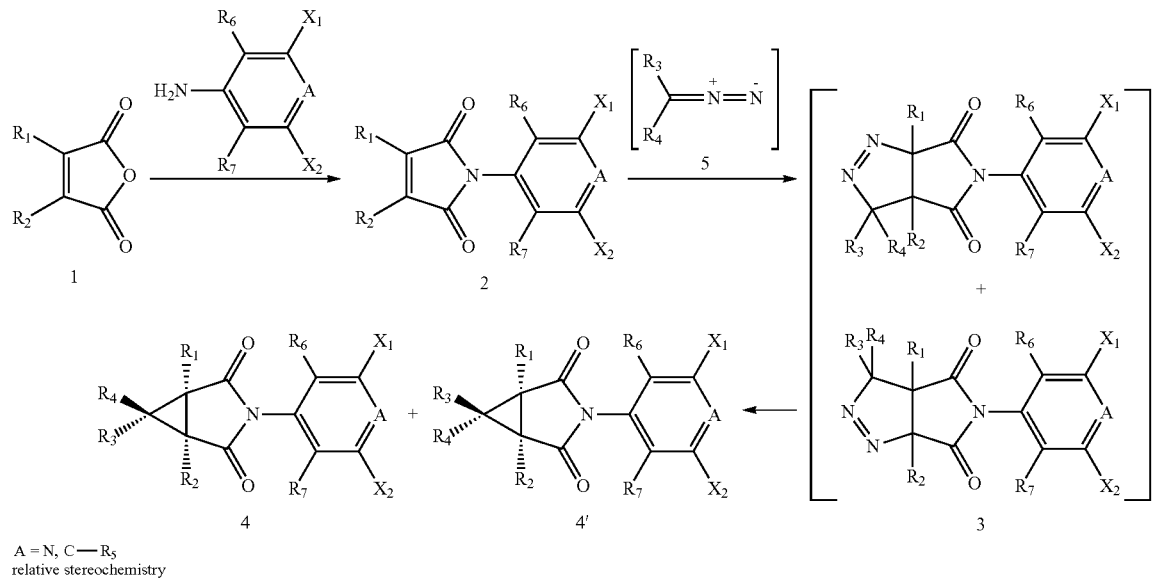

A = N, C—R$_5$
relative stereochemistry

Methods of Scheme A

To a solution of anhydride 1 (1 eq.) in acetic acid amine (1 eq.) can be added. The reaction mixture can be boiled for 2-10 h. The solvent can be removed at reduced pressure. The residue dissolved in DCM and washed with sat. aq. NaHCO$_3$, aq. 1N HCl and sat. aq. NaCl, dried over Na$_2$SO$_4$ and the solvent can be removed at reduced pressure. The crude product can be purified by silica gel flash chromatography. [Shults 2005]

To a solution of maleimide 2 (1 eq.) in DCM or toluene a solution of diazo compound in DCM or toluene can be added. The mixture can be stirred at rt for 2-10 days till disappearance of the diazo colour. The precipitate can be filtered off and washed with ethanol [Molchanov 2002]. In cases without a precipitate, the solution can be used directly in the next step.

A mixture of pyrazoline-intermediate 3 and toluene can be heated to 100° C. for 1-2 h at 100° C. The solvent can be removed at reduced pressure and the crude product can be purified by silica gel flash chromatography. [Molchanov 2002]

Scheme B

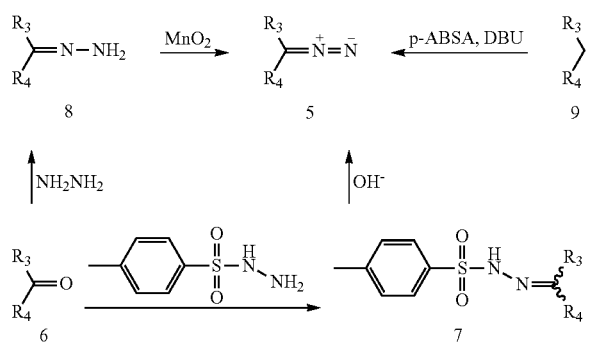

Methods of Scheme B

To the hydrazone 8 (1 eq.) in DCM MnO$_2$ can be added. The suspension can be stirred for 15 min at rt. The mixture can be filtered and the purple solution of 5 can be used directly in the next step [Kotera 2005].

To a stirred suspension of 4-toluenesulfonohydrazide (1 eq.) and MeOH the aldehyde or ketone 6 (1 eq.) can be added. After 1-14 h stirring at different temperatures (rt until 60° C.) the reaction can be complete and the suspension can be filtered or centrifuged, washed with small amounts of MeOH to afford solid 7. [Aggarwal 2003]

The hydrazone 7 (1 eq.) and TEBAC (0.25 eq.) can be stirred in aq. NaOH (15%, 10 eq.) and toluene under nitrogen. After 1-2 h strong stirring at 70° C. the reaction is usually complete.

The deep red/purple organic layer can be washed with sat. aq. NH$_4$Cl, sat. aq. NaCl and dried with Na$_2$SO$_4$. This solution of 5 can be used directly in the next step [Zhou 2009].

To a solution of the ester 9 (1 eq.) and p-ABSA (1.5 eq.) in 10 mL dry CH$_3$CN at 0° C. DBU (1.5 eq.) can be added over 30 min. After stirring for 1 h at rt, the mixture can be partitioned between water and EtOAc. The combined organic extract can be dried and concentrated. The residue can be purified by silica gel flash chromatography to afford 5[Taber 2005].

To the ketone 6 (1 eq.) in ethanol hydrazine (14 eq.) can be added. The mixture can be refluxed for 10 h. The hydrazone can be isolated by extraction [Reimlinger 1964].

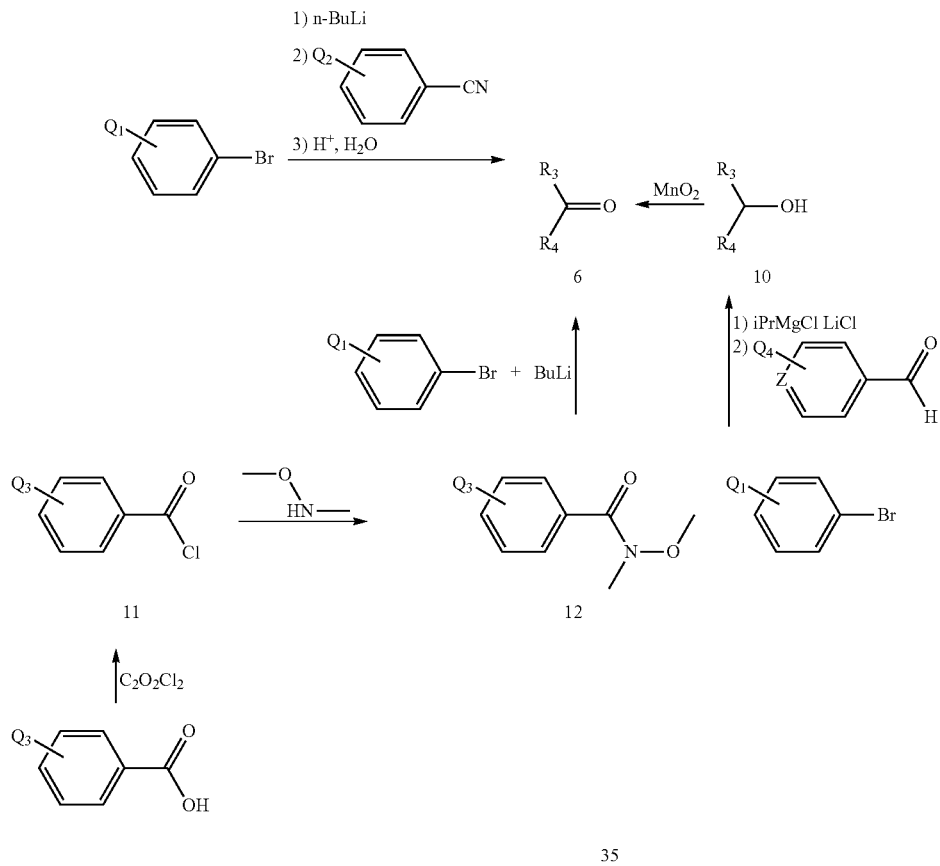

Method of Scheme C

To the substituted bromobenzene (1 eq.) in THF at −78° C. n-BuLi (2.5 M in hexane, 1 eq.) can be added dropwise and the mixture can be stirred at −78° C. for 1 h [WO2008/64057 A1 2008]. To the solution of substituted phenyllithium in ether (1 eq.) benzonitrile (1 eq.) in ether can be added at 0° C. and the mixture can be stirred at rt overnight. The reaction mixture can be poured onto ice (in some cases acidified). The resulting mixture can be allowed to warm to rt and extracted with ether, dried and concentrated at reduced pressure. The crude product can be purified by chromatography on alumina [Cook 1980].

To a 1.3 M i-PrMgCl.LiCl solution (1 eq.) an aromatic bromide (1.05 eq.) in THF can be added at 0° C. After 2 h the aldehyde (1.05 eq.) can be added at −10° C. After 20 min the mixture can be quenched with sat. aqueous NH$_4$Cl solution, worked up by extraction and purified by silica gel flash chromatography to afford the alcohol 10 [Krasovskiy 2004].

To the alcohol 10 (1 eq.) in methylene chloride MnO$_2$ (10 eq.) can be added. The suspension can be stirred for 1 h at rt, worked up by filtration and purified by silica gel flash chromatography to afford the ketone 6 [Nakayama 2006].

To a solution of acid (1 eq.) in DMF/DCM (1:5) oxalyl chloride (1.4 eq.) can be added. After 5 h at 45° C. N,O-dimethylhydroxylamine hydrochloride (1.5 eq.) and pyridine (2 eq.) can be added at 0° C. After 2 h at rt the reaction mixture can be worked-up by extraction and purified by silica gel flash chromatography to afford the Weinreb amide 12 [Aidhen 2013].

Diagnostic and Therapeutic Use

The compounds according to the invention as described supra stabilize the leukocyte integrin LFA-1 in its inactive state, preventing the binding of activated LFA-1 to its natural counter ligands. These molecules have diagnostic, preventive and therapeutic utility in human and veterinary diseases mediated by LFA-1 bearing cells, with these cells including lymphocytes, monocytes/macrophages, dendritic cells, neutrophils, eosinophils, basophils, mast cells, plasma cells among other leukocyte populations, also including malignant leukocyte populations. Diseases mediated by LFA-1 bearing cells include inflammatory, immune-mediated, infectious and malignant conditions as well as conditions mediated by reperfusion injury. Immune-mediated conditions include autoimmune diseases, transplantion indications and allergic diseases. Transplantation indications include allo- and xeno-transplantation of organs, tissues and/or cells.

Infectious diseases are diseases caused by pathogenic microorganisms, e.g. bacteria, viruses, fungi, helminths or protozoa. Malignant diseases are characterized by abnormal cells which divide uncontrollably and have the ability to infiltrate and destroy normal body tissue, e.g. carcinomas, sarcomas, melanomas, leukaemias, multiple myeloma, lymphomas. Autoimmune diseases are diseases in which body cells or tissues are attacked by the immune system, e.g. systemic and cutaneous lupus erythematosus, non-infectious posterior uveitis, Crohn's disease, rheumatoid arthritis, psoriasis, multiple sclerosis, Sjogren syndrome, type I diabetes mellitus, multiple sclerosis, myositis, dermatomyositis, autoimmune hepatitis, vasculitis. Transplantation indications are e.g. kidney, heart, liver, lung, pancreas, islet cell, small bowel, cornea, middle ear, skin, bone, bone marrow, heart valve, connective tissue, stem cell and progenitor cell transplantation. Allergic diseases are e.g. allergic rhinitis, allergic conjunctivitis, asthma, food allergies, insect venom allergies, contact dermatitis and eczema (atopic dermatitis).

Multiple organ injury syndromes secondary to septicemia or trauma are e.g. sepsis or trauma-induced multiple organ dysfunction or failure; acute respiratory distress syndrome; sepsis-associated encephalopathy; mucosal inflammatory disease affects oral, nasal, sinus and gastrointestinal mucosal linings, e.g. stomatitis, periodontitis, mucositis, rhinosinusitis, esophagitis, gastritis and intestinal mucosal lesional diseases; reactive forms of arthritis are e.g. *yersinia*-, *campylobacter*-, *salmonella*-, *shigella*- and *chlamydia trachomatis*-associated arthritis; autoimmune rheumatic diseases are e.g. rheumatoid arthritis, systemic lupus erythematosus, Sjogren syndrome, systemic vasculitides, scleroderma, mixed connective tissue disease, dermatomyositis and antiphospholipid syndrome leukotoxin-producing bacterial infections are e.g. infections caused by Aggregatibacter *actinomycetemcomitans*, *Mannheimia haemolytica*; other malignancies involving cells expressing LFA-1 or its ligands are e.g. melanoma, lung cancer, renal cell carcinoma, hepatocellular carcinoma; indications which are candidates for the induction of regulatory cell populations and/or immune tolerance i.e. indications in which induction of immune tolerance is sought, are e.g. autoimmune diseases, allergies and transplantation indications. Indications which are candidates for the induction of immune tolerance are e.g. immune-mediated diseases in which disease-driving antigens or allergens are known.

Tolerance inducing regimens in transplantation and immune-mediated diseases is e.g. use as a single agent or in combination with other immunomodulatory modalities to induce immunological tolerance, e.g. use for the generation of regulatory T-cell populations in vivo, ex vivo or in vitro for inducing immunological tolerance or use within adjunctive cell therapy in the context of transplantation indications.

Conditions which may be treated with the compounds according to the invention include, but are not limited to, acute respiratory distress syndrome, shock, oxygen toxicity, sepsis, multiple organ injury syndromes secondary to septicemia or trauma; reperfusion injury of tissues due to cardiopulmonary bypass, myocardial infarction, stroke or use of thrombolysis agents; thermal injury; transfusion related injury; hemodialysis; inflammatory and immune-mediated skin diseases including psoriasis, atopic dermatitis, contact dermatitis, cutaneous lupus erythematodes, vitiligo, rosacea, acne, lichen planus, pemphigus vulgaris, bullous pemphigoid, scleroderma and neutrophilic dermatoses; chronic urticaria, alopecia; paradontal and mucosal inflammatory disease; inflammatory and immune-mediated diseases afflicting the eye including conjunctivitis, dry eye disease, diabetic macular edema, Behcet's disease, Sjogren syndrome, uveitis; vasculitis; myositis and dermatomyositis; rheumatoid arthritis, ankylosing spondylitis, psoriatric arthritis, reactive forms of arthritis; osteoarthritis, osteoporosis; multiple sclerosis, acute and chronic glomerulonephritis, diabetes mellitus, pancreatitis, viral and autoimmune hepatitis, gastritis, inflammatory bowel disease including Crohn's disease and ulcerative colitis, necrotizing enterocolitis; systemic lupus erythematosus, systemic sclerosis, autoimmune rheumatic diseases and other systemic or organ/tissue specific autoimmune diseases; chronic obstructive pulmonary disease (COPD), emphysema; pulmonary fibrosis; chronic bronchitis; asthma, allergic rhinitis, atopic and allergic diseases; autoimmune polyglandular disease, Addison's disease, Grave's disease, autoimmune thyroiditis; acute and chronic rejection of organ/tissue transplants (e.g. kidney, heart, lung, liver, islet cells, small bowel, cornea, skin, bone marrow, stem cells and/or other cells derived from such organs/tissues) and graft-versus-host-disease; tolerance inducing regimens in transplantation and immune-mediated diseases; indications for cell therapy involving cell populations treated with LFA-1 inhibitors in vitro, ex vivo, in vivo; Alzheimer's disease; atherosclerosis and chronic cardiovascular disease; wound healing; malaria, HIV infection and leukotoxin-producing bacterial infections, multiple myeloma, lymphoma, leukemia or other malignancies involving LFA-1 expressing cells including malignancies involving cells expressing LFA-1 or its ligands. Indications for cell therapy involving cell populations treated with LFA-1 inhibitors in vitro, ex vivo, in vivo are e.g. indications for cell therapy involving cell treatment with LFA-1 inhibitors in vitro, ex vivo, in vivo.

Preferred conditions which may be treated with the compounds according to the invention are selected from the group consisting of non-infectious uveitis, dry eye disease, diabetic macular edema, inflammatory and immune-mediated diseases afflicting the eye; cutaneous lupus erythematosus, psoriasis, atopic dermatitis, lichen planus, pemphigus, pemphigoid, neutophilic dermatoses, inflammatory and immune-mediated skin diseases; systemic lupus erythematosus; vasculitis; myositis; rheumatoid arthritis, ankylosing spondylitis, psoriatic arthritis, arthritis; transplantation indications; indications which are candidates for the induction of regulatory cell populations and/or immune tolerance; multiple sclerosis; type I diabetes mellitus; autoimmune hepatitis; asthma and allergic diseases; immune-mediated diseases in which disease-driving antigens or allergens are known; indications for cell therapy involving cell populations treated with LFA-1 inhibitors in vitro, ex vivo, in vivo; and malignancies involving LFA-1 expressing cells including malignancies involving cells expressing LFA-1 or its ligands.

More preferred conditions which may be treated with the compounds according to the invention are selected from the group consisting of non-infectious uveitis, dry eye disease, diabetic macular edema, inflammatory and immune-mediated diseases afflicting the eye; cutaneous lupus erythematosus, psoriasis, atopic dermatitis, lichen planus, pemphigus, pemphigoid, neutophilic dermatoses, inflammatory and immune-mediated skin diseases; systemic lupus erythematosus; vasculitis; myositis; rheumatoid arthritis, ankylosing spondylitis, psoriatic arthritis, arthritis; transplantation indications; indications which are candidates for the induction of regulatory cell populations and/or immune tolerance; multiple sclerosis; type I diabetes mellitus; autoimmune hepatitis; asthma and allergic diseases; immune-mediated diseases in which disease-driving antigens or allergens are known; indications for cell therapy involving cell populations treated with LFA-1 inhibitors in vitro, ex vivo, in vivo; malignancies involving LFA-1 expressing cells including malignancies involving cells expressing LFA-1 or its ligands, inflammatory bowel disease including Crohn's disease and ulcerative colitis, wound healing, and HW infection.

Most preferred conditions which may be treated with the compounds according to the invention are selected from the group consisting of non-infectious uveitis, conjunctivitis, dry eye disease, diabetic macular edema, cutaneous lupus erythematosus, psoriasis, atopic dermatitis, lichen planus, pemphigus, pemphigoid, neutophilic dermatoses; systemic lupus erythematosus; vasculitis, myositis, rheumatoid arthritis, ankylosing spondylitis, psoriatic arthritis, arthritis, multiple sclerosis, type I diabetes mellitus; autoimmune hepatitis, asthma, allergic diseases, inflammatory bowel disease including Crohn's disease and ulcerative colitis, wound healing, and HIV infection, in particular non-infectious uveitis, conjunctivitis, dry eye disease, diabetic macular edema, cutaneous lupus erythematosus, psoriasis, atopic dermatitis, lichen planus, pemphigus, pemphigoid, neutophilic dermatoses, systemic lupus erythematosus; vasculitis, myositis, rheumatoid arthritis, ankylosing spondylitis, psoriatic arthritis, arthritis, multiple sclerosis, type I diabetes mellitus; autoimmune hepatitis, asthma and allergic diseases.

Thus, in a further aspect the present invention provides the use of the compounds as described supra and the use of the pharmaceutical composition described below for diagnostic, preventive and/or therapeutic purposes.

In one embodiment of the present invention, the compounds according to the invention as described supra may be used as a medicament, preferably for use in human medicine and/or veterinarian medicine.

In another embodiment, the compounds according to the invention as described supra may be used in a method for preventing or treating a condition associated with LFA-1 or its counter-ligands in a subject.

In another embodiment, the compounds according to the invention as described supra may be used in a method for preventing or treating aberrant immune responses (e.g. in immune-mediated disease and transplantation) and/or for inducing immune tolerance.

In another embodiment, the compounds according to the invention as described supra may be used in diagnosis and/or prognosis of a condition associated with LFA-1 or its counter ligands. In another embodiment, the compounds according to the invention as described supra may be used in the mobilization of LFA-1 bearing cells e.g. in the context of e.g. stem or progenitor cell transplantation or the treatment of malignant diseases, e.g. leukemias or e.g. for harvesting or for sensitizing cells.

In another embodiment, the compounds according to the invention as described supra may be used as an adjunct to minimize the toxicity of combination regimens e.g. used for the treatment of immune-mediated diseases, transplantation indications and malignant diseases.

In another embodiment, the compounds according to the invention as described supra may be used to treat leukocyte populations in vitro, ex vivo and in vivo in the context of cell therapy i.e. cell-based therapy, e.g. within cell therapy regimens involving regulatory cell populations or for the ex-vivo or in vitro generation of regulatory T-cell populations in the treatment of autoimmune or allergic diseases or transplantation indications.

In another embodiment, the compounds according to the invention as described supra may be used in a method for preventing and treating a condition associated with LFA-1 or its counter-ligands to enhance the effectiveness of combination regimens, e.g. for the use in combination with other modalities providing additive or synergistic therapeutic effect, e.g. immunomodulatory combination regimens for immune-mediated diseases or cytotoxic combination regimens for malignant diseases.

In another embodiment, the compounds according to the invention as described supra may be used as carriers directing drugs and marker molecules to LFA-1 bearing cells both for diagnostic (e.g. imaging of inflammatory and malignant lesions; assessment of tumor load; identification of different prognostic sub-groups) and therapeutic purposes (e.g. for targeting immunomodulatory and cancer therapies).

In another embodiment, the compounds according to the invention as described supra may be used in a method for treating LFA-1 expressing malignancies to enhance the effectiveness of apoptosis-inducing or anti-proliferative regimens.

Preferably a condition associated with LFA-1 or its counter-ligands is selected from non-infectious uveitis, dry eye disease, diabetic macular edema, inflammatory and immune-mediated diseases afflicting the eye; cutaneous lupus erythematosus, psoriasis, atopic dermatitis, lichen planus, pemphigus, pemphigoid, neutophilic dermatoses, inflammatory and immune-mediated skin diseases; systemic lupus erythematosus; vasculitis; myositis; rheumatoid arthritis, ankylosing spondylitis, psoriatic arthritis, arthritis; transplantation indications; indications which are candidates for the induction of regulatory cell populations and/or immune tolerance; multiple sclerosis; type I diabetes mellitus; autoimmune hepatitis; asthma and allergic diseases; immune-mediated diseases in which disease-driving antigens or allergens are known; indications for cell therapy involving cell populations treated with LFA-1 inhibitors in vitro, ex vivo, in vivo; or malignancies involving LFA-1 expressing cells.

Compounds according to the invention as described supra may also be used to treat LFA-1 expressing malignancies, e.g. in conjunction with apoptosis-inducing or anti-proliferative regimens.

The veterinary utility of the compounds will be for immune-mediated, inflammatory, malignant and infectious diseases corresponding to human disease pathologies included above, including species-specific diseases (such as leukotoxin-producing *Mannheimia haemolytica* infections).

When provided preventively, the immunosuppressive compound(s) are provided in advance of established disease (for example, prior to, at, or shortly after the time of an organ or tissue transplant but in advance of symptoms of organ rejection). The preventive administration of a compound of the present invention serves to prevent or attenuate the evolution of disease (such as, for example, rejection of a transplanted organ or tissue, etc.). The therapeutic administration of a compound of the present invention serves to attenuate established disease (such as, for example, the rejection of a transplanted organ or tissue). Thus, in accordance with the invention, a compound of the present invention can be administered either prior to the onset of disease or during the course of disease.

The compounds of the present invention may, in accordance with the invention, be administered in single or divided doses by oral, parenteral, inhalatory, rectal or topical administration including cutaneous, ophthalmic, mucosal scalp, sublingual, buccal and intranasal routes of administration; further, the compounds provided by the invention may be formulated to be used for the treatment of leukocyte populations ex vivo and in vitro.

When the compounds of the present invention are to be administered e.g. by the oral route, they may be administered as medicaments in the form of pharmaceutical compositions which contain them in association with a pharmaceutically acceptable carrier material. Thus the present invention also provides a pharmaceutical composition comprising the compounds according to the invention as described supra and one or more pharmaceutically acceptable carrier. The pharmaceutical compositions can be prepared in a conventional manner and finished dosage forms can be solid dosage forms, for example, tablets, dragees, capsules, and the like, or liquid dosage forms, for example solutions, suspensions, emulsions and the like. Pharmaceutically acceptable carriers include sterile aqueous solutions or dispersions and sterile powders for the extemporaneous preparation of sterile injectable solutions or dispersion. The use of such media and agents for pharmaceutically active substances is known in the art.

For parenteral use, a compound according to the invention as described supra can be administered in an aqueous or non-aqueous solution, suspension or emulsion in a pharmaceutically acceptable oil or a mixture of liquids.

For topical and localized use, a compound according to the invention as described supra can be administered as a liquid, gel, cream, ointments and the like.

The compounds of this invention may also be administered as solutions for nasal and inhaled application.

The compounds provided by the invention can be administered by suppository.

Additionally, the compounds provided by the invention can be used within in vitro and ex vivo cultures of leukocyte populations, e.g. within cell therapy regimens.

In accordance with the method and the pharmaceutical composition provided by the invention, the compounds according to the invention as described supra may be administered for either a "preventive" or "therapeutic" purpose either alone or with other pharmaceutical active agents such as anti-inflammatory, immunosuppressive, immunomodulatory, anti-fibrotic, anti-proliferative, anti-viral, anti-bacterial, anti-fungal or anti-malarial agents, used in combination or sequentially.

Assays

The biological properties of compounds of the present invention can be investigated by assays known in the art e.g. by way of the experimental protocols described in the experimental section. Assays which are useful to determine the physiological effect of the compounds are e.g. a cell-based assays to determine the effect of the compounds on LFA-1-mediated cell adhesion like an adhesion assay measuring the ability of the compounds to interfere with LFA-1-mediated binding to its counter ligands at cellular level, a cell-based assay to determine the selectivity of the compounds over the integrin VLA-4 like a cell adhesion assay measuring the effect of the compounds on VLA-4-mediated Jurkat cell binding to VCAM-1, an assay measuring mAb R7.1 binding to LFA-1 (mAb R7.1 binding), like a flow cytometry assay determining the effect of the compounds on the binding of the anti-LFA-1 mAb R7.1 to LFA-1 expressed on leukocytes, assays to quantify mAb MEM148 binding to LFA-1 (mAb MEM148 binding), using e.g. a flow cytometry assay to determine the effect of the compounds on the binding of the conformation-sensitive anti-LFA-1 mAb MEM148 to LFA-1 expressed on leukocytes, and assays to assess cellular toxicity using e.g. the Toxilight™ BioAssay (Lonza) or the CellTiter-Glo™ Luminescent Cell Viability Assay (Promega).

REFERENCES CITED IN THE DESCRIPTION

This list of references cited by the applicant does not form part of the patent document. It is for the reader's convenience only.

[Aggarwal 2003] Aggarwal V K, Alonso E, Bae I, Hynd G, Lydon K M, Palmer M J, Patel M, Porcelloni M, Richardson J, Stenson R A, Studley J R, Vasse J L, Winn C L. A new protocol for the in situ generation of aromatic, heteroaromatic, and unsaturated diazo compounds and its application in catalytic and asymmetric epoxidation of carbonyl compounds. Extensive studies to map out scope and limitations, and rationalization of diastereo- and enantioselectivities. J Am Chem Soc. 2003 Sep. 10; 125(36):10926-40.

[Ahrens 2008] Ahrens I, Peter K. Therapeutic integrin inhibition: allosteric and activation-specific inhibition strategies may surpass the initial ligand-mimetic strategies. Thromb Haemost. 2008 May; 99(5):803-4.

[Aidhen 2013] I. S. Aidhen, K. Harikrishna, A. Rakshit, *Eur. J. Org. Chem.* 2013, 4918.

[Arefanian 2010] Arefanian H, Tredget E B, Rajotte R V, Gill R G, Korbutt G S, Rayat G R. Short-term administrations of a combination of anti-LFA-1 and anti-CD154 monoclonal antibodies induce tolerance to neonatal porcine islet xenografts in mice. Diabetes. 2010 April; 59(4): 958-66.

[Bourget 2005] Bourget C, Trévisiol E, Bridon I, Kotera M, Lhomme J, Laayoun A. Biotin-phenyldiazomethane conjugates as labeling reagents at phosphate in mono and polynucleotides. Bioorg Med Chem. 2005 March 1; 13(5):1453-61.

[Chittasupho 2010] Chittasupho C, Manikwar P, Krise J P, Siahaan T J, Berkland C. cIBR effectively targets nanoparticles to LFA-1 on acute lymphoblastic T cells. Mol Pharm. 2010 Feb. 1; 7(1):146-55

[Cook 1980] Cook L S, Wakefield B J. Enamidines. Part 1. Synthesis of enamidines and dihydrntriazines by the reaction of organolithium and organomagnesium compounds with aromatic nitriles. J. Chem. Soc., Perkin Trans. 1, 1980, 2392-2397.

[Faia 2011] Faia L J, Sen H N, Li Z, Yeh S, Wroblewski K J, Nussenblatt R B. Treatment of inflammatory macular edema with humanized anti-CD11a antibody therapy. Invest Ophthalmol Vis Sci. 2011 Sep. 1; 52(9):6919-24.

[Giblin 2006] Giblin P A, Lemieux R M. LFA-1 as a key regulator of immune function: approaches toward the development of LFA-1-based therapeutics. Curr Pharm Des. 2006; 12(22):2771-95.

[Glawe 2009] Glawe J D, Patrick D R, Huang M, Sharp C D, Barlow S C, Kevil C G. Genetic deficiency of Itgb2 or ItgaL prevents autoimmune diabetes through distinctly different mechanisms in NOD/LtJ mice. Diabetes. 2009 June; 58(6):1292-301.

[Hogg 2011] Hogg N, Patzak I, Willenbrock F. The insider's guide to leukocyte integrin signalling and function. Nat Rev Immunol. 2011 June; 11(6):416-26

[Jabado 1996] Jabado N, Le Deist F, Cant A, De Graeff-Meeders E R, Fasth A, Morgan G, Vellodi A, Hale G, Bujan W, Thomas C, Cavazzana-Calvo M, Wijdenes J, Fischer A. Bone marrow transplantation from genetically HLA-nonidentical donors in children with fatal inherited disorders excluding severe combined immunodeficiencies: use of two monoclonal antibodies to prevent graft rejection. Pediatrics. 1996 September; 98(3 Pt 1):420-8.

[Kapp T G] Kapp T G, Rechenmacher F, Sobahi T R, Kessler H. Integrin modulators: a patent review. Expert Opin Ther Pat. 2013 October; 23(10):1273-95.

[Ke 2007] Ke Y, Sun D, Zhang P, Jiang G, Kaplan H J, Shao H. Suppression of established experimental autoimmune uveitis by anti-LFA-1alpha Ab. Invest Ophthalmol Vis Sci. 2007 June; 48(6):2667-75.

[Krasovskiy 2004] A. Krasovskiy, P. Knochel, Angew. Chem. Int. Ed. 2004, 43, 3333.

[Lebwohl 2003] Lebwohl M, Tyring S K, Hamilton T K, Toth D, Glazer S, Tawfik N H, Walicke P, Dummer W, Wang X, Garovoy M R, Pariser D; Efalizumab Study Group. A novel targeted T-cell modulator, efalizumab, for plaque psoriasis. N Engl J Med. 2003 Nov. 20; 349(21): 2004-13.

[Lee 2008] Lee S H, Prince J E, Rais M, Kheradmand F, Ballantyne C M, Weitz-Schmidt G, Smith C W, Corry D B. Developmental control of integrin expression regulates Th2 effector homing. J Immunol. 2008 Apr. 1; 180(7): 4656-67.

[Molchanov 2002] Molchanov A P, Diev V V, Kostikov R R. Reactions of aliphatic diazo compounds: IV. Reaction of diphenyldiazomethane with substituted imides of maleic and itaconic acids. Russian Journal of Organic Chemistry. February 2002; 38(2):259-263.

[Nakayama 2006] Nakayama et al., Patent No. US2006/0202197 A1.

[Navarini 2010] Navarini A A, Kerl K, French L E, Trüeb R M. Control of widespread hypertrophic lupus erythematosus with T-cell-directed biologic efalizumab. Dermatology. 2010; 220(3):249-53.

[Nicolls 2006] Nicolls M R, Gill R G. LFA-1 (CD11a) as a therapeutic target. Am J Transplant. 2006; 6(1):27-36.

[Poria 2006] Poria R B, Norenberg J P, Anderson T L, Erion J, Wagner C R, Arterburn J B, Larson R S. Characterization of a radiolabeled small molecule targeting leukocyte function-associated antigen-1 expression in lymphoma and leukemia. Cancer Biother Radiopharm. 2006 October; 21(5):418-26.

Posselt A M, Bellin M D, Tavakol M, Szot G L, Frassetto L A, Masharani U, Kerlan R K, Fong L, Vincenti F G, Hering B J, Bluestone J A, Stock P G. Islet transplantation in type 1 diabetics using an immunosuppressive protocol based on the anti-LFA-1 antibody efalizumab. Am J Transplant. 2010 August; 10(8):1870-80.

[Reimlinger 1964] H. Reimlinger, Chem. Ber. 1964, 97, 3493.

[Salas 2004] Salas A, Shimaoka M, Kogan A N, Harwood C, von Andrian U H, Springer T A. Rolling adhesion through an extended conformation of integrin alphaLbeta2 and relation to alpha I and beta I-like domain interaction. Immunity. 2004 April; 20(4):393-406.

[Seminara 2010] Seminara N M, Gelfand J M. Assessing long-term drug safety: lessons (re) learned from raptiva. Semin Cutan Med Surg. 2010 March; 29(1):16-9.

[Sheppard 2014] Sheppard J D, Torkildsen G L, Lonsdale J D, D'Ambrosio F A Jr, McLaurin E B, Eiferman R A, Kennedy K S, Semba C P; OPUS-1 Study Group. Lifitegrast ophthalmic solution 5.0% for treatment of dry eye disease: results of the OPUS-1 phase 3 study. Ophthalmology. 2014 February; 121(2):475-83.

[Shults 2005] Shults E E, Shakirov M M, Tolstikov G A, Kalinin V N, Schmidhammer G. Thebaine adducts with maleimides. Synthesis and transformations. Russian Journal of Organic Chemistry, 2005; 41 (8): 1132-1144.

[Suchard 2010] Suchard S J, Stetsko D K, Davis P M, Skala S, Potin D, Launay M, Dhar T G, Barrish J C, Susulic V, Shuster D J, McIntyre K W, McKinnon M, Salter-Cid L. An LFA-1 (alphaLbeta2) small-molecule antagonist reduces inflammation and joint destruction in murine models of arthritis. J Immunol. 2010 Apr. 1; 184(7):3917-26.

[Taber 2005] Taber D F, Sheth R B, Joshi P V. Simple preparation of alpha-diazo esters. J Org Chem. 2005 Apr. 1; 70(7):2851-4.

[Tan S M 2012] Tan S M. The leucocyte β2 (CD18) integrins: the structure, functional regulation and signalling properties. Biosci Rep. 2012 June; 32(3):241-69.

[Usmani 2007] Usmani N, Goodfield M. Efalizumab in the treatment of discoid lupus erythematosus. Arch Dermatol. 2007 July; 143(7):873-7. [Verma 2012] Verma N K, Dempsey E, Long A, Davies A, Barry S P, Fallon P G, Volkov Y, Kelleher D. Leukocyte function-associated antigen-1/intercellular adhesion molecule-1 interaction induces a novel genetic signature resulting in T-cells refractory to transforming growth factor-β signaling. J Biol Chem. 2012 Aug. 3; 287(32):27204-16.

[Weitz-Schmidt 2004] Weitz-Schmidt G, Welzenbach K, Dawson J, Kallen J. Improved lymphocyte function-associated antigen-1 (LFA-1) inhibition by statin derivatives: molecular basis determined by x-ray analysis and monitoring of LFA-1 conformational changes in vitro and ex vivo. J Biol Chem. 2004 Nov. 5; 279(45):46764-71.

[Weitz-Schmidt 2012] Weitz-Schmidt G, Chreng S. Cell adhesion assays. Methods Mol Biol. 2012; 757:15-30.

[WO2008/064057 A1] Wang A X, Zheng B Z, D'Andrea, S, Meanwell, N A, Scola P M. Macrocyclic peptides as hepatitis C virus inhibitors. WO2008/064057 A1, 2008

[Yuki 2012] Yuki K, Bu W, Xi J, Sen M, Shimaoka M, Eckenhoff R G. Isoflurane binds and stabilizes a closed conformation of the leukocyte function-associated antigen-1. FASEB J. 2012 November; 26(11):4408-17

[Zhou 2009] Zhou Y, Trewyn B G, Angelici R J, Woo L K. Catalytic reactions of carbene precursors on bulk gold metal. J Am Chem Soc. 2009 Aug. 26; 131(33):11734-43.

EXAMPLES

Abbreviations of the Description
aq. aqueous

BCECF 2',7'-Bis-(2-Carboxyethyl)-5-(and-6)-Carboxyfluorescein, Acetoxymethyl Ester
BSA bovine serum albumin
DAD diode array detector
DBU 1,8-diazabicyclo[5.4.0]undec-7-ene
DCM dichloromethane
DMSO dimethylsulfoxide
EtOAc ethylacetate
EtOH ethylalcohol
FCS fetal calf serum
FITC fluorescein isothiocyanate
hept heptane (isomeric mixture)
HPLC high-performance liquid chromatography
ICAM intercellular adhesion molecule
JAM-1 junctional adhesion molecule-A
LAD-I leukocyte adhesion deficiency-I
LFA-1 lymphocyte-function-associated antigen-1
mAb monoclonal antibody
MeOH methylalcohol
MFI mean fluorescence intensity
n-BuLi n-butyllithium
p-ABSA 4-acetoamidobenzenesulfonylazide
PBMC peripheral blood mononuclear cell
PBS phosphate buffered saline
PE phycoerythrin
sat. saturated
TBME tert-butylmethylether
TEBAC triethylbenzylammoniumchloride
THF tetrahydrofuran
TLC thin layer chromatography
VCAM-1 vascular cell adhesion molecule-1
VLA-4 very late antigen-4

The compounds have been prepared in accordance to the following Schemes/methods. However other methods are known for the synthesis.

Scheme A

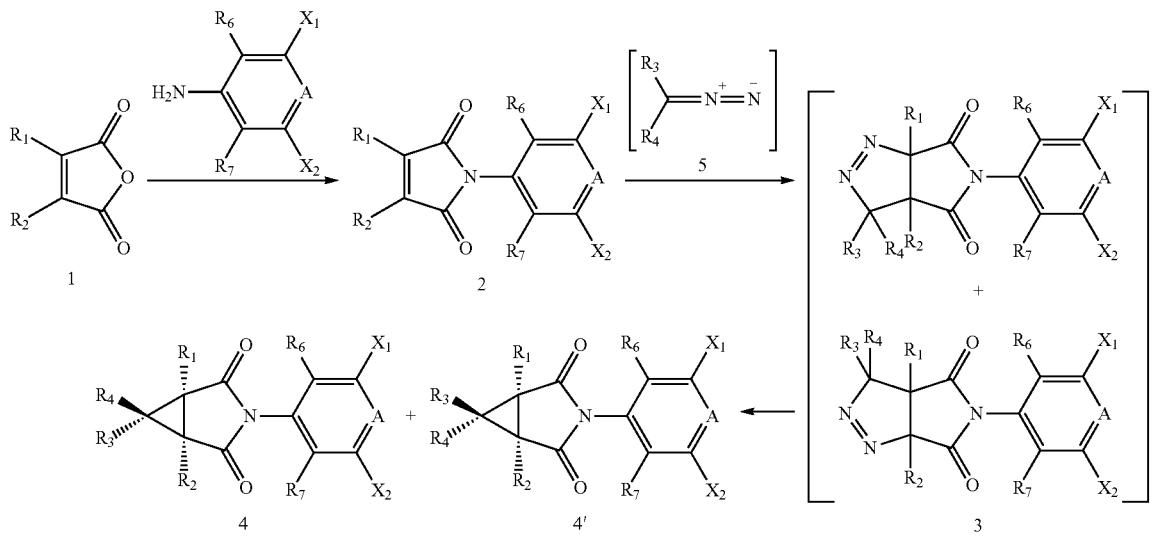

A = N, C—R$_5$
relative stereochemistry

Scheme B

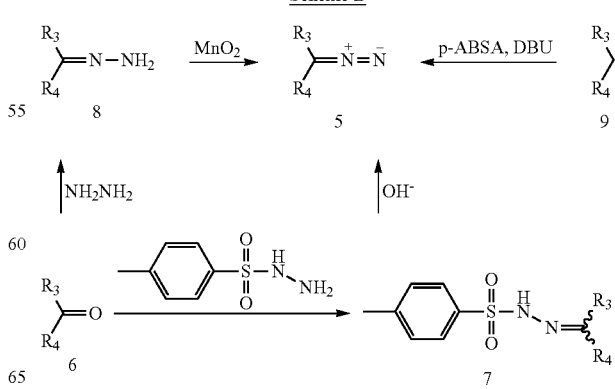

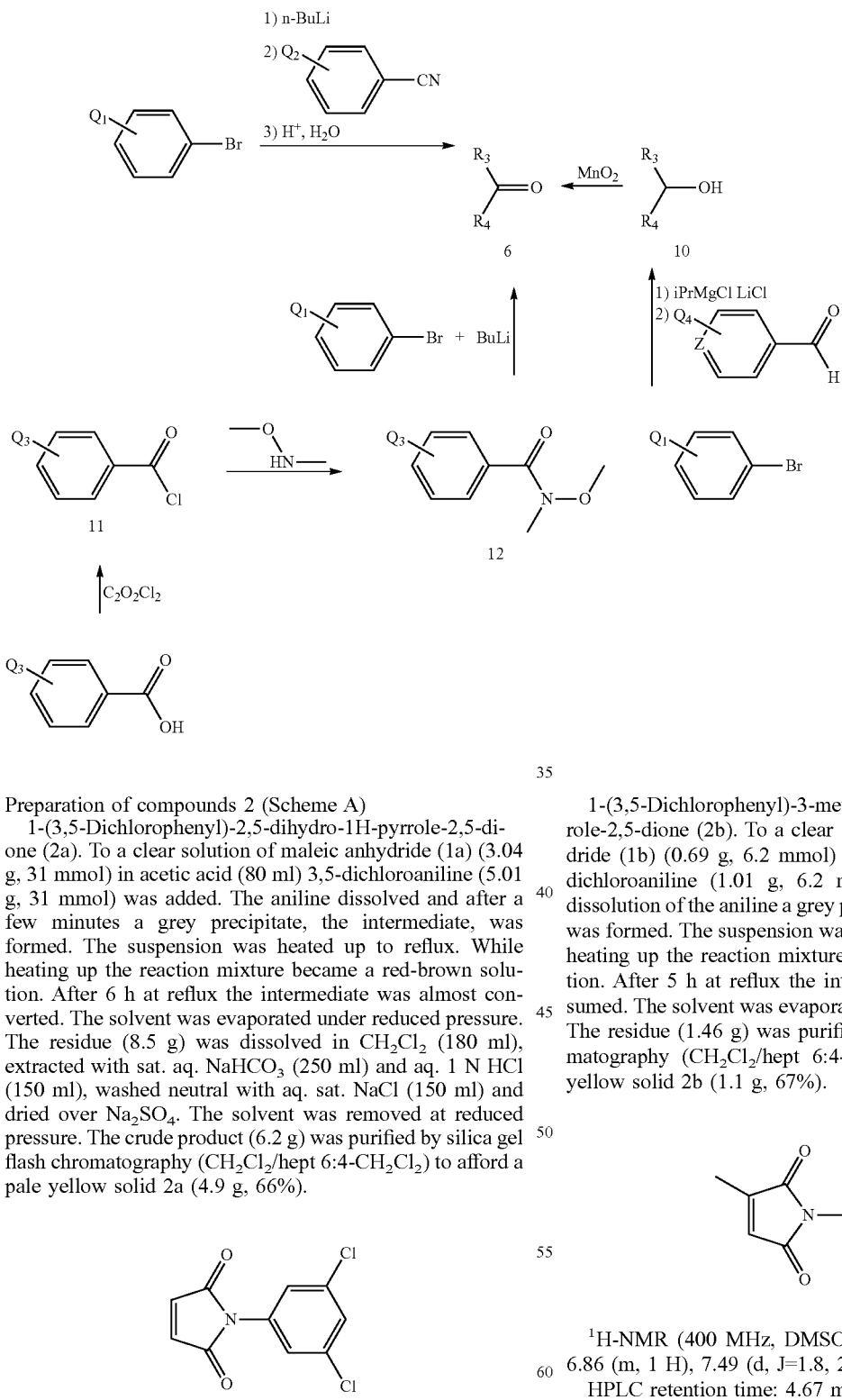

Scheme C

Preparation of compounds 2 (Scheme A)

1-(3,5-Dichlorophenyl)-2,5-dihydro-1H-pyrrole-2,5-dione (2a). To a clear solution of maleic anhydride (1a) (3.04 g, 31 mmol) in acetic acid (80 ml) 3,5-dichloroaniline (5.01 g, 31 mmol) was added. The aniline dissolved and after a few minutes a grey precipitate, the intermediate, was formed. The suspension was heated up to reflux. While heating up the reaction mixture became a red-brown solution. After 6 h at reflux the intermediate was almost converted. The solvent was evaporated under reduced pressure. The residue (8.5 g) was dissolved in $CH_2Cl_2$ (180 ml), extracted with sat. aq. $NaHCO_3$ (250 ml) and aq. 1 N HCl (150 ml), washed neutral with aq. sat. NaCl (150 ml) and dried over $Na_2SO_4$. The solvent was removed at reduced pressure. The crude product (6.2 g) was purified by silica gel flash chromatography ($CH_2Cl_2$/hept 6:4-$CH_2Cl_2$) to afford a pale yellow solid 2a (4.9 g, 66%).

$^1$H-NMR (400 MHz, DMSO-$d_6$): 7.24 (s, 2 H); 7.51 (d, J=1.9, 2 H); 7.68 (t, J=1.9, 1 H).

$^{13}$C-NMR (400 MHz, DMSO-$d_6$): 125.26, 127.21, 133.84, 133.88, 134.92, 169.13. HPLC retention time: 4.34 min 1-(3,5-Dichlorophenyl)-3-methyl-2,5-dihydro-1H-pyrrole-2,5-dione (2b). To a clear solution of citraconic anhydride (1b) (0.69 g, 6.2 mmol) in acetic acid (30 ml) 3,5-dichloroaniline (1.01 g, 6.2 mmol) was added. During dissolution of the aniline a grey precipitate, the intermediate, was formed. The suspension was heated up to reflux. While heating up the reaction mixture became a red-brown solution. After 5 h at reflux the intermediate was totally consumed. The solvent was evaporated under reduced pressure. The residue (1.46 g) was purified by silica gel flash chromatography ($CH_2Cl_2$/hept 6:4-$CH_2Cl_2$) to afford a pale yellow solid 2b (1.1 g, 67%).

$^1$H-NMR (400 MHz, DMSO-$d_6$): 2.08 (d, J=1.8, 3 H), 6.86 (m, 1 H), 7.49 (d, J=1.8, 2 H), 7.66 (t, J=1.8, 1 H).

HPLC retention time: 4.67 min

Preparation of ketone 6i (Scheme C, $Q_1$=p-$OCF_3$, $Q_2$=p-CN)

4-{[4-(Trifluoromethoxy)phenyl]carbonyl}benzonitrile (6i). To a solution of n-butyl lithium (8.87 ml, 12.5 mmol) in THF (30 ml) at −70° C. 4-bromotrifluoromethoxybenzene (3.00 g, 12.5 mmol) in THF (10 ml) was added without allowing the temperature to exceed −70° C. To the grey-brown solution 1,4-dicyanobenzene (1.60 g, 12.5 mmol) was added as a suspension in THF (10 ml). After 2 h at −70° C. the red suspension was quenched with aq. 2N HCl (75 ml) and ice (about 25 g) and TBME (150 ml) was added. After separation of the organic layer the inorganic phase was extracted with TBME (2×30 ml). The organic phases were combined, dried over Na$_2$SO$_4$ and concentrated at reduced pressure. The crude product (2 g) was purified by silica gel flash chromatography (TBME/hept 1:8) to afford a white solid 6i (1.2 g, 33%).

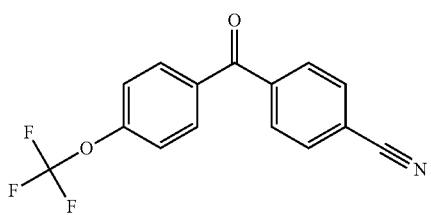 [SMILES: N#Cc1ccc(C(=O)c2ccc(OC(F)(F)F)cc2)cc1]

$^1$H-NMR (400 MHz, CDCl$_3$): 7.35 (m, 2 H), 7.78-7.91 (m, 6 H).

HPLC retention time: 4.95 min

Preparation of diazo compounds 5 from hydrazone 8 (with MnO$_2$) (Scheme B)

Diphenyldiazomethane (5a). To a clear solution of benzophenonhydrazone (8a) (101 mg, 0.5 mmol) in CH$_2$Cl$_2$ (9 ml) activated MnO$_2$ (370 mg, 85%, 3.6 mmol) was added. This purple suspension was stirred for 30 min at rt. After stirring, the purple clear solution containing 5a was removed from the precipitated MnO$_2$ and used directly in the next step for the preparation of the pyrazoline-intermediate 3.

Preparation of diazo compounds 5 through DBU and p-ABSA (Scheme B)

Ethyl-2-(4-bromophenyl)-2-diazoacetate (5j). To a solution of ethyl-4-bromophenylacetate (9j) (400 mg, 1.65 mmol) and 4-acetamidobenzenesulfonylazide (p-ABSA) (593 mg, 2.47 mmol) in dry CH$_3$CN (4 mL) at 0° C. 1,8-diazabicyclo[5.4.0]undec-7-ene (DBU) (376 mg, 2.47 mmol) was added. The mixture was stirred at rt overnight, poured onto water (30 mL) and extracted with EtOAc (3×30 mL) The combined organic layers were washed with brine (40 mL), dried over Na$_2$SO$_4$ and the solvent evaporated under reduced pressure. The residue was dissolved in CH$_2$Cl$_2$ (30 mL) whereby the side product 4-acetamidobenzenesulfonamide precipitated as a white solid. The suspension was filtered through silica gel and concentrated to afford an orange solid 5j (359 mg, 81%).

Preparation of diazo compounds from aldehydes or ketones through tosylhydrazones 7 (Scheme B)

a) Tosylhydrazones (7)

4-Methyl-N'-(1-phenylmethylidene)benzene-1-sulfonohydrazide (7c). To a stirred white suspension of 4-toluenesulfonohydrazide (5.16 g, 28 mmol) and MeOH (12 ml) benzaldehyde (3.24 g, 30 mmol) was added dropwise during 15 min. The reaction was slightly exothermic; the temperature didn't exceed 30° C. and there resulted a clear and yellow solution. After 45 min stirring at rt a white precipitate was formed. 75 min after addition the reaction was complete. The suspension was cooled to 1° C., filtered and washed with cooled MeOH (4 ml). The filtrate was concentrated under reduced pressure and filtered again. Both filter cakes were combined and dried in vacuo to afford a white solid 7c (6.3 g, 75%).

N'-[1-(4-Bromophenyl)methylidene]-4-methylbenzene-1-sulfonohydrazide (7e/f). To a stirred white suspension of 4-toluenesulfonohydrazide (2.50 g, 13.4 mmol) and MeOH (7 ml) 4-bromobenzaldehyde (2.96 g, 14.4 mmol) was added in portions during 10-15 min. The reaction was slightly exothermic. After stirring overnight (about 14 h) at rt the reaction was complete and the white suspension was filtered, washed with MeOH (4 ml) and dried in vacuo to afford a white solid 7e (4.70 g, 92%).

4-Methyl-N'-[1-(4-[trifluoromethoxy]phenyl)methylidene]benzene-1-sulfonohydrazide (7g). To a stirred white suspension of 4-toluenesulfonohydrazide (2.00 g, 11 mmol) and MeOH (5 ml) 4-(trifluoromethoxy)benzaldehyde (2.33 g, 12 mmol) was added dropwise during 15 min. The reaction was slightly exothermic, the temperature didn't exceed 32° C. During the addition, the hydrazide dissolved and there resulted a clear, colourless solution. After 2-3 h stirring at rt the reaction was complete and the white suspension was cooled to 2-5° C., filtered, washed with MeOH (2.5 ml) and dried in vacuo to afford a white solid 7g (2.73 g, 69%).

N'[1-(4-Cyanophenyl)methylidene]-4-methylbenzene-1-sulfonohydrazide (7h). To a stirred white suspension of 4-toluenesulfonohydrazide (2.00 g, 11 mmol) and MeOH (5 ml) 4-cyanobenzaldehyde (1.59 g, 12 mmol) in MeOH (3 ml) was added dropwise during 5 min. The reaction was slightly exothermic. During the addition, the hydrazide almost dissolved. The reaction mixture was a yellow solution. After 1.5 h stirring at rt the reaction was complete and the now slightly yellow suspension was cooled to 2-5° C., filtered, washed with MeOH (2.5 ml) and dried in vacuo to afford a white solid 7h (2.77 g, 84%).

N'-[(1E/Z)-(4-Cyanophenyl)[4-(trifluoromethoxy)phenyl]methylidene]-4-methylbenzene-1-sulfonohydrazide (7i). To a stirred white suspension of 4-toluenesulfonohydrazide (129 mg, 0.69 mmol) and MeOH (1 ml) 4-{[4-(trifluoromethoxy)phenyl]carbonyl}benzonitrile (6i) (201 mg, 0.69 mmol) was added in portions during 5 min. The reaction mixture was heated to 45° C. and the starting materials almost dissolved. After 2 h stirring at 45° C. the reaction mixture was a fine, slightly yellow suspension. Centrifugation led to a white solid (30 mg, 10%). The supernatant was concentrated by a N$_2$ flow, centrifuged again and dried in vacuo to afford a pale yellow solid 7i (100 mg, 31%).

b) Diazo Compounds (5)

Phenyldiazomethane (5c). 4-Methyl-N'-(1-phenylmethylidene)benzene-1-sulfonohydrazide (7c) (233 mg, 0.85 mmol) and TEBAC (55 mg, 0.24 mmol) were stirred in aq. NaOH (15%, 3 ml) and toluene (3 ml). After stirring 5 min at 70° C. the two phases were clear and the organic phase got slightly red. After 1 h strong stirring the reaction was complete and the organic phase was deep red. The organic phase was washed with aq. sat. NH$_4$Cl (3 ml), aq. sat. NaCl (2×2 ml) and dried with Na$_2$SO$_4$. The red solution 5c was used directly in the next step.

4-Bromophenyldiazomethane (5e). N'-[1-(4-Bromophenyl)methylidene]-4-methylbenzene-1-sulfonohydrazide (7e) (200 mg, 0.57 mmol) and TEBAC (40 mg, 0.18 mmol) were stirred in aq. NaOH (15%, 3 ml) and toluene (3 ml). After stirring a few min at 70° C. the two phases were clear and the organic phase got slightly purple. After 1 h strong stirring the reaction was complete and the organic phase was deep purple. The organic phase was washed with aq. sat. NH$_4$Cl (3 ml), aq. sat. NaCl (3 ml) and dried with Na$_2$SO$_4$. The purple solution 5e was used directly in the next step.

4-Trifluoromethoxyphenyldiazomethane (5g). 4-Methyl-N'-[1-(4-[trifluoromethoxy]phenyl)methylidene]-benzene-1-sulfonohydrazide (7g) (300 mg, 0.84 mmol) and TEBAC (51 mg, 0.22 mmol) were stirred in aq. NaOH (15%, 3 ml) and toluene (3 ml). After stirring a few min at 70° C. the two phases were clear and the organic phase got slightly red. After 1 h strong stirring the reaction was complete and the organic phase was deep red. The organic phase was washed with aq. sat. $NH_4Cl$ (3 ml), aq. sat. NaCl (2×3 ml) and dried with $Na_2SO_4$. The red solution 5g was used directly in the next step.

4-Cyanophenyldiazomethane (5h). N'[1-(4-Cyanophenyl)methylidene]-4-methylbenzene-1-sulfonohydrazide (7h) (303 mg, 1 mmol) and TEBAC (60 mg, 0.26 mmol) were stirred in aq. NaOH (15%, 3 ml) and toluene (3 ml). After stirring a few min at 70° C. the two phases were clear and the organic phase got slightly red. After 1.5 h strong stirring the reaction was complete and the organic phase was deep red. The organic phase was washed with aq. sat. $NH_4Cl$ (3 ml), aq. sat. NaCl (2×3 ml) and dried with $Na_2SO_4$. The red solution 5h was used directly in the next step.

4-{Diazo[4-(trifluoromethoxy)phenyl]methyl}benzonitril (5i). N'-[(1E/Z)-(4-Cyanophenyl)[4-(trifluoro-methoxy)phenyl]methylidene]-4-methylbenzene-1-sulfonohydrazide (7i) (100 mg, 0.22 mmol) and TEBAC (23 mg, 0.5 mmol) were stirred in aq. NaOH (15%, 1.5 ml) and toluene (1.5 ml). After stirring a few min at 70° C. the two phases were clear and the organic phase got slightly red. After 0.5 h strong stirring the reaction was complete and the organic phase was deep red. The organic phase was washed with aq. sat. $NH_4Cl$ (1.5 ml), aq. sat. NaCl (1.5 ml) and dried with $Na_2SO_4$. The red solution 5i was used directly in the next step.

Preparation of compounds 9 (Scheme B)

2-(4-Bromophenyl)-1-(morpholin-4-yl)ethan-1-one (9k). A solution of 4-bromophenylacetic acid (1.0 g, 4.7 mmol) and morpholine (0.41 g, 4.7 mmol) in DCM (20 ml) was cooled to 0° C. and a mixture of DCC (0.96 g, 4.7 mmol) and DMAP (6.4 mg, 0.05 mmol) in DCM (10 ml) was added dropwise. After 16 h at rt the suspension was filtered over hyflo and the filtrate was concentrated at reduced pressure. The residue was suspended in small amounts of DCM and filtrated again. The filtrate was concentrated at reduced pressure to afford a white solid 9k (1.2 g, 90%).

1-(Morpholin-4yl)-2-[4-(trifluoromethyl)phenyl]ethan-1-one (9l). A solution of 4-(trifluoromethyl)phenylacetic acid (1.0 g, 4.9 mmol) and morpholine (0.43 g, 4.9 mmol) in DCM (20 ml) was cooled to 0° C. and a mixture of DCC (1.0 g, 4.9 mmol) and DMAP (5 mg, 0.04 mmol) in DCM (10 ml) was added dropwise. After 2 h at rt the suspension was filtered over hyflo and the filtrate was concentrated at reduced pressure. The residue was suspended in small amounts of DCM and filtrated again. The filtrate was concentrated at reduced pressure to afford a yellow oil 9l (1.29 g, 96%).

1-(Morpholin-4yl)-2-[4-(trifluoromethoxy)phenyl]ethan-1-one (9m). A solution of 4-(trifluoromethoxy)phenylacetic acid (1.0 g, 4.5 mmol) and morpholine (0.40 g, 4.5 mmol) in DCM (20 ml) was cooled to 0° C. and a mixture of DCC (0.94 g, 4.5 mmol) and DMAP (7 mg, 0.06 mmol) in DCM (10 ml) was added dropwise. After 2 h at rt the suspension was filtered over hyflo and the filtrate was concentrated at reduced pressure, the residue was dissolved in EtOAc (20 ml), and washed with aq. sat. $NH_4Cl$ (15 ml). The inorganic layer was extracted with EtOAc (2×20 ml). The organic layers were combined, washed with aq. sat. NaCl (30 ml), dried over $Na_2SO_4$ and concentrated at reduced pressure to afford a slightly brown solid 9m (1.38 g, quant.).

4-[2-(Morpholin-4-yl)-2-oxoethyl]benzonitrile (9n). A solution of 4-cyanophenylacetic acid (0.5 g, 3.1 mmol) and morpholine (0.27 g, 3.1 mmol) in DCM (20 ml) was cooled to 0° C. and a mixture of DCC (0.64 g, 3.1 mmol) and DMAP (6 mg, 0.046 mmol) in DCM (5 ml) was added dropwise. After 1 h at rt the suspension was filtered over hyflo and the filtrate was concentrated at reduced pressure, the residue was dissolved in EtOAc (20 ml), and washed with aq. sat. $NH_4Cl$ (30 ml). The inorganic layer was extracted with EtOAc (2×30 ml). The organic layers were combined, washed with aq. sat. NaCl (60 ml), dried over $Na_2SO_4$ and concentrated at reduced pressure to afford a white solid 9n (0.71 g, 99%).

Preparation of Weinreb amide 12 (Scheme C)

N-Methoxy-N-methyl-4-(trifluoromethoxy)benzamide (12q, $Q_3=OCF_3$). To a suspension of 4-(trifluoromethoxy)benzoyl chloride (2.01 g, 8.9 mmol) and N,O-dimethylhydroxylamine hydrochloride (1.04 g, 10.7 mmol) in DCM (22 ml) triethylamine (3.1 ml, 2.25 g, 22.2 mmol) was added dropwise at 0° C. After 1 h at 0° C. and 20 h at rt the reaction mixture was washed with aq. 2.5 N HCl (50 ml), aq. 1.1 N $NaHCO_3$ (3×50 ml), aq. sat. NaCl (50 ml), dried over $Na_2SO_4$ and concentrated at reduced pressure to afford a clear colourless oil 12q (1.78 g, 80%).

N,4-Dimethoxy-N-methylbenzamide (12s, $Q_3=OCH_3$). To a suspension of 4-methoxyphenylacetic acid (1.02 g, 6.6 mmol) in DCM (21 ml) oxalyl chloride (1.2 ml, 13.8 mmol, 2.1 eq.) was added at 0° C. After 3.5 h at 0° C. a slightly yellow solution was formed. The solution was added dropwise during 1 h to a suspension of N,O-dimethylhydroxylamine hydrochloride (1.09 g, 11 mmol) and triethylamine (9.6 ml, 6.91 g, 68 mmol, 10 eq.) in DCM (17 ml) at 0° C. After 4 h when the temperature had reached rt water (25 ml) was added to the reaction mixture. The organic phase was separated, washed with aq. sat. $NaHCO_3$ (2×25 ml), aq. sat. NaCl (20 ml), dried over $Na_2SO_4$ and concentrated at reduced pressure to afford a slightly yellow oil (0.83 g, 64%). The crude product was purified by silica gel flash chromatography (hept/EtOAc 3:1 to 0:1) to afford a colourless oil 12s (0.71 g, 55%).

Preparation of ketones 6 from Weinreb amide 12 (Scheme C)

Bis[4-(trifluoromethoxy)phenyl]methanone (6q, $Q_1=OCF_3$, $Q_3=OCF_3$). To a solution of 1-bromo-4-(trifluoromethoxy)benzene (1.45 g, 6 mmol) in THF (30 ml) n-buthyllithium solution (2.5 M in hexane, 2.3 ml, 0.35 g, 5.7 mmol) was added dropwise at −60° C. After 3 h at −60° C. Weinreb amide 12q (1.02 g, 4 mmol) in THF (12 ml) was added dropwise at −60° C. The orange solution was allowed to warm up overnight (about 16 h) to rt, quenched with aq. sat. $NH_4Cl$ (50 ml) and water (50 ml) and extracted with TBME (100 ml+2×50 ml). The organic layers were washed with aq. sat. $NaHCO_3$ and aq. sat. NaCl, combined, dried over $Na_2SO_4$ and concentrated at reduced pressure to afford an orange solid 6q (1.5 g, quant).

(4-Chlorophenyl)(4-methoxyphenyl)methanone (6s, $Q_1=Cl$, $Q_3=OCH_3$). To a solution of Weinreb amide 12s (0.46 g, 2.3 mmol) in THF (5 ml) 4-chlorophenylmagnesium bromide (1 M in $Et_2O$, 6.2 mL, 6.2 mmol) was added dropwise at 0° C. over 5 min. After 14 h at rt the reaction mixture was quenched with aq. sat. $NH_4Cl$ (15 ml) and EtOAc. The organic layer was washed with water (15 ml). The water layer was extracted with EtOAc (2×15 ml). The organic layers were combined, dried over $Na_2SO_4$ and concentrated at reduced pressure to afford a yellow solid (0.8 g). The crude product was purified by silica gel flash chromatography (hept/EtOAc 12:1-1:1) to afford a white solid 12s (0.55 g, 95%).

Preparation of alcohol compounds 10 through iPrMgCl (Scheme C)

4-[(4-Cyanophenyl)(hydroxy)methyl]benzonitrile (10u, $Q_1$=CN, $Q_4$=CN). To a solution of iPrMgCl LiCl complex 1.3 M in THF (10.5 ml) at −15° C. 4-bromobenzonitrile (1.4 g, 7.6 mmol) in THF (4 ml) was added dropwise over 15 min. The brown solution was stirred for 30 min at −15° C. and 1.5 h at rt. The solution was added dropwise to a yellowish solution of 4-formylbenzonitrile (1.0 g, 7.6 mmol) in THF (4 ml) over 10 min at −15° C. After 1 h stirring at 0° C. the light green solution was quenched with aq. sat. $NH_4Cl$ (20 ml), TBME (30 ml) and water (20 ml) were added. After separation of the organic layer the inorganic phase was extracted with TBME (2×20 ml). The organic layers were washed with aq. sat. NaCl, combined, dried over $Na_2SO_4$ and concentrated at reduced pressure. To the liquid crude product (2 g) EtOAc/hept 1:2 was added. An insoluble pale yellow solid (0.54 g) was filtered off, dissolved in diethylether and precipitated with pentane to afford a pale yellow solid 10u (0.49 g, 27.5%). The mother liquor was concentrated at reduced pressure and was purified by silica gel flash chromatography (EtOAc/hept 1:2) to afford a pale yellow solid 10u (0.23 g, 13%).

Pyridin-4-yl[4-(trifluoromethoxy)phenyl]methanol (10w, th=$OCF_3$, Z=N). To an iPrMgCl LiCl complex solution 1.3 M in THF (17 ml, 13 mmol) 1-bromo-4-trifluoromethoxybenzene (3 g, 12.4 mmol) was added dropwise over 15 min between −15° C. and −5° C. The brown suspension was stirred for 1 h at 0° C., for 2 h at 10° C. and overnight (about 16 h) at rt. To this brown solution 4-pyridinecarboxaldehyde (1.2 ml, 12.4 mmol) was added dropwise over 30 min between −15° C. and 0° C. and THF (10 ml) was added. The orange solution was allowed to warm up to rt and was added to a solution of aq. sat. $NH_4Cl$ (25 ml) and water (25 ml) at 0° C. The inorganic layer was extracted with EtOAc (100 ml+2×50 ml). The organic layers were combined, washed with aq. sat. NaCl, dried over $Na_2SO_4$ and concentrated at reduced pressure to afford a yellow oil (3.6 g). The crude product was purified by silica gel flash chromatography (EtOAc/hept 2:1) to afford a pale yellow solid 10w (2.8 g, 84%).

Preparation of ketones 6 from alcohols 10 (Scheme C)

4-[(4-Cyanophenyl)carbonyl]benzonitrile (6u). A suspension of 4-[(4-cyanophenyl)(hydroxy)methyl]benzonitrile (10u) (0.68 g, 2.9 mmol), $CHCl_3$ (25 ml) and $MnO_2$ (1.7 g, 17.4 mmol) was stirred for 1 h at rt. $MnO_2$ (0.8 g, 8.7 mmol) was added again and the suspension was stirred for 1.5 h at rt. The suspension was filtered and to the yellow solution $MnO_2$ (1.7 g, 17.4 mmol) was added and stirred for 2 h again. After a new addition of $MnO_2$ (0.3 g, 2.9 mmol) and stirring for 1 h the starting material was totally consumed. The $MnO_2$ was filtered off and the filtrate was concentrated at reduced pressure to afford a pale yellow solid 6u (0.57 g, 85%).

4-{[4-(Trifluoromethoxy)phenyl]carbonyl}pyridine (6w). To a solution of pyridin-4-yl[4-(trifluoromethoxy)phenyl]methanol (10w) (2.75 g, 10.2 mmol) in $CHCl_3$ (10 ml) $MnO_2$ (6.2 g, 61 mmol) was added and the suspension stirred overnight (about 16 h) at rt. The $MnO_2$ was removed by filtration and new $MnO_2$ (3 g, 29 mmol) was added. After 5 h stirring at rt more $MnO_2$ (3 g, 29 mmol) was added. After 2 h stirring at rt the $MnO_2$ was removed and the filtrate concentrated at reduced pressure to afford a pale yellow solid 6w (2.2 g, 81%).

4-[(Pyridin-4-yl)Carbonyl]Benzonitrile (6y). To a solution of 4-[hydroxy(pyridin-4-yl)methyl]benzonitrile (10y) (5 g, 23.8 mmol) in DCM (50 ml) $MnO_2$ (10.4 g, 102 mmol) was added and the suspension stirred for 44 h; after 16.5 h, 19.5 h, 22.5 h, 40.5 h fresh $MnO_2$ was added (each time 2.07 g, 20 mmol). The $MnO_2$ was removed and the filtrate concentrated at reduced pressure to afford a white solid 6y (4.49 g, 91%).

Preparation of hydrazones 8 from ketones 6 (Scheme B)

4-{[4-(Trifluoromethoxy)phenyl]methanehydrazonoyl}benzonitrile (8i). To a mixture of 4-{[4-(trifluoromethoxy)phenyl]carbonyl}benzonitrile (6i) (3.5 g, 12 mmol) and EtOH (65 ml) hydrazine monohydrate (7.6 ml, 7.8 g, 156 mmol) was added dropwise over 30 min. The yellow solution was stirred overnight (about 16 h) at 80° C., the mixture was allowed to cool to rt and EtOAc (200 ml) and $H_2O$ (80 ml) were added. The organic layer was washed neutral with water (2×50 ml) and aq. sat. NaCl (2×25 ml). The organic layer was dried over $Na_2SO_4$ and concentrated at reduced pressure to afford a slightly yellow solid 8i (3.35 g, 90%).

{Bis[4-(trifluoromethoxy)phenyl]methylidene}hydrazine (8q). To a solution of bis[4-(trifluoromethoxy)phenyl]methanone (6q) (1.0 g, 2.9 mmol) in EtOH (10 ml) hydrazine monohydrate (1.8 g, 36 mmol) was added dropwise. After stirring 4 h at 80° C. the mixture was allowed to cool down over weekend (about 60 h) to rt and EtOAc (50 ml) and water (50 ml) were added. The inorganic layer was extracted with EtOAc (2×50 ml). The organic layers were combined, washed with aq. sat. NaCl, dried over $Na_2SO_4$ and concentrated at reduced pressure to afford a slightly brown oil 8q (0.51 g, 48%).

[(4-Chlorophenyl)(4-methoxyphenyl)methylidene]hydrazine (8s). To a solution of (4-chlorophenyl)(4-methoxyphenyl)methanone (6s) (0.53 g, 2.15 mmol) in EtOH (5 ml) hydrazine monohydrate (0.32 ml, 6.4 mmol) was added. After stirring 4 h at 80° C. and 60 h at rt water (50 ml) was added. The inorganic layer was extracted with EtOAc (2×50 ml). The organic layers were combined, washed with water, aq. sat. NaCl, dried over $Na_2SO_4$ and concentrated at reduced pressure to afford a slightly orange oil 8s.

[Furan-2-yl(phenyl)methylidene]hydrazine (8t). To a mixture of 2-benzoylfuran (6t) (1.54 g, 8.9 mmol) and EtOH (25 ml) hydrazine monohydrate (5.5 ml, 113 mmol) was added dropwise. After stirring 25 h at 80° C., the mixture was allowed to cool to rt and TBME (50 ml) and water (50 ml) were added. The inorganic layer was extracted with TMBE (2×50 ml). The organic layers were combined, washed neutral with aq. sat. NaCl (25 ml), dried over $Na_2SO_4$ and concentrated at reduced pressure to afford a slightly yellow oil 8t (0.51 g, 32%).

4-[(4-Cyanophenyl)methanehydrazonoyl]benzonitrile (8u). To a mixture of 4-[(4-cyanophenyl)carbonyl]benzonitrile (6u) (0.56 g, 2.4 mmol) and EtOH (30 ml) hydrazine monohydrate (1.8 g, 36 mmol) was added dropwise over 5 min. The yellow solution was stirred overnight (about 16 h) at 80° C., the mixture was allowed to cool to rt and EtOAc (150 ml) was added. The organic layer was washed with water (50 ml+2×25 ml). The inorganic wash layers were extracted with EtOAc (2×25 ml). The organic layers were combined, washed neutral with aq. sat. NaCl (25 ml), dried over $Na_2SO_4$ and concentrated at reduced pressure to afford a slightly red solid 8u (0.51 g, 86%).

4-{[4-(Trifluoromethoxy)phenyl]methanehydrazonoyl}pyridine (8w). To a solution of 4-{[4-(trifluoromethoxy)phenyl]carbonyl}pyridine (6w) (2.1 g, 7.8 mmol) in EtOH (10 ml) hydrazine monohydrate (3.8 ml, 78 mmol) was added dropwise over 5 min. After stirring overnight (about 16 h) at 60° C. the mixture was allowed to cool down to rt and EtOAc (150 ml) was added. The organic layer was washed with water (2×50 ml). The inorganic wash layers were extracted with EtOAc (2×50 ml). The organic layers were combined, washed with aq. sat. NaCl (2×10 ml), dried over $Na_2SO_4$ and concentrated at reduced pressure to afford a pale yellow solid 8w (2.2 g, 100%).

4-(Pyridin-4-ylmethanehydrazonoyl)benzonitrile (8y).

To a solution of 4-[(pyridin-4-yl)carbonyl]benzonitrile (6y) (4.0 g, 19.2 mmol) in EtOH (100 ml) hydrazine monohydrate (12.1 ml, 250 mmol) was added. After stirring overnight (about 15 h) at 78° C. the mixture was allowed to cool down to rt and was poured into cold water (200 ml). The yellow suspension was stirred for 30 min and filtrated. The residue was dried at reduced pressure to afford a yellow solid 8y (3.4 g, 80%).

Preparation of diazo compounds 5 from hydrazone 8 (with $MnO_2$) (Scheme B)

4-[Diazo(phenyl)methyl]pyridine (5o). To a solution of 4-(phenylmethanehydrazonoyl)pyridine (8o) (0.24 g, 1.22 mmol) in $CHCl_3$ (5 ml) $MnO_2$ (0.64 g, 7.4 mmol) was added. After 30 min the $MnO_2$ was removed by filtration and the red solution 5o was used directly in the next step.

4-{Diazo[4-(trifluoromethoxy)phenyl]methyl}benzonitrile (5i). To a solution of 4-{[4-(trifluoromethoxy)phenyl]methanehydrazonoyl}benzonitrile (8i) (0.20 g, 0.65 mmol) in $CHCl_3$ (2 ml) $MnO_2$ (0.335 g, 3.28 mmol) was added. After 30 min stirring at rt $MnO_2$ was removed and the red solution 5i was used directly in the next step.

1-{Diazo[4-(trifluoromethoxy)phenyl]methyl}-4-(trifluoromethoxy)benzene (5q). To a solution of {bis[4-(trifluoromethoxy)phenyl]methylidene}hydrazine (8q) (0.89 g, 2.44 mmol) in $CHCl_3$ (5 ml) $MnO_2$ (0.686 g, 6.7 mmol) was added. After 1 h $MnO_2$ (0.686 g, 6.7 mmol) was added again. After 30 min the suspension was filtered, the red filtrate 5q was used directly in the next step.

4-[(4-Cyanophenyl)(diazo)methyl]benzonitrile (5u). To a solution of 4-[(4-cyanophenyl)methanehydrazonoyl]benzonitrile (8u) (0.2 g, 0.81 mmol) in $CHCl_3$ (4 ml) $MnO_2$ (0.41 g, 4 mmol) was added. After 1 h the $MnO_2$ was removed by filtration and the red solution 5u was used directly in the next step.

4-{Diazo[4-(trifluoromethoxy)phenyl]methyl}pyridine (5w). To a solution of 4-{[4-(trifluoromethoxy)phenyl]methanehydrazonoyl}pyridine (8w) (0.4 g, 1.4 mmol) in $CHCl_3$ (3 ml) $MnO_2$ (0.73 g, 7.1 mmol) was added and the suspension was stirred for 1.5 h at rt. $MnO_2$ was removed and the red solution 5w was used directly in the next step.

4-[Diazo(pyridin-4-yl)methyl]benzonitrile (5y). To a solution of 4-(pyridin-4-ylmethanehydrazonoyl)benzonitrile (8y) (0.3 g, 1.4 mmol) in $CHCl_3$ (3 ml) $MnO_2$ (0.94 g, 9.2 mmol) was added and the suspension was stirred for 1 h at rt. $MnO_2$ was removed and the red solution 5y was used directly in the next step.

Preparation of diazo compounds 5 through DBU and p-ABSA (Scheme B)

2-(4-Bromophenyl)-2-diazo-1-(morpholin-4-yl)ethan-1-one (5k).

To a mixture of p-ABSA (0.51 g, 2.1 mmol) and 2-(4-bromophenyl)-1-(morpholin-4-yl)ethan-1-one (9k) (0.4 g, 1.4 mmol) in acetonitrile (4 ml) at 0° C. DBU (0.32 ml, 0.32 g, 2.1 mmol) was added dropwise. After stirring 18 h at rt the orange mixture was added to water (30 ml) and extracted with EtOAc (3×30 ml). The organic layers were combined, washed with aq. sat. NaCl (50 ml), dried over $Na_2SO_4$ and concentrated at reduced pressure. The residue was suspended in DCM, the insoluble part was filtered off and the filtrate was concentrated at reduced pressure to afford an orange oil (0.5 g). The crude product was purified by silica gel flash chromatography (EtOAc/Hept 1:1) to afford an orange oil 5k (0.17 g, 39%).

2-Diazo-1-(morpholin-4-yl)-2-[4-(trifluoromethyl)phenyl]ethan-1-one (5l). To a mixture of p-ABSA (0.54 g, 2.2 mmol) and 1-(morpholin-4-yl)-2-[4-(trifluoromethyl)phenyl]ethan-1-one (9l) (0.4 g, 1.5 mmol) in acetonitrile (4 ml) at 0° C. DBU (0.34 ml, 0.34 g, 2.2 mmol) was added dropwise. After stirring 19 h at rt the orange mixture was added to water (30 ml) and extracted with EtOAc (3×30 ml). The organic layers were combined, washed with aq. sat. NaCl (50 ml), dried over $Na_2SO_4$ and concentrated at reduced pressure. The residue was suspended in DCM, the insoluble part was filtered off and the filtrate was concentrated at reduced pressure to afford a yellow oil. The crude product was purified by silica gel flash chromatography (DCM/MeOH 98:2) to afford an orange oil 5l (0.17 g, 39%).

2-Diazo-1-(morpholin-4-yl)-2-[4-(trifluoromethoxy)phenyl]ethan-1-one (5m). To a mixture of p-ABSA (1.67 g, 6.7 mmol) and 1-(morpholin-4-yl)-2-[4-(trifluoromethoxy)phenyl]ethan-1-one (9m) (1.3 g, 4.5 mmol) in acetonitrile (15 ml) at 0° C. DBU (1.0 ml, 1.03 g, 6.7 mmol) was added dropwise. After stirring over weekend (about 64 h) at rt the orange mixture was added to water (40 ml). EtOAc (40 ml) was added and the inorganic layer was extracted with EtOAc (2×40 ml). The organic layers were combined, washed with aq. sat. NaCl (60 ml), dried over $Na_2SO_4$ and concentrated at reduced pressure. The residue was suspended in DCM, the insoluble part was filtered off and the filtrate was concentrated at reduced pressure to afford an orange oil (1.96 g). The crude product was purified by silica gel flash chromatography (TBME) to afford an orange oil 5m (0.45 g, 32%).

4-[1-Diazo-2-(morpholin-4-yl)-2-oxoethyl]benzonitrile (5n). To a mixture of p-ABSA (1.08 g, 4.4 mmol) and 4-[2-(morpholin-4-yl)-2-oxoethyl]benzonitrile (9n) (0.67 g, 2.9 mmol) in DCM (10 ml) at 0° C. DBU (0.65 ml, 0.66 g, 4.4 mmol) was added dropwise. After stirring overnight (about 14 h) at rt the reaction mixture was purified by silica gel flash chromatography (TBME) to afford an orange oil 5n (0.34 g, 45%).

Compounds of Type 3 (Scheme A)

5-(3,5-Dichlorophenyl)-3,3-diphenyl-3a,6a-dihydropyrrolo[3,4-c]pyrazole-4,6(3H,5H)-dione (3a). The purple diphenyldiazomethane (5a) solution in $CH_2Cl_2$ (9 ml, max. 0.52 mmol) was reduced to a volume of about 5 ml and then 1-(3,5-dichlorophenyl)-2,5-dihydro-1H-pyrrole-2,5-dione 2a (121 mg, 0.50 mmol) was added. While stirring this solution 3 h at rt, it turned into a white suspension. After centrifugation the residue was washed with EtOH (3 ml) to afford a white solid 3a (195 mg, 89%).

5-(3,5-Dichlorophenyl)-6a-methyl-3, 3-diphenyl-3a, 6a-dihydropyrrolo[3, 4-c]pyrazole-4, 6(3H, 5H)-dione and 5-(3,5-dichlorophenyl)-3a-methyl-3,3-diphenyl-3a,6a-dihydropyrrolo[3,4-c]pyrazole-4,6(3H,5H)-dione (3b). The purple diphenyldiazomethane (5a) solution in $CH_2Cl_2$ (10 ml, max. 0.51 mmol) was reduced to a volume of about 2 ml and then 1-(3,5-dichlorophenyl)-3-methyl-2,5-dihydro-1H-pyrrole-2,5-dione (2b) (133 mg, 0.52 mmol) was added. While stirring this solution 1 d at rt, it turned into a clear, slightly orange solution. The diazo compound was fully consumed and beside of imide 2b and the pyrazoline-intermediates 3b the 3-membered ring product 4b was formed. The solvent was removed and the residue was washed with EtOH (total 10 ml) to remove the starting material to afford a white solid 3b (95 mg, 40%).

5-(3,5-Dichlorophenyl)-3-phenyl-3a,6a-dihydropyrrolo[3,4-c]pyrazole-4, 6(3H, 5H)-dione (3c). To the red phenyldiazomethane (5c) solution in toluene (7 ml, max. 1.1 mmol) 1-(3,5-dichlorophenyl)-2,5-dihydro-1H-pyrrole-2,5-dione (2a) (225 mg, 0.9 mmol) was added. The red solution turned immediately to a slightly yellow solution and 5 min later a white precipitate was observed. After 15 min the slightly yellow suspension contained the pyrazoline-intermediates 3c and the diazo was fully consumed. The suspension was used directly in the next step.

5-(3,5-Dichlorophenyl)-6a-methyl-3-phenyl-3a, 6a-dihydropyrrolo[3,4-c]pyrazole-4,6(3H,5H)-dione and 5-(3,5-dichlorophenyl)-3a-methyl-3-phenyl-3a,6a-dihydropyrrolo[3,4-c]pyrazole-4,6(3H,5H)-dione (3d). To the red phenyldiazomethane (5c) solution in toluene (7 ml, max. 1.5 mmol) 1-(3,5-dichlorophenyl)-3-methyl-2,5-dihydro-1H-pyrrole-2,5-dione (2b) (471 mg, 1.8 mmol) was added in portions. The red solution turned immediately to a slightly yellow solution. After 70 min the diazo compound was fully converted and there resulted a slightly yellow suspension which contained the pyrazoline-intermediates 3d. The suspension was used directly in the next step.

3-(4-Bromophenyl)-5-(3,5-dichlorophenyl)-3a,6a-dihydropyrrolo[3,4-c]pyrazole-4,6(3H,5H)-dione (3e). To the purple solution of 4-bromophenyldiazomethane (5e) in toluene (3 ml, max. 0.57 mmol) 1-(3,5-dichlorophenyl)-2,5-dihydro-1H-pyrrole-2,5-dione (2a) (115 mg, 0.48 mmol) was added in portions. During the addition, the purple solution turned to a slightly purple solution and a precipitate was observed. After 20 min the reaction was complete and the pyrazoline-intermediates 3e were formed. The slightly yellow suspension was used directly in the next step.

3-(4-Bromophenyl)-5-(3,5-dichlorophenyl)-6a-methyl-3a,6a-dihydropyrrolo[3,4-c]pyrazole-4, 6(3H, 5H)-dione and 3-(4-bromophenyl)-5-(3,5-dichlorophenyl)-3a-methyl-3a,6a-dihydropyrrolo[3,4-c]pyrazole-4,6(3H,5H)-dione (3f). To the red 4-bromophenyldiazomethane (5e) solution in toluene (5 ml, max. 0.7 mmol) 1-(3,5-dichlorophenyl)-3-methyl-2,5-dihydro-1H-pyrrole-2,5-dione (2b) (180 mg, 0.7 mmol) was added. After 1 h the red-orange solution became less coloured, first precipitates were formed and 2 h later the reaction mixture became a yellow suspension. The reaction was complete and the pyrazoline-intermediates 3f were formed and were used directly in the next step.

5-(3,5-Dichlorophenyl)-6a-methyl-3-[4-(trifluoromethoxy)phenyl]-3a, 6a-dihydropyrrolo[3, 4-c]pyrazole-4,6-(3H,5H)-dione and 5-(3,5-dichlorophenyl)-3a-methyl-3-[4-(trifluoromethoxy)phenyl]-3a,6a-dihydropyrrolo-[3,4-c]pyrazole-4,6(3H,5H)-dione (3g). To the red solution of 4-trifluoromethoxyphenyldiazomethane (5g) in toluene (4.5 ml, max. 1 mmol) 1-(3,5-dichlorophenyl)-3-methyl-2,5-dihydro-1H-pyrrole-2,5-dione (2b) (218.3 mg, 0.85 mmol) was added and the reaction mixture became a red-orange solution. After 3.5 h the reaction was finished and the pyrazoline-intermediates 3g were formed. This slightly orange solution was used directly in the next step.

4-[5-(3,5-Dichlorophenyl)-6a-methyl-4,6-dioxo-3,3a,4,5,6,6a-hexahydropyrrolo[3, 4-c]pyrazol-3-yl]benzo-nitrile and 4-[5-(3,5-dichlorophenyl)-3a-methyl-4,6-dioxo-3,3a,4,5,6,6a-hexahydropyrrolo[3,4-c]pyrazol-3-yl]benzonitrile (3h). To the red solution of 4-cyanophenyldiazomethane (5h) in toluene (4.5 ml, max. 1 mmol) 1-(3,5-dichlorophenyl)-3-methyl-2,5-dihydro-1H-pyrrole-2,5-dione (2b) (192.1 mg, 0.75 mmol) was added and the reaction mixture became a red-orange solution. After about 20 h there was no diazo compound left and the slightly yellow, fine suspension of the pyrazoline-intermediates 3h was used directly in the next step.

4-[5-(3,5-Dichlorophenyl)-6a-methyl-4,6-dioxo-3-[4-(trifluoromethoxy)phenyl]-3, 3a,4,5,6,6a-hexahydro-pyrrolo[3, 4-c]pyrazol-3-yl]benzonitrile and 4-[5-(3,5-dichlorophenyl)-3a-methyl-4,6-dioxo-3-[4-(trifluoro-methoxy)phenyl]-3,3a,4,5,6,6a-hexahydropyrrolo[3, 4-c]pyrazol-3-yl]benzonitrile (3i). To the red solution of 4-{diazo[4-(trifluoromethoxy)-phenyl]methyl}benzonitrile (5i) in toluene (1.5 ml, max. 0.22 mmol) 1-(3,5-dichlorophenyl)-3-methyl-2,5-dihydro-1H-pyrrole-2,5-dione (2b) (80 mg, 0.31 mmol) was added and the red solution was stirred at rt. After about 16 h the toluene was reduced by $N_2$ flow and $CH_2Cl_2$ (0.5 ml) was added. After 10 d the red colour of the diazo compound was gone and the slightly yellow solution was used directly in the next step. (Afterwards in became clear, that after 10 d already the 3-membered ring products were formed under these conditions).

Compounds of Type 4/4' (Scheme A)

3-(3,5-Dichlorophenyl)-6,6-diphenyl-3-azabicyclo[3.1.0]hexane-2, 4-dione (4a). A white suspension of the pyrazoline-intermediate 3a (149 mg, 0.34 mmol) in toluene (2 ml) was heated to 100° C. While heating a clear solution resulted. After 1 h the reaction was complete and the toluene was removed at reduced pressure. The crude product was purified by silica gel flash chromatography ($CH_2Cl_2$/hept 6:4) to afford a white solid 4a (81 mg, 58%).

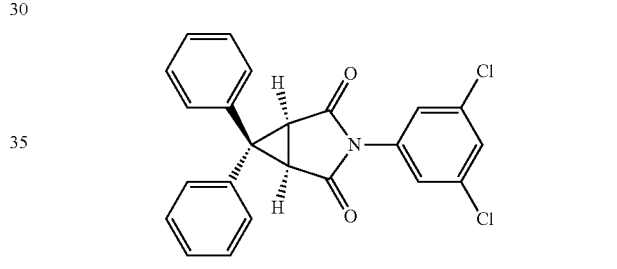

$^1$H-NMR (400 MHz, DMSO-$d_6$): 3.66 (s, 2 H), 6.29 (d, J=1.9, 2 H), 7.23-7.49 (m, 10 H), 7.59 (t, J=1.9, 1 H).

HPLC retention time: 5.49 min rac-(1S,5S)-3-(3,5-Dichlorophenyl)-1-methyl-6,6-diphenyl-3-azabicyclo[3.1.0]hexane-2, 4-dione (4b). A clear, colourless solution of the pyrazoline-intermediates 3b (65 mg, 0.14 mmol) in toluene (2 ml) was heated to 100° C. After 50 min the reaction was complete, the toluene was removed at reduced pressure to afford a white solid 4b (58 mg, 95%). A further purification wasn't necessary.

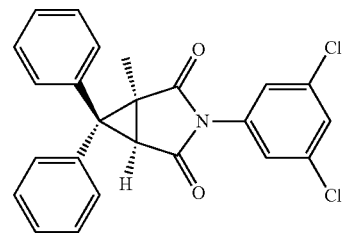

relative stereochemistry $^1$H-NMR (400 MHz, DMSO-$d_6$): 1.34 (s, 3 H), 3.69 (s, 1 H), 6.28 (d, J=1.8, 2 H), 7.25-7.38 (m, 8 H), 7.51-7.55 (m, 2 H), 7.59 (t, J=1.8, 2 H).

HPLC retention time: 5.60 min

The racemate was separated by fractionation on analytical HPLC by a chiral column.
Column: Reprosil 100 chiral NR 250×4.6 mm 8 μm
Flow: 1.5 ml/min Detector: DAD 200-400 nm (210 nm)
Eluent: 25% H$_2$O/75% MeOH isocratic
Retention time: 12.73 min (first peak) (Enantiomer A of 4b), 14.51 min (second peak) (Enantiomer B of 4b)

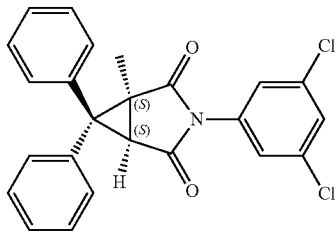

(1S,5S)-3-(3,5-Dichlorophenyl)-1-methyl-6,6-diphenyl-3-azabicyclo[3.1.0]hexane-2,4-dione.

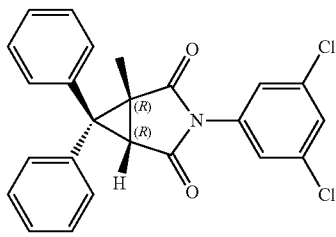

(1R,5R)-3-(3,5-Dichlorophenyl)-1-methyl-6,6-diphenyl-3-azabicyclo[3.1.0]hexane-2,4-dione.

rel-(1R,5S,6s)- and rel-(1R,5S,6r)-3-(3,5-Dichlorophenyl)-6-phenyl-3-azabicyclo[3.1.0]hexane-2,4-dione (4c and 4'c). The suspension 3c turned into a slightly yellow solution (in toluene, 7 ml, max. 0.9 mmol) while heating up to 100° C. After 1 h the reaction was complete, the solvent was removed at reduced pressure. The residue was washed with EtOH (1 ml) to remove a part of the impurities. The residue was washed again with EtOH (4×0.6 ml) and was further purified by silica gel flash chromatography (CH$_2$Cl$_2$/hept 6:4) to afford a white solid 4c (55 mg, 18%). The EtOH wash phases (3.4 ml) were reduced at reduced pressure and purified by two silica gel flash chromatographies (EtOAc/hept 1:9 and EtOAc/hept 2:8) to afford a white solid 4'c (12 mg, 4%).

rel-(1R,5S,6s)-3-(3,5-Dichlorophenyl)-6-phenyl-3-azabicyclo[3.1.0]hexane-2,4-dione (4c)

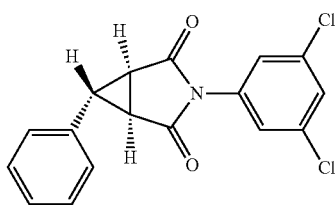

relative stereochemistry $^1$H-NMR (400 MHz, DMSO-d$_6$): 3.22 (d, J=3.3, 2 H), 3.54 (t, J=3.3, 1 H), 7.23-7.40 (m, 5 H), 7.52 (d, J=1.9, 2 H), 7.71 (t, J=1.9, 1 H).

HPLC retention time: 5.00 min rel-(1R,5S,6r)-3-(3,5-Dichlorophenyl)-6-phenyl-3-azabicyclo[3.1.0]hexane-2,4-dione (4'c)

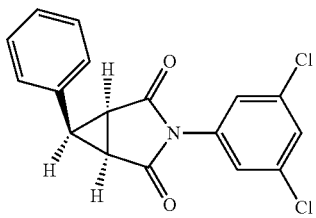

relative stereochemistry $^1$H-NMR (400 MHz, DMSO-d$_6$): 3.23 (d, J=8.3, 2H), 3.47 (t, J=8.3, 1H), 6.28 (d, J=1.9, 2H), 7.25-7.32 (m, 2H), 7.34-7.44 (m, 3H), 7.57 (t, J=1.9, 1H).

HPLC retention time: 4.80 min rac-(1R,5S,6R)- and rac-(1R,5S,6S)-3-(3,5-Dichlorophenyl)-1-methyl-6-phenyl-3-azabicyclo[3.1.0]hexane-2,4-dione (4d and 4'd). The suspension 3d turned into a slightly yellow solution (in toluene, 7 ml, max. 1.5 mmol) while heating up to 100° C. After 1.5 h the reaction was complete, the solvent was removed at reduced pressure. The residue was purified by silica gel flash chromatography (CH$_2$Cl$_2$/hept 8:2-CH$_2$Cl$_2$) to afford a white solid 4d (30 mg, 11%). A further purification by preparative TLC (TBME/hept 1:3) was necessary to afford a white solid 4'd (13 mg, 3%).

rac-(1R,5S,6R)-3-(3,5-Dichlorophenyl)-1-methyl-6-phenyl-3-azabicyclo[3.1.0]hexane-2,4-dione (4d)

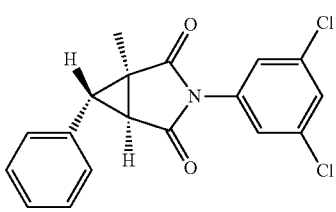

relative stereochemistry $^1$H-NMR (400 MHz, DMSO-d$_6$): 1.18 (s, 3H), 3.42 (d, J=3.6, 1H), 3.57 (d, J=3.6, 1H), 7.30-7.44 (m, 4H), 7.54 (d, J=1.9, 2H), 7.71 (t, J=1.9, 1H).

HPLC retention time: 5.22 min rac-(1R,5S,6S)-3-(3,5-Dichlorophenyl)-1-methyl-6-phenyl-3-azabicyclo[3.1.0]hexane-2,4-dione (4'd)

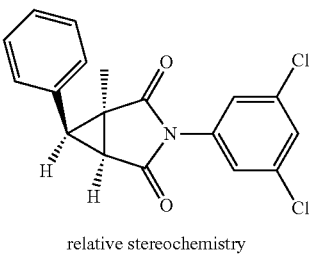 [SMILES: C[C@]12C(=O)N(c3cc(Cl)cc(Cl)c3)C(=O)[C@H]1[C@H]2c1ccccc1]

relative stereochemistry

¹H-NMR (400 MHz, DMSO-d₆): 1.65 (s, 3 H), 3.09 (d, J=8.3, 1 H), 3.37 (d, J=8.3, 1 H), 6.28 (d, J=1.9, 2 H), 7.20-7.27 (m, 2 H), 7.32-7.42 (m, 2 H), 7.56 (t, J=1.9, 1 H).

HPLC retention time: 5.06 min rel-(1R,5S,6s)- and rel-(1R,5S,6r)-6-(4-Bromophenyl)-3-(3,5-dichlorophenyl)-3-azabicyclo[3.1.0]hexane-2,4-dione (4e and 4'e). The suspension 3e turned into a slightly yellow solution (in toluene, 3 ml, max. 0.48 mmol) while heating up to 100° C. After 1.5 h the reaction was complete and overnight a solid precipitated. After centrifugation (the solid was impure product) the supernatant was concentrated at reduced pressure. The residue was purified by silica gel flash chromatography (CH₂Cl₂/hept 6:4-8:2) to afford a white solid 4e (35 mg, 20%) and a white solid 4'e (12 mg, 7%).

rel-(1R,5S,6s)-6-(4-Bromophenyl)-3-(3,5-dichlorophenyl)-3-azabicyclo[3.1.0]hexane-2,4-dione (4e)

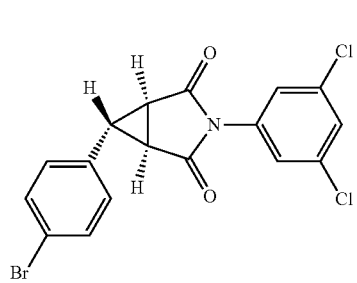

relative stereochemistry

¹H-NMR (400 MHz, DMSO-d₆): 3.25 (d, J=3.3, 2 H), 3.54 (t, J=3.3, 1 H), 7.23 (m, 2H), 7.51 (d, J=1.9, 2 H), 7.56 (m, 2H), 7.71 (t, J=1.9, 1 H).

HPLC retention time: 5.34 min rel-(1R,5S,6r)-6-(4-Bromophenyl)-3-(3,5-dichlorophenyl)-3-azabicyclo[3.1.0]hexane-2,4-dione (4'e)

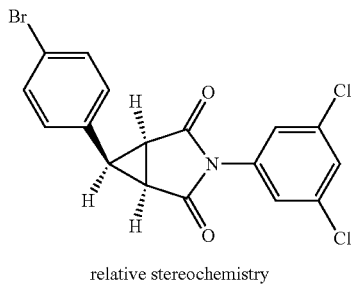 [SMILES: O=C1[C@@H]2[C@H](C(=O)N1c1cc(Cl)cc(Cl)c1)[C@@H]2c1ccc(Br)cc1]

relative stereochemistry

¹H-NMR (400 MHz, DMSO-d₆): 3.24 (d, J=8.2, 2 H), 3.43 (t, J=8.2, 1 H), 6.33 (d, J=1.9, 2 H), 7.23 (m, 2 H), 7.61 (t, J=1.9, 1 H), 7.62 (m, 2 H).

HPLC retention time: 5.15 min rac-(1R,5S,6R)- and rac-(1R,5S,6S)-6-(4-Bromophenyl)-3-(3,5-dichlorophenyl)-1-methyl-3-azabicyclo[3.1.0]-hexane-2,4-dione (4f and 4'f). The suspension 3f turned into a slightly yellow solution (in toluene, 5 ml, max. 0.7 mmol) while heating up to 100° C. After 45 min the reaction was complete, the solvent was removed at reduced pressure. The residue (313 mg) was purified by silica gel flash chromatography (CH₂Cl₂/hept 1:1) to afford a white solid 4f (134 mg, 42%). For the second product 4'f a preparative TLC was necessary (TBME/hept 1:1) to afford a slightly yellow solid (12 mg, 4%).

rac-(1R,5S,6R)-6-(4-Bromophenyl)-3-(3,5-dichlorophenyl)-1-methyl-3-azabicyclo[3.1.0]hexane-2,4-dione (4f)

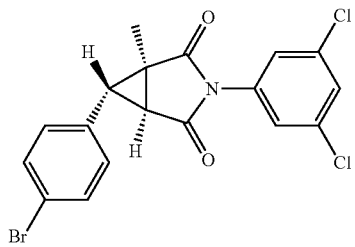

relative stereochemistry

¹H-NMR (400 MHz, DMSO-d₆): 1.17 (s, 3 H), 3.46 (d, J=3.7, 1 H), 3.56 (d, J=3.7, 1 H), 7.31 (m, 2 H), 7.52 (d, J=1.9, 2 H), 7.59 (m, 2 H), 7.71 (t, J=1.9, 1 H).

HPLC retention time: 5.55 min rac-(1R,5S,6S)-6-(4-Bromophenyl)-3-(3,5-dichlorophenyl)-1-methyl-3-azabicyclo[3.1.0]hexane-2,4-dione (4'f)

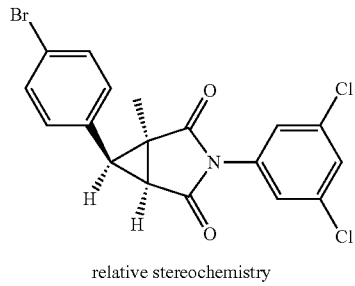 [SMILES: C[C@]12C(=O)N(c3cc(Cl)cc(Cl)c3)C(=O)[C@H]1[C@H]2c1ccc(Br)cc1]

relative stereochemistry $^1$H-NMR (400 MHz, DMSO-d$_6$): 1.64 (s, 3 H), 3.11 (d, J=8.3, 1 H), 3.33 (d, J=8.3, 1 H), 6.33 (d, J=1.9, 2 H), 7.18 (m, 2 H), 7.60 (t, J=1.9, 1 H), 7.61 (m, 2 H).

HPLC retention time: 5.39 min rac-(1R,5S,6R)- and rac-(1R,5S,6S)-3-(3, 5-Dichlorophenyl) -1-methyl-6-[4-(trifluoromethoxy)phenyl]-3-aza-bicyclo[3.1.0.]hexane-2,4-dione (4g and 4'g). The suspension 3g turned into a slightly yellow solution (in toluene, 4.5 ml, max. 0.85 mmol) while heating up to 100° C. After 40 min the reaction was terminated, the solvent was removed at reduced pressure. The residue was purified by silica gel flash chromatography (TBME/hept 2:8) to afford both products impure. For each product a further purification by silica gel flash chromatography was necessary to afford a white solid 4g (EtOAc/hept 1.5:8.5) (74 mg, 20%) and a white solid 4'g (toluene/hept 95:5) (5 mg, 2%).

rac-(1R,5S,6R)-3-(3,5-Dichlorophenyl)-1-methyl-6-[4-(trifluoromethoxy)phenyl]-3-azabicyclo[3.1.0] hexane-2,4-dione (4g)

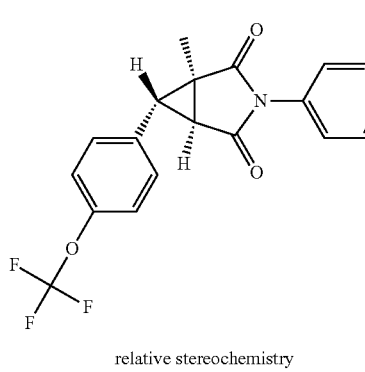

relative stereochemistry $^1$H-NMR (400 MHz, DMSO-d$_6$): 1.18 (s, 3 H), 3.47 (d, J=3.6, 1 H), 3.61 (d, J=3.6, 1 H), 7.39 (m, 2 H), 7.49 (m, 2 H), 7.53 (d, J=1.9, 2 H), 7.71 (t, J=1.9, 1 H).

HPLC retention time: 5.61 min rac-(1R,5S,6S)-3-(3,5-Dichlorophenyl)-1-methyl-6-[4-(trifluoromethoxy)phenyl]-3-azabicyclo[3.1.0] hexane-2,4-dione (4'g)

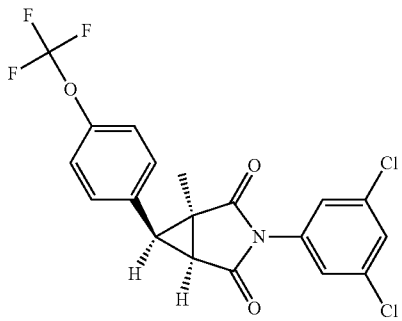

relative stereochemistry $^1$H-NMR (400 MHz, DMSO-d$_6$): 1.66 (s, 3 H), 3.13 (d, J=8.3, 1 H), 3.39 (d, J=8.3, 1 H), 6.40 (d, J=1.9, 2 H), 7.39 (m, 4 H), 7.59 (t, J=1.9, 1 H).

HPLC retention time: 5.46 min rac-(1R,5S,6R)- and rac-(1R,5S,6S)-4-[3-(3,5-Dichlorophenyl)-1-methyl-2,4-dioxo-3-azabicyclo[3.1.0]hexan-6-yl] benzonitrile (4h and 4'h). From the pyrazoline -intermediate in toluene 3h (4.5 ml, max. 0.75 mmol) the solvent was removed and the residue was heated at 280° C. for 1h. The crude product (104.6 mg) was purified by silica gel flash chromatography (TBME/hept 8:2) to afford a white solid 4h (10 mg, 4%). A further purification by preparative TLC (EtOAc/hept 7:3) was necessary to afford a white solid 4'h (4 mg, 2%).

rac-4-[(1R,5S,6R)-3-(3,5-Dichlorophenyl)-1-methyl-2,4-dioxo-3-azabicyclo[3.1.0]hexan-6-yl]benzonitrile (4h)

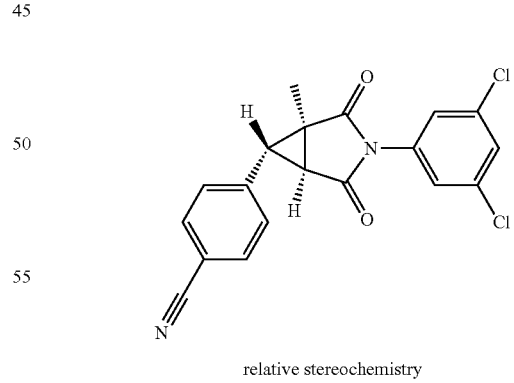

relative stereochemistry $^1$H-NMR (400 MHz, DMSO-d$_6$): 1.18 (s, 3 H), 3.59 (d, J=3.7, 1 H), 3.67 (d, J=3.7, 1 H), 7.52 (d, J=1.9, 2 H), 7.56 (m, 2 H), 7.72 (t, J=1.9, 1 H), 7.88 (m, 2 H).

HPLC retention time: 4.95 min rac-4-[(1R,5S,6S)-3-(3,5-Dichlorophenyl)-1-methyl-2,4-dioxo-3-azabicyclo[3.1.0]hexan-6-yl]benzonitrile (4'h)

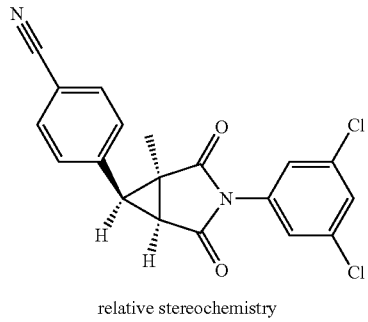 [SMILES: C[C@]12C(=O)N(c3cc(Cl)cc(Cl)c3)C(=O)[C@H]1[C@H]2c1ccc(C#N)cc1]

relative stereochemistry

¹H-NMR (400 MHz, CDCl₃): 1.81 (s, 3 H), 2.93 (d, J=8.4, 1 H), 3.16 (d, J=8.4, 1 H), 6.30 (d, J=1.9, 2 H), 7.26 (t, J=1.9, 1 H), 7.49 (m, 2 H), 7.68 (m, 2 H).

HPLC retention time: 4.65 min rac-4-[(1 S, 5S, 6S)- and rac-4-(1 S, 5S, 6R)-3-(3,5-Dichlorophenyl)-1-methyl-2,4-dioxo-6-[4-(trifluoromethoxy)-phenyl]-3-azabicyclo[3.1.0]hexan-6-yl]benzonitrile (4i/4'i diastereomer I and 4i/4'i diastereomer II). The CH₂Cl₂ of the solution 3i was removed by N₂ flow and toluene (0.5 ml) was added. After 45 min at 100° C. there was no change of the product. The 3-membered ring products 4 were formed already in the step before. After the long stirring there weren't any pyrazoline-intermediates 3 left. The solvent was removed and the crude product (90 mg) was purified by silica gel flash chromatography (TBME/hept 3:7) to afford a white solid (4i/4'i diastereomer I: 7 mg, 6%) and a white solid (4i/4'i diastereomer II: 12 mg, 10%).

4i/4'i diastereomer I: ¹H-NMR (400 MHz, DMSO-d₆): 1.37 (s, 3H), 3.82 (s, 1H), 6.28 (d, J=1.9, 2H), 7.37 (m, 2H), 7.63 (t, J=1.9, 1H), 7.65-7.83 (m, 4H), 7.91 (m, 2H). LC retention time: 5.57 min 4i/4'i diastereomer II: ¹H-NMR (400 MHz, DMSO-d₆): 1.35 (s, 3H), 3.85 (s, 1H), 6.42 (d, J=1.9, 2H), 7.42 (m, 2H), 7.62 (t, J=1.9, 1H), 7.45-7.75 (m, 2H), 7.83 (m, 4H). LC retention time: 5.67 min

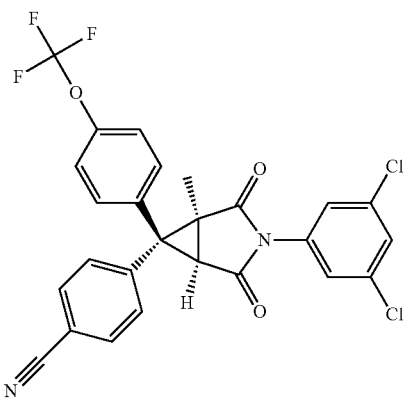

relative stereochemistry rac-4-[(1S,5S,6R)-3-(3,5-Dichlorophenyl)-1-methyl-2,4-dioxo-6-[4-(trifluoromethoxy)phenyl]-3-azabicyclo-[3.1.0]hexan-6-yl]benzonitrile (4'i)

The racemate (4i/4'i diastereomer II) was separated by fractionation on analytical HPLC by a chiral column.

Column: Reprosil 100 chiral NR 250×4.6 mm 8 µm

Flow: 1.5 ml/min Detector: DAD 200-400 nm (210 nm)

Eluent: 30% H₂O/70% MeOH isocratic

Retention time: 24.53 min (first peak) (Enantiomer A of 4i/4'i diastereomer II) 26.88 min (second peak) (Enantiomer B of 4i/4'i diastereomer II)

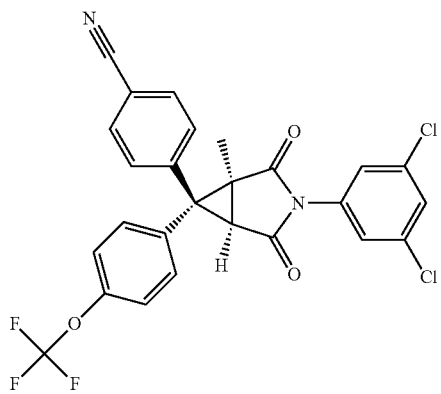

relative stereochemistry rac-4-[(1S,5S,6S)-3-(3,5-Dichlorophenyl)-1-methyl-2,4-dioxo-6-[4-(trifluoromethoxy)phenyl]-3-azabicyclo-[3.1.0]hexan-6-yl]benzonitrile (4i)

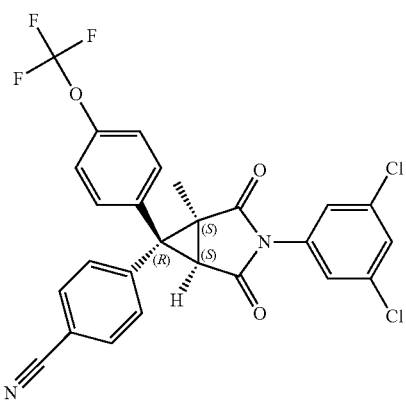

4-[(1S,5S,6R)-3-(3,5-Dichlorophenyl)-1-methyl-2,4-dioxo-6-[4-(trifluoromethoxy)phenyl]-3-azabicyclo[3.1.0]hexan-6-yl]benzonitrile -continued

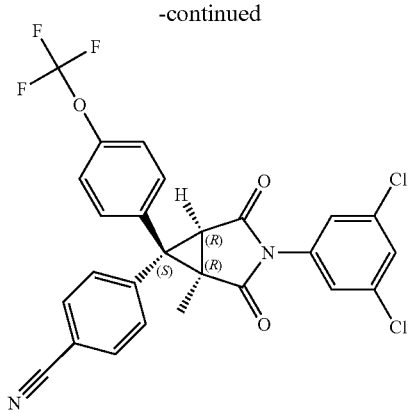

4-[(1R,5R,6S)-3-(3,5-Dichlorophenyl)-1-
methyl-2,4-dioxo-6-[4-
(trifluoromethoxy)phenyl]-3-
azabicyclo[3.1.0]hexan-6-yl]benzonitrile

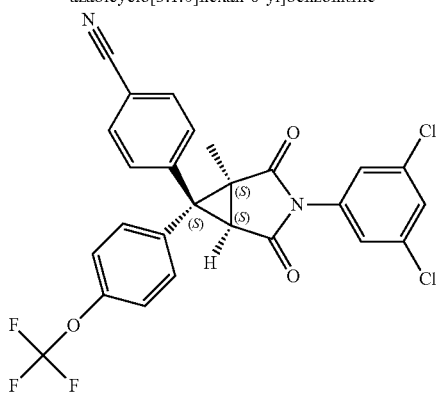

4-[(1S,5S,6S)-3-(3,5-Dichlorophenyl)-1-
methyl-2,4-dioxo-6-[4-
(trifluoromethoxy)phenyl]-3-
azabicyclo[3.1.0]hexan-6-yl]benzonitrile

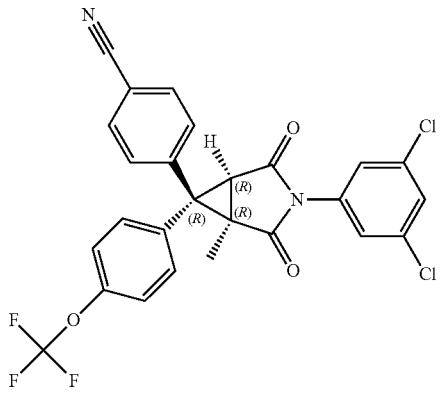

4-[(1R,5R,6R)-3-(3,5-Dichlorophenyl)-1-
methyl-2,4-dioxo-6-[4-
(trifluoromethoxy)phenyl]-3-
azabicyclo[3.1.0]hexan-6-yl]benzonitrile rac-Ethyl-(1 S, 5R, 6R)-6-(4-bromophenyl)-3-(3,5-dichlorophenyl)-1-methyl-2,4-dioxo-3-azabicyclo[3.1.0]-hexane-6-carboxylate (4'j). To an orange solution of the diazo compound 5j (395 mg, 1.47 mmol) in toluene (3 mL) 1-(3,5-dichlorophenyl)-3-methyl-2,5-dihydro-1H-pyrrole-2,5-dione (2b) (375 mg, 1.47 mmol) in toluene (2 mL) was added. The solution was heated up to 100° C. and stirred for 3 h. The orange solution became yellowish. The solvent was evaporated under reduced pressure and the residue (538 mg, orange solid) was purified by silica gel flash chromatography (TBME/hexane 2:3-1:1) to afford a white, crystalline solid 4'j (16 mg, 2%).

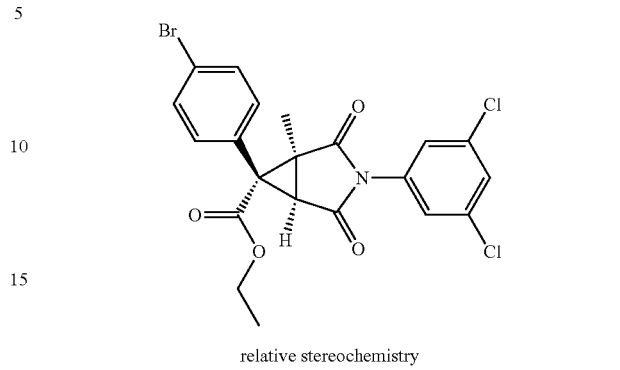

relative stereochemistry

¹H-NMR (400 MHz, DMSO-$d_6$): 7.65 (d, J=8.6, 2 H), 7.62 (t, J=1.8, 1 H), 7.24 (d, J=8.6, 2 H), 6.27 (d, J=1.8, 2 H), 4.14 (m, 2 H),20 3.54 (s, 1 H), 1.64 (s, 3 H), 1.14 (t, J=7.1, 3 H).

HPLC retention time: 5.77 min

HPLC conditions for determining retention time of the prepared compounds:
Column: Poroshell 120 EC-C18, 50×4.6 mm 2.7 μm P.N. 699975-902 Temp: 25° C.
Flow: 1.5 ml/min Detector: 210 nm
Eluent: A=H$_2$O (0.1V % H$_3$PO$_4$)/B=CH$_3$CN (t=0 min; 95% A/t=5.5 min; 5% A/t=5.5-7.5 min; 5% A)
Compounds of Type 4/4' (Scheme A)

rac-(1 S, 5R, 6S)- and rac-(1 S, 5R, 6R)-6-(4-Bromophenyl)-3-(3,5-dichlorophenyl)-1-methyl-6-[(morpholin-4-yl) carbonyl]-3-azabicyclo[3.1.0]hexane-2,4-dione (4k and 4'k). To a solution of 2-(4-bromophenyl)-2-diazo-1-(morpholin-4-yl)ethan-1-one (5k) (0.14 g, 0.45 mmol) in toluene (2 ml) 1-(3,5-dichlorophenyl)-3-methyl-2,5-dihydro-1H-pyrrole-2,5-dione (2b) (0.116 g, 0.45 mmol) in toluene (1 ml) was added dropwise and the orange mixture was stirred overnight (about 15 h) at 60° C. and 2 h at 90° C. The reaction mixture was concentrated at reduced pressure to afford a yellow oil (0.29 g). The crude product was purified by two silica gel flash chromatographies (isopropylacetate/hept 1:1-3:1) and (isopropylether/DCM/hept 80:18:2) and by preparative TLC (AcOEt/DCM 1:1) to afford a white solid 4'k (5 mg, 2%). 4k was not isolated.

rac-(1S,5R,6R)-6-(4-Bromophenyl)-3-(3,5-dichlorophenyl)-1-methyl-6-[(morpholin-4-yl)carbonyl]-3-azabicyclo[3.1.0]hexane-2,4-dione (4'k)

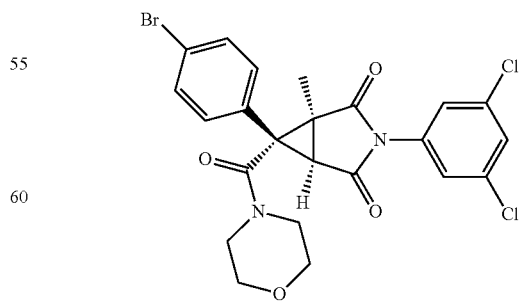

relative stereochemistry $^1$H-NMR (400 MHz, CDCl$_3$): 1.70 (s, 3 H), 3.43 (s, 1 H), 3.45-3.73 (m, 8 H), 6.32 (d, J=1.9, 2 H), 7.27 (t, J=1.9, 1 H), 7.38 (m, 2 H), 7.52 (m, 2 H).

HPLC retention time: 4.99 min rac-(1 S, 5R, 6S)- and rac-(1 S, 5R, 6R)-3-(3,5-Dichlorophenyl)-1-methyl-6-[(morpholin-4-yl)carbonyl]-6-[4-(trifluoromethyl)phenyl]-3-azabicyclo[3.1.0]hexane-2,4-dione (4l and 4'l).

To a solution of 2-diazo-1-(morpholin-4-yl)-2-[4-(trifluoromethyl)phenyl]ethan-1-one (5i) (0.1 g, 0.33 mmol) in toluene (2 ml) 1-(3,5-dichlorophenyl)-3-methyl-2,5-dihydro-1H-pyrrole-2,5-dione (2b) (0.09 g, 0.33 mmol) in toluene (1 ml) was added dropwise and the orange mixture was stirred 5 h at rt, overnight (about 18 h) at 80° C. and 2 h at 90° C. The yellow solution was concentrated at reduced pressure to afford a yellow oil. The crude product was purified by silica gel flash chromatography (EtOAc/hept 1:1), by preparative TLC (EtOAc/hept 2:1) and by preparative TLC (C18, acetonitrile/H$_2$O 3:2) to afford a white solid 4'l (5 mg, 3%). 4l was not isolated.

rac-(1S,5R,6R)-3-(3,5-Dichlorophenyl)-1-methyl-6-[(morpholin-4-yl)carbonyl]-6-[4-(trifluoromethyl)phenyl]-3-azabicyclo[3.1.0]hexane-2,4-dione (4'l)

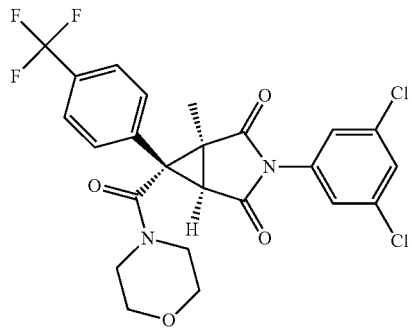

relative stereochemistry $^1$H-NMR (400 MHz, DMSO-d$_6$): 1.63 (s, 3 H), 3.45 (s, 1 H), 3.38-3.74 (m, 8 H), 6.28 (d, J=1.9, 2 H), 7.60 (m, 2 H), 7.62 (t, J=1.9, 1 H), 7.83 (m, 2 H).

HPLC retention time: 5.02 min rac-(1 S, 5R, 6S)- and rac-(1 S, 5R, 6R)-3-(3, 5-Dichlorophenyl)-1-methyl-6-[(morpholin-4-yl)carbonyl]-6-[4-(trifluoromethoxy)phenyl]-3-azabicyclo[3.1.0]hexane-2,4-dione (4m and 4'm). To a solution of 2-diazo-1-(morpholin-4-yl)-2-[4-(trifluoromethoxy)phenyl]ethan-1-one (5m) (0.44 g, 1.4 mmol) in toluene (2 ml) 1-(3,5-dichlorophenyl)-3-methyl-2,5-dihydro-1H-pyrrole-2,5-dione (2b) (0.36 g, 1.4 mmol) in toluene (3 ml) was added dropwise and the orange mixture was stirred 14 h at 50° C. and 18 h at 80° C. The yellow solution was concentrated at reduced pressure to afford a yellow oil (0.7 g). The crude product was purified by two silica gel flash chromatographies (TBME/hept 1:1-7:3) and (isopropylacetate/hept 2:1) and by preparative TLC (isopropylacetate/hept 2:1) to afford a white solid 4'm (30 mg, 4%). 4m was not isolated.

rac-(1S,5R,6R)-3-(3,5-Dichlorophenyl)-1-methyl-6-[(morpholin-4-yl)carbonyl]-6-[4-(trifluoromethoxy)phenyl]-3-azabicyclo[3.1.0]hexane-2,4-dione (4'm)

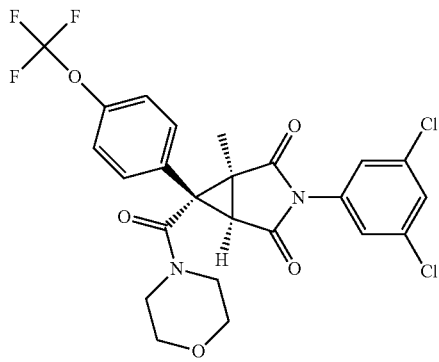

relative stereochemistry $^1$H-NMR (400 MHz, DMSO-d$_6$): 1.61 (s, 3 H), 3.40 (s, 1 H), 3.27-3.73 (m, 8 H), 6.47 (d, J=1.9, 2 H), 7.45 (m, 2 H), 7.50 (m, 2 H), 7.63 (t, J=1.9, 1 H).

HPLC retention time: 5.11 min rac-4-[(1 S, 5R, 6S)- and rac-4-[(1 S, 5R, 6R)-3-(3,5-Dichlorophenyl)-1-methyl-6-[(morpholin-4-yl)carbonyl]-2,4-dioxo-3-azabicyclo[3.1.0]hexan-6-yl]benzonitrile (4n and 4'n). To a solution of 4-[1-diazo-2-(morpholin-4-yl)-2-oxoethyl]benzonitrile 5n (0.32 g, 1.25 mmol) in toluene (2.5 ml) 1-(3,5-dichlorophenyl)-3-methyl-2,5-dihydro-1H-pyrrole-2,5-dione (2b) (0.32 g, 1.25 mmol) in toluene (3 ml) was added dropwise and the orange mixture was stirred overnight (about 18 h) at 60° C. and 3 h at 100° C. The yellow solution was concentrated at reduced pressure to afford a yellow oil (0.63 g). The crude product was purified by silica gel flash chromatography (EtOAc/hept 1:1-2:3) and by two preparative TLC (diethylether/THF 4:1 and diethylether/isobutylmethylketone 2:1) to afford a white solid 4'n (21 mg, 4%). 4n was not isolated.

rac-4-[(1S,5R,6R)-3-(3,5-Dichlorophenyl)-1-methyl-6-[(morpholin-4-yl)carbonyl]-2,4-dioxo-3-azabicyclo[3.1.0]hexan-6-yl]benzonitrile (4'n)

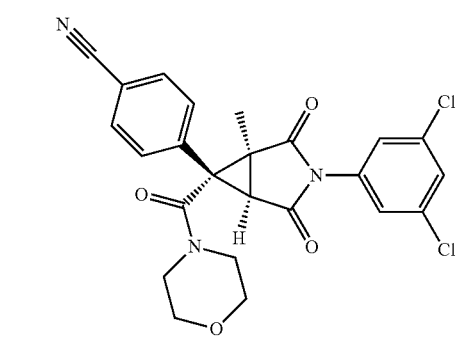

relative stereochemistry $^1$H-NMR (400 MHz, DMSO-d$_6$): 1.62 (s, 3H), 3.46 (s, 1 H), 3.34-3.73 (m, 8 H), 6.32 (d, J=1.9, 2 H), 7.56 (m, 2 H), 7.64 (t, J=1.9, 1 H), 7.95 (m, 2 H).

HPLC retention time: 4.39 min rac-(1 S, 5S, 6S)- and rac-(1 S, 5S, 6R)-3-(3,5-Dichlorophenyl)-1-methyl-6-phenyl-6-(pyridin-4-yl)-3-azabicyclo[3.1.0]hexane-2,4-dione (4o and 4'o). To a red solution of 4-[diazo(phenyl)methyl]pyridine (5o) (0.23 g, 1.22 mmol) in CHCl$_3$ (6 ml) 1-(3,5-dichlorophenyl)-3-methyl-2,5-dihydro-1H-pyrrole-2,5-dione (2b) (0.20 g, 1.17 mmol) was added. After 23 h rt and 23 h at 50° C. the brown solution was concentrated at reduced pressure to afford a brown oil (0.52 g). The crude product was purified by silica gel flash chromatography (EtOAc/hept 3:7) to afford a pale yellow solid 4o or 4'o (diastereomer I) (70 mg, 14%). A further purification by silica gel flash chromatography (EtOAc/hept 9:1) afforded a white solid 4o or 4'o (diastereomer II) (50 mg, 10%).

4o or 4'o (diastereomer I): $^1$H-NMR (400 MHz, DMSO-d$_6$): 1.35 (s, 3 H), 3.77 (s, 1 H), 6.39 (d, J=1.9, 2 H), 7.31 (m, 1 H), 7.39 (m, 2 H), 7.47 (m, 2 H), 7.58 (m, 2 H), 7.62 (t, J=1.9, 1 H), 8.56 (m, 2 H).

HPLC retention time: 4.38 min 4o or 4'o (diastereomer II): $^1$H-NMR (400 MHz, DMSO-d$_6$): 1.35 (s, 3 H), 3.83 (s, 1 H), 6.28 (d, J=1.9, 2 H), 7.32-7.53 (m, 5 H), 7.56 (m, 2 H), 7.60 (t, J=1.9, 1 H), 8.55 (m, 2 H).

HPLC retention time: 3.94 min

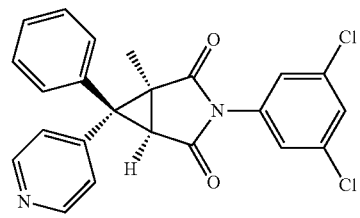

relative stereochemistry rac-(1S,5S,6S)-3-(3,5-Dichlorophenyl)-1-methyl-6-phenyl-6-(pyridin-4-yl)-3-azabicyclo[3.1.0]hexane-2,4-dione (4o)

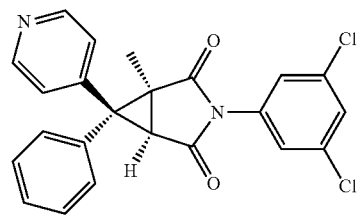

relative stereochemistry rac-(1S,5S,6R)-3-(3,5-Dichlorophenyl)-1-methyl-6-phenyl-6-(pyridin-4-yl)-3-azabicyclo[3.1.0]hexane- 3-(3,5-Dichlorophenyl)-6,6-bis[4-(trifluoromethoxy)phenyl]-3-azabicyclo[3.1.0.]hexane-2, 4-dione (4p). To the red solution of 1-{diazo[4-(trifluoromethoxy)phenyl]methyl}-4-(trifluoromethoxy)benzene (5q) (1.8 mmol) in CHCl$_3$ (5 ml) 1-(3,5-dichlorophenyl)-2,5-dihydro-1H-pyrrole-2,5-dione (2a) (0.5 g, 1.7 mmol) was added. The red solution was stirred overnight at 60° C. The slightly yellow reaction mixture was concentrated at reduced pressure, purified by silica gel flash chromatography (heptane/isopropylacetate 8.5:1.5) to afford a slightly yellow solid 4p (85 mg, 6%).

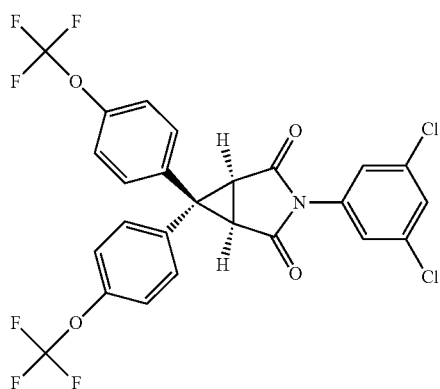

$^1$H-NMR (400 MHz, CDCl$_3$): 3.34 (s, 2 H), 6.36 (d, J=1.8, 2 H), 7.19 (m, 2 H), 7.24-7.31 (m, 5 H), 7.55 (m, 2 H).

HPLC retention time: 6.09 min rac-(1S,5S)-3-(3,5-Dichlorophenyl)-1-methyl-6,6-bis[4-(trifluoromethoxy)phenyl]-3-azabicyclo[3.1.0]hexane-2,4-dione (4q). To the red solution of 1-{diazo[4-(trifluoromethoxy)phenyl]methyl}-4-(trifluoromethoxy)benzene (5q) (2.44 mmol) in CHCl$_3$ (12 ml) 1-(3,5-dichlorophenyl)-3-methyl-2,5-dihydro-1H-pyrrole-2,5-dione (2b) (0.6 g, 2.36 mmol) was added. The red solution was stirred overnight at 60° C. The slightly yellow reaction mixture was concentrated at reduced pressure, purified by silica gel flash chromatography (heptane/isopropylacetate 8.5:1.5) to afford a slightly yellow solid 4q (85 mg, 6%).

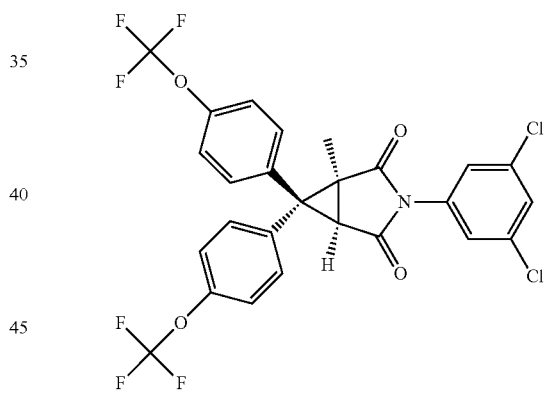

relative stereochemistry $^1$H-NMR (400 MHz, CDCl$_3$): 1.49 (s, 3 H), 3.25 (s, 1 H), 6.37 (d, J=1.8, 2 H), 7.16-7.25 (m, 4 H), 7.26 (t, J=1.8, 1 H), 7.41 (m, 2 H), 7.49 (m, 2 H).

HPLC retention time: 6.17 min rel-4-[(1S,5R,6r)- and rel-4-[(1 S, 5R, 6s)-4-3-(3, 5-Dichlorophenyl)-2, 4-dioxo-6-[4-(trifluoromethoxy)phenyl]-3-azabicyclo[3.1.0]hexan-6-yl]benzonitrile (4r and 4'r). To the red solution of 4-{diazo[4-(trifluoromethoxy)phenyl]methyl}benzonitrile (5i) (0.65 mmol) in CHCl$_3$ (2 ml) 1-(3,5-dichlorophenyl)-2,5-dihydro-1H-pyrrole-2,5-dione (2a) (158.5 mg, 0.655 mmol) was added. After 18 h stirring between 35° C. and 48° C. the green-brown solution was concentrated at reduced pressure and purified by silica gel flash chromatography (hept/TBME 6:1 to 1:1) and by washing with pentane to afford a white solid 4r or 4'r (diastereomer I) (100 mg, 29%) and a white solid 4r or 4'r (diastereomer II) (60 mg, 17.4%).

4r or 4'r (diastereomer I): ¹H-NMR (400 MHz, CDCl₃): 3.38 (s, 2 H), 6.27 (d, J=1.9, 2 H), 7.21 (m, 2 H), 7.27 (t, J=1.9, 1 H), 7.31 (m, 2 H), 7.64 (m, 2 H), 7.73 (m, 2 H).

HPLC retention time: 5.45 min 4r or 4'r (diastereomer II): ¹H-NMR (400 MHz, CDCl₃): 3.36 (s, 2 H), 6.36 (d, J=1.7, 2 H), 7.24-7.39 (m, 5 H), 7.54 (m, 2 H), 7.65 (m, 2 H).

HPLC retention time: 5.58 min

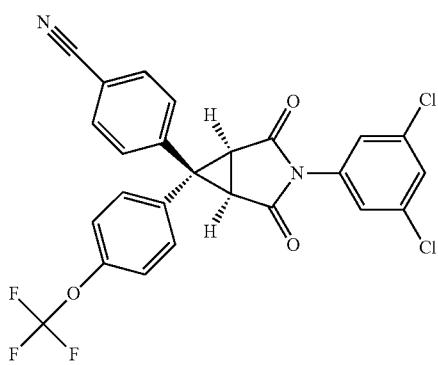

relative stereochemistry rel-4-[(1S,5R,6r)-3-(3,5-dichlorophenyl)-2,4-dioxo-6-[4-(trifluoromethoxy)phenyl]-3-azabicyclo[3.1.0]hexan-6-yl]benzonitrile 4r

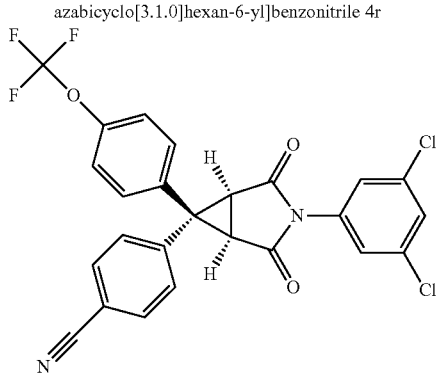

relative stereochemistry rel-4-[(1S,5R,6s)-3-(3,5-dichlorophenyl)-2,4-dioxo-6-[4-(trifluoromethoxy)phenyl]-3-azabicyclo[3.1.0]hexan-6-yl]benzonitrile 4'r rac-(1S, 5S, 6R)- and rac-(1S, 5S, 6S)-6-(4-Chlorophenyl)-3-(3,5-dichlorophenyl)-6-(4-methoxyphenyl)-1-methyl-3-azabicyclo[3.1.0]hexane-2,4-dione (4s and 4's). To a solution of [(4-chlorophenyl)(4-methoxyphenyl)methylidene]hydrazine (8s) (0.42 g, 1.6 mmol) in CHCl₃ (2 ml) MnO₂ (0.82 g, 8 mmol) was added. After 75 min at rt 1-(3,5-dichlorophenyl)-3-methyl-2,5-dihydro-1H-pyrrole-2,5-dione (2b) (0.388 mg, 1.6 mmol) in CHCl₃ (2 ml) was added. After 8 h at 40° C. and 14 h at 60° C. the suspension was filtered over celite, the filtrate was concentrated at reduced pressure to afford a yellow oil. The crude product was purified by silica gel flash chromatography (hept/TBME 4:1) and by washing with pentane to afford a white solid 4s or 4's (diastereomer I) (12 mg, 1.5%) and a white solid 4s or 4's (diastereomer II) (10 mg, 1%).

4s or 4's (diastereomer I): ¹H-NMR (400 MHz, CDCl₃): 1.45 (s, 3 H), 3.22 (s, 1 H), 3.76 (s, 3 H), 6.26 (d, J=1.8, 2 H), 6.85 (m, 2 H), 7.23 (t, J=1.8, 1 H), 7.27-7.38 (m, 6 H).

HPLC retention time: 5.74 min 4s or 4's (diastereomer II): ¹H-NMR (400 MHz, CDCl₃): 1.46 (s, 3 H), 3.24 (s, 1 H), 3.77 (s, 3 H), 6.28 (d, J=1.8, 2 H), 6.87 (m, 2 H), 7.22-7.28 (m, 3 H), 7.31 (m, 2 H), 7.37 (m, 2 H).

HPLC retention time: 5.80 min

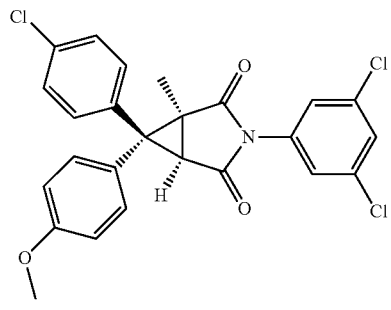

relative stereochemistry rac-(1S,5S,6R)-6-(4-Chlorophenyl)-3-(3,5-dichlorophenyl)-6-(4-methoxyphenyl)-1-methyl-3-azabicyclo[3.1.0]hexane-2,4-dione (4s)

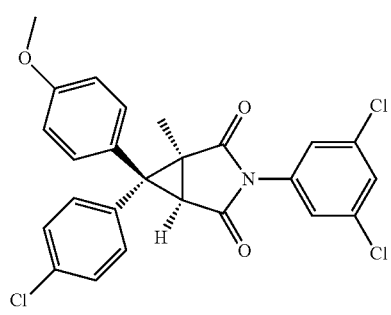

relative stereochemistry rac-(1S,5S,6S)-6-(4-Chlorophenyl)-3-(3,5-dichlorophenyl)-6-(4-methoxyphenyl)-1-methyl-3-azabicyclo[3.1.0]hexane-2,4-dione (4's)

rac-(1S, 5S, 6R)- and rac-(1S, 5S, 6S)-3-(3,5-Dichlorophenyl)-6-(furan-2-yl)-1-methyl-6-phenyl-3-azabicyclo[3.1.0]hexane-2,4-dione (4t and 4't). To a suspension of 1-(3,5-dichlorophenyl)-3-methyl-2,5-dihydro-1H-pyrrole-2,5-dione (2b) (0.53 g, 2.1 mmol) and MnO₂ (1.17 g, 11.4 mmol) in CHCl₃ (5 ml) [furan-2-yl(phenyl)methylidene]hydrazine (8t) (0.42 g, 2.2 mmol) in CHCl₃ (3.5 ml) was added. After 2 h the MnO₂ was removed. The clear solution was stirred overnight (about 16 h) at rt and 2 h at 60° C. and concentrated at reduced pressure to afford an oil (0.78 g). The crude product was purified by two silica gel flash chromatographies (toluene/TBME 99:1-8:2) and (hept/TBME 8:2) to afford solid 4t or 4't (diastereomer I) (2 mg, 0.2%). 4t or 4't (diastereomer II) was not isolated.

4t or 4't (diastereomer I): ¹H-NMR (400 MHz, CDCl₃): 1.64 (s, 3 H), 3.50 (s, 1 H), 5.96 (m, 1 H), 6.22 (d, J=1.9, 2 H), 6.33 (m, 1 H), 7.23 (t, J=1.9, 1 H), 7.37-7.52 (m, 6 H).

HPLC retention time: 5.51 min

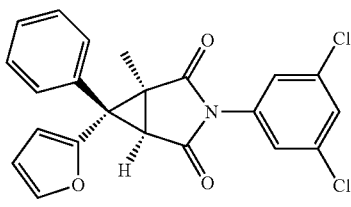

relative stereochemistry rac-(1S,5S,6R)-3-(3,5-Dichlorophenyl)-6-
(furan-2-yl)-1-methyl-6-phenyl-3-
azabicyclo[3.1.0]hexane-2,4-dione (4t)

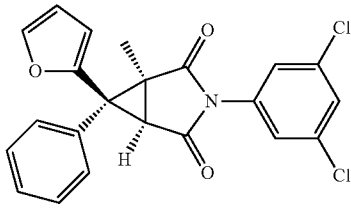

relative stereochemistry rac-(1S,5S,6S)-3-(3,5-Dichlorophenyl)-6-
(furan-2-yl)-1-methyl-6-phenyl-3-
azabicyclo[3.1.0]hexane-2,4-dione (4′t)

4-[6-(4-Cyanophenyl)-3-(3,5-dichlorophenyl)-2,4-dioxo-3-azabicyclo[3.1.0]hexan-6-yl]benzonitrile (4u). To a red solution of 4-[(4-cyanophenyl)(diazo)methyl]benzonitrile 5u (0.2 g, 0.81 mmol) in CHCl$_3$ (4 ml) 1-(3,5-dichlorophenyl)-2,5-dihydro-1H-pyrrole-2,5-dione (2a) (0.246 g, 1 mmol) was added. The solution was stirred overnight (about 16 h) at rt to afford a pink suspension without diazo compound left. The suspension was stirred for 1.5 h at 60° C., concentrated at reduced pressure to afford a red solid (0.49 g). The crude product was purified by silica gel flash chromatography (EtOAc/hept 1:2) to afford a pink solid 4u (0.15 mg, 40%).

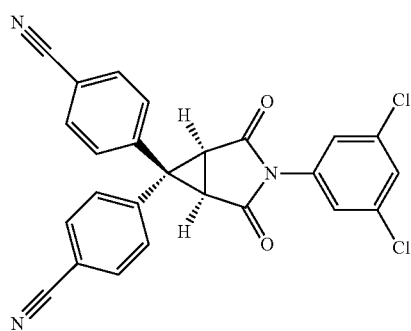

$^1$H-NMR (400 MHz, CDCl$_3$): 3.40 (s, 2 H), 6.27 (d, J=1.9, 2 H), 7.28 (t, J=1.9, 1 H), 7.36 (m, 2 H), 7.60-7.70 (m, 4 H), 7.75 (m, 2 H).

HPLC retention time: 4.87 min rac-4-[(1S,5S)-6-(4-Cyanophenyl)-3-(3,5-dichlorophenyl)-1-methyl-2,4-dioxo-3-azabicyclo[3.1.0]hexan-6-yl]benzonitrile (4v). To a red solution of 4-[(4-cyanophenyl)(diazo)methyl]benzonitrile (5u) (0.53 g, 2.2 mmol) in CHCl$_3$ (20 ml) 1-(3,5-dichlorophenyl)-3-methyl-2,5-dihydro-1H-pyrrole-2,5-dione (2b) (0.55 g, 2.2 mmol) was added. After 17 h at 60° C. a solid precipitated and a filtration afforded an orange solid (1.04 g). The crude product was purified by two silica gel flash chromatographies (DCM) and (TBME/hept 2:1) to afford a white solid 4v (0.23 g, 23%).

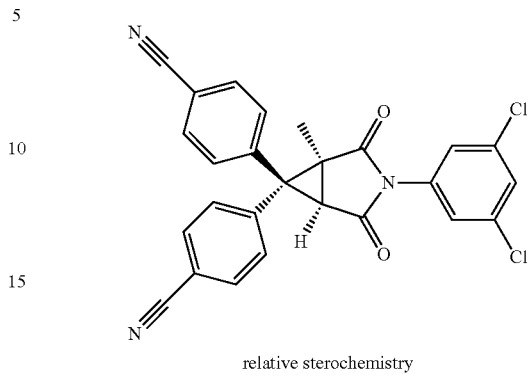

relative sterochemistry $^1$H-NMR (400 MHz, CDCl$_3$): 1.49 (s, 3 H), 3.31 (s, 1 H), 6.26 (d, J=1.8, 2 H), 7.27 (t, J=1.9, 1 H), 7.51 (m, 2 H), 7.58 (m, 2 H), 7.64-7.73 (m, 4 H).

HPLC retention time: 4.98 min rel-(1R,5S,6s)- and rel-(1R,5S,6r)-3-(3,5-Dichlorophenyl)-6-(pyridin-4-yl)-6-[4-(trifluoromethoxy)phenyl]3-azabicyclo[3.1.0]hexane-2,4-dione (4w and 4′w). To a red solution of 4-{diazo[4-(trifluoromethoxy)phenyl]methyl}pyridine (5w) (0.132 g, 0.47 mmol) in CHCl$_3$ (1.5 ml) 1-(3,5-dichlorophenyl)-2,5-dihydro-1H-pyrrole-2,5-dione (2a) (0.11 g, 0.47 mmol) was added and the mixture stirred overnight (about 16 h) at rt. The slightly brown suspension was stirred for 1.5 h at 60° C., concentrated at reduced pressure to afford a red solid (0.4 g). The crude product was suspended in EtOAc, the residue filtered and washed with EtOAc to afford a pale brown solid (0.135 g, 58%). The crude product was purified by silica gel flash chromatography (EtOAc) to afford a white solid 4w or 4′w (diastereomer I) (59 mg, 25%) and a white solid 4w or 4′w (diastereomer II) (61 mg, 26%).

4w or 4′w (diastereomer I): $^1$H-NMR (400 MHz, DMSO-d$_6$): 3.82 (s, 2H), 6.42 (d, J=1.9, 2 H), 7.29 (m, 2H), 7.51 (m, 2H), 7.59 (m, 2H), 7.63 (t, J=1.9, 1 H), 8.53 (m, 2H).

HPLC retention time: 4.41 min 4w or 4′w (diastereomer II): $^1$H-NMR (400 MHz, DMSO-d$_6$): 3.80 (s, 2 H), 6.39 (d, J=1.9, 2 H), 7.36 (m, 2 H), 7.51 (m, 2 H), 7.58-7.65 (m, 3 H), 8.64 (m, 2 H).

HPLC retention time: 4.89 min

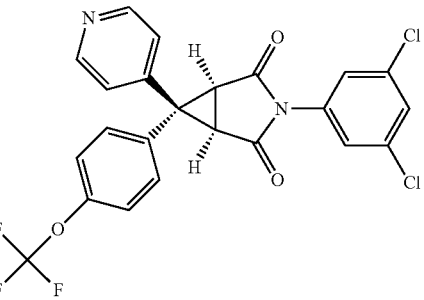

relative stereochemistry rel-(1R,5S,6s)-3-(3,5-Dichlorophenyl)-6-
(pyridin-4-yl)-6-[4-
(trifluoromethoxy)phenyl]-3-
azabicyclo[3.1.0]hexane-2,4-dione (4w)

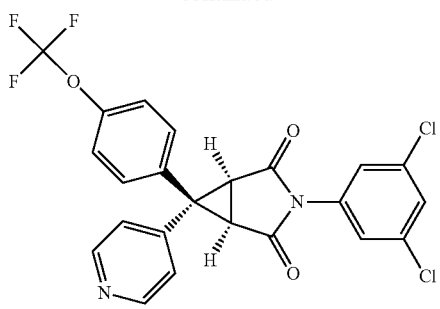

relative stereochemistry rel-(1R,5S,6r)-3-(3,5-Dichlorophenyl)-
6-(pyridin-4-yl)-6-[4-
(trifluoromethoxy)phenyl]-3-
azabicyclo[3.1.0]hexane-2,4-dione
(4'w)

rac-(1 S, 5S, 6R)- and rac-(1 S, 5S, 6S)-3-(3, 5-Dichlorophenyl)-1-methyl-6-(pyridin-4-yl)-6-[4-(trifluoromethoxy)phenyl]-3-azabicyclo[3.1.0]hexane-2, 4-dione (4x and 4'x). To a red solution of 4-{diazo[4-(trifluoromethoxy)phenyl]methyl}pyridine (5w) (0.26 g, 0.94 mmol) in CHCl$_3$ (4 ml) 1-(3,5-dichlorophenyl)-3-methyl-2, 5-dihydro-1H-pyrrole-2,5-dione (2b) (0.24 g, 0.94 mmol) was added and stirred overnight (about 16 h) at rt. The red solution was stirred overnight at 60° C., concentrated at reduced pressure to afford a black oil (0.49 g). The crude product was purified by silica gel flash chromatography (EtOAc/hept 3:1) to afford a white solid 4x or 4'x (diastereomer I) (75 mg, 15%). A further purification by silica gel flash chromatography (EtOAc/hept 1:4) afforded a white solid 4x or 4'x (diastereomer II) (41 mg, 8%).

4x or 4'x (diastereomer I): $^1$H-NMR (400 MHz, CDCl$_3$): 1.48 (s, 3 H), 3.31 (s, 1 H), 6.37 (d, J=1.9, 2 H), 7.22 (m, 2 H), 7.24-7.28 (m, 3 H), 7.49 (m, 2 H), 8.63 (m, 2 H).

HPLC retention time: 4.60 min 4x or 4'x (diastereomer II): $^1$H-NMR (400 MHz, CDCl$_3$): 1.50 (s, 3 H), 3.27 (s, 1 H), 6.37 (d, J=1.9, 2 H), 7.20-7.28 (m, 3 H), 7.37 (m, 2 H), 7.42 (m, 2 H), 8.60 (m, 2 H).

HPLC retention time: 4.99 min

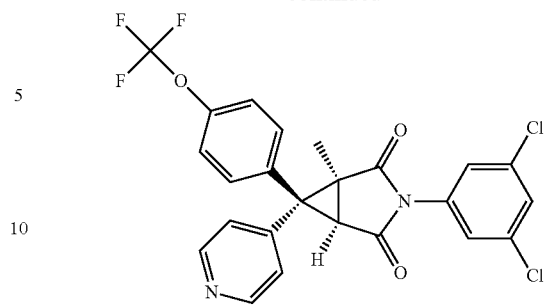

relative stereochemistry rac-(1S,5S,6S)-3-(3,5-dichlorophenyl)-1-
methyl-6-(pyridin-4-yl)-6-[4-
(trifluoromethoxy)phenyl]-3-
azabicyclo[3.1.0]hexane-2,4-dione (4'x)

rel-4-[(1 S, 5R, 6s)- and rel-4-[(1 S, 5R, 6r)-3-(3,5-Dichlorophenyl)-2,4-dioxo-6-(pyridin-4-yl)-3-azabicyclo[3.1.0]hexan-6-yl]benzonitrile (4y and 4'y). The red solution of 4-[diazo(pyridin-4-yl)methyl]benzonitrile (5y) (0.10 g, 0.45 mmol) in CHCl$_3$ (2 ml) was added (over 1 h) to a solution of 1-(3,5-dichlorophenyl)-2,5-dihydro-1H-pyrrole-2,5-dione (2a) (0.11 g, 0.45 mmol) in CHCl$_3$ (0.5 ml) at 60°. The red solution was stirred overnight at 60° C., concentrated at reduced pressure to afford a black oil (0.24 g). The crude product was purified by two silica gel flash chromatographies (EtOAc/hept 1:2-1:0) and (toluene/EtOAc 5:1) to afford a pale yellow solid 4y or 4'y (diastereomer I) (41 mg, 21%) and a further filtration over silica gel to afford a white solid 4y or 4'y (diastereomer II) (40 mg, 20%).

4y or 4'y (diastereomer I): $^1$H-NMR (400 MHz, CDCl$_3$): 3.39 (s, 2 H), 6.37 (d, J=1.9, 2 H), 7.27 (t, J=1.9, 1 H), 7.38 (m, 2 H), 7.43 (m, 2 H), 7.67 (m, 2 H), 8.70 (m, 2 H).

HPLC retention time: 4.18 min 4y or 4'y (diastereomer II): $^1$H-NMR (400 MHz, CDCl$_3$): 3.41 (s, 2 H), 6.27 (d, J=1.9, 2 H), 7.03 (m, 2 H), 7.29 (t, J=1.9, 1 H), 7.64 (m, 2 H), 7.78 (m, 2 H), 8.61 (m, 2 H).

HPLC retention time: 3.66 min

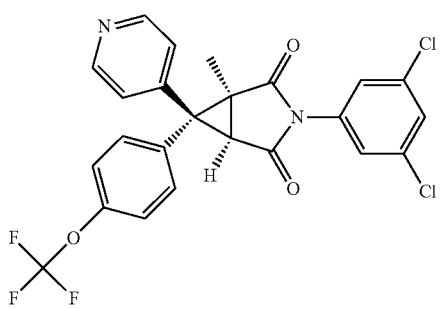

relative stereochemistry rac-(1S,5S,6R)-3-(3,5-dichlorophenyl)-1-
methyl-6-(pyridin-4-yl)-6-[4-
(trifluoromethoxy)phenyl]-3-
azabicyclo[3.1.0]hexane-2,4-dione (4x)

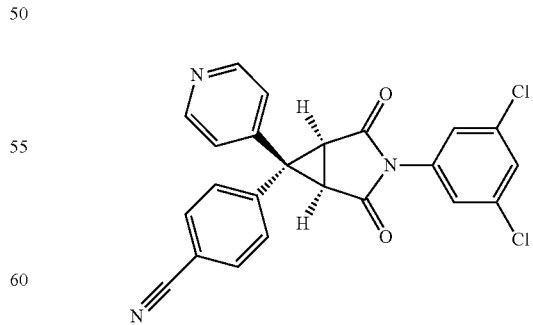

relative stereochemistry rel-4-[(1S,5R,6s)-3-(3,5-Dichlorophenyl)-2,4-
dioxo-6-(pyridin-4-yl)-3-azabicyclo
[3.1.0]hexan-6-yl]benzonitrile (4y)

-continued

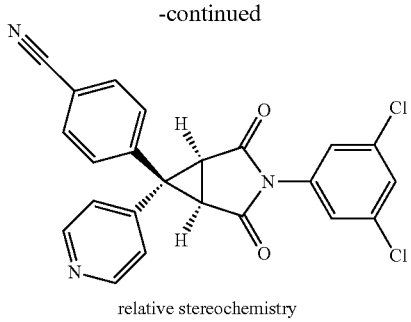

relative stereochemistry rel-4-[(1S,5R,6r)-3-(3,5-Dichlorophenyl)-2,4-
dioxo-6-(pyridin-4-yl)-3-azabicyclo
[3.1.0]hexan-6-yl]benzonitrile (4'y)

rac-4-[(1S,5S,6R)- and rac-4-[(1 S, 5S, 6S)-3-(3,5-Dichlorophenyl)-1-methyl-2,4-dioxo-6-(pyridin-4-yl)-3-azabicyclo[3.1.0]hexan-6-yl]benzonitrile (4z and 4'z). The red solution of 4-[diazo(pyridin-4-yl)methyl]benzonitrile (5y) (0.20 g, 0.9 mmol) in CHCl$_3$ (4 ml) was added (over 7 h with syringe dispenser) to a solution of 1-(3,5-dichlorophenyl)-3-methyl-2,5-dihydro-1H-pyrrole-2,5-dione (2b) (0.23 g, 0.90 mmol) in CHCl$_3$ (1 ml) at 60°. The solution was stirred 45 h at 60° C., concentrated at reduced pressure to afford a black oil (0.47 g). The crude product was purified by silica gel flash chromatography (EtOAc/hept 1:2-1:0) and by recrystallization in EtOAc to afford a pale yellow solid 4z or 4'z (diastereomer I) (25 mg, 6%) and a pale yellow solid 4z or 4'z (diastereomer II) (30 mg, 8%).

4z or 4'z (diastereomer I): $^1$H-NMR (400 MHz, CDCl$_3$): 1.49 (s, 3 H), 3.31 (s, 1 H), 6.36 (d, J=1.9, 2 H), 7.26 (t, J=1.9, 1 H), 7.37 (m, 2 H), 7.53 (m, 2 H), 7.71 (m, 2 H), 8.62 (m, 2 H).

HPLC retention time: 4.30 min 4z or 4'z (diastereomer II): $^1$H-NMR (400 MHz, CDCl$_3$): 1.50 (s, 3 H), 3.34 (s, 1 H), 6.26 (d, J=1.9, 2 H), 7.22-7.28 (m, 3 H), 7.59 (m, 2 H), 7.69 (m, 2 H), 8.65 (m, 2 H).

HPLC retention time: 3.86 min

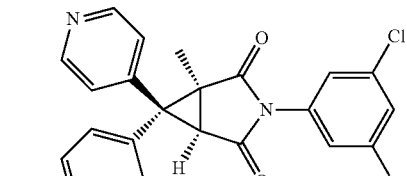

relative stereochemistry rac-4-[(1S,5S,6R)3-(3,5-Dichlorophenyl)-1-
methyl-2,4-dioxo-6-(pyridin-4-yl)-3-azabicyclo
[3.1.0]hexan-6-yl]benzonitrile (4z)

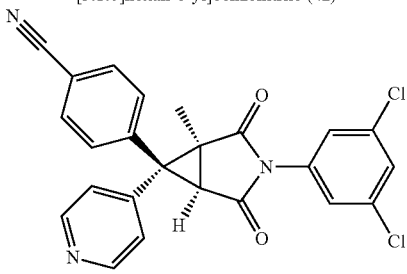

relative stereochemistry rac-4-[(1S,5S,6S)-3-(3,5-Dichlorophenyl)-1-
methyl-2,4-dioxo-6-(pyridin-4-yl)-3-azabicyclo
[3.1.0]hexan-6-yl]benzonitrile (4'z)

TABLE 1

Exemplified compounds with substituents according to formula (Ia) and (Ib)

| | A | X$_1$ | X$_2$ | R$_1$ | R$_2$ | R$_3$ | R$_4$ | R$_6$ | R$_7$ | HPLC ret. time |
|---|---|---|---|---|---|---|---|---|---|---|
| a | CH | Cl | Cl | H | H | phenyl | phenyl | H | H | 4a = 5.49 min |
| b | CH | Cl | Cl | CH$_3$ | H | phenyl | phenyl | H | H | 4b = 5.60 min |
| c | CH | Cl | Cl | H | H | phenyl | H | H | H | 4c = 5.00 min, 4'c = 4.80 min |
| d | CH | Cl | Cl | CH$_3$ | H | phenyl | H | H | H | 4d = 5.22 min, 4'd = 5.06 min |
| e | CH | Cl | Cl | H | H | 4-Br-phenyl | H | H | H | 4e = 5.34 min, 4'e = 5.15 min |

TABLE 1-continued

Exemplified compounds with substituents according to formula (Ia) and (Ib)

| | A | X₁ | X₂ | R₁ | R₂ | R₃ | R₄ | R₆ | R₇ | HPLC ret. time |
|---|---|---|---|---|---|---|---|---|---|---|
| f | CH | Cl | Cl | CH₃ | H | 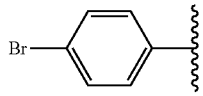 | H | H | H | 4f = 5.55 min<br>4'f = 5.39 min |
| g | CH | Cl | Cl | CH₃ | H | 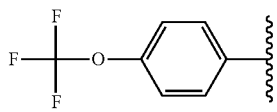 [SMILES: *c1ccc(OC(F)(F)F)cc1] | H | H | H | 4g = 5.61 min<br>4'g = 5.46 min |
| h | CH | Cl | Cl | CH₃ | H | 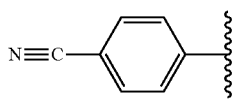 | H | H | H | 4h = 4.95 min<br>4'h = 4.65 min |
| i | CH | Cl | Cl | CH₃ | H | 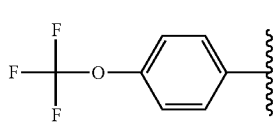 | 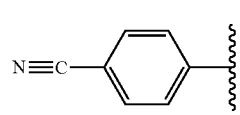 | H | H | 4i/4'i diastereomer I = 5.57 min<br>4i/4'i diastereomer II = 5.67 min |
| j | CH | Cl | Cl | CH₃ | H | 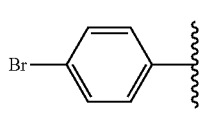 | 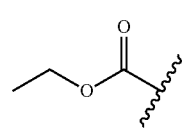 [SMILES: *C(=O)OCC] | H | H | 4'j = 5.77 min |
| k | CH | Cl | Cl | CH₃ | H | 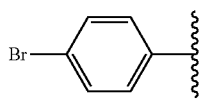 | 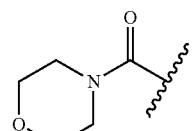 | H | H | 4'k = 4.99 min |
| l | CH | Cl | Cl | CH₃ | H | 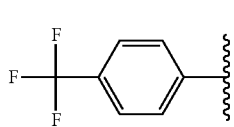 | 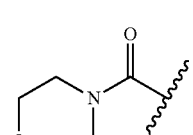 | H | H | 4'l = 5.02 min |
| m | CH | Cl | Cl | CH₃ | H | 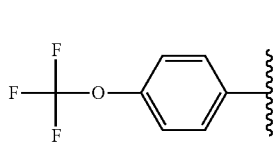 [SMILES: *c1ccc(OC(F)(F)F)cc1] | 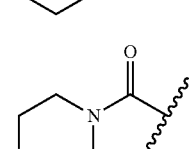 | H | H | 4'm = 5.11 min |
| n | CH | Cl | Cl | CH₃ | H | 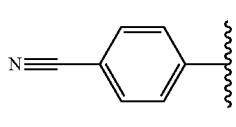 | 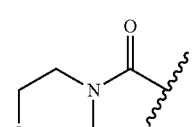 | H | H | 4'n = 4.39 min |
| o | CH | Cl | Cl | CH₃ | H | 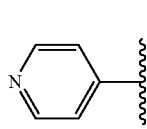 [SMILES: *c1ccncc1] | 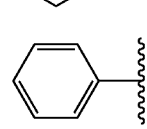 | H | H | 4o or 4'o diastereomer I = 4.38 min<br>4o or 4'o diastereomer II = 3.94 min |
| p | CH | Cl | Cl | H | H | 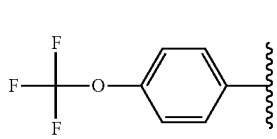 | 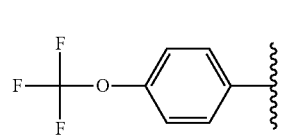 [SMILES: *c1ccc(OC(F)(F)F)cc1] | H | H | 4p = 6.09 min |

TABLE 1-continued

Exemplified compounds with substituents according to formula (Ia) and (Ib)

| | A | $X_1$ | $X_2$ | $R_1$ | $R_2$ | $R_3$ | $R_4$ | $R_6$ | $R_7$ | HPLC ret. time |
|---|---|---|---|---|---|---|---|---|---|---|
| q | CH | Cl | Cl | $CH_3$ | H | 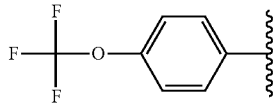 | 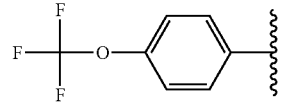 [SMILES: *c1ccc(OC(F)(F)F)cc1] | H | H | 4q = 6.17 min |
| r | CH | Cl | Cl | H | H | 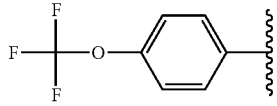 | 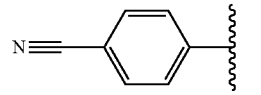 | H | H | 4r or 4'r diastereomer I = 5.45 min<br>4r or 4'r diastereomer II = 5.58 min |
| s | CH | Cl | Cl | $CH_3$ | H | 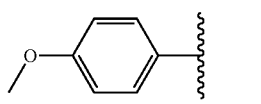 [SMILES: *c1ccc(OC)cc1] | 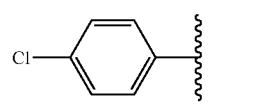 [SMILES: *c1ccc(Cl)cc1] | H | H | 4s or 4's diastereomer I = 5.74 min<br>4s or 4's diastereomer II = 5.80 min |
| t | CH | Cl | Cl | $CH_3$ | H | 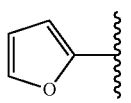 | 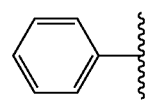 | H | H | 4t or 4't diastereomer I = 5.51 min |
| u | CH | Cl | Cl | H | H | 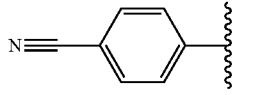 | 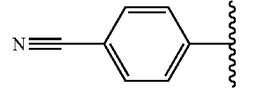 | H | H | 4u = 4.87 min |
| v | CH | Cl | Cl | $CH_3$ | H | 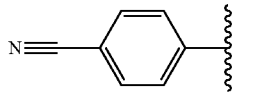 [SMILES: *c1ccc(C#N)cc1] | 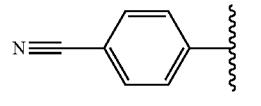 | H | H | 4v = 4.98 min |
| w | CH | Cl | Cl | H | H | 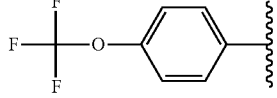 | 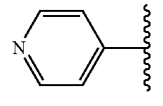 | H | H | 4w or 4'w diastereomer I = 4.41 min<br>4w or 4'w diastereomer II = 4.89 min |
| x | CH | Cl | Cl | $CH_3$ | H | 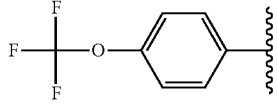 [SMILES: *c1ccc(OC(F)(F)F)cc1] | 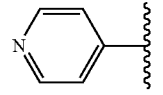 | H | H | 4x or 4'x diastereomer I = 4.60 min<br>4x or 4'x diastereomer II = 4.99 min |
| y | CH | Cl | Cl | H | H | 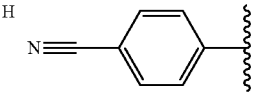 | 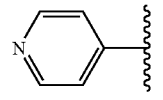 | H | H | 4y or 4'y diastereomer I = 4.18 min<br>4y or 4'y diastereomer II = 3.66 min |
| z | CH | Cl | Cl | $CH_3$ | H | 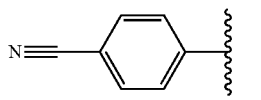 | 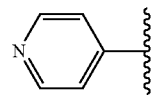 | H | H | 4z or 4'z diastereomer I = 4.30 min<br>4z or 4'z diastereomer II = 3.86 min |

The biological properties of representative compounds were investigated by way of the experimental protocols described below:

Cell-Based Assay to Determine the Effect of the Compounds on LFA-1-Mediated Cell Adhesion (LFA-1 Adhesion)

Purpose of the Assay: The V well cell adhesion assay measures the ability of the compounds to interfere with LFA-1-mediated binding to ICAM-1 at cellular level. The assay has been successfully used in the past to identify and characterize small molecules LFA-1 inhibitors.

Experimental Protocol: The adhesion assay was performed in Vbottom 96-well plates as described previously [Weitz-Schmidt 2012]. Briefly, the plates were coated with anti-human IgG mAb diluted in coating buffer (20 mM Tris containing 150 mM NaCl, pH 8) (1 µg/mL) and incubated overnight at 4° C. The plates were flicked out and blocked with blocking buffer (50 mM Tris base, 150 mM NaCl, 1.5% BSA (w/v), pH 7.2) at 37° C. for 90 min. Then human recombinant ICAM-1/Fc (R&D Systems) diluted in coating buffer (0.3 µg/mL) was added to each well. The plates were incubated at 37° C. for 90 min and washed with binding buffer (50 mM Tris base, 150 mM NaCl, 1.5% BSA (w/v), 2 mM $MgCl_2$, 2 mM $MnCl_2$, 5 mM D-glucose monohydrate, pH 7.2-7.4) to remove unbound ligand.

Jurkat cells were cultured under standard conditions as recommended by the American Type Culture collection (ATCC). The cells were fluorescently labelled with BCECF-AM in PBS (1 µg/mL) at 37° C. for 20 min in the dark, centrifuged and washed with PBS. The test compounds were dissolved in DMSO at 10 mM and serially pre-diluted in DMSO (100%) to avoid precipitation, before performing final dilution steps in binding buffer.

The labelled Jurkat cells were re-suspended in binding buffer and test compounds or solvent control were added. The DMSO concentration was kept constant in all samples (1% DMSO as final assay concentration). After 40 min at 37° C. (LFA-1 activation and compound pre-incubation step) the cell suspension ($3 \times 10^5$ cells/mL in binding buffer) was pipetted up and down and transferred to the ligand-coated microtiter V well plates (30 000 cells/well). The plates were centrifuged for 4 min at room temperature (rt) at 1000 rpm (Centrifuge Eppendorf 5810 R), setting the brake off. Non-adherent cells that accumulated in the center of the Vbottom were quantified using a fluorescence reader with the filter sets allowing excitation at 485 nm and quantification of emission at 535 nm. The determination of the half maximal inhibitory concentration ($IC_{50}$) of the compounds was calculated using the software GraphPad Prism 6.

Cell-Based Assay to Determine the Selectivity of the Compounds Over the Integrin VLA-4 (VLA-4 Adhesion)

Purpose of the Assay: This V well cell adhesion assay measures the effect of the compounds on VLA-4-mediated Jurkat cell binding to VCAM-1. The assay has been successfully used in the past to determine the selectivity of small molecule LFA-1 inhibitors over the integrin VLA-4.

Experimental Protocol: The adhesion assay was performed as described above for the Jurkat/ICAM-1 V well adhesion assay. Briefly, plates were coated with anti-human IgG mAb and blocked with BSA as described above. Instead of ICAM-1, recombinant human VCAM-1/CD106 Fc chimera (R&D Systems) was coated onto the plates (0.3 µg/mL in coating buffer). After incubation, labelled Jurkat cells in binding buffer were transferred to the wells (20,000 cells/well). The plates were immediately centrifuged at 1000 rpm for 4 min at rt (Centrifuge Eppendorf 5810 R) setting the brakeoff. Non-adherent cells were quantified in the tip of the Vbottom well using a fluorescence reader. $IC_{50}$ values of the compounds were calculated using the software GraphPad Prism 6.

Measurement of mAb R7.1 binding to LFA-1 (mAb R7.1 binding)

Purpose of the Assay: This flow cytometry assay determines the effect of the compounds on the binding of the anti-LFA-1 mAb R7.1 to LFA-1 expressed on leukocytes. A concentration-dependent reduction of mAb R7.1 binding indicates that the compounds interact with the alpha I allosteric site of LFA-1 and thus belong to the class of alpha I allosteric inhibitors, stabilizing LFA-1 in an inactive state.

Experimental Protocol: Jurkat cells or human peripheral blood mononuclear cells (PBMCs) were resuspended in assay buffer (50 mM Tris, 150 mM NaCl, 2 mM $MgCl_2$, 1.5% BSA and 5 mM D-glucose monohydrate, pH7.2) at $2 \times 10^6$ cells/mL and 500 µL of this cell suspension ($1 \times 10^6$ cells) were transferred into polypropylene tubes containing the test compounds diluted in 500 µL assay buffer. The samples were pre-incubated at 37° C. for 40 min, and centrifuged. The supernatants were removed and FITC-labelled anti-LFA-1 mAb R7.1 and PE-labeled anti-LFA-1 mAb TS2/4 (mAb TS2/4 is not affected by alpha I allosteric inhibitor binding to LFA-1) or appropriate isotype controls were added directly to each cell pellet. The pellets were then gently pipetted up and down and incubated on ice for 30 min in the dark. After the incubation step the cells were washed twice with PBS and resuspended in PBS.

Antibody binding was analyzed by flow cytometry. Mean fluorescence intensities (MFI) were calculated using the CellQuest software. The values are expressed as % of solvent control (solvent control=100% binding).

Quantification of mAb MEM148 Binding to LFA-1 (mAb MEM148 Binding)

Purpose of the Assay: This flow cytometry assay determines the effect of the compounds on the binding of the conformation-sensitive anti-LFA-1 mAb MEM148 to LFA-1 expressed on leukocytes. The mAb MEM148 detects an epitope which becomes exposed in activated LFA-1 [Yuki 2012]

Experimental Protocol: The assay is performed as the flow cytometry assay described above.

Briefly, Jurkat cells or PBMCs in assay buffer (50 mM Tris, 150 mM NaCl, 1 mM $CaCl_2$, 1 mM $MgCl_2$, 5 mM Glucose, 1.5% BSA, pH 7.3) were pre-incubated with the compounds and appropriate positive controls for 40 min at rt. After incubation, the cell-suspension was centrifuged, the supernatant discarded and PE-labelled anti-LFA-1 mAb MEM148 was directly added to the pellets. After pipetting up and down, the tubes were incubated for 30 min. at 37° C. in the dark. The pellet was washed twice with 1 mL PBS and resuspended in PBS. Antibody binding was quantified by flow cytometry. Mean fluorescence intensities (MFI) were calculated using the CellQuest software. Positive controls in each experiments showed an increase in MEM148 binding over solvent control of at least >2.5 fold.

Assessment of Cellular Toxicity (Toxilight Assay and CellTiter-Glo Assay)

Purpose. To detect potential cellular toxicity of present LFA-1 inhibitors two complementary assays were chosen: the Toxilight™ BioAssay (Lonza) and the CellTiter-Glo™ Luminescent Cell Viability Assay (Promega). The Toxilight assay measures cell death via the release of the cytosolic enzyme adenylate kinase into the supernatant of treated cell cultures. The CellTiter-Glo assay directly determines the key energy metabolite ATP, resulting in sensitive quantitation of the number of healthy cells in culture.

Both assays were used with two different cell lines: the Jurkat and HepG2 cell lines. Jurkat, a human lymphocytic leukemia cell line, was utilized to assess the effect of the compounds on LFA-1 expressing cells. HepG2, a human hepatocyte cell line, was used to assess the response of liver cells where drugs are metabolized. Both assays included the use of untreated cells, and cells treated with amiodarone or 0.5% Triton X 100 as cytotoxic controls.

Experimental Protocols.

Jurkat cells and HepG2 cells were cultured in RPMI 1640 containing 10% FCS or DMEM containing 10% FCS under standard conditions (recommended by ATCC). Compounds were dissolved in DMSO and serially pre-diluted in DMSO (100%) to avoid precipitation of the compounds, before final dilution steps in culture medium containing FCS were performed. The final DMSO concentration was kept constant at 0.5% in all samples.

The test compounds and controls were exposed to the cells for 24 hours respectively at 37° C. Then adenylate kinase activity was quantified in the supernatant of the cell cultures using the ToxiLight™ reagent. In an independent set of experiments ATP content was measured by adding the CellTiter-Glo™ reagent according to manufacturer's instructions.

TABLE 2

Biological properties of selected compounds
(designation according to preparation supra)

| Compound | LFA-1 Adhesion [1] $IC_{50}$ [μM] | VLA-4 Adhesion [2] $IC_{50}$ [μM] | mAb R7.1 binding [3] % inhibition at 1 μM | mAb MEM148 binding [4] binding relative to solvent ctrl at 10 μM | Toxilight Jurkat [5] % viability at 10 μM | Toxilight HepG2 [5] % viability at 10 μM | CellTiter-Glo Jurkat [5] % viability at 10 μM | CellTiter-Glo HepG2 [5] % viability at 10 μM |
|---|---|---|---|---|---|---|---|---|
| 4a | 8.477 | n.d. | n.d. | n.d. | n.d. | n.d. | n.d. | n.d. |
| 4b (racemate) | 1.865 ± 1.269 | >10 | 76.9; 80.0 | 0.974 | 101 ± 9.8 | 124 ± 29.7 | 96.8 ± 4.7 | 98.4 ± 3.8 |
| 4b enantiomer A | 1.342 ± 0.678 | >10 | 87.3 | no | 100 ± 12.9 | 120 ± 40.2 | 92.8 ± 4.7 | 101.5 ± 1.9 |
| 4b enantiomer B | >10 | n.d. | n.d. | n.d. | n.d. | n.d. | n.d. | n.d. |
| 4'c | 1.587 | n.d. | n.d. | n.d. | n.d. | n.d. | n.d. | n.d. |
| 4'd (racemate) | 1.544 ± 0.646 | n.d. | 80.5 | n.d. | n.d. | n.d. | n.d. | n.d. |
| 4'e | 3.326 | n.d. | n.d. | n.d. | n.d. | n.d. | n.d. | n.d. |
| 4'f (racemate) | 0.715 ± 0.618 | >10 | 85.2; 91.7 | 0.96 | 99.9 ± 24.2 | 115.6 ± 35.1 | 115.0 ± 4.8 | 101.6 ± 4.0 |
| 4'g (racemate) | 0.550 ± 0.206 | >10 | 93.6; 94.1 | 0.89 | 116 ± 16.2 | 99.8 ± 26.5 | 111.4 ± 7.4 | 102.6 ± 4.5 |
| 4'h (racemate) | 0.147 | >10 | 96.8; 95.8 | 1.00 | 93.5 ± 2.06 | 78.3 ± 35.2 | 112.6 ± 4.9 | 103.7 ± 3.2 |
| 4i/4'i diastereomer I (racemate) | 0.562; 0.530 | n.d. | n.d. | n.d. | n.d. | n.d. | n.d. | n.d. |
| 4i/4'i diastereomer II (racemate) | 0.018 ± 0.014 | >10 | 98.6 | 0.937 | n.d. | n.d. | n.d. | n.d. |
| 4i/4'i diastereomer II enantiomer A | 0.005, 0.004 | >10 | n.d. | 0.96 | n.d. | n.d. | n.d. | n.d. |
| 4i/4'i diastereomer II enantiomer B | 0.573 | n.d. | n.d. | n.d. | n.d. | n.d. | n.d. | n.d. |
| 4'j (racemate) | 0.375 ± 0.204 | >10 | 93.6 | 0.738 | n.d. | n.d. | n.d. | n.d. |
| 4'k (racemate) | 3.469 | n.d. | n.d. | n.d. | n.d. | n.d. | n.d. | n.d. |
| 4'l (racemate) | >3 | n.d. | n.d. | n.d. | n.d. | n.d. | n.d. | n.d. |
| 4'm (racemate) | 0.405 | n.d. | n.d. | n.d. | n.d. | n.d. | n.d. | n.d. |
| 4'n (racemate) | 0.636 | n.d. | n.d. | n.d. | n.d. | n.d. | n.d. | n.d. |
| 4 o or 4'o diastereomer I (racemate) | >3 | n.d. | n.d. | n.d. | n.d. | n.d. | n.d. | n.d. |
| 4 o or 4'o diastereomer II (racemate) | 0.458 | n.d. | n.d. | n.d. | n.d. | n.d. | n.d. | n.d. |
| 4p | >1 | n.d. | 74.3 | n.d. | n.d. | n.d. | n.d. | n.d. |
| 4q (racemate) | 0.101 | n.d | n.d. | n.d. | n.d. | n.d. | n.d. | n.d. |
| 4r or 4'r diastereomer I | 0.963 | n.d. | n.d. | n.d. | n.d. | n.d. | n.d. | n.d. |
| 4r or 4'r diastereomer II | 0.132 | n.d. | n.d. | n.d. | n.d. | n.d. | n.d. | n.d. |
| 4s or 4's diastereomer I (racemate) | 1.831 | n.d. | n.d. | n.d. | n.d. | n.d. | n.d. | n.d. |
| 4s or 4's diastereomer II (racemate) | 0.153 | n.d. | n.d. | n.d. | n.d. | n.d. | n.d. | n.d. |
| 4t or 4't Diastereomer I (racemate) | 0.870 | n.d. | n.d. | n.d. | n.d. | n.d. | n.d. | n.d. |
| 4u | >1 | n.d. | 87.1 | n.d. | n.d. | n.d. | n.d. | n.d. |
| 4v (racemate) | 0.045 ± 0.014 | >10 | n.d. | | | | | |
| 4w or 4'w diastereomer I | 0.215 ± 0.134 | >10 | 95.7 | n.d. | n.d. | n.d. | n.d. | n.d. |

TABLE 2-continued

Biological properties of selected compounds
(designation according to preparation supra)

| Compound | LFA-1 Adhesion [1)] IC$_{50}$ [μM] | VLA-4 Adhesion [2)] IC$_{50}$ [μM] | mAb R7.1 binding [3)] % inhibition at 1 μM | mAb MEM148 binding [4)] binding relative to solvent ctrl at 10 μM | Toxilight Jurkat [5)] % viability at 10 μM | Toxilight HepG2 [5)] % viability at 10 μM | CellTiter-Glo Jurkat [5)] % viability at 10 μM | CellTiter-Glo HepG2 [5)] % viability at 10 μM |
|---|---|---|---|---|---|---|---|---|
| 4w or 4'w diastereomer II | >1 | n.d. | 45.7 | n.d. | n.d. | n.d. | n.d. | n.d. |
| 4x or 4'x diastereomer I (racemate) | 0.202, 0.286 | >10 | 98.4 | n.d. | n.d. | n.d. | n.d. | n.d. |
| 4x or 4'x diastereomer II (racemate) | >1 | n.d. | 76.9 | n.d. | n.d. | n.d. | n.d. | n.d. |
| 4y or 4'y diastereomer I | >1 | n.d. | n.d. | n.d. | n.d. | n.d. | n.d. | n.d. |
| 4y or 4'y diastereomer II | 1 | n.d. | n.d. | n.d. | n.d. | n.d. | n.d. | n.d. |
| 4z or 4'z diastereomer I (racemate) | >1 | n.d. | n.d. | n.d. | n.d. | n.d. | n.d. | n.d. |
| 4z or 4'z diastereomer II (racemate) | 0.071 | n.d. | n.d. | n.d. | n.d. | n.d. | n.d. | n.d. |

[1)] Mean IC$_{50}$ values ±SD of ≥3 independent experiments run in triplicates or IC$_{50}$ values of single experiments run in triplicates are shown;
[2)] IC$_{50}$ values of single experiments run in triplicates are shown;
[3)] Results are expressed as % of solvent control; IC$_{50}$ values of independent experiments are shown
[4)] mAb MEM148 binding relative to solvent control (=ctrl) is shown; solvent ctrl = 1; positive controls were included in each experiment (not shown);
[5)] 24 hours exposure; mean values ± SD of triplicates are shown

The invention claimed is:

1. A compound according to formula (Ia)

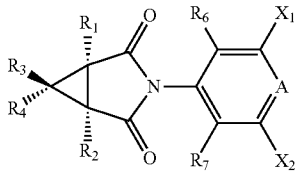

and/or according to formula (Ib),

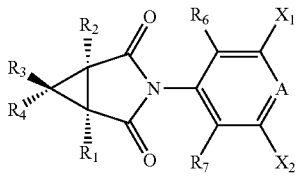

racemates of me according to formula (Ia) and the compound according to formula (Ib), diastereomers of the compound according to formula (Ia) or the compound according to formula (Ib), diastereomeric meso forms of the compound according to formula (Ia) wherein $R_1$ and $R_2$ are the same, pharmaceutically-acceptable salts, hydrates, or solvates, thereof, in which:

$X_1$ is selected from H, halogen or $CF_3$,
$X_2$ is selected from H, halogen or $CF_3$,
wherein at least one of $X_1$ and $X_2$ is halogen or $CF_3$;
A is N or $CR_5$, wherein $R_5$ is selected from H, halogen, branched or unbranched alkyl of 1 to 6 carbon atoms, branched or unbranched alkenyl of 2 to 6 carbon atoms, $CF_3$, $CCl_3$, CN, $NO_2$, O-alkyl with branched or unbranched alkyl of 1 to 6 carbon atoms, S-alkyl with branched or unbranched alkyl of 1 to 6 carbon atoms, aryl, substituted aryl, heteroaryl or substituted heteroaryl;

$R_1$ is selected from H, branched or unbranched alkyl of 1 to 6 carbon atoms, branched or unbranched alkenyl of 2 to 6 carbon atoms, or cycloalkyl of 3 to 6 carbon atoms;

$R_2$ and $R_4$ are independently selected from
(A) H,
(B) branched or unbranched alkyl of 1 to 6 carbon atoms or cycloalkyl of 3 to 6 carbon atoms, wherein said alkyl or cycloalkyl group may optionally be substituted with:
(a) a group of the formula —$OR_8$, wherein $R_8$ is an alkyl or acyl group of 1 to 6 carbon atoms, or
(b) a group of the formula —$NR_9R_{10}$, wherein $R_9$ and $R_{10}$ are each, independently, an alkyl or acyl group of 1 to 2 carbon atoms,
(C) $(CH_2)_n$-aryl, substituted $(CH_2)_n$-aryl, $(CH_2)_n$-heteroaryl or substituted $(CH_2)_n$- heteroaryl,
wherein one or more of the hydrogen atoms of the aryl group of said substituted $(CH_2)_n$-aryl group or one or more of the hydrogen atoms of the heteroaryl group of said substituted $(CH_2)_n$-heteroaryl group may be optionally and independently replaced with:
(i) $R_{11}$, which is aryl or heteroaryl selected from phenyl, 2-naphthyl, 2-, 3-, 5- or 6- indolyl, 2- or 3-thiophenyl, 2-, 3- or 4-pyridyl, 2-, 4- or 5-pyrimidinyl, 2- or 3-furyl, 1-, 2- or 3-pyrrolyl, 2-, 4- or 5-oxazolyl, 2-, 4- or 5-thiazolyl, 1-, 3-, 4- or 5-pyrazolyl, 3-, 4- or 5-isoxazolyl, 1-, 2-, 4- or 5-imidazolyl, 3-, 4- or 5-isothiazolyl, 4- or 5- oxadiazolyl, 1-, 4- or 5-triazolyl, 2-thiadiazolyl, 3- or 4-pyridazinyl, 2-pyrazinyl, 2- triazinyl, 2-, 3-, 6- or 7-indolyzinyl, 2-, 3-, 5- or 6-isoindolyl, 2-, 3-, 5- or 6- benzo[b]furanyl, 2-, 3-, 5- or 6-benzo[b]thiophenyl, 3-, 5- or 6-indazolyl, 2-, 5- or 6- benzthiazolyl, 2-, 5- or 6-benzimidazolyl, 2-, 3-, 6- or 7-quinolinyl, 3-, 6- or 7- isoquinolinyl, 2- or 8- purinyl, 2-, 3-, 7- or 8-quinolizinyl, 3-, 6- or 7-cinnolinyl, 6- or 7- phthalazinyl, 2-, 3-, 6- or 7-quinoxalinyl, 2-, 3-, 6- or 7-naphthyridinyl, 2-, 6- or 7- pteridinyl or 2-, 6- or 7-quinazolinyl, wherein one or more of the hydrogen atoms of said aryl or heteroaryl group may be optionally and independently replaced with:

(a) branched or unbranched alkyl of 1 to 6 carbon atoms or cycloalkyl of 3 to 6 carbon atoms, which alkyl or cycloakyl group may be mono or polysubstituted with halogen or oxo, (b) —COOH, (c) —SO$_2$OH, (d) —PO(OH)$_2$, (e) a group of the formula —COOR$_{12}$, wherein R$_{12}$ is unbranched or branched alkyl of 1 to 6 carbon atoms or cycloalkyl of 3 to 6 carbon atoms, (f) a group of the formula —NR$_{13}$R$_{14}$, wherein R$_{13}$ and R$_{14}$ are each, independently, H, alkyl or fluoroalkyl of 1 to 6 carbon atoms, cycloalkyl of 3 to 6 carbon atoms or acyl of 1 to 6 carbon atoms, or wherein R$_{13}$ and R$_{14}$ constitute a saturated hydrocarbon bridge of 3 to 5 carbon atoms which together with the nitrogen atom between them form a heterocyclic ring, (g) a group of the formula —CONR$_{15}$R$_{16}$, wherein R$_{15}$ and R$_{16}$ are each, independently H, alkyl or fluoroalkyl of 1 to 6 carbon atoms or cycloalkyl of 3 to 6 carbon atoms, or wherein R$_{15}$ and R$_{16}$ constitute a saturated hydrocarbon bridge of 3 to 5 carbon atoms which together with the nitrogen atom between them form a heterocyclic ring, (h) a group of the formula —OR$_{17}$, wherein R$_{17}$ is H, alkyl or fluoroalkyl of 1 to 6 carbon atoms or acyl of 1 to 6 carbon atoms, (i) a group of the formula —SR$_{18}$, wherein R$_{18}$ is H, alkyl or fluoroalkyl of 1 to 6 carbon atoms or acyl of 1 to 6 carbon atoms, (j) cyano, (k) nitro, (l) an amidino group of the formula —C(NR$_{19}$)—NR$_{20}$R$_{21}$ wherein R$_{19}$, R$_{20}$ and R$_{21}$ are each, independently, H or alkyl of 1 to 3 carbon atoms, and wherein two of R$_{19}$, R$_{20}$ and R$_{21}$ may additionally constitute a saturated hydrocarbon bridge of 3 to 5 carbon atoms which together with the nitrogen atom(s) between them form a heterocyclic ring, or (m) halogen, (ii) methyl, which may be mono- or polysubstituted with fluorine atoms and additionally may be monosubstituted with R$_{11}$, (iii) branched or unbranched alkyl of 2 to 6 carbon atoms or cycloalkyl of 3 to 6 carbon atoms, which alkyl or cycloakyl group may be mono- or polysubstituted with halogen or oxo, (iv) a group of the formula —COOR$_{22}$, wherein R$_{22}$ is unbranched or branched alkyl of 1 to 6 carbon atoms or cycloalkyl of 3 to 6 carbon atoms, (v) a group of the formula —NR$_{23}$R$_{24}$, wherein R23 and R24 are each, independently, H, alkyl or fluoroalkyl of 1 to 6 carbon atoms, cycloalkyl of 3 to 6 carbon atoms or acyl of 1 to 6 carbon atoms, or wherein R$_{23}$ and R$_{24}$ constitute a saturated hydrocarbon bridge of 3 to 5 carbon atoms which together with the nitrogen atom between them form a heterocyclic ring, or wherein one of R$_{23}$ and R$_{24}$ is the group R$_{11}$, (vi) a group of the formula —CONR$_{25}$R$_{26}$, wherein R$_{25}$ and R$_{26}$ are each, independently, H, alkyl or fluoroalkyl of 1 to 6 carbon atoms or cycloalkyl of 3 to 6 carbon atoms, or wherein R$_{25}$ and R$_{26}$ constitute a saturated hydrocarbon bridge of 3 to 5 carbon atoms which together with the nitrogen atom between them form a heterocyclic ring, or wherein one of R$_{25}$ and R$_{26}$ is the group R$_{11}$, (vii) a group of the formula —COR$_{27}$, wherein R$_{27}$ is H, unbranched or branched alkyl of 1 to 6 carbon atoms, cycloalkyl of 3 to 6 carbon atoms or R11, (viii) a group of the formula —OR$_{28}$, wherein R$_{28}$ is H, alkyl or fluoroalkyl of 1 to 6 carbon atoms or acyl of 1 to 6 carbon atoms, or R$_{11}$, (ix) a group of the formula —SR$_{29}$, wherein R$_{29}$ is H, alkyl or fluoroalkyl of 1 to 6 carbon atoms or acyl of 1 to 6 carbon atoms, or R$_{11}$, (x) cyano, (xi) nitro, or (xii) halogen, or, (D) a substituent selected from (i) a group of the formula —(CH$_2$)$_n$COOR$_{30}$, wherein R$_{30}$ is independently H, unbranched or branched alkyl of 1 to 6 carbon atoms or cycloalkyl of 3 to 6 carbon atoms and wherein said unbranched or branched alkyl of 1 to 6 carbon atoms or cycloalkyl of 3 to 6 carbon atoms may be optionally and independently substituted with —CH$_2$OR$_{31}$, —COOR$_{31}$, —CON(R$_{31}$)$_2$, —CH$_2$NHCOR$_{31}$, —SO$_2$N(R$_{31}$)$_2$, —CH$_2$NHSO$_2$R$_{31}$, —CH$_2$N(R$_{31}$)$_2$, —SO$_2$OH, —PO(OH)$_2$ wherein R$_{31}$ is independently selected from H, unbranched or branched alkyl of 1 to 6 carbon atoms, (ii) a group of the formula —(CH$_2$)$_n$CONR$_{32}$R$_{33}$, wherein R$_{32}$ and R$_{33}$ are each, independently, H, unbranched or branched alkyl of 1 to 6 carbon atoms or cycloalkyl of 3 to 6 carbon atoms and wherein said unbranched or branched alkyl of 1 to 6 carbon atoms or cycloalkyl of 3 to 6 carbon atoms may be optionally and independently substituted with —CH$_2$OR$_{31}$, —COOR$_{31}$, —CON(R$_{31}$)$_2$, —CH$_2$NHCOR$_{31}$, —SO$_2$N(R$_{31}$)$_2$, —CH$_2$NHSO$_2$R$_{31}$, —CH$_2$N(R$_{31}$)$_2$,—SO$_2$OH, —PO(OH)$_2$ wherein R$_{31}$ is independently selected from H, unbranched or branched alkyl of 1 to 6 carbon atoms or wherein NR$_{32}$ is N-alkyl-4-piperidinylamino, N-carboxymethyl-4-piperidinylamino, pyridin-4- ylmethylamino, 4-amidinobenzylamino, 4-carboxybenzylamino, or 4-hydroxybenzylamino and R$_{33}$ is H or wherein NR$_{32}$R$_{33}$ constitute a heterocyclic ring selected from 4-alkyl-1-piperazinyl, wherein alkyl is unbranched or branched alkyl of 1 to 6 carbon atoms, or 1-morpholinyl, (iii) a group of the formula —(CH$_2$)$_n$NHR$_{34}$, wherein R$_{34}$ is H, unbranched or branched alkyl of 1 to 6 carbon atoms, cycloalkyl of 3 to 6 carbon atoms or an acyl group of 1 to 6 carbon atoms and wherein said unbranched or branched alkyl of 1 to 6 carbon atoms or cycloalkyl of 3 to 6 carbon atoms may be optionally and independently substituted with —CH$_2$OR$_{31}$, —COOR$_{31}$, —CON(R$_{31}$)$_2$, —CH$_2$NHCOR$_{31}$, —SO$_2$N(R$_{31}$)$_2$, —CH$_2$NHSO$_2$R$_{13}$, —CH$_2$N(R$_{31}$)$_2$, —SO$_2$OH, —PO(OH)$_2$ wherein R$_{31}$ is independently selected from H, unbranched or branched alkyl of 1 to 6 carbon atoms or wherein R$_{34}$ is —COR$_{36}$ wherein R$_{36}$ is 1-alkyl-4-piperidyl, wherein alkyl is unbranched or branched alkyl of 1 to 6 carbon atoms, or —(CH$_2$)$_n$COR$_{36}$ wherein R$_{36}$ is 4-pyridyl or 4-hydroxyphenyl, (iv) a group of the formula —(CH$_2$)$_n$PO(OH)$_2$, —(CH$_2$)$_n$SO$_2$OH, —(CH$_2$)$_n$OR$_{31}$, —(CH$_2$)$_n$SO$_2$N(R$_{31}$)$_2$, or —(CH$_2$)$_n$NHSO$_2$R$_{31}$ wherein R$_{31}$ is independently selected from H, unbranched or branched alkyl of 1 to 6 carbon atoms, (v) (CH$_2$)$_n$-aryl, substituted (CH$_2$)$_n$-aryl, (CH$_2$)$_n$-heteroaryl or substituted (CH$_2$)$_n$-heteroaryl, wherein one or more of the hydrogen atoms of the aryl group of said substituted (CH$_2$)$_n$-aryl group or one or more of the hydrogen atoms of the heteroaryl group of said substituted (CH$_2$)$_n$-heteroaryl group may be optionally and independently replaced with:

(a) a group of the formula —COOR$_{30}$, wherein R$_{30}$ is independently H, unbranched or branched alkyl of 1 to 6 carbon atoms or cycloalkyl of 3 to 6 carbon atoms and wherein said unbranched or branched alkyl of 1 to 6 carbon atoms or cycloalkyl of 3 to 6 carbon atoms may be optionally and independently substituted with —CH$_2$OR$_{31}$, —COOR$_{31}$, —CON(R$_{31}$)$_2$, —CH$_2$NHCOR$_{31}$, —SO$_2$N(R$_{31}$)$_2$, —CH$_2$NHSO$_2$R$_{31}$, —CH$_2$N(R$_{31}$)$_2$, —SO$_2$OH, —PO(OH)$_2$ wherein R$_{31}$ is independently selected from H, unbranched or branched alkyl of 1 to 6 carbon atoms, (b) a group of the formula —CONR$_{32}$R$_{33}$, wherein R$_{32}$ and R$_{33}$ are each, independently, H, unbranched or branched alkyl of 1 to 6 carbon atoms or cycloalkyl of 3 to 6 carbon atoms and wherein said unbranched or branched alkyl of 1 to 6 carbon atoms or cycloalkyl of 3 to 6 carbon atoms may be optionally and independently substituted with —CH$_2$OR$_{31}$, —COOR$_{31}$, —CON(R$_{31}$)$_2$, —CH$_2$NHCOR$_{31}$, —SO$_2$N(R$_{31}$)$_2$, —CH$_2$NHSO$_2$R$_{31}$, —CH$_2$N(R$_{31}$)$_2$, —SO$_2$OH, —PO(OH)$_2$ wherein R$_{31}$ is independently selected from H, unbranched or branched alkyl of 1 to 6 carbon atoms or wherein NR$_{32}$ is N-alkyl-4-piperidinylamino, N-carboxymethyl-4-piperidinylamino, pyridin-4-ylmethylamino, 4-amidinobenzylamino, 4-carboxybenzylamino, or 4-hydroxybenzylaminoand R$_{33}$ is H or wherein NR$_{32}$R$_{33}$ constitute a heterocyclic ring selected from 4-alkyl1piperazinyl, wherein alkyl is unbranched or branched alkyl of 1 to 6 carbon atoms, or 1-morpholinyl, (c) a group of the formula —NHR$_{35}$, wherein R$_{35}$ is H, unbranched or branched alkyl of 1 to 6 carbon atoms, cycloalkyl of 3 to 6 carbon atoms or an acyl group of 1 to 6 carbon atoms and wherein said unbranched or branched alkyl of 1 to 6 carbon atoms or cycloalkyl of 3 to 6 carbon atoms may be optionally and independently substituted with —CH$_2$OR$_{31}$, —COOR$_{31}$, —CON(R$_{31}$)$_2$, —CH$_2$NHCOR$_{31}$, —SO$_2$N(R$_{31}$)$_2$, —CH$_2$NHSO$_2$R$_{31}$, —CH$_2$N(R$_{31}$)$_2$, —SO$_2$OH, —PO(OH)$_2$ wherein R$_{31}$ is independently selected from H, unbranched or branched alkyl of 1 to 6 carbon atoms or wherein R$_{35}$ is —COR$_{36}$ wherein R$_{36}$ is 1-alkyl-4-piperidyl, wherein alkyl is unbranched or branched alkyl of 1 to 6 carbon atoms, or —(CH$_2$)$_n$ COR$_{36}$ wherein R$_{36}$ is 4-pyridyl or 4-hydroxyphenyl, (d) a group of the formula —(CH$_2$)$_n$PO(OH)$_2$, —(CH$_2$)$_n$SO$_2$OH, —(CH$_2$)$_n$OR$_{31}$, —(CH$_2$)$_n$SO$_2$N(R$_{31}$)$_2$, or —(CH$_2$)$_n$NHHSO$_2$R$_{31}$ wherein R$_{31}$ is independently selected from H, unbranched or branched alkyl of 1 to 6 carbon atoms;

R$_3$ is selected from (A) H, (B) branched or unbranched alkyl of 1 to 6 carbon atoms or cycloalkyl of 3 to 6 carbon atoms, wherein said alkyl or cycloalkyl group may optionally be substituted with a group of the formula —OR$_8$, wherein R$_8$ is an alkyl or acyl group of 1 to 6 carbon atoms, (C) (CH$_2$)$_n$-aryl, substituted (CH$_2$)$_n$-aryl, (CH$_2$)$_n$-heteroaryl or substituted (CH$_2$)$_n$-heteroaryl, wherein one or more of the hydrogen atoms of the aryl group of said substituted (CH$_2$)$_n$-aryl group or one or more of the hydrogen atoms of the heteroaryl group of said substituted (CH$_2$)$_n$-heteroaryl group may be optionally and independently replaced with:

(i) R$_{11}$, which is aryl or heteroaryl selected from phenyl, 2-naphthyl, 2-, 3-, 5- or 6-indolyl, 2- or 3-thiophenyl, 2-, 3- or 4-pyridyl, 2-, 4- or 5-pyrimidinyl, 2- or 3-furyl, 1-, 2- or 3-pyrrolyl, 2-, 4- or 5-oxazolyl, 2-, 4- or 5-thiazolyl, 1-, 3-, 4- or 5-pyrazolyl, 3-, 4- or 5-isoxazolyl, 1-, 2-, 4- or 5-imidazolyl, 3-, 4- or 5-isothiazolyl, 4- or 5- oxadiazolyl, 1-, 4- or 5-triazolyl, 2-thiadiazolyl, 3- or 4-pyridazinyl, 2-pyrazinyl, 2-triazinyl, 2-, 3-, 6- or 7-indolyzinyl, 2-, 3-, 5- or 6-isoindolyl, 2-, 3-, 5- or 6-benzo[b]furanyl, 2-, 3-, 5- or 6-benzo[b]thiophenyl, 3-, 5- or 6-indazolyl, 2-, 5- or 6-benzthiazolyl, 2-, 5- or 6-benzimidazolyl, 2-, 3-, 6- or 7-quinolinyl, 3-, 6- or 7-isoquinolinyl, 2- or 8- purinyl, 2-, 3-, 7- or 8-quinolizinyl, 3-, 6- or 7-cinnolinyl, 6- or 7- phthalazinyl, 2-, 3-, 6- or 7-quinoxalinyl, 2-, 3-, 6- or 7-naphthyridinyl, 2-, 6- or 7-pteridinyl or 2-, 6- or 7-quinazolinyl, wherein one or more of the hydrogen atoms of said aryl or heteroaryl group may be optionally and independently replaced with:

(a) branched or unbranched alkyl of 1 to 6 carbon atoms or cycloalkyl of 3 to 6 carbon atoms, which alkyl or cycloakyl group may be mono or poly-substituted with halogen or oxo, (b) a group of the formula —COOR$_{12}$, wherein R$_{12}$ is unbranched or branched alkyl of 1 to 6 carbon atoms or cycloalkyl of 3 to 6 carbon atoms, (c) a group of the formula -NR$_{13}$R$_{14}$, wherein R$_{13}$ and R$_{14}$ are each, independently, H, alkyl or fluoroalkyl of 1 to 6 carbon atoms, cycloalkyl of 3 to 6 carbon atoms or acyl of 1 to 6 carbon atoms, or wherein R$_{13}$ and R$_{14}$ constitute a saturated hydrocarbon bridge of 3 to 5 carbon atoms which together with the nitrogen atom between them form a heterocyclic ring, (d) a group of the formula —CONR$_{15}$R$_{16}$, wherein R$_{15}$ and R$_{16}$ are each independently H, alkyl or fluoroalkyl of 1 to 6 carbon atoms or cycloalkyl of 3 to 6 carbon atoms, or wherein R$_{15}$ and R$_{16}$ constitute a saturated hydrocarbon bridge of 3 to 5 carbon atoms which together with the nitrogen atom between them form a heterocyclic ring, (e) a group of the formula —$OR_{17}$, wherein $R_{17}$ is H, alkyl or fluoroalkyl of 1 to 6 carbon atoms or acyl of 1 to 6 carbon atoms,
(f) a group of the formula —$SR_{18}$, wherein $R_{18}$ is H, alkyl or fluoroalkyl of 1 to 6 carbon atoms or acyl of 1 to 6 carbon atoms,
(g) cyano,
(h) nitro,
(i) an amidino group of the formula —$C(NR_{19})$—$NR_{20}R_{21}$ wherein $R_{19}$, $R_{20}$ and $R_{21}$ are each, independently, H or alkyl of 1 to 3 carbon atoms, and wherein two of $R_{19}$, $R_{20}$ and $R_{21}$ may additionally constitute a saturated hydrocarbon bridge of 3 to 5 carbon atoms which together with the nitrogen atom(s) between them form a heterocyclic ring, or
(j) halogen,
(ii) methyl, which may be mono- or polysubstituted with fluorine atoms and additionally may be monosubstituted with $R_{11}$,
(iii) branched or unbranched alkyl of 2 to 6 carbon atoms or cycloalkyl of 3 to 6 carbon atoms, which alkyl or cycloakyl group may be mono- or polysubstituted with halogen or oxo,
(iv) a group of the formula —$COOR_{22}$, wherein $R_{22}$ is unbranched or branched alkyl of 1 to 6 carbon atoms or cycloalkyl of 3 to 6 carbon atoms,
(v) a group of the formula —$NR_{23}R_{24}$, wherein $R_{23}$ and $R_{24}$ are each, independently, H, alkyl or fluoroalkyl of 1 to 6 carbon atoms, cycloalkyl of 3 to 6 carbon atoms or acyl of 1 to 6 carbon atoms, or wherein $R_{23}$ and $R_{24}$ constitute a saturated hydrocarbon bridge of 3 to 5 carbon atoms which together with the nitrogen atom between them form a heterocyclic ring, or wherein one of $R_{23}$ and $R_{24}$ is the group $R_{11}$,
(vi) a group of the formula —$CONR_{25}R_{26}$, wherein $R_{25}$ and $R_{26}$ are each, independently, H, alkyl or fluoroalkyl of 1 to 6 carbon atoms or cycloalkyl of 3 to 6 carbon atoms, or wherein $R_{25}$ and $R_{26}$ constitute a saturated hydrocarbon bridge of 3 to 5 carbon atoms which together with the nitrogen atom between them form a heterocyclic ring, or wherein one of $R_{25}$ and $R_{26}$ is the group $R_{11}$,
(vii) a group of the formula —$COR_{27}$, wherein $R_{27}$ is H, unbranched or branched alkyl of 1 to 6 carbon atoms, cycloalkyl of 3 to 6 carbon atoms or $R_{11}$,
(viii) a group of the formula —$COOR_{28}$, wherein $R_{28}$ is H, alkyl or fluoroalkyl of 1 to 6 carbon atoms or acyl of 1 to 6 carbon atoms, or $R_{11}$,
(ix) a group of the formula —$SR_{29}$, wherein $R_{29}$ is H, alkyl or fluoroalkyl of 1 to 6 carbon atoms or acyl of 1 to 6 carbon atoms, or $R_{11}$,
(x) cyano,
(xi) nitro, or
(xii) halogen,
wherein at least one of $R_2$ and $R_3$ is $(CH_2)_n$-aryl, substituted $(CH_2)_n$-aryl, $(CH_2)_n$-heteroaryl or substituted $(CH_2)_n$-heteroaryl;
$R_6$ and $R_7$ are independently selected from H, branched or unbranched alkyl of 1 to 6 carbon atoms or cycloalkyl of 3 to 6 carbon atoms, wherein said alkyl or cycloalkyl group may optionally be substituted with:
(a) a group of the formula —$OR_8$, wherein $R_8$ is an alkyl or acyl group of 1 to 6 carbon atoms, or
(b) a group of the formula —$NR_9R_{10}$, wherein $R_9$ and $R_{10}$ are each, independently, an alkyl or acyl group of 1 to 2 carbon atoms;

n is 0, 1, 2 or 3;
with the proviso that the following compounds are excluded from the invention:
Ethyl 3-(3-chlorophenyl)-1-(4-chlorophenyl)-2,4-dioxo-3-azabicyclo[3.1.0]hexane-6-carboxylate
3-(3-Chlorophenyl)-6,6-diphenyl-3-azabicyclo[3.1.0]hexane-2,4-dione
3-(3-Bromophenyl)-6,6-diphenyl-3-azabicyclo[3.1.0]hexane-2,4-dione
3-(3-Chlorophenyl)-1-methyl-6,6-diphenyl-3-azabicyclo[3.1.0]hexane-2,4-dione
3-(3,5-Dichlorophenyl)-6,6-diphenyl-3-azabicyclo[3.1.0]hexane-2,4-dione
3-(3,5-Dichlorophenyl)-1-methyl-6,6-diphenyl-3-azabicyclo[3.1.0]hexane-2,4-dione
3-(3,4-Dichlorophenyl)-1-methyl-6,6-diphenyl-3-azabicyclo[3.1.0]hexane-2,4-dione
3-(3-Bromophenyl)-1-methyl-6,6-diphenyl-3-azabicyclo[3.1.0]hexane-2,4-dione
1-Methyl-6,6-diphenyl-3-(3-(trifluoromethyl)phenyl)-3-azabicyclo[3.1.0]hexane-2,4-dione
3-(3-Chlorophenyl)-1,6,6-triphenyl-3-azabicyclo[3.1.0]hexane-2,4-dione
3-(3,4-Dichlorophenyl)-1,6,6-triphenyl-3-azabicyclo[3.1.0]hexane-2,4-dione
1,6,6-Triphenyl-3-(3-(trifluoromethyl)phenyl)-3-azabicyclo[3.1.0]hexane-2,4-dione
3-(3-Bromophenyl)-1,6,6-triphenyl-3-azabicyclo[3.1.0]hexane-2,4-dione
3-(3-Chlorophenyl)-1-(4-chlorophenyl)-6,6-diphenyl-3-azabicyclo[3.1.0]hexane-2,4-dione
1-(4-Chlorophenyl)-3-(3,5-dichlorophenyl)-6,6-diphenyl-3-azabicyclo[3.1.0]hexane-2,4-dione
3-(3,5-Dichlorophenyl)-1-(4-nitrophenyl)-6,6-diphenyl-3-azabicyclo[3.1.0]hexane-2,4-dione
3-(3,4-Dichlorophenyl)-1-(4-nitrophenyl)-6,6-diphenyl-3-azabicyclo[3.1.0]hexane-2,4-dione
1-(4-Nitrophenyl)-6,6-diphenyl-3-[3-(trifluoromethyl)phenyl]-3-azabicyclo[3.1.0]hexane-2,4-dione
1-(4-Nitrophenyl)-6,6-diphenyl-3-(3-chloro-4-methylphenyl)-3-azabicyclo[3.1.0]hexane-2,4-dione
3-(3-Chloro-6-methoxy-phenyl)-6,6-diphenyl-3-azabicyclo[3.1.0]hexane-2,4-dione.
2. Diastereomeric mesoforms of a compound according to formula (Ia)

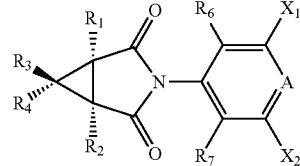

pharmaceutically-acceptable salts, hydrates, or solvates thereof, in which:
$X_1$ is selected from H, halogen or $CF_3$,
$X_2$ is selected from H, halogen or $CF_3$,
wherein at least one of $X_1$ and $X_2$ is halogen or $CF_3$,
A is N or $CR_5$, wherein $R_5$ is selected from H, halogen, branched or unbranched alkyl of 1 to 6 carbon atoms, branched or unbranched alkenyl of 2 to 6 carbon atoms, $CF_3$, $CCl_3$, CN, $NO_2$, O-alkyl with branched or unbranched alkyl of 1 to 6 carbon atoms, S-alkyl with branched or unbranched alkyl of 1 to 6 carbon atoms, aryl, substituted aryl, heteroaryl or substituted heteroaryl;

$R_1$ and $R_2$ are the same and are selected from H, branched or unbranched alkyl of 1 to 6 carbon atoms, or cycloalkyl of 3 to 6 carbon atoms;

$R_4$ is H;

$R_3$ is selected from $(CH_2)_n$-aryl, substituted $(CH_2)_n$-aryl, $(CH_2)_n$-heteroaryl or substituted $(CH_2)_n$-heteroaryl, wherein one or more of the hydrogen atoms of the aryl group of said substituted $(CH_2)_n$-aryl group or one or more of the hydrogen atoms of the heteroaryl group of said substituted $(CH_2)_n$-heteroaryl group may be optionally and independently replaced with:

(i) $R_{11}$, which is aryl or heteroaryl selected from phenyl, 2-naphthyl, 2-, 3-, 5- or 6-indolyl, 2- or 3-thiophenyl, 2-, 3- or 4-pyridyl, 2-, 4- or 5-pyrimidinyl, 2- or 3-furyl, 1-, 2- or 3-pyrrolyl, 2-, 4- or 5-oxazolyl, 2-, 4- or 5-thiazolyl, 1-, 3-, 4- or 5-pyrazolyl, 3-, 4- or 5-isoxazolyl, 1-, 2-, 4- or 5-imidazolyl, 3-, 4- or 5-isothiazolyl, 4- or 5-oxadiazolyl, 1-, 4- or 5-triazolyl, 2-thiadiazolyl, 3- or 4-pyridazinyl, 2-pyrazinyl, 2- triazinyl, 2-, 3-, 6- or 7-indolyzinyl, 2-, 3-, 5- or 6-isoindolyl, 2-, 3-, 5- or 6-benzo[b]furanyl, 2-, 3-, 5- or 6-benzo[b]thiophenyl, 2-, 5- or 6-indazolyl, 2-, 5- or 6-benzthiazolyl, 2-, 5- or 6-benzimidazolyl, 2-, 3-, 6- or 7-quinolinyl, 3-, 6- or 7-isoquinolinyl, 2- or 8- purinyl, 2-, 3-, 7- or 8-quinolizinyl, 3-, 6- or 7-cinnolinyl, 6- or 7-phthalazinyl, 2-, 3-, 6- or 7-quinoxalinyl, 2-, 3-, 6- or 7-naphthyridinyl, 2-, 6- or 7-pteridinyl or 2-, 6- or 7-quinazolinyl, wherein one or more of the hydrogen atoms of said aryl or heteroaryl group may be optionally and independently replaced with:

(a) branched or unbranched alkyl of 1 to 6 carbon atoms or cycloalkyl of 3 to 6 carbon atoms, which alkyl or cycloakyl group may be mono or polysubstituted with halogen or oxo, (b) a group of the formula —$COOR_{12}$, wherein $R_{12}$ is unbranched or branched alkyl of 1 to 6 carbon atoms or cycloalkyl of 3 to 6 carbon atoms, (c) a group of the formula —$NR_{13}R_{14}$, wherein $R_{13}$ and $R_{14}$ are each, independently, H, alkyl or fluoroalkyl of 1 to 6 carbon atoms, cycloalkyl of 3 to 6 carbon atoms, or acyl of 1 to 6 carbon atoms, or wherein $R_{13}$ and $R_{14}$ constitute a saturated hydrocarbon bridge of 3 to 5 carbon atoms which together with the nitrogen atom between them form a heterocyclic ring, (d) a group of the formula —$CONR_{15}R_{16}$, wherein $R_{15}$ and $R_{16}$ are each independently H, alkyl or fluoroalkyl of 1 to 6 carbon atoms or cycloalkyl of 3 to 6 carbon atoms, or wherein $R_{15}$ and $R_{16}$ constitute a saturated hydrocarbon bridge of 3 to 5 carbon atoms which together with the nitrogen atom between them form a heterocyclic ring, (e) a group of the formula —$OR_{17}$, wherein $R_{17}$ is H, alkyl or fluoroalkyl of 1 to 6 carbon atoms or acyl of 1 to 6 carbon atoms, (f) a group of the formula —$SR_{18}$, wherein $R_{18}$ is H, alkyl or fluoroalkyl of 1 to 6 carbon atoms or acyl of 1 to 6 carbon atoms, (g) cyano, (h) nitro, (i) an amidino group of the formula —$C(NR_{19})$—$NR_{20}R_{21}$ wherein $R_{19}$, $R_{20}$ and $R_{21}$ are each, independently, H or alkyl of 1 to 3 carbon atoms, and wherein two of $R_{19}$, $R_{20}$ and $R_{21}$ may additionally constitute a saturated hydrocarbon bridge of 3 to 5 carbon atoms which together with the nitrogen atom(s) between them form a heterocyclic ring, or (j) halogen, (ii) methyl, which may be mono- or polysubstituted with fluorine atoms and additionally may be monosubstituted with $R_{11}$, (iii) branched or unbranched alkyl of 2 to 6 carbon atoms or cycloalkyl of 3 to 6 carbon atoms, which alkyl or cycloakyl group may be mono- or polysubstituted with halogen or oxo, (iv) a group of the formula —$COOR_{22}$, wherein $R_{22}$ is unbranched or branched alkyl of 1 to 6 carbon atoms or cycloalkyl of 3 to 6 carbon atoms, (v) a group of the formula —$NR_{23}R_{24}$, wherein $R_{23}$ and $R_{24}$ are each, independently, H, alkyl or fluoroalkyl of 1 to 6 carbon atoms, cycloalkyl of 3 to 6 carbon atoms or acyl of 1 to 6 carbon atoms, or wherein $R_{23}$ and $R_{24}$ constitute a saturated hydrocarbon bridge of 3 to 5 carbon atoms which together with the nitrogen atom between them form a heterocyclic ring, or wherein one of $R_{23}$ and $R_{24}$ is the group $R_{11}$, (vi) a group of the formula —$CONR_{25}R_{26}$, wherein $R_{25}$ and $R_{26}$ are each, independently, H, alkyl or fluoroalkyl of 1 to 6 carbon atoms or cycloalkyl of 3 to 6 carbon atoms, or wherein $R_{25}$ and $R_{26}$ constitute a saturated hydrocarbon bridge of 3 to 5 carbon atoms which together with the nitrogen atom between them form a heterocyclic ring, or wherein one of $R_{25}$ and $R_{26}$ is the group $R_{11}$, (vii) a group of the formula —$COR_{27}$, wherein $R_{27}$ is H, unbranched or branched alkyl of 1 to 6 carbon atoms, cycloalkyl of 3 to 6 carbon atoms or $R_{11}$, (viii) a group of the formula —$OR_{28}$, wherein $R_{28}$ is H, alkyl or fluoroalkyl of 1 to 6 carbon atoms or acyl of 1 to 6 carbon atoms, or $R_{11}$, (ix) a group of the formula —$SR_{29}$, wherein $R_{29}$ is H, alkyl or fluoroalkyl of 1 to 6 carbon atoms or acyl of 1 to 6 carbon atoms, or $R_{11}$, (x) cyano, (xi) nitro, or (xii) halogen;

$R_6$ and $R_7$ are independently selected from H, branched or unbranched alkyl of 1 to 6 carbon atoms or cycloalkyl of 3 to 6 carbon atoms, wherein said alkyl or cycloalkyl group may optionally be substituted with:

(a) a group of the formula —$OR_8$, wherein $R_8$ is an alkyl or acyl group of 1 to 6 carbon atoms, or (b) a group of the formula —$NR_9R_{10}$, wherein $R_9$ and $R_{10}$ are each, independently, an alkyl or acyl group of 1 to 2 carbon atoms;

n is 0, 1, 2 or 3.

3. The compound according to claim 1, wherein A is $CR_5$ and wherein $R_5$ is H or halogen.

4. The compound according to claim 1, wherein $R_3$ is selected from $(CH_2)_n$-aryl, substituted $(CH_2)_n$-aryl, $(CH_2)_n$-heteroaryl or substituted $(CH_2)_n$-heteroaryl, wherein one or more of the hydrogen atoms of the aryl group of said substituted $(CH_2)_n$-aryl group or one or more of the hydrogen atoms of the heteroaryl group of said substituted $(CH_2)_n$-heteroaryl group may be optionally and independently replaced with:

(i) $R_{11}$, which is aryl or heteroaryl selected from phenyl, 2-naphthyl, 2-, 3-, 5- or 6-indolyl, 2- or 3-thiophenyl, 2-, 3- or 4-pyridyl, 2-, 4- or 5-pyrimidinyl, 2- or 3-furyl, 1-, 2- or 3-pyrrolyl, 2-, 4- or 5-oxazolyl, 2-, 4- or 5-thiazolyl, 1-, 3-, 4- or 5-pyrazolyl, 3-, 4- or 5-isoxazolyl, 1-, 2-, 4- or 5-imidazolyl, 3-, 4- or 5-isothiazolyl, 4- or 5-oxadiazolyl, 1-, 4- or 5-triazolyl, 2-thiadiazolyl, 3- or 4-pyridazinyl, 2-pyrazinyl, 2- triazinyl, 2-, 3-, 6- or 7-indolyzinyl, 2-, 3-, 5- or 6-isoindolyl, 2-, 3-, 5- or 6-benzo[b]furanyl, 2-, 3-, 5- or 6-benzo[b]thiophenyl, 3-, 5- or 6-indazolyl, 2-, 5- or 6-benzthiazolyl, 2-, 5- or 6-benzimidazolyl, 2-, 3-, 6- or 7-quinolinyl, 3-, 6- or 7-isoquinolinyl, 2- or 8- purinyl, 2-, 3-, 7- or 8-quinolizinyl, 3-, 6- or 7-cinnolinyl, 6- or 7-phthalazinyl, 2-, 3-, 6- or 7-quinoxalinyl, 2-, 3-, 6- or 7-naphthyridinyl, 2-, 6- or 7-pteridinyl or 2-, 6- or 7-quinazolinyl, wherein one or more of the hydrogen atoms of said aryl or heteroaryl group may be optionally and independently replaced with:
  (a) branched or unbranched alkyl of 1 to 6 carbon atoms or cycloalkyl of 3 to 6 carbon atoms, which alkyl or cycloakyl group may be mono or polysubstituted with halogen or oxo,
  (b) a group of the formula —$COOR_{12}$, wherein $R_{12}$ is unbranched or branched alkyl of 1 to 6 carbon atoms or cycloalkyl of 3 to 6 carbon atoms,
  (c) a group of the formula —$NR_{13}R_{14}$, wherein $R_{11}$ and $R_{12}$ are each, independently, H, alkyl or fluoroalkyl of 1 to 6 carbon atoms, cycloalkyl of 3 to 6 carbon atoms or acyl of 1 to 6 carbon atoms, or wherein $R_{11}$ and $R_{12}$ constitute a saturated hydrocarbon bridge of 3 to 5 carbon atoms which together with the nitrogen atom between them form a heterocyclic ring,
  (d) a group of the formula —$CONR_{15}R_{16}$, wherein $R_{15}$ and $R_{16}$ are each independently H, alkyl or fluoroalkyl of 1 to 6 carbon atoms or cycloalkyl of 3 to 6 carbon atoms, or wherein $R_{15}$ and $R_{16}$ constitute a saturated hydrocarbon bridge of 3 to 5 carbon atoms which together with the nitrogen atom between them form a heterocyclic ring,
  (e) a group of the formula —$OR_{15}$, wherein $R_{17}$ is H, alkyl or fluoroalkyl of 1 to 6 carbon atoms or acyl of 1 to 6 carbon atoms,
  (f) a group of the formula —$SR_{18}$, wherein $R_{18}$ is H, alkyl or fluoroalkyl of 1 to 6 carbon atoms or acyl of 1 to 6 carbon atoms,
  (g) cyano,
  (h) nitro,
  (i) an amidino group of the formula —$C(NR_{19})$—$NR_{20}R_{21}$ wherein $R_{19}$, $R_{20}$ and $R_{21}$ are each, independently, H or alkyl of 1 to 3 carbon atoms, and wherein two of $R_{19}$, $R_{20}$ and $R_{21}$ may additionally constitute a saturated hydrocarbon bridge of 3 to 5 carbon atoms which together with the nitrogen atom(s) between them form a heterocyclic ring, or
  (m) halogen,
(ii) methyl, which may be mono- or polysubstituted with fluorine atoms and additionally may be monosubstituted with $R_{11}$,
(iii) branched or unbranched alkyl of 2 to 6 carbon atoms or cycloalkyl of 3 to 6 carbon atoms, which alkyl or cycloakyl group may be mono- or polysubstituted with halogen or oxo,
(iv) a group of the formula —$COOR_{22}$, wherein $R_{22}$ is unbranched or branched alkyl of 1 to 6 carbon atoms or cycloalkyl of 3 to 6 carbon atoms,
(v) a group of the formula —$NR_{23}R_{24}$, wherein $R_{23}$ and $R_{24}$ are each, independently, H, alkyl or fluoroalkyl of 1 to 6 carbon atoms, cycloalkyl of 3 to 6 carbon atoms or acyl of 1 to 6 carbon atoms, or wherein $R_{23}$ and $R_{24}$ constitute a saturated hydrocarbon bridge of 3 to 5 carbon atoms which together with the nitrogen atom between them form a heterocyclic ring, or wherein one of $R_{23}$ and $R_{24}$ is the group $R_{11}$,
(vi) a group of the formula —$CONR_{25}R_{26}$, wherein $R_{25}$ and $R_{26}$ are each, independently, H, alkyl or fluoroalkyl of 1 to 6 carbon atoms or cycloalkyl of 3 to 6 carbon atoms, or wherein $R_{25}$ and $R_{26}$ constitute a saturated hydrocarbon bridge of 3 to 5 carbon atoms which together with the nitrogen atom between them form a heterocyclic ring, or wherein one of $R_{25}$ and $R_{26}$ is the group $R_{11}$,
(vii) a group of the formula —$COR_{27}$, wherein $R_{27}$ is H, unbranched or branched alkyl of 1 to 6 carbon atoms, cycloalkyl of 3 to 6 carbon atoms or R11,
(viii) a group of the formula —$OR_{28}$, wherein $R_{28}$ is H, alkyl or fluoroalkyl of 1 to 6 carbon atoms or acyl of 1 to 6 carbon atoms, or $R_{11}$,
(ix) a group of the formula —$SR_{29}$, wherein $R_{29}$ is H, alkyl or fluoroalkyl of 1 to 6 carbon atoms or acyl of 1 to 6 carbon atoms, or $R_{11}$,
(x) cyano,
(xi) nitro, or
(xii) halogen;
and
$R_4$ is selected from $(CH_2)_n$-aryl, substituted $(CH_2)_n$-aryl, $(CH_2)_n$-heteroaryl or substituted $(CH_2)_n$-heteroaryl,
wherein one or more of the hydrogen atoms of the aryl group of said substituted $(CH_2)_n$-aryl group or one or more of the hydrogen atoms of the heteroaryl group of said substituted $(CH_2)_n$-heteroaryl group may be optionally and independently replaced with:
  (i) $R_{11}$, which is aryl or heteroaryl selected from phenyl, 2-naphthyl, 2-, 3-, 5- or 6-indolyl, 2- or 3-thiophenyl, 2-, 3- or 4-pyridyl, 2-, 4- or 5-pyrimidinyl, 2- or 3-furyl, 1-, 2- or 3-pyrrolyl, 2-, 4- or 5-oxazolyl, 2-, 4- or 5-thiazolyl, 1-, 3-, 4- or 5-pyrazolyl, 3-, 4- or 5-isoxazolyl, 1-, 2-, 4- or 5-imidazolyl, 3-, 4- or 5-isothiazolyl, 4- or 5-oxadiazolyl, 1-, 4- or 5-triazolyl, 2-thiadiazolyl, 3- or 4-pyridazinyl, 2-pyrazinyl, 2-triazinyl, 2-, 3-, 6- or 7-indolyzinyl, 2-, 3-, 5- or 6-isoindolyl, 2- , 3-, 5- or 6-benzo[b]furanyl, 2-, 3-, 5- or 6-benzo[b]thiophenyl, 3-, 5- or 6-indazolyl, 2-, 5- or 6-benzthiazolyl, 2-, 5- or 6-benzimidazolyl, 2-, 3-, 6- or 7-quinolinyl, 3-, 6- or 7-isoquinolinyl, 2- or 8- purinyl, 2-, 3-, 7- or 8-quinolizinyl, 3-, 6- or 7-cinnolinyl, 6- or 7-phthalazinyl, 2-, 3-, 6- or 7-quinoxalinyl, 2-, 3-, 6- or 7-naphthyridinyl, 2-, 6- or 7-pteridinyl or 2-, 6- or 7-quinazolinyl,
wherein one or more of the hydrogen atoms of said aryl or heteroaryl group may be optionally and independently replaced with:
  (a) branched or unbranched alkyl of 1 to 6 carbon atoms or cycloalkyl of 3 to 6 carbon atoms, which alkyl or cycloakyl group may be mono or polysubstituted with halogen or oxo,
  (b) —COOH,
  (c) —$SO_2OH$,
  (d) —$PO(OH)_2$,
  (e) a group of the formula —$COOR_{12}$, wherein $R_{12}$ is unbranched or branched alkyl of 1 to 6 carbon atoms or cycloalkyl of 3 to 6 carbon atoms,
  (f) a group of the formula —$NR_{13}R_{14}$, wherein $R_{13}$ and $R_{14}$ are each, independently, H, alkyl or fluoroalkyl of 1 to 6 carbon atoms, cycloalkyl of 3 to 6 carbon atoms or acyl of 1 to 6 carbon atoms, or wherein $R_{13}$ and $R_{14}$ constitute a saturated hydrocarbon bridge of 3 to 5 carbon atoms which together with the nitrogen atom between them form a heterocyclic ring, (g) a group of the formula —CONR$_{15}$R$_{16}$, wherein R$_{15}$ and R$_{16}$ are each independently H, alkyl or fluoroalkyl of 1 to 6 carbon atoms or cycloalkyl of 3 to 6 carbon atoms, or wherein R$_{15}$ and R$_{16}$ constitute a saturated hydrocarbon bridge of 3 to 5 carbon atoms which together with the nitrogen atom between them form a heterocyclic ring, (h) a group of the formula —OR$_{15}$, wherein R$_{17}$ is H, alkyl or fluoroalkyl of 1 to 6 carbon atoms or acyl of 1 to 6 carbon atoms, (i) a group of the formula —SR$_{18}$, wherein R$_{18}$ is H, alkyl or fluoroalkyl of 1 to 6 carbon atoms or acyl of 1 to 6 carbon atoms, (j) cyano, (k) nitro, (l) an amidino group of the formula —C(NR$_{19}$)—NR$_{20}$R$_{21}$ wherein R$_{19}$, R$_{20}$ and R$_{21}$ are each, independently, H or alkyl of 1 to 3 carbon atoms, and wherein two of R$_{19}$, R$_{20}$ and R$_{21}$ may additionally constitute a saturated hydrocarbon bridge of 3 to 5 carbon atoms which together with the nitrogen atom(s) between them form a heterocyclic ring, or (m) halogen, (ii) methyl, which may be mono- or polysubstituted with fluorine atoms and additionally may be monosubstituted with R$_{11}$, (iii) branched or unbranched alkyl of 2 to 6 carbon atoms or cycloalkyl of 3 to 6 carbon atoms, which alkyl or cycloakyl group may be mono- or polysubstituted with halogen or oxo, (iv) a group of the formula —COOR$_{22}$, wherein R$_{22}$ is unbranched or branched alkyl of 1 to 6 carbon atoms or cycloalkyl of 3 to 6 carbon atoms, (v) a group of the formula —NR$_{23}$R$_{24}$, wherein R$_{23}$ and R$_{24}$ are each, independently, H, alkyl or fluoroalkyl of 1 to 6 carbon atoms, cycloalkyl of 3 to 6 carbon atoms or acyl of 1 to 6 carbon atoms, or wherein R$_{23}$ and R$_{24}$ constitute a saturated hydrocarbon bridge of 3 to 5 carbon atoms which together with the nitrogen atom between them form a heterocyclic ring, or wherein one of R$_{23}$ and R$_{24}$ is the group R$_{11}$, (vi) a group of the formula —CONR$_{25}$ R$_{26}$, wherein R$_{25}$ and R$_{26}$ are each, independently, H, alkyl or fluoroalkyl of 1 to 6 carbon atoms or cycloalkyl of 3 to 6 carbon atoms, or wherein R$_{25}$ and R$_{26}$ constitute a saturated hydrocarbon bridge of 3 to 5 carbon atoms which together with the nitrogen atom between them form a heterocyclic ring, or wherein one of R$_{25}$ and R$_{26}$ is the group R$_{11}$, (vii) a group of the formula —COR$_{27}$, wherein R$_{27}$ is H, unbranched or branched alkyl of 1 to 6 carbon atoms, cycloalkyl of 3 to 6 carbon atoms or R$_{11}$, (viii) a group of the formula —OR$_{28}$, wherein R$_{28}$ is H, alkyl or fluoroalkyl of 1 to 6 carbon atoms or acyl of 1 to 6 carbon atoms, or R$_{11}$, (ix) a group of the formula —SR$_{29}$, wherein R$_{29}$ is H, alkyl or fluoroalkyl of 1 to 6 carbon atoms or acyl of 1 to 6 carbon atoms, or R$_{11}$, (x) cyano, (xi) nitro, or (xii) halogen, or is selected from a substituent as defined by (D).

5. The compound according to claim 1, wherein R$_3$ is selected from (CH$_2$)$_n$-aryl, substituted (CH$_2$)$_n$-aryl, (CH$_2$)$_n$-heteroaryl or substituted (CH$_2$)$_n$-heteroaryl, wherein one or more of the hydrogen atoms of the aryl group of said substituted (CH$_2$)$_n$-aryl group or one or more of the hydrogen atoms of the heteroaryl group of said substituted (CH$_2$)$_n$-heteroaryl group may be optionally and independently replaced with:

(i) R$_{11}$, which is aryl or heteroaryl selected from phenyl, 2-naphthyl, 2-, 3-, 5- or 6-indolyl, 2- or 3-thiophenyl, 2-, 3- or 4-pyridyl, 2-, 4- or 5-pyrimidinyl, 2- or 3-furyl, 1-, 2- or 3-pyrrolyl, 2-, 4- or 5-oxazolyl, 2-, 4- or 5-thiazolyl, 1-, 3-, 4- or 5-pyrazolyl, 3-, 4- or 5-isoxazolyl, 1-, 2-, 4- or 5-imidazolyl, 3-, 4- or 5-isothiazolyl, 4- or 5-oxadiazolyl, 1-, 4- or 5-triazolyl, 2-thiadiazolyl, 3- or 4-pyridazinyl, 2-pyrazinyl, 2- triazinyl, 2-, 3-, 6- or 7-indolyzinyl, 2-, 3-, 5- or 6-isoindolyl, 2-, 3-, 5- or 6-benzo[b]furanyl, 2-, 3-, 5- or 6-benzo[b]thiophenyl, 3-, 5- or 6-indazolyl, 2-, 5- or 6-benzthiazolyl, 2-, 5- or 6-benzimidazolyl, 2-, 3-, 6- or 7-quinolinyl, 3-, 6- or 7-isoquinolinyl, 2- or 8- purinyl, 2-, 3-, 7- or 8-quinolizinyl, 3-, 6- or 7-cinnolinyl, 6- or 7-phthalazinyl, 2-, 3-, 6- or 7-quinoxalinyl, 2-, 3-, 6- or 7-naphthyridinyl, 2-, 6- or 7-pteridinyl or 2-, 6- or 7-quinazolinyl, wherein one or more of the hydrogen atoms of said aryl or heteroaryl group may be optionally and independently replaced with:

(a) branched or unbranched alkyl of 1 to 6 carbon atoms or cycloalkyl of 3 to 6 carbon atoms, which alkyl or cycloakyl group may be mono or polysubstituted with halogen or oxo, (b) a group of the formula —COOR$_{12}$, wherein R$_{12}$ is unbranched or branched alkyl of 1 to 6 carbon atoms or cycloalkyl of 3 to 6 carbon atoms, (c) a group of the formula —NR$_{13}$R$_{14}$, wherein R$_{13}$ and R$_{14}$ are each, independently, H, alkyl or fluoroalkyl of 1 to 6 carbon atoms, cycloalkyl of 3 to 6 carbon atoms or acyl of 1 to 6 carbon atoms, or wherein R$_{13}$ and R$_{14}$ constitute a saturated hydrocarbon bridge of 3 to 5 carbon atoms which together with the nitrogen atom between them form a heterocyclic ring, (d) a group of the formula —CONR$_{15}$R$_{16}$, wherein R$_{15}$ and R$_{16}$ are each independently H, alkyl or fluoroalkyl of 1 to 6 carbon atoms or cycloalkyl of 3 to 6 carbon atoms, or wherein R$_{15}$ and R$_{16}$ constitute a saturated hydrocarbon bridge of 3 to 5 carbon atoms which together with the nitrogen atom between them form a heterocyclic ring, (e) a group of the formula —OR$_{15}$, wherein R$_{17}$ is H, alkyl or fluoroalkyl of 1 to 6 carbon atoms or acyl of 1 to 6 carbon atoms, (f) a group of the formula —SR$_{18}$, wherein R$_{18}$ is H, alkyl or fluoroalkyl of 1 to 6 carbon atoms or acyl of 1 to 6 carbon atoms, (g) cyano, (h) nitro, (i) an amidino group of the formula —C(NR$_{19}$)—NR$_{20}$R$_{21}$ wherein R$_{19}$, R$_{20}$ and R$_{21}$ are each, independently, H or alkyl of 1 to 3 carbon atoms, and wherein two of R$_{19}$, R$_{20}$ and R$_{21}$ may additionally constitute a saturated hydrocarbon bridge of 3 to 5 carbon atoms which together with the nitrogen atom(s) between them form a heterocyclic ring, or (m) halogen, (ii) methyl, which may be mono- or polysubstituted with fluorine atoms and additionally may be monosubstituted with R$_{11}$, (iii) branched or unbranched alkyl of 2 to 6 carbon atoms or cycloalkyl of 3 to 6 carbon atoms, which alkyl or cycloakyl group may be mono- or polysubstituted with halogen or oxo,
(iv) a group of the formula —COOR$_{22}$, wherein R$_{22}$ is unbranched or branched alkyl of 1 to 6 carbon atoms or cycloalkyl of 3 to 6 carbon atoms,
(v) a group of the formula —NR$_{23}$R$_{24}$, wherein R$_{23}$ and R$_{24}$ are each, independently, H, alkyl or fluoroalkyl of 1 to 6 carbon atoms, cycloalkyl of 3 to 6 carbon atoms or acyl of 1 to 6 carbon atoms, or wherein R$_{23}$ and R$_{24}$ constitute a saturated hydrocarbon bridge of 3 to 5 carbon atoms which together with the nitrogen atom between them form a heterocyclic ring, or wherein one of R$_{23}$ and R$_{24}$ is the group R$_{11}$,
(vi) a group of the formula —CONR$_{25}$R$_{26}$, wherein R$_{25}$ and R$_{26}$ are each, independently, H, alkyl or fluoroalkyl of 1 to 6 carbon atoms or cycloalkyl of 3 to 6 carbon atoms, or wherein R$_{25}$ and R$_{26}$ constitute a saturated hydrocarbon bridge of 3 to 5 carbon atoms which together with the nitrogen atom between them form a heterocyclic ring, or wherein one of R$_{25}$ and R$_{26}$ is the group R$_{11}$,
(vii) a group of the formula —COR$_{27}$, wherein R$_{27}$ is H, unbranched or branched alkyl of 1 to 6 carbon atoms, cycloalkyl of 3 to 6 carbon atoms or R$_{11}$,
(viii) a group of the formula —OR$_{28}$, wherein R$_{28}$ is H, alkyl or fluoroalkyl of 1 to 6 carbon atoms or acyl of 1 to 6 carbon atoms, or R$_{11}$,
(ix) a group of the formula —SR$_{29}$, wherein R$_{29}$ is H, alkyl or fluoroalkyl of 1 to 6 carbon atoms or acyl of 1 to 6 carbon atoms, or R$_{11}$,
(x) cyano,
(xi) nitro, or
(xii) halogen;
and R$_4$ is H.

6. The compound according to claim 1, wherein
A is CR$_5$, wherein R$_5$ is H or halogen;
R$_1$ is selected from H, branched or unbranched alkyl of 1 to 6 carbon atoms;
R$_2$ and R$_4$ are independently selected from H, (CH$_2$)$_n$-aryl, substituted (CH$_2$)$_n$-aryl or (CH$_2$)$_n$-heteroaryl, wherein one or more of the hydrogen atoms of the aryl group of said substituted (CH$_2$)$_n$-aryl group may be optionally replaced with:
(i) R$_{11}$, which is aryl or heteroaryl selected from phenyl, 2-naphthyl, 2-, 3-, 5- or 6-indolyl, 2- or 3-thiophenyl, 2-, 3- or 4-pyridyl, 2-, 4- or 5-pyrimidinyl, 2- or 3-furyl, 1-, 2- or 3-pyrrolyl, 2-, 4- or 5-oxazolyl, 2-, 4- or 5-thiazolyl, 1-, 3-, 4- or 5-pyrazolyl, 3-, 4- or 5-isoxazolyl, 1-, 2-, 4- or 5-imidazolyl, 3-, 4- or 5-isothiazolyl, 4- or 5-oxadiazolyl, 1-, 4- or 5-triazolyl, 2-thiadiazolyl, 3- or 4-pyridazinyl, 2-pyrazinyl, 2-triazinyl, 2-, 3-, 6- or 7-indolyzinyl, 2-, 3-, 5- or 6-isoindolyl, 2-, 3-, 5- or 6-benzo[b]furanyl, 2-, 3-, 5- or 6-benzo[b]thiophenyl, 3-, 5- or 6-indazolyl, 2-, 5- or 6-benzthiazolyl, 2-, 5- or 6-benzimidazolyl, 2-, 3-, 6- or 7-quinolinyl, 3-, 6- or 7-isoquinolinyl, 2- or 8- purinyl, 2-, 3-, 7- or 8-quinolizinyl, 3-, 6- or 7-cinnolinyl, 6- or 7-phthalazinyl, 2-, 3-, 6- or 7-quinoxalinyl, 2-, 3-, 6- or 7-naphthyridinyl, 2-, 6- or 7-pteridinyl or 2-, 6- or 7-quinazolinyl,
(ii) methyl, which may be mono- or polysubstituted with fluorine atoms and additionally may be monosubstituted with R$_{11}$,
(iii) branched or unbranched alkyl of 2 to 6 carbon atoms or cycloalkyl of 3 to 6 carbon atoms, which alkyl or cycloakyl group may be mono- or polysubstituted with halogen or oxo,
(iv) a group of the formula —OR$_{28}$, wherein R$_{28}$ is H, alkyl or fluoroalkyl of 1 to 6 carbon atoms or acyl of 1 to 6 carbon atoms, or R$_{11}$,
(v) cyano,
(vi) halogen, or
from a substituent of (D) selected from
(i) a group of the formula —(CH$_2$)$_n$COOR$_{30}$, wherein R$_{30}$ is independently H, unbranched or branched alkyl of 1 to 6 carbon atoms or cycloalkyl of 3 to 6 carbon atoms and wherein said unbranched or branched alkyl of 1 to 6 carbon atoms or cycloalkyl of 3 to 6 carbon atoms may be optionally and independently substituted with —CH$_2$OR$_{31}$, —COOR$_{31}$, —CON(R$_{31}$)$_2$, —CH$_2$NHCOR$_{31}$, —SO$_2$N(R$_{31}$)$_2$, —CH$_2$NHSO$_2$R$_{31}$, —CH$_2$N(R$_{30}$)$_2$, —SO$_2$OH, —PO(OH)$_2$ wherein R$_{31}$ is independently selected from H, unbranched or branched alkyl of 1 to 6 carbon atoms; or
(ii) a group of the formula —(CH$_2$)$_n$CONR$_{32}$R$_{33}$, wherein R$_{32}$ and R$_{33}$ are each, independently, H, unbranched or branched alkyl of 1 to 6 carbon atoms or cycloalkyl of 3 to 6 carbon atoms and wherein said unbranched or branched alkyl of 1 to 6 carbon atoms or cycloalkyl of 3 to 6 carbon atoms may be optionally and independently substituted with —CH$_2$OR$_{31}$, —COOR$_{31}$, —CON(R$_{31}$)$_2$, —CH$_2$NHCOR$_{31}$, —SO$_2$N(R$_{31}$)$_2$, —CH$_2$NHSO$_2$R$_{31}$, —CH$_2$N(R$_{31}$)$_2$,—SO$_2$OH, —PO(OH)$_2$ wherein R$_{31}$ is independently selected from H, unbranched or branched alkyl of 1 to 6 carbon atoms or wherein NR$_{32}$ is N-alkyl-4-piperidinylamino, N-carboxymethyl-4-piperidinylamino, pyridin-4-ylmethylamino, 4-amidinobenzylamino, 4-carboxybenzylamino, or 4-hydroxybenzylamino and R$_{33}$ is H or wherein NR$_{32}$R$_{33}$ constitute a heterocyclic ring selected from 4-alkyl-1-piperazinyl, wherein alkyl is unbranched or branched alkyl of 1 to 6 carbon atoms, or 1-morpholinyl;
R$_3$ is selected from H, (CH$_2$)$_n$-aryl, substituted (CH$_2$)$_n$-aryl, (CH$_2$)$_n$-heteroaryl and substituted (CH$_2$)$_n$-heteroaryl, wherein one or more of the hydrogen atoms of the aryl group of said substituted (CH$_2$)$_n$-aryl group or one or more of the hydrogen atoms of the heteroaryl group of said substituted (CH$_2$)$_n$-heteroaryl group may be optionally and independently replaced with:
(i) R$_{11}$, which is aryl or heteroaryl selected from phenyl, 2-naphthyl, 2-, 3-, 5- or 6-indolyl, 2- or 3-thiophenyl, 2-, 3- or 4-pyridyl, 2-, 4- or 5-pyrimidinyl, 2- or 3-furyl, 1-, 2- or 3-pyrrolyl, 2-, 4- or 5-oxazolyl, 2-, 4- or 5-thiazolyl, 1-, 3-, 4- or 5-pyrazolyl, 3-, 4- or 5-isoxazolyl, 1-, 2-, 4- or 5-imidazolyl, 3-, 4- or 5-isothiazolyl, 4- or 5-oxadiazolyl, 1-, 4- or 5-triazolyl, 2-thiadiazolyl, 3- or 4-pyridazinyl, 2-pyrazinyl, 2-triazinyl, 2-, 3-, 6- or 7-indolyzinyl, 2-, 3-, 5- or 6-isoindolyl, 2-, 3-, 5- or 6-benzo[b]furanyl, 2-, 3-, 5- or 6-benzo[b]thiophenyl, 3-, 5- or 6-indazolyl, 2-, 5- or 6-benzthiazolyl, 2-, 5- or 6-benzimidazolyl, 2-, 3-, 6- or 7-quinolinyl, 3-, 6- or 7-isoquinolinyl, 2- or 8- purinyl, 2-, 3-, 7- or 8-quinolizinyl, 3-, 6- or 7-cinnolinyl, 6- or 7-phthalazinyl, 2-, 3-, 6- or 7-quinoxalinyl, 2-, 3-, 6- or 7-naphthyridinyl, 2-, 6- or 7-pteridinyl or 2-, 6- or 7-quinazolinyl,
(ii) methyl, which may be mono- or polysubstituted with fluorine atoms and additionally may be monosubstituted with $R_{11}$,
(iii) branched or unbranched alkyl of 2 to 6 carbon atoms or cycloalkyl of 3 to 6 carbon atoms, which alkyl or cycloakyl group may be mono- or polysubstituted with halogen or oxo,
(iv) a group of the formula —$OR_{28}$, wherein $R_{28}$ is H, alkyl or fluoroalkyl of 1 to 6 carbon atoms or acyl of 1 to 6 carbon atoms, or $R_{11}$,
(v) cyano, or
(vi) halogen;
$R_6$ and $R_7$ are both H;
and n is 0, 1 or 2.

7. The compound according to claim 1, wherein
A is $CR_5$, wherein $R_5$ is H or halogen;
$R_1$ is selected from H, branched or unbranched alkyl of 1 to 6 carbon atoms;
$R_2$ and $R_4$ are independently selected from H, $(CH_2)_n$-aryl, or substituted $(CH_2)_n$-aryl, wherein one or more of the hydrogen atoms of the aryl group of said substituted $(CH_2)_n$-aryl group may be optionally replaced with:
(i) $R_{11}$, which is aryl or heteroaryl selected from phenyl, 2-naphthyl, 2-, 3-, 5- or 6-indolyl, 2- or 3-thiophenyl, 2-, 3- or 4-pyridyl, 2-, 4- or 5-pyrimidinyl, 2- or 3-furyl, 1-, 2- or 3-pyrrolyl, 2-, 4- or 5-oxazolyl, 2-, 4- or 5-thiazolyl, 1-, 3-, 4- or 5-pyrazolyl, 3-, 4- or 5-isoxazolyl, 1-, 2-, 4- or 5-imidazolyl, 3-, 4- or 5-isothiazolyl, 4- or 5-oxadiazolyl, 1-, 4- or 5-triazolyl, 2-thiadiazolyl, 3- or 4-pyridazinyl, 2-pyrazinyl, 2-triazinyl, 2-, 3-, 6- or 7-indolyzinyl, 2-, 3-, 5- or 6-isoindolyl, 2-, 3-, 5- or 6-benzo[b]furanyl, 2-, 3-, 5- or 6-benzo[b]thiophenyl, 3-, 5- or 6-indazolyl, 2-, 5- or 6-benzthiazolyl, 2-, 5- or 6-benzimidazolyl, 2-, 3-, 6- or 7-quinolinyl, 3-, 6- or 7-isoquinolinyl, 2- or 8- purinyl, 2-, 3-, 7- or 8-quinolizinyl, 3-, 6- or 7-cinnolinyl, 6- or 7-phthalazinyl, 2-, 3-, 6- or 7-quinoxalinyl, 2-, 3-, 6- or 7-naphthyridinyl, 2-, 6- or 7-pteridinyl or 2-, 6- or 7-quinazolinyl,
(ii) methyl, which may be mono- or polysubstituted with fluorine atoms and additionally may be monosubstituted with $R_{11}$,
(iii) branched or unbranched alkyl of 2 to 6 carbon atoms or cycloalkyl of 3 to 6 carbon atoms, which alkyl or cycloakyl group may be mono- or polysubstituted with halogen or oxo,
(iv) a group of the formula —$OR_{28}$, wherein $R_{28}$ is H, alkyl or fluoroalkyl of 1 to 6 carbon atoms or acyl of 1 to 6 carbon atoms, or $R_{11}$,
(v) cyano,
(vi) halogen, or
from a substituent of (D) selected from
(i) a group of the formula —$(CH_2)COOR_{30}$, wherein $R_{30}$ is independently H, unbranched or branched alkyl of 1 to 6 carbon atoms or cycloalkyl of 3 to 6 carbon atoms and wherein said unbranched or branched alkyl of 1 to 6 carbon atoms or cycloalkyl of 3 to 6 carbon atoms may be optionally and independently substituted with —$CH_2OR_{31}$, —$COOR_{31}$, —$CON(R_{31})_2$, —$CH_2NHCOR_{31}$, —$SO_2N(R_{31})_2$, —$CH_2NHSO_2R_{31}$, —$CH_2N(R_{31})_2$, —$SO_2OH$, —$PO(OH)_2$ wherein $R_{31}$ is independently selected from H, unbranched or branched alkyl of 1 to 6 carbon atoms; or
(ii) a group of the formula —$(CH_2)_nCONR_{32}R_{33}$, wherein $R_{32}$ and $R_{33}$ are each, independently, H, unbranched or branched alkyl of 1 to 6 carbon atoms or cycloalkyl of 3 to 6 carbon atoms and wherein said unbranched or branched alkyl of 1 to 6 carbon atoms or cycloalkyl of 3 to 6 carbon atoms may be optionally and independently substituted with —$CH_2OR_{31}$, —$COOR_{31}$, —$CON(R_{31})_2$, —$CH_2NHCOR_{31}$, —$SO_2N(R_{31})_2$, —$CH_2NHSO_2R_{31}$, —$CH_2N(R_{31})_2$, —$SO_2OH$, —$PO(OH)_2$ wherein $R_{31}$ is independently selected from H, unbranched or branched alkyl of 1 to 6 carbon atoms or wherein $NR_{32}$ is N-alkyl-4-piperidinylamino, N-carboxymethyl-4-piperidinylamino, pyridin-4-ylmethylamino, 4-amidinobenzylamino, 4-carboxybenzylamino, or 4-hydroxybenzylamino and $R_{33}$ is H or wherein $NR_{32}R_{33}$ constitute a heterocyclic ring selected from 4-alkyl-1-piperazinyl, wherein alkyl is unbranched or branched alkyl of 1 to 6 carbon atoms, or 1-morpholinyl;
$R_3$ is selected from H, $(CH_2)_n$-aryl, substituted $(CH_2)_n$-aryl, $(CH_2)_n$-heteroaryl and substituted $(CH_2)_n$-heteroaryl, wherein one or more of the hydrogen atoms of the aryl group of said substituted $(CH_2)_n$-aryl group or one or more of the hydrogen atoms of the heteroaryl group of said substituted $(CH_2)_n$-heteroaryl group may be optionally and independently replaced with:
(i) $R_{11}$, which is aryl or heteroaryl selected from phenyl, 2-naphthyl, 2-, 3-, 5- or 6-indolyl, 2- or 3-thiophenyl, 2-, 3- or 4-pyridyl, 2-, 4- or 5-pyrimidinyl, 2- or 3-furyl, 1-, 2- or 3-pyrrolyl, 2-, 4- or 5-oxazolyl, 2-, 4- or 5-thiazolyl, 1-, 3-, 4- or 5-pyrazolyl, 3-, 4- or 5-isoxazolyl, 1-, 2-, 4- or 5-imidazolyl, 3-, 4- or 5-isothiazolyl, 4- or 5-oxadiazolyl, 1-, 4- or 5-triazolyl, 2-thiadiazolyl, 3- or 4-pyridazinyl, 2-pyrazinyl, 2-triazinyl, 2-, 3-, 6- or 7-indolyzinyl, 2-, 3-, 5- or 6-isoindolyl, 2-, 3-, 5- or 6-benzo[b]furanyl, 2-, 3-, 5- or 6-benzo[b]thiophenyl, 3-, 5- or 6-indazolyl, 2-, 5- or 6-benzthiazolyl, 2-, 5- or 6-benzimidazolyl, 2-, 3-, 6- or 7-quinolinyl, 3-, 6- or 7-isoquinolinyl, 2- or 8- purinyl, 2-, 3-, 7- or 8-quinolizinyl, 3-, 6- or 7-cinnolinyl, 6- or 7-phthalazinyl, 2-, 3-, 6- or 7-quinoxalinyl, 2-, 3-, 6- or 7-naphthyridinyl, 2-, 6- or 7-pteridinyl or 2-, 6- or 7-quinazolinyl,
(ii) methyl, which may be mono- or polysubstituted with fluorine atoms and additionally may be monosubstituted with $R_{11}$,
(iii) branched or unbranched alkyl of 2 to 6 carbon atoms or cycloalkyl of 3 to 6 carbon atoms, which alkyl or cycloakyl group may be mono- or polysubstituted with halogen or oxo,
(iv) a group of the formula —$OR_{28}$, wherein $R_{28}$ is H, alkyl or fluoroalkyl of 1 to 6 carbon atoms or acyl of 1 to 6 carbon atoms, or $R_{11}$,
(v) cyano, or
(vi) halogen;
$R_6$ and $R_7$ are both H;
and n is 0, 1 or 2.

8. The compound according to claim 1, wherein
A is $CR_5$, wherein $R_5$ is H or halogen;
$R_1$ is selected from H, branched or unbranched alkyl of 1 to 6 carbon atoms;

$R_2$ is selected from H, branched or unbranched alkyl of 1 to 6 carbon atoms;

$R_4$ is selected from H, $(CH_2)_n$-aryl, substituted $(CH_2)_n$-aryl or $(CH_2)_n$-heteroaryl, wherein one or more of the hydrogen atoms of the aryl group of said substituted $(CH_2)_n$-aryl group may be optionally replaced with:
(i) methyl, which may be mono- or polysubstituted with fluorine atoms,
(ii) branched or unbranched alkyl of 2 to 6 carbon atoms or cycloalkyl of 3 to 6 carbon atoms, which alkyl or cycloakyl group may be mono- or polysubstituted with halogen or oxo,
(iii) a group of the formula —$OR_{28}$, wherein $R_{28}$ is H, alkyl or fluoroalkyl of 1 to 6 carbon atoms or acyl of 1 to 6 carbon atoms,
(iv) cyano, or
(v) halogen, or from a substituent of (D) selected from
i) a group of the formula —$(CH_2)_nCOOR_{30}$, wherein $R_{30}$ is independently H, unbranched or branched alkyl of 1 to 6 carbon atoms or cycloalkyl of 3 to 6 carbon atoms and wherein said unbranched or branched alkyl of 1 to 6 carbon atoms or cycloalkyl of 3 to 6 carbon atoms may be optionally and independently substituted with —$CH_2OR_{31}$, —$COOR_{31}$, —$CON(R_{31})_2$, —$CH_2NHCOR_{31}$, —$SO_2N(R_{31})_2$, —$CH_2NHSO_2R_{31}$, —$CH_2N(R_{31})_2$, —$SO_2OH$, —$PO(OH)_2$ wherein $R_{31}$ is independently selected from H, unbranched or branched alkyl of 1 to 6 carbon atoms, ii) a group of the formula —$(CH_2)_nCONR_{32}R_{33}$, wherein $NR_{32}R_{33}$ constitute a heterocyclic ring selected from 4-alkyl-1-piperazinyl, wherein alkyl is unbranched or branched alkyl of 1 to 6 carbon atoms, or 1-morpholinyl;

$R_3$ is selected from H, $(CH_2)_n$-aryl, substituted $(CH_2)_n$-aryl, $(CH_2)_n$-heteroaryl or substituted $(CH_2)_n$-heteroaryl, wherein one or more of the hydrogen atoms of the aryl group of said substituted $(CH_2)_n$-aryl group or one or more of the hydrogen atoms of the heteroaryl group of said substituted $(CH_2)_n$-heteroaryl group may be optionally and independently replaced with:
(i) methyl, which may be mono- or polysubstituted with fluorine atoms and additionally may be mono-substituted with $R_{11}$,
(ii) branched or unbranched alkyl of 2 to 6 carbon atoms or cycloalkyl of 3 to 6 carbon atoms, which alkyl or cycloakyl group may be mono- or polysubstituted with halogen or oxo,
(iii) a group of the formula —$OR_{28}$, wherein $R_{28}$ is H, alkyl or fluoroalkyl of 1 to 6 carbon atoms or acyl of 1 to 6 carbon atoms, or $R_{11}$,
(iv) cyano, or
(v) halogen;

$R_6$ and $R_7$ are both H;
and n is 0 or 1.

9. The compound according to claim 1, wherein
A is $CR_5$, wherein $R_5$ is H or halogen;
$R_1$ is selected from H, branched or unbranched alkyl of 1 to 6 carbon atoms;
$R_2$ is selected from H, branched or unbranched alkyl of 1 to 6 carbon atoms;
$R_4$ is selected from H, $(CH_2)_n$-aryl, or substituted $(CH_2)_n$-aryl, wherein one or more of the hydrogen atoms of the aryl group of said substituted $(CH_2)_n$-aryl group may be optionally replaced with:
(i) methyl, which may be mono- or polysubstituted with fluorine atoms,
(ii) branched or unbranched alkyl of 2 to 6 carbon atoms or cycloalkyl of 3 to 6 carbon atoms, which alkyl or cycloakyl group may be mono- or polysubstituted with halogen or oxo,
(iii) a group of the formula —$OR_{28}$, wherein $R_{28}$ is H, alkyl or fluoroalkyl of 1 to 6 carbon atoms or acyl of 1 to 6 carbon atoms,
(iv) cyano, or
(v) halogen, or from a substituent of (D) selected from
a group of the formula —$(CH_2)_nCOOR_{30}$, wherein $R_{30}$ is independently H, unbranched or branched alkyl of 1 to 6 carbon atoms or cycloalkyl of 3 to 6 carbon atoms and wherein said unbranched or branched alkyl of 1 to 6 carbon atoms or cycloalkyl of 3 to 6 carbon atoms may be optionally and independently substituted with —$CH_2OR_{31}$, —$COOR_{31}$, —$CON(R_{31})2$, —$CH_2NHCOR_{31}$, —$SO_2N(R_{31})_2$, —$CH_2NHSO_2R_{31}$, —$CH_2N(R_{31})_2$, —$SO_2OH$, —$PO(OH)_2$ wherein $R_{31}$ is independently selected from H, unbranched or branched alkyl of 1 to 6 carbon atoms;

$R_3$ is selected from H, $(CH_2)_n$-aryl, substituted $(CH_2)_n$-aryl, $(CH_2)_n$-heteroaryl or substituted $(CH_2)_n$-heteroaryl, wherein one or more of the hydrogen atoms of the aryl group of said substituted $(CH_2)_n$-aryl group or one or more of the hydrogen atoms of the heteroaryl group of said substituted $(CH_2)_n$-heteroaryl group may be optionally and independently replaced with:
(i) methyl, which may be mono- or polysubstituted with fluorine atoms and additionally may be mono-substituted with $R_{11}$,
(ii) branched or unbranched alkyl of 2 to 6 carbon atoms or cycloalkyl of 3 to 6 carbon atoms, which alkyl or cycloakyl group may be mono- or polysubstituted with halogen or oxo,
(iii) a group of the formula —$OR_{28}$, wherein $R_{28}$ is H, alkyl or fluoroalkyl of 1 to 6 carbon atoms or acyl of 1 to 6 carbon atoms, or $R_{11}$,
(iv) cyano, or
(v) halogen;

$R_6$ and $R_7$ are both H;
and n is 0 or 1.

10. The compound according to claim 1, wherein
$X_1$ and $X_2$ are halogen;
A is $CR_5$ and wherein $R_5$ is H;
$R_1$ is selected from H, branched or unbranched alkyl of 1 to 6 carbon atoms;
$R_2$ is selected from H, branched or unbranched alkyl of 1 to 6 carbon atoms;
$R_4$ is selected from H, $(CH_2)_n$-aryl, substituted $(CH_2)_n$-aryl or $(CH_2)_n$-heteroaryl, wherein one or more of the hydrogen atoms of the aryl group of said substituted $(CH_2)_n$-aryl group may be optionally replaced with:
(i) methyl, which may be mono- or polysubstituted with fluorine atoms,
(ii) branched or unbranched alkyl of 2 to 6 carbon atoms or cycloalkyl of 3 to 6 carbon atoms, which alkyl or cycloakyl group may be mono- or polysubstituted with halogen or oxo,
(iii) a group of the formula —$OR_{28}$, wherein $R_{28}$ is H, alkyl or fluoroalkyl of 1 to 6 carbon atoms or acyl of 1 to 6 carbon atoms,
(iv) cyano, or
(v) halogen, or from a substituent of (D) selected from
i) a group of the formula —(CH$_2$)$_n$COOR$_{30}$, wherein R$_{30}$ is independently H, unbranched or branched alkyl of 1 to 6 carbon atoms,
ii) a group of the formula —(CH$_2$)$_n$CONR$_{32}$R$_{33}$, wherein NR$_{32}$R$_{33}$ constitute a heterocyclic ring selected from 4-alkyl-1-piperazinyl, wherein alkyl is unbranched or branched alkyl of 1 to 6 carbon atoms, or 1-morpholinyl;

R$_3$ is selected from H, (CH$_2$)$_n$-aryl, substituted (CH$_2$)$_n$-aryl or (CH$_2$)$_n$-heteroaryl, wherein one or more of the hydrogen atoms of the aryl group of said substituted (CH$_2$)$_n$-aryl group may be optionally and independently replaced with:
  (i) methyl, which may be mono- or polysubstituted with fluorine atoms and additionally may be monosubstituted with R$_{11}$,
  (ii) branched or unbranched alkyl of 2 to 6 carbon atoms or cycloalkyl of 3 to 6 carbon atoms, which alkyl or cycloakyl group may be mono- or polysubstituted with halogen or oxo,
  (iii) a group of the formula —OR$_{28}$, wherein R$_{28}$ is H, alkyl or fluoroalkyl of 1 to 6 carbon atoms or acyl of 1 to 6 carbon atoms, or R$_{11}$,
  (iv) cyano, or
  (v) halogen;

R$_6$ and R$_7$ are both H;
and n is 0.

11. The compound according to claim 1, wherein
X$_1$ and X$_2$ are halogen;
A is CR$_5$ and wherein R$_5$ is H;
R$_1$ is selected from H, branched or unbranched alkyl of 1 to 6 carbon atoms;
R$_2$ is selected from H, branched or unbranched alkyl of 1 to 6 carbon atoms;
R$_4$ is selected from H, (CH$_2$)$_n$-aryl, or substituted (CH$_2$)$_n$-aryl, wherein one or more of the hydrogen atoms of the aryl group of said substituted (CH$_2$)$_n$-aryl group may be optionally replaced with:
  (i) methyl, which may be mono- or polysubstituted with fluorine atoms,
  (ii) branched or unbranched alkyl of 2 to 6 carbon atoms or cycloalkyl of 3 to 6 carbon atoms, which alkyl or cycloakyl group may be mono- or polysubstituted with halogen or oxo,
  (iii) a group of the formula —OR$_{28}$, wherein R$_{28}$ is H, alkyl or fluoroalkyl of 1 to 6 carbon atoms or acyl of 1 to 6 carbon atoms,
  (iv) cyano, or
  (v) halogen, or
from a substituent of (D) selected from
a group of the formula —(CH$_2$)$_n$COOR$_{30}$, wherein R$_{30}$ is independently H, unbranched or branched alkyl of 1 to 6 carbon atoms;

R$_3$ is selected from H, (CH$_2$)$_n$-aryl, or substituted (CH$_2$)$_n$-aryl, wherein one or more of the hydrogen atoms of the aryl group of said substituted (CH$_2$)$_n$-aryl group may be optionally and independently replaced with:
  (i) methyl, which may be mono- or polysubstituted with fluorine atoms and additionally may be monosubstituted with R$_{11}$,
  (ii) branched or unbranched alkyl of 2 to 6 carbon atoms or cycloalkyl of 3 to 6 carbon atoms, which alkyl or cycloakyl group may be mono- or polysubstituted with halogen or oxo,
  (iii) a group of the formula —OR$_{28}$, wherein R$_{28}$ is H, alkyl or fluoroalkyl of 1 to 6 carbon atoms or acyl of 1 to 6 carbon atoms, or R$_{11}$,
  (iv) cyano, or
  (v) halogen;

R$_6$ and R$_7$ are both H;
and n is 0.

12. A compound selected from the group consisting of:

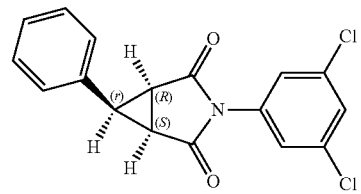

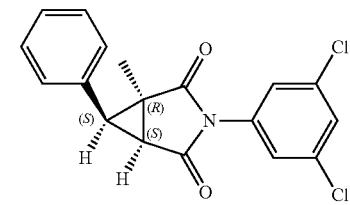

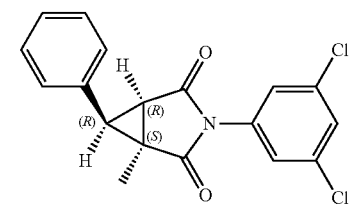

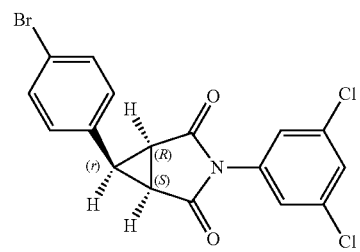

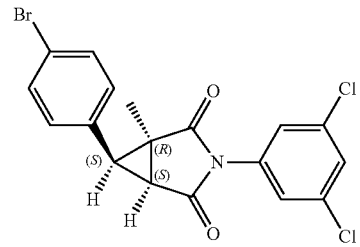

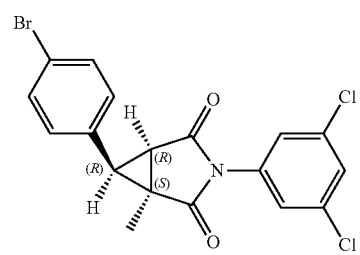

-continued
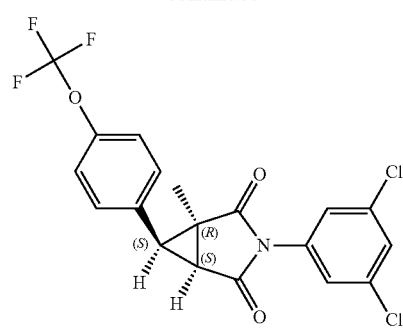
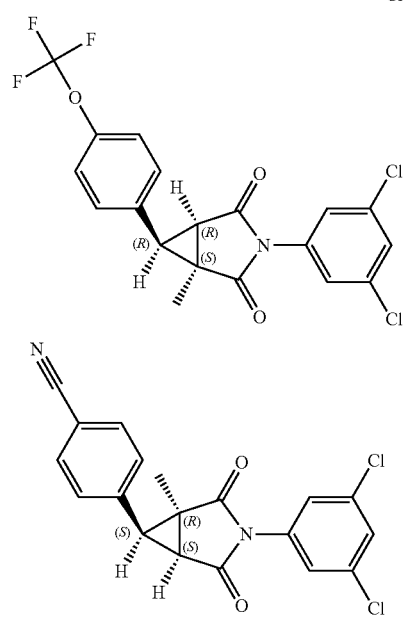
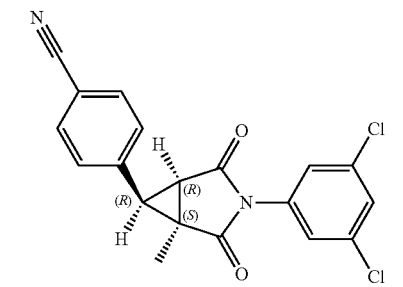
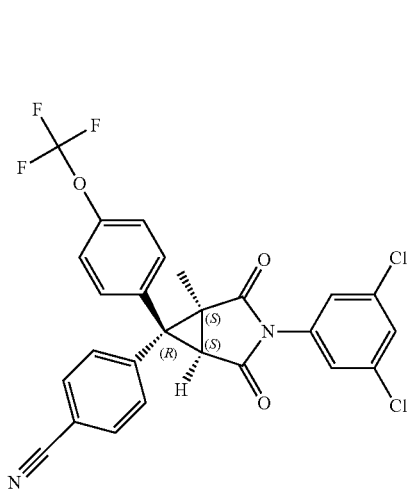
-continued
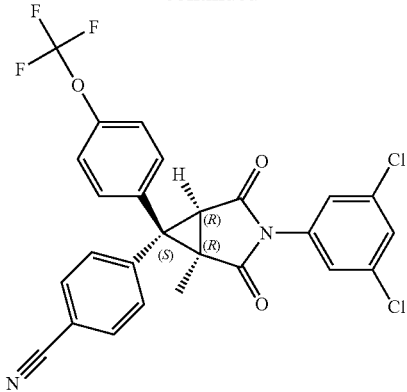
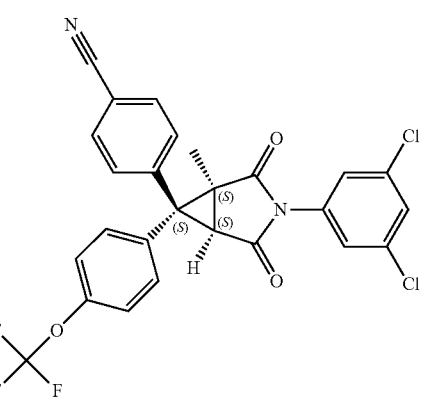
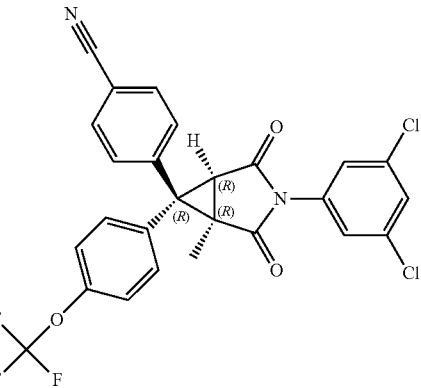
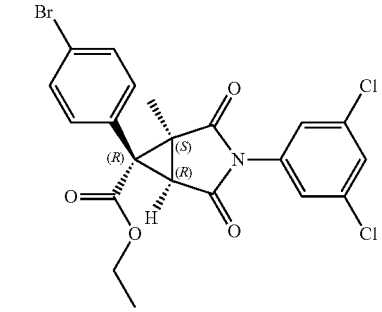

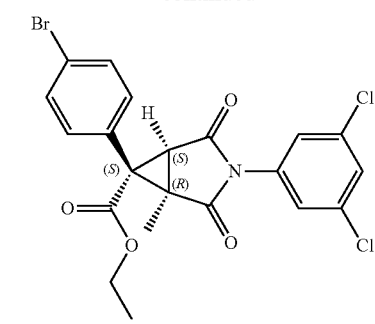
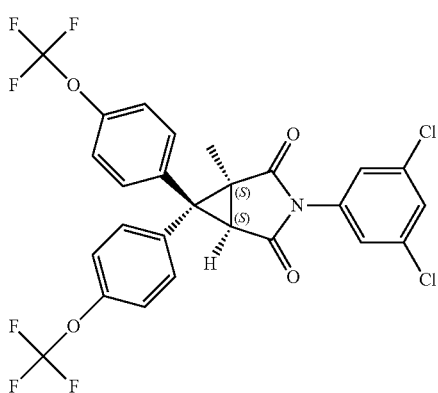
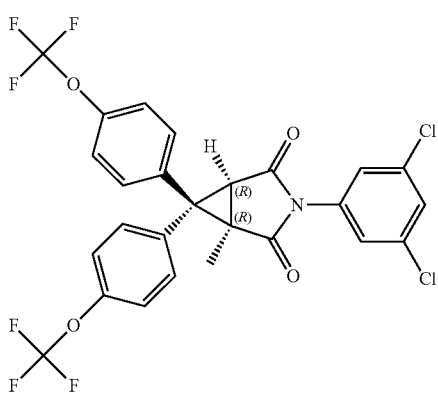
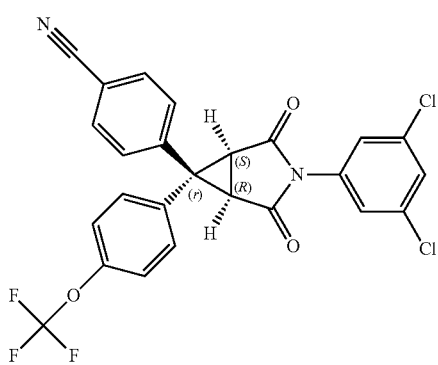
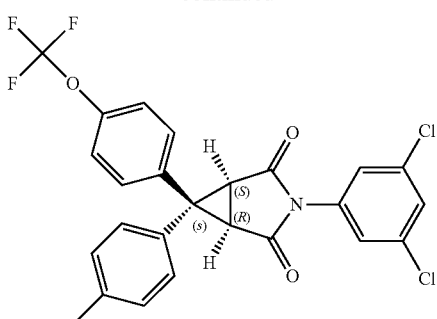
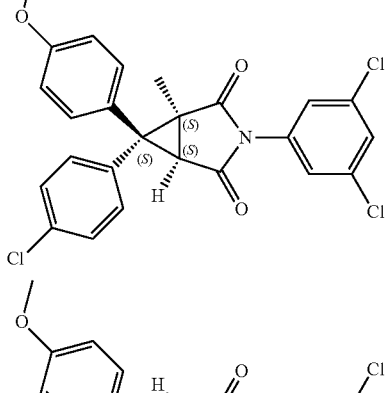
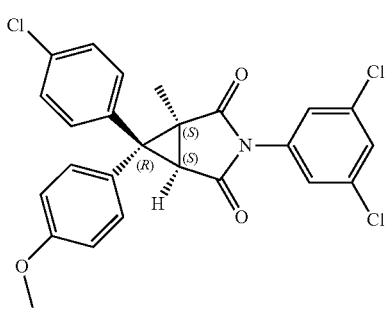
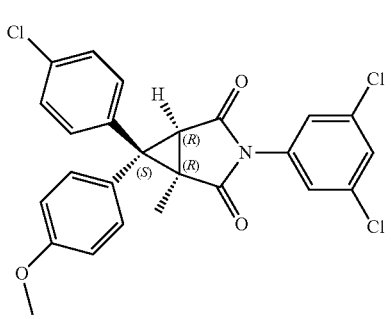

-continued

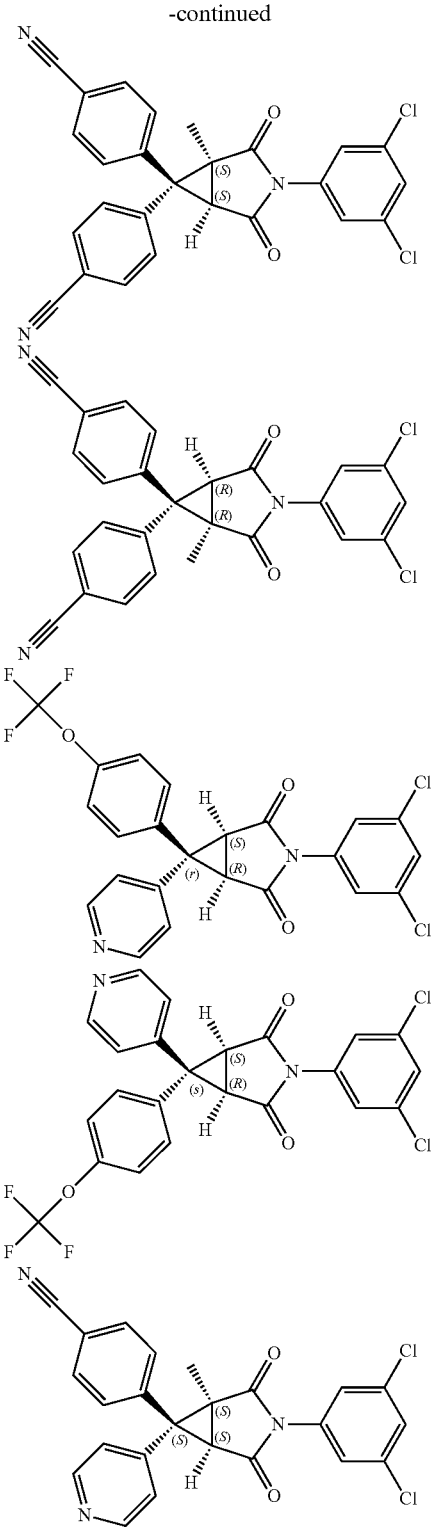

-continued

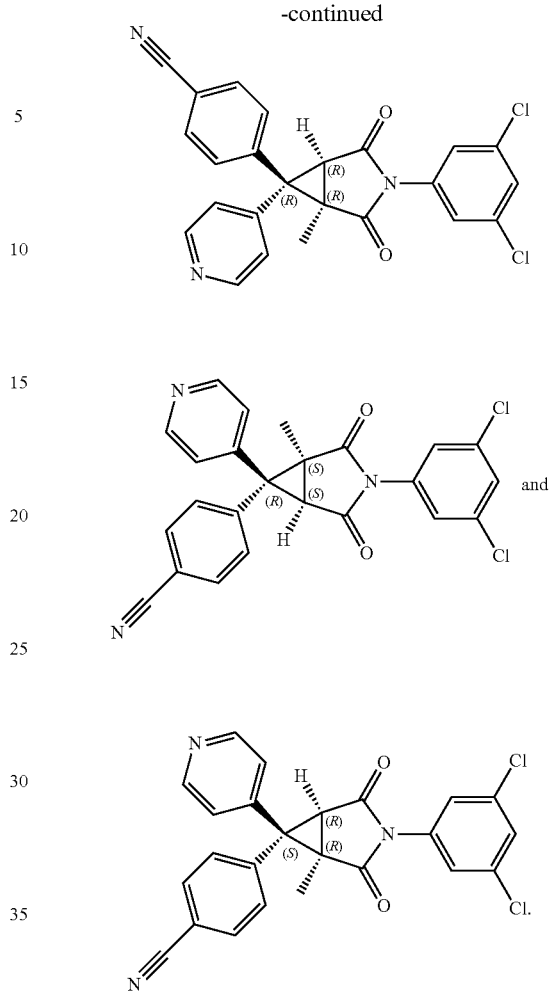

and

13. A pharmaceutical composition comprising a compound according to claim 1 and a pharmaceutically acceptable carrier.

14. The pharmaceutical composition according to claim 13, further comprising another pharmaceutical active agent.

15. The pharmaceutical composition according to claim 14, wherein the compound according to formula Ia or the compound according to formula Ib is a carrier for directing said pharmaceutical active agent to LFA-1 bearing cells.

16. A pharmaceutical composition comprising a compound according to claim 2 and a pharmaceutically acceptable carrier.

17. The pharmaceutical composition according to claim 16, further comprising another pharmaceutical active agent.

18. The pharmaceutical composition according to claim 17, wherein the compound according to formula Ia is a carrier for directing said pharmaceutical active agent to LFA-1 bearing cells.

* * * * *